(12) United States Patent
Murata et al.

(10) Patent No.: US 8,686,159 B2
(45) Date of Patent: Apr. 1, 2014

(54) OXADIAZOLE DERIVATIVE, AND LIGHT EMITTING ELEMENT, LIGHT EMITTING DEVICE, AND ELECTRONIC DEVICE USING THE OXADIAZOLE DERIVATIVE

(71) Applicant: Semiconductor Energy Laboratory Co., Ltd., Kanagawa-ken (JP)

(72) Inventors: Hiroko Murata, Kanagawa (JP); Harue Nakashima, Kanagawa (JP); Sachiko Kawakami, Kanagawa (JP); Nobuharu Ohsawa, Kanagawa (JP); Ryoji Nomura, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 13/780,737

(22) Filed: Feb. 28, 2013

(65) Prior Publication Data

US 2013/0200344 A1     Aug. 8, 2013

Related U.S. Application Data

(62) Division of application No. 11/646,224, filed on Dec. 27, 2006, now Pat. No. 8,389,735.

(30) Foreign Application Priority Data

Dec. 28, 2005   (JP) .................. 2005-378843

(51) Int. Cl.
  *C07D 271/107*  (2006.01)
  *C09K 11/00*  (2006.01)
  *H01L 51/54*  (2006.01)
(52) U.S. Cl.
  USPC ............ 548/145; 548/143; 257/40; 313/503; 428/917

(58) Field of Classification Search
  None
  See application file for complete search history.

(56) References Cited

U.S. PATENT DOCUMENTS

| | | | |
|---|---|---|---|
| 4,629,671 | A | 12/1986 | Everhardus et al. |
| 5,747,183 | A | 5/1998 | Shi et al. |
| 6,406,804 | B1 | 6/2002 | Higashi et al. |
| 6,528,657 | B2 | 3/2003 | Nakaya et al. |
| 6,773,831 | B2 | 8/2004 | Higashi et al. |
| 2002/0105005 | A1 | 8/2002 | Seo et al. |
| 2002/0136924 | A1 | 9/2002 | Higashi et al. |
| 2003/0205696 | A1 | 11/2003 | Thoms et al. |
| 2004/0234814 | A1 | 11/2004 | Nakaya et al. |
| 2006/0243970 | A1 | 11/2006 | Seo et al. |
| 2007/0059553 | A1 | 3/2007 | Egawa et al. |
| 2007/0069197 | A1 | 3/2007 | Leclerc |

FOREIGN PATENT DOCUMENTS

| | | |
|---|---|---|
| EP | 0 175 402 A1 | 3/1986 |
| EP | 0 992 564 A1 | 4/2000 |
| EP | 1 477 544 A2 | 11/2004 |
| JP | 57-68839 | 4/1982 |
| JP | 61-83173 | 4/1986 |
| JP | 62-200359 | 9/1987 |
| JP | 62-201454 | 9/1987 |
| JP | 63-165855 | 7/1988 |
| JP | 1-185527 | 7/1989 |
| JP | 1-208873 | 8/1989 |
| JP | 2-272570 | 11/1990 |
| JP | 6-258852 | 9/1994 |
| JP | 8-245954 | 9/1996 |
| JP | 8-311051 | 11/1996 |
| JP | 9-288364 | 11/1997 |
| JP | 10-161329 | 6/1998 |
| JP | 11-204262 | 7/1999 |
| JP | 2001-220578 | 8/2001 |
| JP | 2002-352957 | 12/2002 |
| JP | 2003-7467 | 1/2003 |
| JP | 2003-20477 | 1/2003 |
| JP | 2003-86381 | 3/2003 |
| JP | 2003-317966 | 11/2003 |
| JP | 2004-71500 | 3/2004 |
| JP | 2004-234952 | 8/2004 |
| JP | 2004-295012 | 10/2004 |
| JP | 2004-303636 | 10/2004 |
| JP | 2005-154404 | 6/2005 |
| JP | 2005-179488 | 7/2005 |

| WO | WO 99/52992 A1 | 10/1999 |
| WO | WO 2005/016882 A1 | 2/2005 |
| WO | WO 2006/072470 A1 | 7/2006 |

OTHER PUBLICATIONS

Thomas et al. Chem. Mater. 2004, 16, 5437-5444.*
Thomas et al. Chem. Mater. 2002, 14, 3852-3859.*
Baldo, M.A. et al, "Very High-Efficiency Green Organic Light-Emitting Devices Based on Electrophosphorescence," Applied Physics Letters, vol. 75, No. 1, Jul. 5, 1999, pp. 4-6.
Thomas, K.R.J. et al., "Green and Yellow Electroluminescent Dipolar Carbazole Derivatives: Features and Benefits of Electron-Withdrawing Segments", Chemistry of Materials, 2002, vol. 14, No. 9, pp. 3852-3859.
Thomas, K.R.J. et al, "New Carbazole-Oxadiazole Dyads for Electroluminescent Devices: Influence of Acceptor Substituents on Luminescent and Thermal Properties," Chemistry of Materials, 2004, vol. 16, No. 25, pp. 5437-5444.
Brunner, K. et al, "Carbazole Compounds as Host Materials for Triplet Emitters in Organic Light-Emitting Diodes: Tuning the HOMO Level Without Influencing the Triplet Energy in Small Molecules," Journal of the American Chemical Society, vol. 126, No. 19, Apr. 23, 2004, pp. 6035-6042.
International Search Report re Application No. PCT/JP2006/326177, dated Feb. 13, 2007.
Written Opinion re Application No. PCT/JP2006/326177, dated Feb. 13, 2007.
STN Structure Search Results, dated Apr. 20, 2010 (27 pages).

* cited by examiner

*Primary Examiner* — Vu A Nguyen
(74) *Attorney, Agent, or Firm* — Husch Blackwell LLP

(57) ABSTRACT

An oxadiazole derivative represented by the following general formula (G1) is synthesized and applied to the light emitting element,

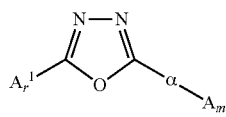
(G1)

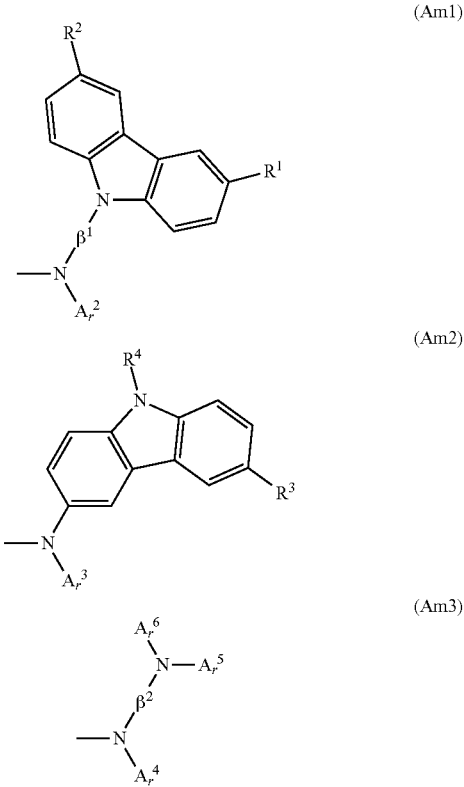

wherein $A_m$ is a substituent represented by a general formula (Am1), (Am2), or (Am3); each of $\alpha$, $\beta^1$, and $\beta^2$ represents an arylene group having 6 to 25 carbon atoms; each of $A_r^1$ to $A_r^6$ represents an aryl group having 6 to 25 carbon atoms; each of $R^1$ to $R^3$ represents hydrogen, an alkyl group having 1 to 4 carbon atoms, or an aryl group having 6 to 25 carbon atoms; and $R^4$ represents an alkyl group having 1 to 4 carbon atoms or an aryl group having 6 to 25 carbon atoms.

23 Claims, 33 Drawing Sheets

> US 8,686,159 B2

OXADIAZOLE DERIVATIVE, AND LIGHT EMITTING ELEMENT, LIGHT EMITTING DEVICE, AND ELECTRONIC DEVICE USING THE OXADIAZOLE DERIVATIVE

This application is a divisional of copending U.S. application Ser. No. 11/646,224 filed on Dec. 27, 2006.

TECHNICAL FIELD

The present invention relates to an oxadiazole derivative. In addition, the present invention relates to a light emitting element, a light emitting device, and an electronic device using the oxadiazole derivative.

BACKGROUND ART

There are more kinds of organic compounds than inorganic compounds. Therefore, in organic compounds, there is a possibility to design and synthesize a substance which has various functions. From such an aspect, in recent years, electronics using an organic compound has attracted attention. For example, a solar battery, a light emitting element, a transistor, and the like using an organic compound as a functional material are typical examples.

These examples are devices utilizing an electrical property and an optical property of an organic compound, and above all, research and development of a light emitting element which uses an organic compound as a light emitting substance has remarkably progressed.

This light emitting element has a simple structure in which a light emitting layer containing an organic compound that is a light emitting substance is provided between electrodes, and has attracted attention as a next-generation flat panel display element because of its characteristics such as a thin shape, lightweight, high response speed, and low direct current voltage driving. In addition, a display using this light emitting element has a feature that it is excellent in contrast and image quality, and has a wide viewing angle.

A light emission mechanism of a light emitting element using an organic compound as a light emitting substance is a carrier injecting type. In other words, when voltage is applied between electrodes with a light emitting layer interposed therebetween, a hole and an electron injected from the electrodes are recombined, a light emitting substance is in an excited state, and light is emitted when the excited state returns to a ground state. As a type of an excited state, a singlet excited state (S*) and a triplet excited state (T*) are given. A statistical generation ratio thereof in a light emitting element is considered to be S*:T*=1:3.

In a compound which converts a singlet excited state into light emission (hereinafter referred to as a fluorescent compound), light emission from a triplet excited state (phosphorescence) is not observed at room temperature, and only light emission from a singlet excited state (fluorescence) is observed. Therefore, in a light emitting element using a fluorescent compound, the theoretical limit of internal quantum efficiency (the ratio of generated photons to injected carriers) is considered to be 25% based on S*:T*=1:3.

On the other hand, when a compound which converts a triplet excited state into light emission (hereinafter referred to as a phosphorescent compound) is used, internal quantum efficiency can be theoretically 75 to 100%. In other words, light emitting efficiency can be three to four times as high as that of a fluorescent compound. From such a reason, in order to achieve a high efficiency light emitting element, a light emitting element using a phosphorescent compound has been actively developed recently (for example, see Non Patent Document 1).

When a light emitting layer of a light emitting element is formed by using the above phosphorescent compound, in order to suppress concentration quenching of the phosphorescent compound or quenching due to triplet-triplet annihilation, the light emitting layer is often formed so that the phosphorescent compound is dispersed in a matrix of another substance. At this time, the substance which serves as a matrix is referred to as a host material; and the substance which is dispersed in a matrix such as a phosphorescent substance is referred to as a guest material.

When the phosphorescent compound is used as a guest material, a host material is required to have higher triplet excitation energy (an energy difference between a ground state and a triplet excited state) than that of the phosphorescent compound. It is known that CBP that is used as a host material in Non Patent Document 1 has higher triplet excitation energy than that of a phosphorescent compound which exhibits emission of green to red light, and is widely used as a host material of the phosphorescent compound.

However, although CBP has high triplet excitation energy, it is poor in ability to receive a hole or an electron; therefore, there is a problem in that driving voltage gets higher. Accordingly, as a host material of a phosphorescent compound, a substance which has high triplet excitation energy and can easily receive or transport both a hole and an electron (i.e. a bipolar substance) is required.

In addition, since singlet excitation energy (an energy difference between a ground state and a singlet excited state) is higher than triplet excitation energy, a substance having high triplet excitation energy also has high singlet excitation energy. Therefore, a substance which has high triplet excitation energy and is bipolar as described above is also effective in a light emitting element using a fluorescent compound as a light emitting substance.

[Non Patent Document 1]

M. A. Baldo, and four others, Applied Physics Letters, vol. 75, No. 1, 4-6 (1999)

DISCLOSURE OF INVENTION

In view of the foregoing, it is an object of the present invention to provide a substance having high excitation energy, in particular, a substance having high triplet excitation energy. In addition, it is another object to provide a bipolar substance.

In addition, it is also an object of the present invention to provide a light emitting element with high light emitting efficiency and with low driving voltage by applying such a substance to the light emitting element.

Further, it is an object to provide a light emitting device with low power consumption by manufacturing the light emitting device using the light emitting element as described above and to provide an electronic device with low power consumption by applying such a light emitting device to the electronic device.

As a result of diligent studies, the present inventors found that the problems can be solved by an oxadiazole derivative represented by the following general formula (G1). Therefore, one structure of the present invention is the oxadiazole derivative represented by the following general formula (G1).

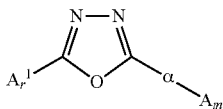

(G1)

$A_m$;

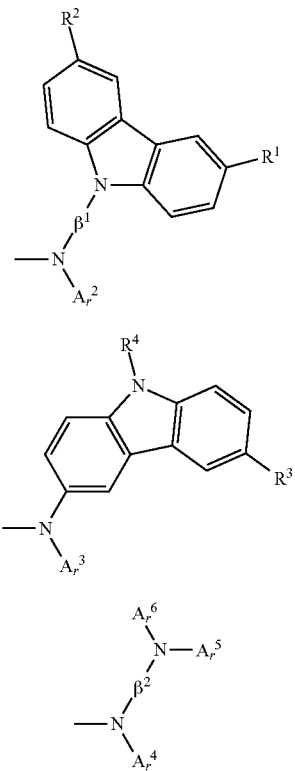

wherein $A_m$ is a substituent represented by a general formula (Am1), (Am2), or (Am3); each of α, $β^1$, and $β^2$ represents an arylene group having 6 to 25 carbon atoms; each of $A_r^1$ to $A_r^6$ represents an aryl group having 6 to 25 carbon atoms; each of $R^1$ to $R^3$ represents hydrogen, an alkyl group having 1 to 4 carbon atoms, or an aryl group having 6 to 25 carbon atoms; and $R^4$ represents an alkyl group having 1 to 4 carbon atoms or an aryl group having 6 to 25 carbon atoms.

In the above general formula (G1), when the general formula (Am1) is employed as the substituent $A_m$, the oxadiazole derivative of the present invention is represented by the following general formula (G2). Therefore, another structure of the present invention is the oxadiazole derivative represented by the following general formula (G2).

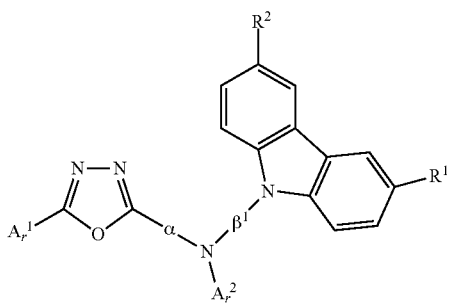

wherein each of α and $β^1$ represents an arylene group having 6 to 25 carbon atoms; each of $A_r^1$ and $A_r^2$ represents an aryl group having 6 to 25 carbon atoms; and each of $R^1$ and $R^2$ represents hydrogen, an alkyl group having 1 to 4 carbon atoms, or an aryl group having 6 to 25 carbon atoms.

Here, in order to obtain chemical stability as well as much higher triplet excitation energy, $β^1$ in the above general formula (G2) is preferably a phenylene group. Therefore, a preferable structure of the present invention is an oxadiazole derivative represented by the following general formula (G3).

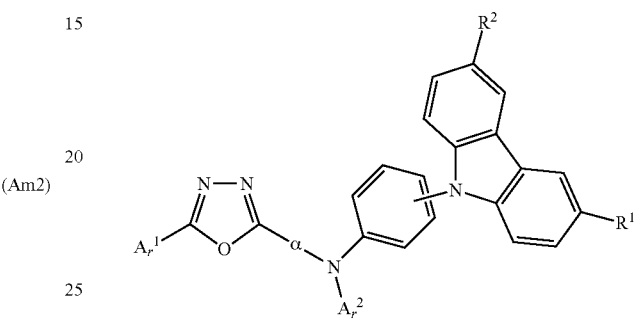

wherein α represents an arylene group having 6 to 25 carbon atoms; each of $A_r^1$ and $A_r^2$ represents an aryl group having 6 to 25 carbon atoms; and each of $R^1$ and $R^2$ represents hydrogen, an alkyl group having 1 to 4 carbon atoms, or an aryl group having 6 to 25 carbon atoms.

In addition, since much higher triplet excitation energy can be obtained and synthesis is easy, $A_r^1$ is preferably a substituted or unsubstituted phenyl group. Therefore, another structure of the present invention is an oxadiazole derivative represented by the following general formula (G4). Since synthesis can be carried out at low cost and with high yield, it is preferable that α be any of a 1,2-phenylene group, a 1,3-phenylene group, or a 1,4-phenylene group.

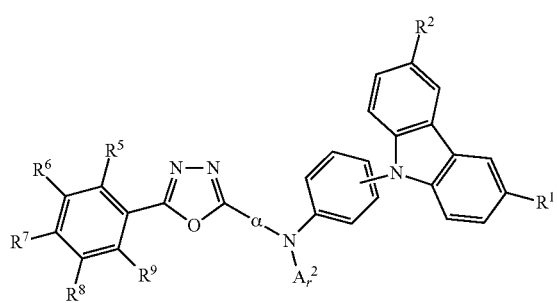

wherein α represents an arylene group having 6 to 25 carbon atoms; $A_r^2$ represents an aryl group having 6 to 25 carbon atoms; each of $R^1$ and $R^2$ represents hydrogen, an alkyl group having 1 to 4 carbon atoms, or an aryl group having 6 to 25 carbon atoms; and each of $R^5$ to $R^9$ represents hydrogen, an alkyl group having 1 to 4 carbon atoms, an alkoxy group having 1 to 4 carbon atoms, or a phenyl group.

In addition, since chemical stability and a high carrier transporting property can be obtained, α is preferably a 1,4-phenylene group. Therefore, another structure of the present invention is an oxadiazole derivative represented by the following general formula (G5).

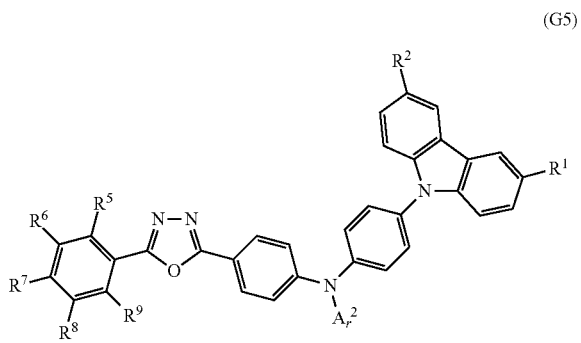

(G5)

wherein $A_r^2$ represents an aryl group having 6 to 25 carbon atoms; each of $R^1$ and $R^2$ represents hydrogen, an alkyl group having 1 to 4 carbon atoms, or an aryl group having 6 to 25 carbon atoms; and each of $R^5$ to $R^9$ represents hydrogen, an alkyl group having 1 to 4 carbon atoms, an alkoxy group having 1 to 4 carbon atoms, or a phenyl group.

Further, in order to obtain much higher triplet excitation energy, $A_r^2$ is preferably a substituted or unsubstituted phenyl group. Therefore, another structure of the present invention is an oxadiazole derivative represented by the following general formula (G6).

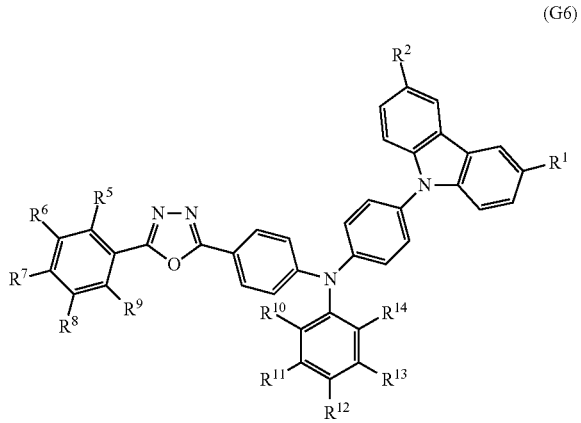

(G6)

wherein each of $R^1$ and $R^2$ represents hydrogen, an alkyl group having 1 to 4 carbon atoms, or an aryl group having 6 to 25 carbon atoms; each of $R^5$ to $R^9$ represents hydrogen, an alkyl group having 1 to 4 carbon atoms, an alkoxy group having 1 to 4 carbon atoms, or a phenyl group; and each of $R^{10}$ to $R^{14}$ represents hydrogen, an alkyl group having 1 to 4 carbon atoms, or a phenyl group.

Subsequently, in the above general formula (G1), when the general formula (Am2) is employed as the substituent $A_m$, the oxadiazole derivative of the present invention is represented by the following general formula (G7). Therefore, another structure of the present invention is the oxadiazole derivative represented by the following general formula (G7).

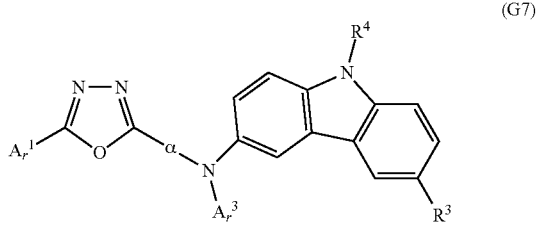

(G7)

wherein $\alpha$ represents an arylene group having 6 to 25 carbon atoms; each of $Ar^1$ and $Ar^3$ represents an aryl group having 6 to 25 carbon atoms; $R^3$ represents hydrogen, an alkyl group having 1 to 4 carbon atoms, or an aryl group having 6 to 25 carbon atoms; and $R^4$ represents an alkyl group having 1 to 4 carbon atoms or an aryl group having 6 to 25 carbon atoms.

Here, since much higher triplet excitation energy can be obtained and synthesis is easy, $A_r^1$ is preferably a substituted or unsubstituted phenyl group. Therefore, another structure of the present invention is an oxadiazole derivative represented by the following general formula (G8). Since synthesis can be carried out at low cost and with high yield, it is preferable that $\alpha$ be any of a 1,2-phenylene group, a 1,3-phenylene group, or a 1,4-phenylene group.

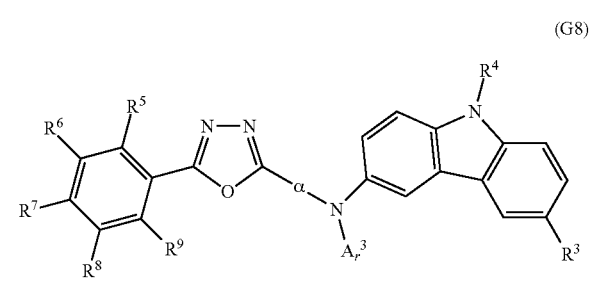

(G8)

wherein $\alpha$ represents an arylene group having 6 to 25 carbon atoms; $Ar^3$ represents an aryl group having 6 to 25 carbon atoms; $R^3$ represents hydrogen, an alkyl group having 1 to 4 carbon atoms, or an aryl group having 6 to 25 carbon atoms; $R^4$ represents an alkyl group having 1 to 4 carbon atoms or an aryl group having 6 to 25 carbon atoms; and each of $R^5$ to $R^9$ represents hydrogen, an alkyl group having 1 to 4 carbon atoms, an alkoxy group having 1 to 4 carbon atoms, or a phenyl group.

In addition, since chemical stability and a high carrier transporting property can be obtained, $\alpha$ is preferably a 1,4-phenylene group. Further, since synthesis is easy, $R^3$ is preferably hydrogen. Therefore, another structure of the present invention is an oxadiazole derivative represented by the following general formula (G9).

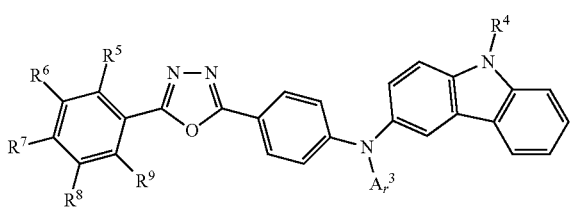

(G9)

wherein $Ar^3$ represents an aryl group having 6 to 25 carbon atoms; $R^4$ represents an alkyl group having 1 to 4 carbon atoms or an aryl group having 6 to 25 carbon atoms; and each of $R^5$ to $R^9$ represents hydrogen, an alkyl group having 1 to 4 carbon atoms, an alkoxy group having 1 to 4 carbon atoms, or a phenyl group.

Further, in order to obtain much higher triplet excitation energy, $A_r^3$ is preferably a substituted or unsubstituted phenyl group. Therefore, another structure of the present invention is an oxadiazole derivative represented by the following general formula (G10).

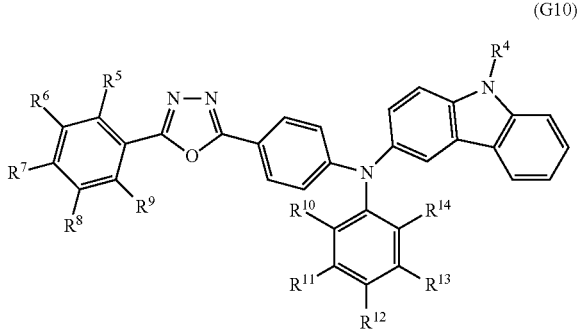

(G10)

wherein $R^4$ represents an alkyl group having 1 to 4 carbon atoms or an aryl group having 6 to 25 carbon atoms; each of $R^5$ to $R^9$ represents hydrogen, an alkyl group having 1 to 4 carbon atoms, an alkoxy group having 1 to 4 carbon atoms, or a phenyl group; and each of $R^{10}$ to $R^{14}$ represents hydrogen, an alkyl group having 1 to 4 carbon atoms, or a phenyl group.

Subsequently, in the above general formula (G1), when the general formula (Am3) is employed as the substituent $A_m$, the oxadiazole derivative of the present invention is represented by the following general formula (G11). Therefore, another structure of the present invention is the oxadiazole derivative represented by the following general formula (G11).

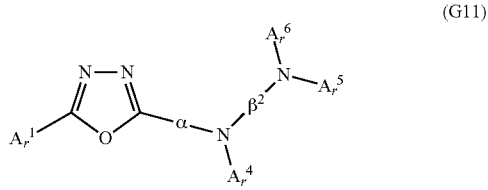

(G11)

wherein each of α and $β^2$ represents an arylene group having 6 to 25 carbon atoms; and each of $A_r^1$ and $A_r^4$ to $A_r^6$ represents an aryl group having 6 to 25 carbon atoms.

Here, in order to obtain chemical stability as well as much higher triplet excitation energy, $β^1$ in the above general formula (G11) is preferably a phenylene group. Therefore, a preferable structure of the present invention is an oxadiazole derivative represented by the following general formula (G12).

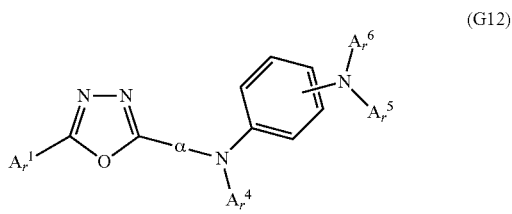

(G12)

wherein α represents an arylene group having 6 to 25 carbon atoms; and each of $A_r^1$ and $A_r^4$ to $A_r^6$ represents an aryl group having 6 to 25 carbon atoms.

In addition, in order to obtain much higher triplet excitation energy, each of $A_r^5$ and $A_r^6$ is preferably a substituted or unsubstituted phenyl group. Therefore, another structure of the present invention is an oxadiazole derivative represented by the following general formula (G13).

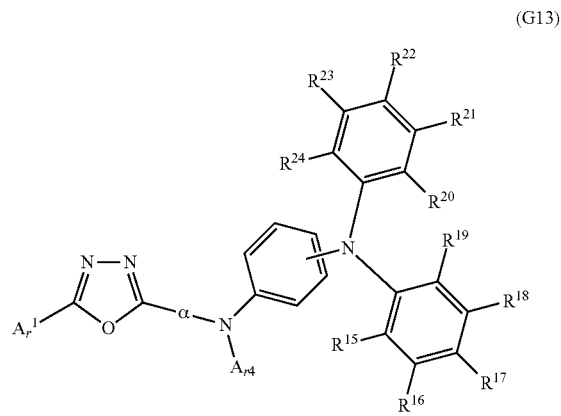

(G13)

wherein α represents an arylene group having 6 to 25 carbon atoms; each of $A_r^1$ and $A_r^4$ represents an aryl group having 6 to 25 carbon atoms; and each of $R^{15}$ to $R^{24}$ represents hydrogen, an alkyl group having 1 to 4 carbon atoms, or a phenyl group.

In addition, since much higher triplet excitation energy can be obtained and synthesis is easy, $A_r^1$ is preferably a substituted or unsubstituted phenyl group. Therefore, another structure of the present invention is an oxadiazole derivative represented by the following general formula (G14). Since synthesis can be carried out at low cost and with high yield, it is preferable that α be any of a 1,2-phenylene group, a 1,3-phenylene group, or a 1,4-phenylene group.

(G14)

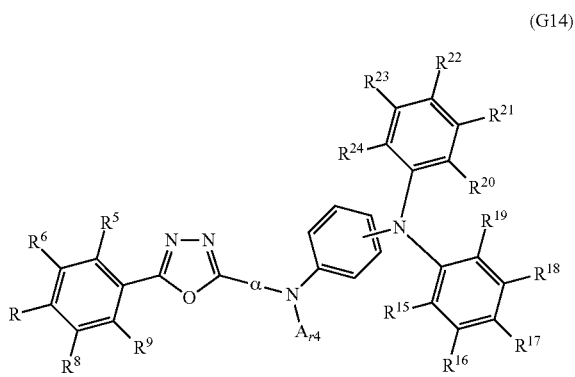

wherein α represents an arylene group having 6 to 25 carbon atoms; $A_r^4$ represents an aryl group having 6 to 25 carbon atoms; each of $R^5$ to $R^9$ represents hydrogen, an alkyl group having 1 to 4 carbon atoms, an alkoxy group having 1 to 4 carbon atoms, or a phenyl group; and each of $R^{15}$ to $R^{24}$ represents hydrogen, an alkyl group having 1 to 4 carbon atoms, or a phenyl group.

In addition, since chemical stability and a high carrier transporting property can be obtained, α is preferably a 1,4-phenylene group. Further, since synthesis is easy, each of $R^{15}$ to $R^{24}$ is preferably hydrogen. Therefore, another structure of the present invention is an oxadiazole derivative represented by the following general formula (G15).

(G15)

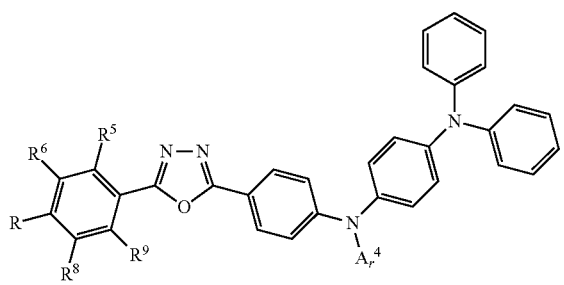

wherein $A_r^4$ represents an aryl group having 6 to 25 carbon atoms; and each of $R^5$ to $R^9$ represents hydrogen, an alkyl group having 1 to 4 carbon atoms, an alkoxy group having 1 to 4 carbon atoms, or a phenyl group.

In addition, in order to obtain much higher triplet excitation energy, $A_r^4$ is preferably a substituted or unsubstituted phenyl group. Therefore, another structure of the present invention is an oxadiazole derivative represented by the following general formula (G16).

(G16)

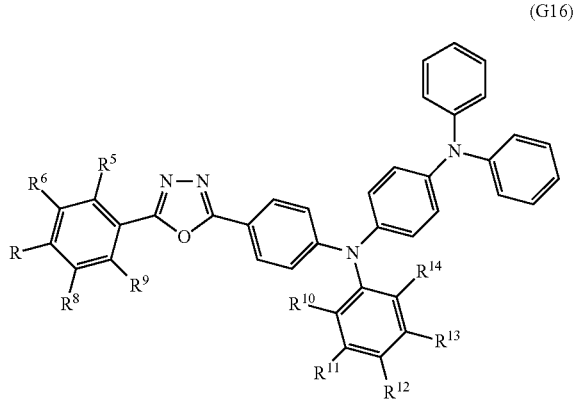

wherein each of $R^5$ to $R^9$ represents hydrogen, an alkyl group having 1 to 4 carbon atoms, an alkoxy group having 1 to 4 carbon atoms, or a phenyl group; and each of $R^{10}$ to $R^{14}$ represents hydrogen, an alkyl group having 1 to 4 carbon atoms, or a phenyl group.

In the oxadiazole derivatives of the present invention represented by the general formulas (G1) to (G16), as an alkyl group having 1 to 4 carbon atoms, a methyl group, an ethyl group, an isopropyl group, an isobutyl group, a tert-butyl group, and the like are given. In addition, as an alkoxy group having 1 to 4 carbon atoms, a methoxy group, an ethoxy group, an isopropoxy group, an isobutoxy group, a tert-butoxy group, and the like are given. As an aryl group having 6 to 25 carbon atoms, a phenyl group, an o-tolyl group, an m-tolyl group, a p-tolyl group, a 4-tert-butylphenyl group, a 1-naphthyl group, a 2-naphthyl group, a 2-biphenyl group, a 3-biphenyl group, a 4-biphenyl group, a 99-dimethylfluoren-2-yl group, a spiro-9,9'-bifluoren-2-yl group, and the like are given. In addition, as an arylene group having 6 to 25 carbon atoms, a 1,2-phenylene group, a 1,3-phenylene group, a 1,4-phenylene group, a 2,5-dimethyl-1,4-phenylene group, a 1,4-naphthylen group, a 1,5-naphthylen group, a 4,4'-biphenylene group, a 9-dimethylfluorene-2,7-diyl group, a spiro-9,9'-bifluorene-2,7-diyl group, and the like are given.

Since the oxadiazole derivatives of the present invention represented by the general formulas (G1) to (G16) have a light emitting property, they can be applied to a light emitting element. Therefore, another structure of the present invention is a light emitting element containing the oxadiazole derivative as described above.

In addition, the oxadiazole derivative of the present invention has high excitation energy and can transport both a hole and an electron, and is thus suitable for a host material of a light emitting layer in a light emitting element. Therefore, another structure of the present invention is a light emitting element including a light emitting layer containing a light emitting substance and the oxadiazole derivative as described above.

In particular, since the oxadiazole derivative of the present invention has a feature of high triplet excitation energy, a phosphorescent compound is suitable for the light emitting substance. By such a structure, a light emitting element that is excellent in light emitting efficiency and driving voltage can be obtained.

Further, one mode of the present invention is a light emitting element in which a layer containing the oxadiazole derivative of the present invention is provided to be in contact with a light emitting layer. Since the oxadiazole derivative of the present invention has high excitation energy, an exciton generated in the light emitting layer can be prevented from diffusing into another layer by such a structure. Consequently, a light emitting element with high light emitting efficiency can be obtained.

In addition, the light emitting element of the present invention obtained as described above has high light emitting efficiency and low driving voltage. Therefore, a light emitting device using the light emitting element (an image display device or a light emitting device) can achieve low power consumption. Therefore, the present invention also includes a light emitting device using the light emitting element of the present invention and an electronic device using the light emitting device.

Note that the light emitting device in this specification includes an image display device or a light emitting device using a light emitting element. In addition, the light emitting device also includes a module in which a light emitting element is provided with a connector such as an anisotropic conductive film, TAB (Tape Automated Bonding) tape, or a TCP (Tape Carrier Package); a module in which the top of a TAB tape or a TCP is provided with a printed wiring board; or a module in which a light emitting element is directly installed with an IC (Integrated Circuit) by a COG (Chip On Glass) method. Further, a light emitting device used for lighting equipment or the like can also be included.

By implementing the present invention, a substance having high excitation energy, in particular, a substance having high triplet excitation energy can be obtained. In addition, a bipolar substance can be obtained.

By applying such a substance to a light emitting element, a light emitting element with high light emitting efficiency and with low driving voltage can be provided.

Further, by manufacturing a light emitting device using the light emitting element as described above, a light emitting device with low power consumption can be provided. Moreover, by applying such a light emitting device to an electronic device, an electronic device with low power consumption can be provided.

BEST MODE FOR CARRYING OUT THE INVENTION

Figure 1:
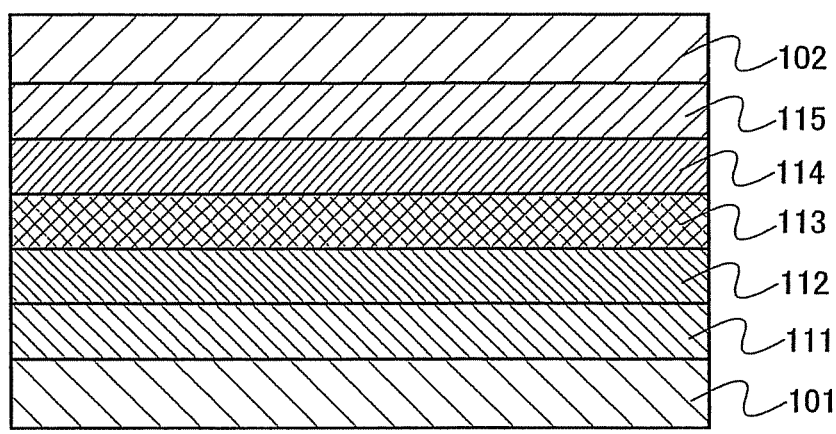
FIG. 1 is a view explaining an element structure of a light emitting element containing an oxadiazole derivative of the present invention.

Hereinafter, embodiment modes and embodiments of the present invention will be explained in detail with reference to the accompanying drawings. Note that the present invention is not limited to the following description, and it is easily understood by those skilled in the art that modes and details thereof can be modified in various ways without departing from the purpose and the scope of the invention. Therefore, the present invention should not be interpreted as being limited to the following description of the embodiment modes and the embodiments.

[Embodiment Mode 1]

Embodiment Mode 1 will explain an oxadiazole derivative of the present invention. The oxadiazole derivative of the present invention is represented by the following general formula (G1).

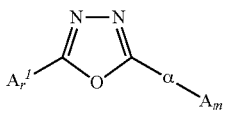
(G1)

$A_m$:

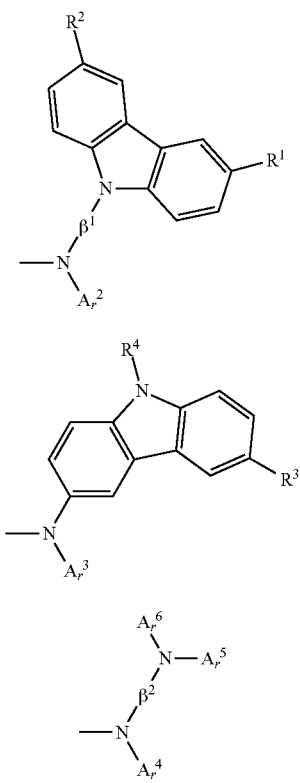

(wherein $A_m$ is a substituent represented by a general formula (Am1), (Am2), or (Am3); each of α, $β^1$, and $β^2$ represents an arylene group having 6 to 25 carbon atoms; each of $A_r^1$ to $A_r^6$ represents an aryl group having 6 to 25 carbon atoms; each of $R^1$ to $R^3$ represents hydrogen, an alkyl group having 1 to 4 carbon atoms, or an aryl group having 6 to 25 carbon atoms; and $R^4$ represents an alkyl group having 1 to 4 carbon atoms or an aryl group having 6 to 25 carbon atoms.)

The oxadiazole derivative represented by the above general formula (G1) can be obtained by coupling a halogenated oxadiazole derivative represented by the following general formula (OXD1) to secondary amine represented by the following formula (Am1'), (Am2'), or (Am3') using a metal catalyst or the like. Hereinafter, a synthesis method of the following (OXD1) will be first explained.

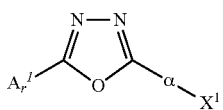
(OXD1)

(wherein α represents an arylene group having 6 to 25 carbon atoms; $A_r^1$ represents an aryl group having 6 to 25 carbon atoms; and $X^1$ represents a halogen group, preferably, a bromo group or an iodo group.)

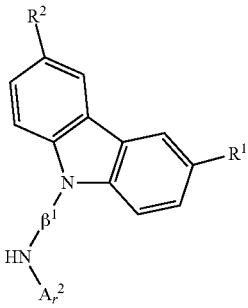
(Am1')

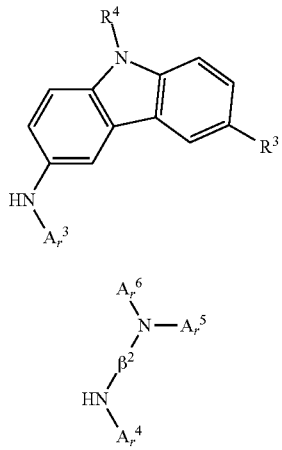

(wherein each of $β^1$ and $β^2$ represents an arylene group having 6 to 25 carbon atoms; each of $A_r^2$ to $A_r^6$ represents an aryl group having 6 to 25 carbon atoms; each of $R^1$ to $R^3$ represents hydrogen, an alkyl group having 1 to 4 carbon atoms, or an aryl group having 6 to 25 carbon atoms; and $R^4$ represents an alkyl group having 1 to 4 carbon atoms or an aryl group having 6 to 25 carbon atoms.)

<<a. Synthesis Method of a Halogenated Oxadiazole Derivative (OXD1)>>

The halogenated oxadiazole derivative represented by the above general formula (OXD1) can be synthesized as shown in the following synthesis scheme (a). That is, first, ester of halogenated aryl carboxylic acid (A) is reacted with hydrazine to synthesize halogenated aryl hydrazide (B). Subsequently, halogenated aryl hydrazide (B) is reacted with aryl carboxylic acid halide (C) to obtain a diacyl hydrazine derivative (D). Further, ring-closing is performed to the diacyl hydrazine derivative (D) by dehydration using a dehydrator to form a 1,3,4-oxadiazole ring; accordingly, the halogenated oxadiazole derivative (OXD1) can be obtained. Note that, in the scheme (a), R represents an alkyl group; α represents an arylene group having 6 to 25 carbon atoms; $A_r^1$ represents an aryl group having 6 to 25 carbon atoms; and each of $X^1$ and $X^2$ represents a halogen group, preferably, a bromo group or an iodo group.

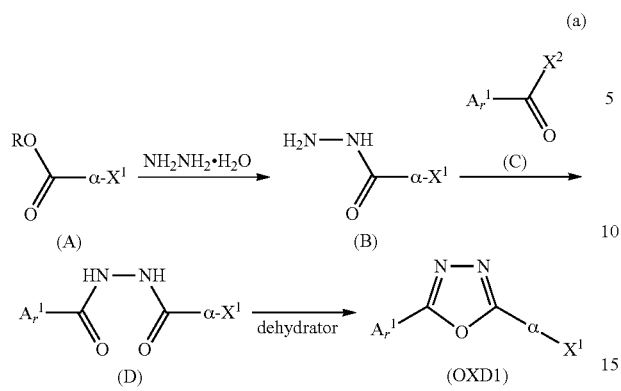

(a)

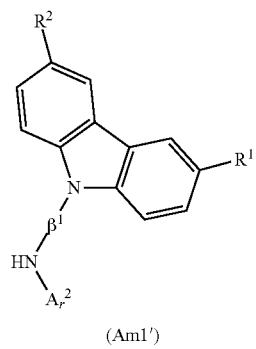

(Am1′)

Note that phosphoryl chloride, thionyl chloride, or the like can be used as the dehydrator.

In addition, a method for synthesizing the halogenated oxadiazole derivative (OXD1) is not limited to the above scheme (a), and other known methods can also be used.

<<b. Synthesis Method of Secondary Amine (Am1′), (Am2′), and (Am3′)>>

Next, a synthesis method of each secondary amine represented by the above general formulas (Am1′), (Am2′), and (Am3′) will be explained.

<b1. Synthesis Method of Secondary Amine (Am1′)>

The secondary amine represented by the above general formula (Am1′) can be synthesized as shown in the following synthesis scheme (b1). That is, first, dihalogenated arene (E) and a carbazole derivative (F) are coupled in the presence of a base using a metal catalyst to synthesize a halogenated aryl carbazole derivative (G). Then, the halogenated aryl carbazole derivative (G) and arylamine (H) are coupled in the presence of a base using a metal catalyst to obtain the secondary amine (Am1′). Note that, in the following scheme (b1), $\beta^1$ represents an arylene group having 6 to 25 carbon atoms; $A_r^2$ represents an aryl group having 6 to 25 carbon atoms; each of $R^1$ and $R^2$ represents hydrogen, an alkyl group having 1 to 4 carbon atoms, or an aryl group having 6 to 25 carbon atoms; and each of $X^3$ and $X^4$ represents a halogen group, preferably, a bromo group or an iodo group.

Note that, as the base, an inorganic base such as potassium carbonate or sodium carbonate, or an organic base typified by metal alkoxide such as sodium tert-butoxide can be used. In addition, as the metal catalyst, a palladium catalyst or monovalent copper can be used. Specifically, palladium acetate, palladium chloride, bis(dibenzylidineacetone)palladium (0), copper (I) iodide, or the like can be used.

In addition, a method for synthesizing the secondary amine (Am1′) is not limited to the above scheme (b1), and other known methods can also be used.

<b2. Synthesis Method of Secondary Amine (Am2′)>

The secondary amine represented by the above general formula (Am2′) can be synthesized as shown in the following synthesis scheme (b2). That is, first, 3 position of a carbazole derivative (I) is halogenated by using a halogenating agent to synthesize a halogenated carbazole derivative (J). Then, the halogenated carbazole derivative (J) and arylamine (K) are coupled in the presence of a base using a metal catalyst to obtain the secondary amine (Am2′). Note that, in the following scheme (b2), $A_r^3$ represents an aryl group having 6 to 25 carbon atoms; $R^3$ represents hydrogen, an alkyl group having 1 to 4 carbon atoms, or an aryl group having 6 to 25 carbon atoms; $R^4$ represents an alkyl group having 1 to 4 carbon atoms, or an aryl group having 6 to 25 carbon atoms; and $X^5$ represents a halogen group, preferably, a bromo group or an iodo group.

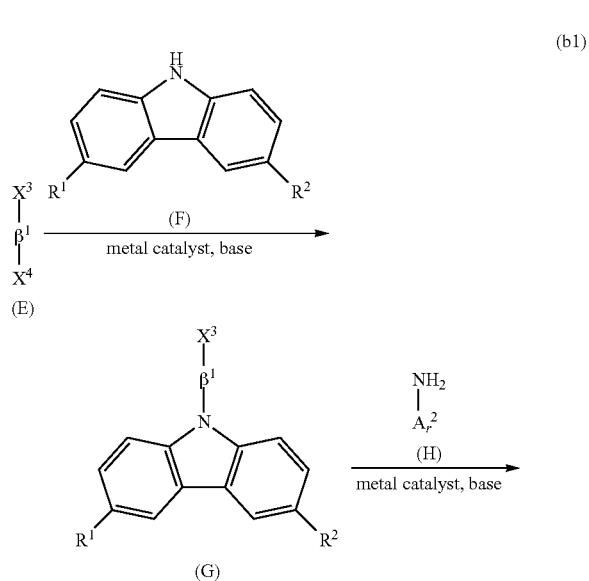

(b1)

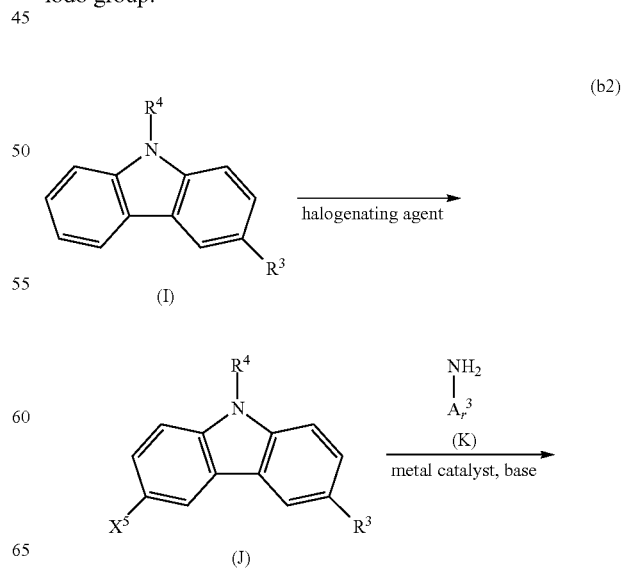

(b2)

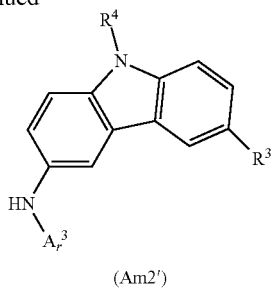

(Am2')

Note that, as the halogenating agent, N-bromosuccinimide (NBS), N-iodosuccinimide (NIS), or the like can be used. In addition, as the base and the metal catalyst, the substances mentioned in <b1. Synthesis Method of secondary amine (Am1')> can be used.

In addition, a method for synthesizing the secondary amine (Am2') is not limited to the above scheme (b2), and other known methods can also be used.

<b3. Synthesis Method of Secondary Amine (Am3')>

The secondary amine represented by the above general formula (Am3') can be synthesized as shown in the following synthesis scheme (b3). That is, first, triarylamine (L) is halogenated by using a halogenating agent to synthesize monohalogenated triarylamine (M). Then, monohalogenated triarylamine (M) and arylamine (N) are coupled in the presence of a base using a metal catalyst to obtain the secondary amine (Am3'). Note that, in the following scheme (b3), $\beta^2$ represents an arylene group having 6 to 25 carbon atoms; each of $A_r^4$ to $A_r^6$ represents an aryl group having 6 to 25 carbon atoms; and $X^6$ represents a halogen group, preferably, a bromo group or an iodo group.

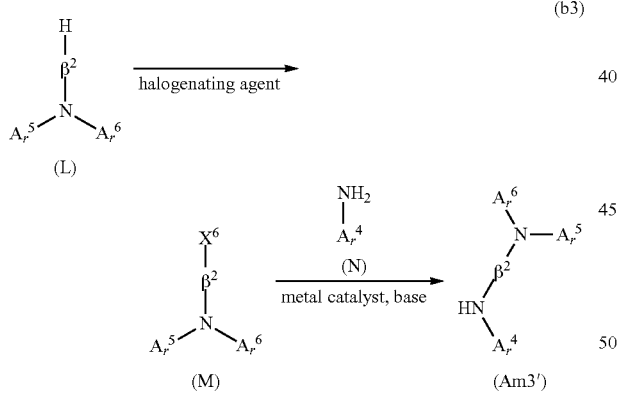

Note that, as the halogenating agent, N-bromosuccinimide (NBS), N-iodosuccinimide (NIS), or the like can be used. In addition, as the base and the metal catalyst, the substances mentioned in <b1. Synthesis Method of secondary amine (Am1> can be used.

In addition, a method for synthesizing the secondary amine (Am3') is not limited to the above scheme (b3), and other known methods can also be used.

21 <c. Synthesis Method of an Oxadiazole Derivative of the Present Invention Represented by the General Formula (G1) >>

The halogenated oxadiazole derivative (OXD1) obtained in the above scheme (a) and the secondary amine (Am1'), (Am2'), or (Am3') obtained in the above scheme (b1), (b2), or (b3) are coupled in the presence of a base using a metal catalyst to obtain the oxadiazole derivative of the present invention represented by the general formula (G1). The scheme is shown in the following scheme (c). Note that, in the following scheme (c), $A_m$ is a substituent represented by the general formula (Am1), (Am2), or and (Am3); each of $\alpha$, $\beta^1$, $\beta^2$ represents an arylene group having 6 to 25 carbon atoms; each of $A_r^1$ to $A_r^6$ represents an aryl group having 6 to 25 carbon atoms; each of $R^1$ to $R^3$ represents hydrogen, an alkyl group having 1 to 4 carbon atoms, or an aryl group having 6 to 25 carbon atoms; $R^4$ represents an alkyl group having 1 to 4 carbon atoms or an aryl group having 6 to 25 carbon atoms, and $X^1$ represents a halogen group, preferably, a bromo group or an iodo group.

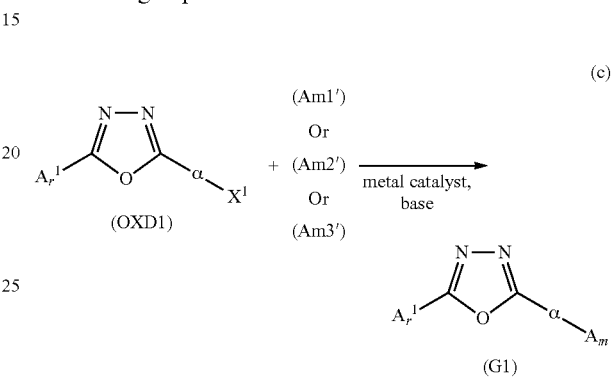

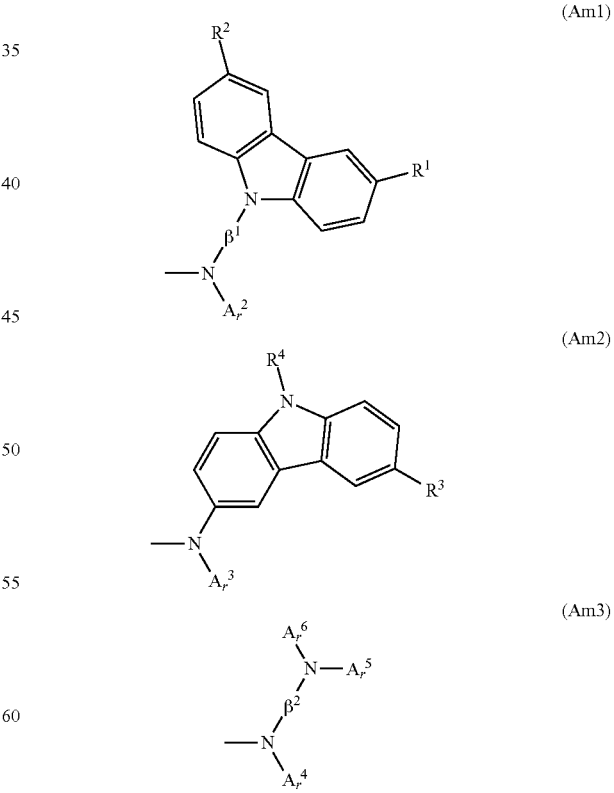

Note that, as the base and the metal catalyst, the substances mentioned in <b1. Synthesis Method of secondary amine (Am1')> can be used.

Note that a substance obtained by coupling (OXD1) and (Am1') corresponds to the oxadiazole derivative represented by the above general formula (G2), a substance obtained by coupling (OXD1) and (Am2') corresponds to the oxadiazole derivative represented by the above general formula (G7), and a substance obtained by coupling (OXD1) and (Am3') corresponds to the oxadiazole derivative represented by the above general formula (G11).

<<Specific Structural Formula of the Oxadiazole Derivative of the Present Invention Represented by the General Formula (G1)>>

Subsequently, a specific structure of the oxadiazole derivative of the present invention will be explained by using the following general formula (G1).

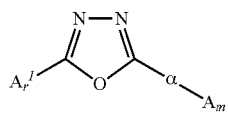

(G1)

$A_m$:

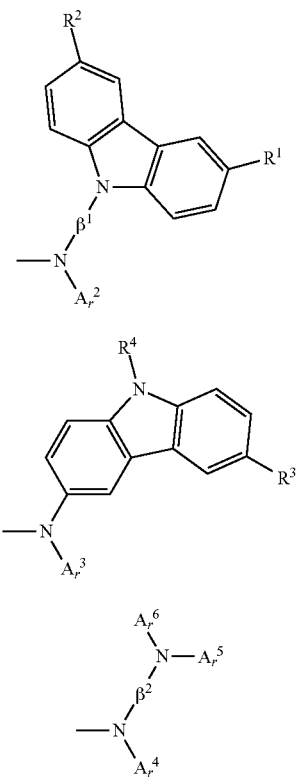

(Am1)

(Am2)

(Am3)

(wherein $A_m$ is a substituent represented by the general formula (Am1), (Am2), or (Am3); each of α, $β^1$, and $β^2$ represents an arylene group having 6 to 25 carbon atoms; each of $A_r^1$ to $A_r^6$ represents an aryl group having 6 to 25 carbon atoms; each of $R^1$ to $R^3$ represents hydrogen, an alkyl group having 1 to 4 carbon atoms, or an aryl group having 6 to 25 carbon atoms; and $R^4$ represents an alkyl group having 1 to 4 carbon atoms or an aryl group having 6 to 25 carbon atoms.)

As a structure of the arylene group α in the general formula (G1), more specifically, any structure in the following structural formula group (α) can be employed. Note that the present invention is not limited thereto.

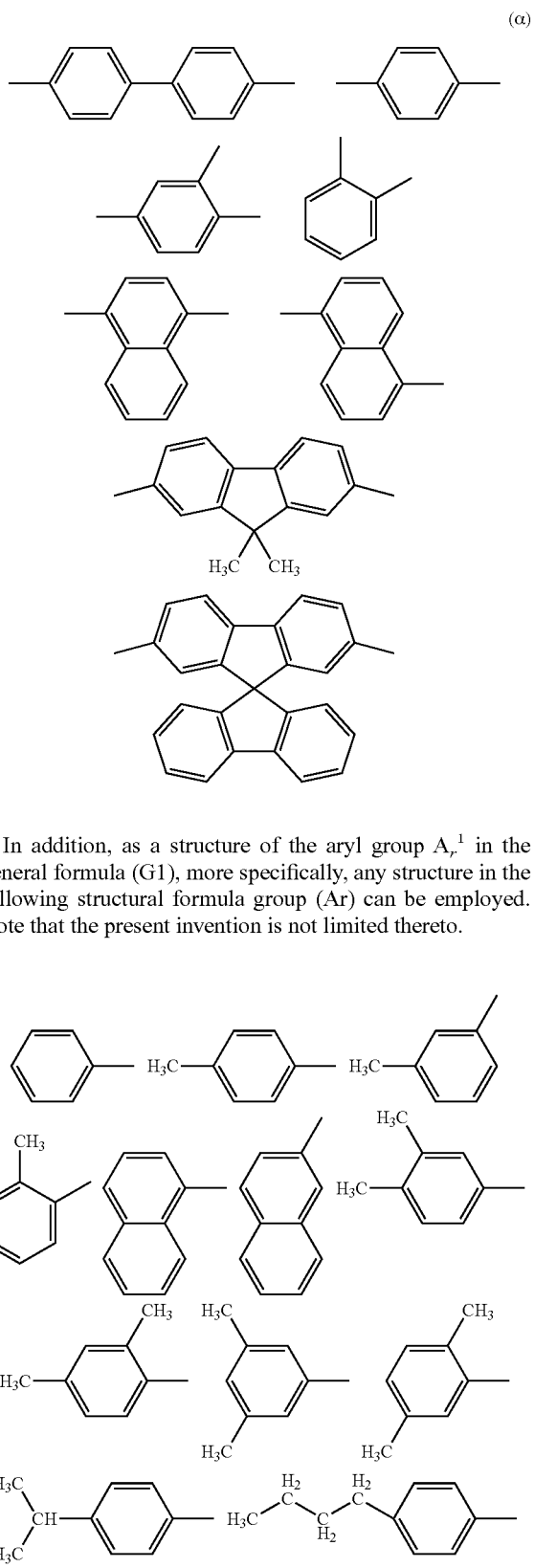

(α)

In addition, as a structure of the aryl group $A_r^1$ in the general formula (G1), more specifically, any structure in the following structural formula group (Ar) can be employed. Note that the present invention is not limited thereto.

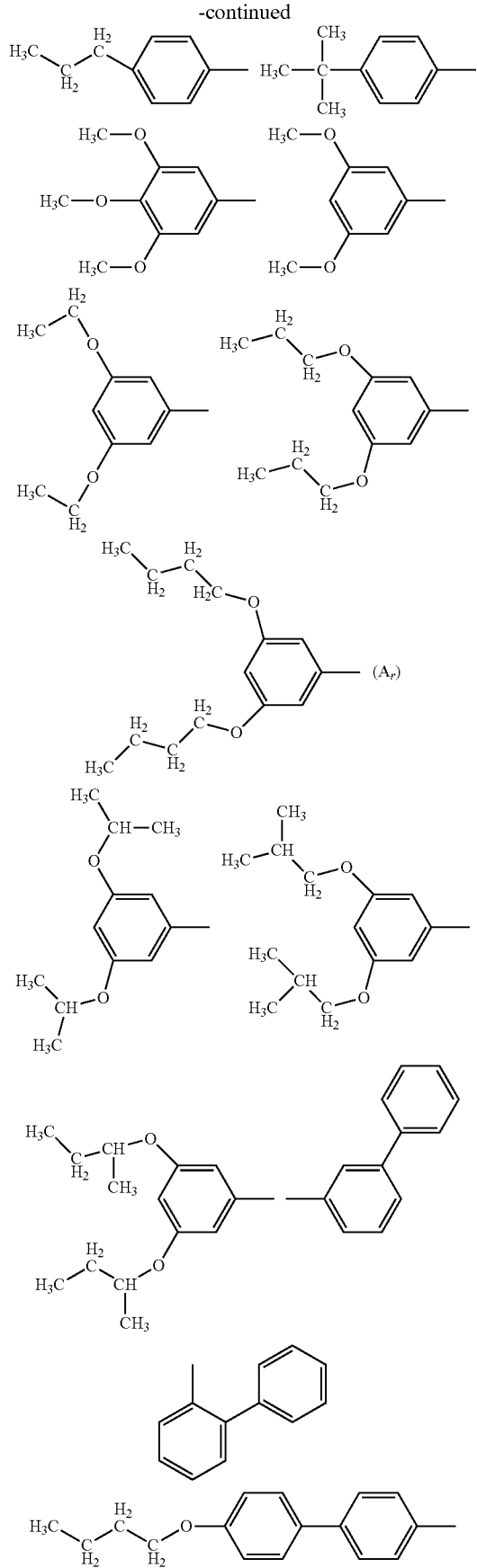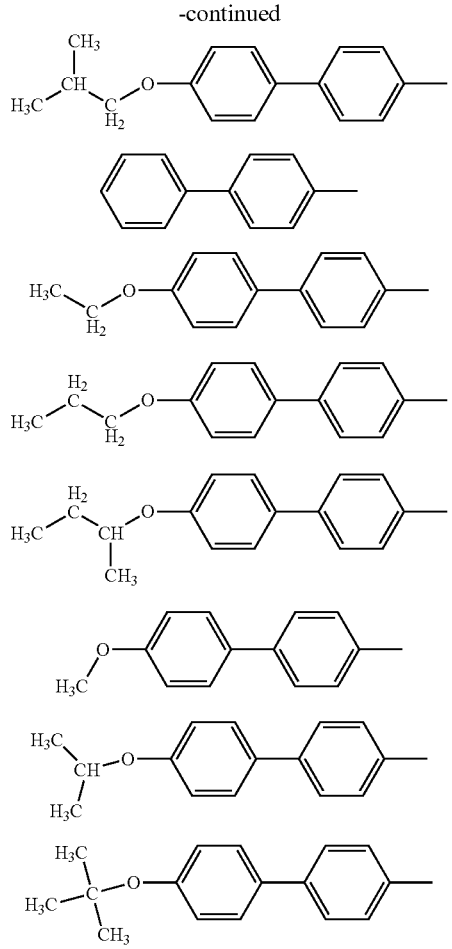

Subsequently, the substituent $A_m$ in the general formula (G1) will be explained. The substituent $A_m$ is represented by (Am1), (Am2), or (Am3) as shown in the general formula (G1). More specifically, any structure in the following structural formula groups (Am1-1) to (Am1-10), the structural formula groups (Am2-1) to (Am2-5), or the structural formula groups (Am3-1) to (Am3-9) can be employed. Note that the present invention is not limited thereto:

(Am1-1)

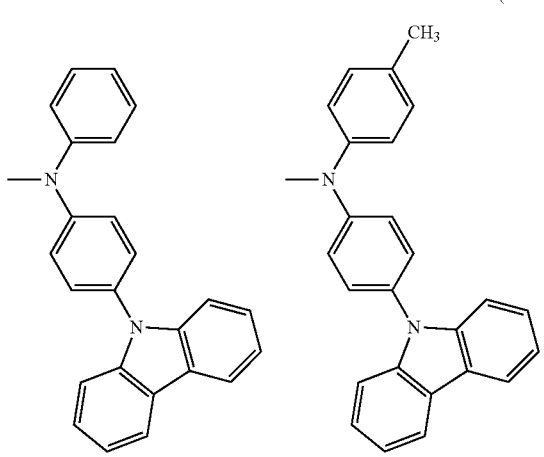

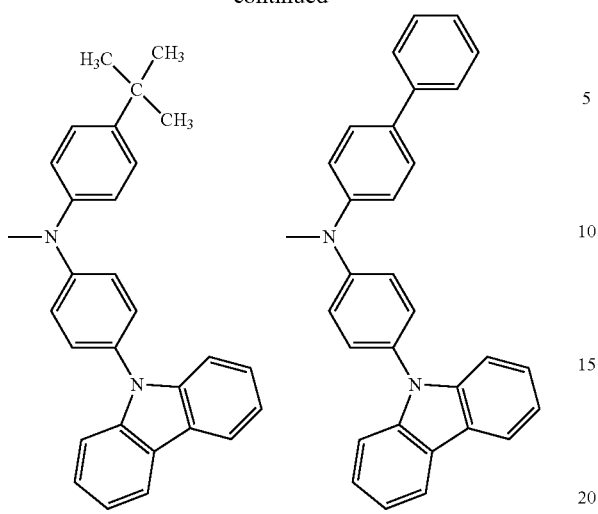
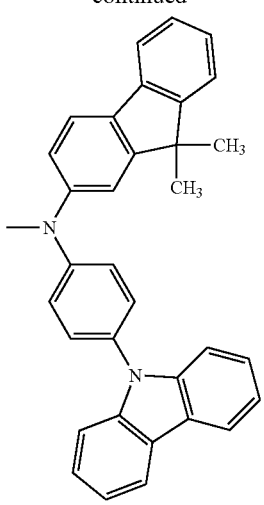
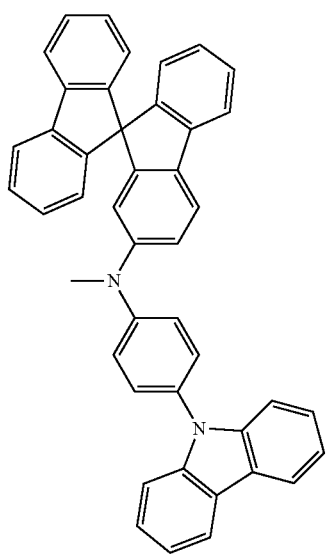
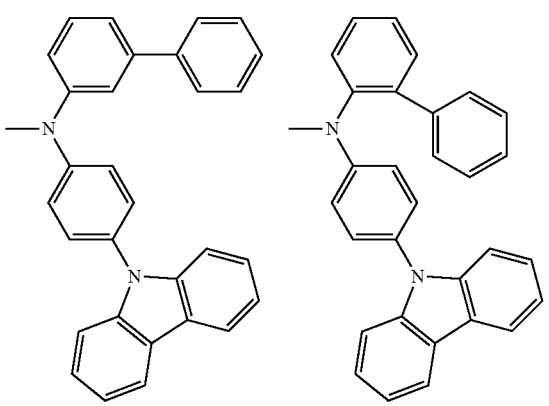
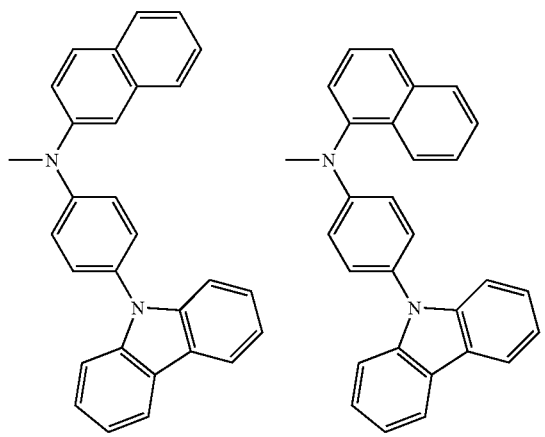
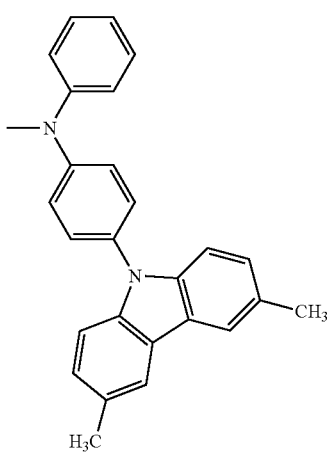
(Am1-2)

25
-continued
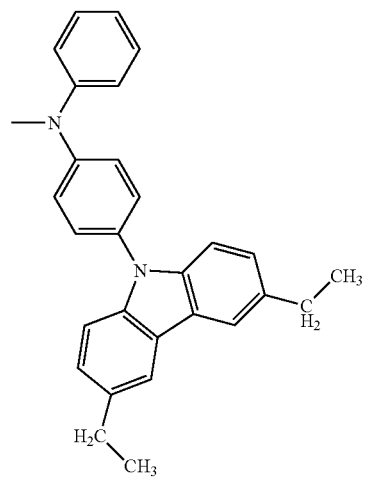
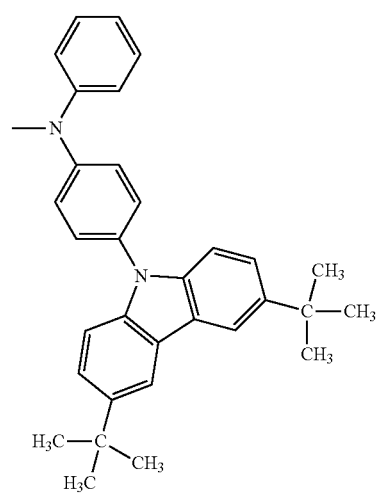
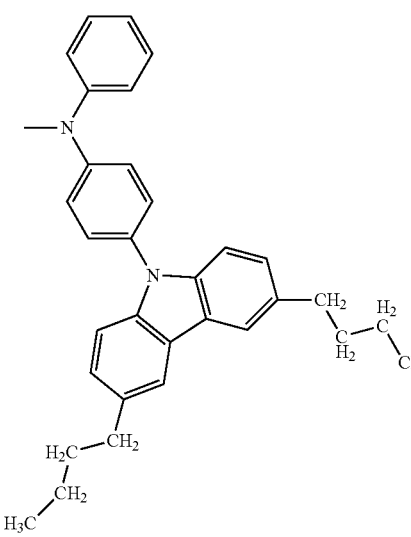
26
-continued
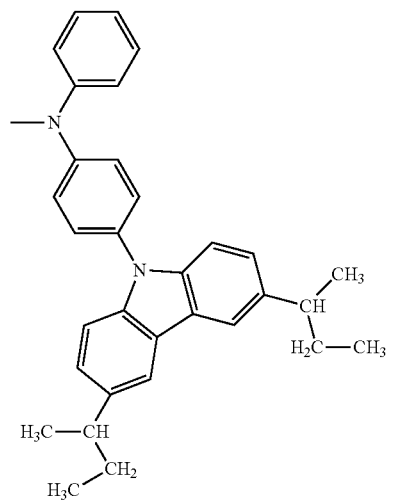
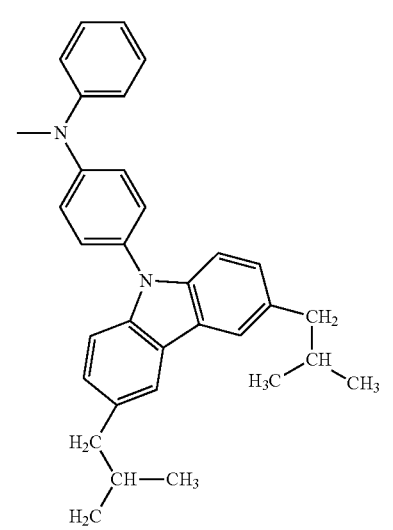
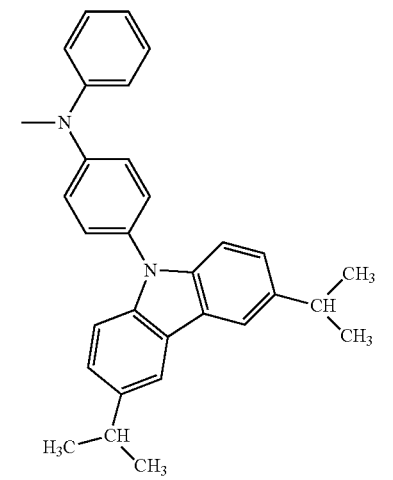

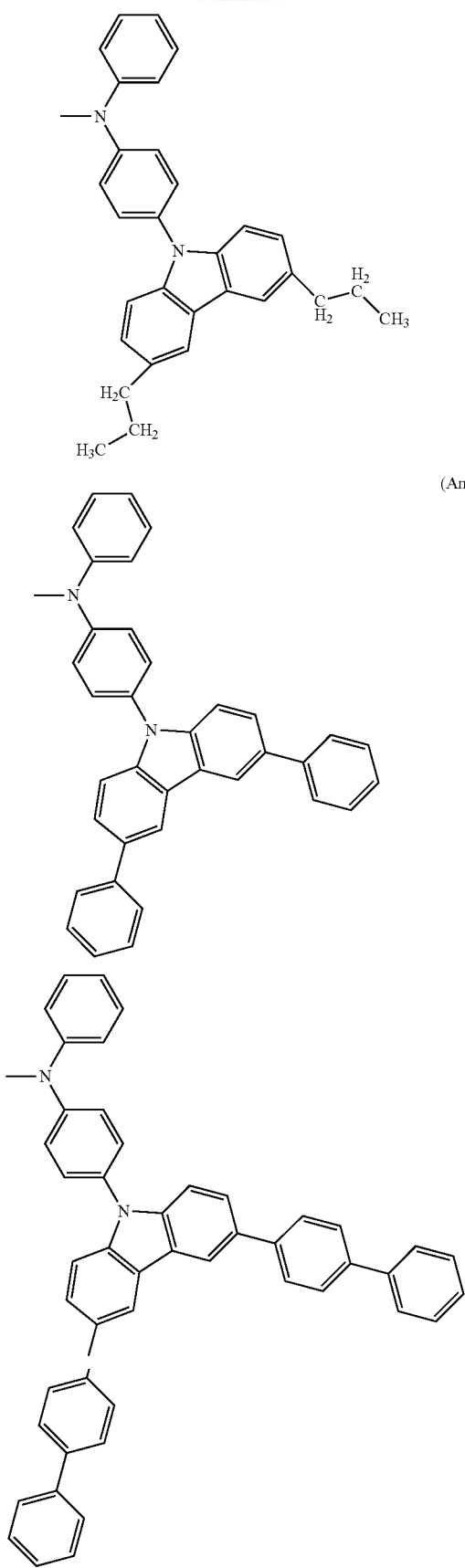
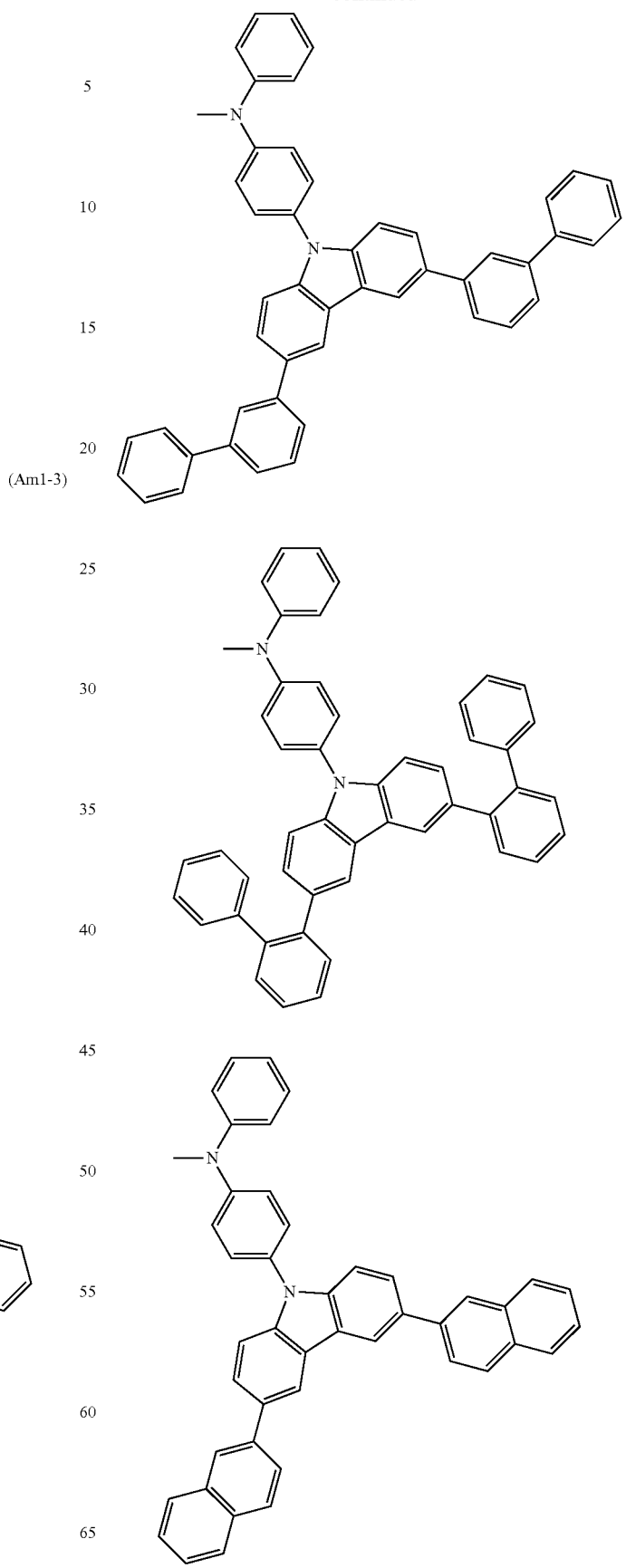
(Am1-3)

29
-continued
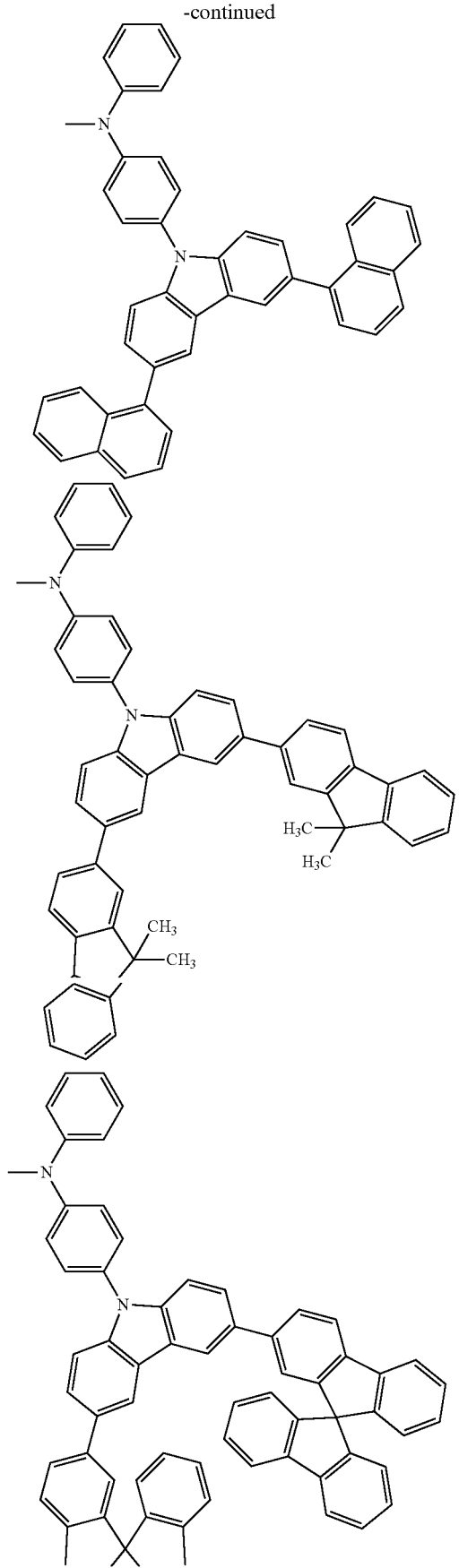
30
-continued
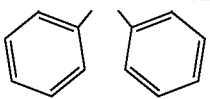
(Am1-4)
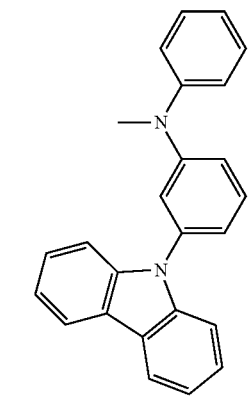
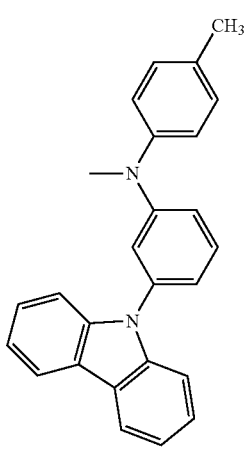
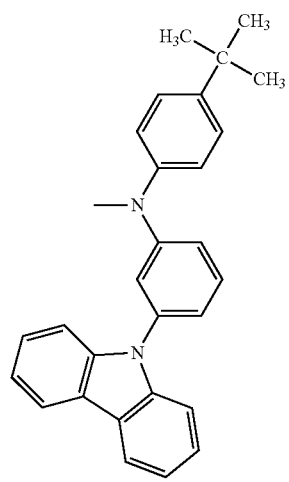

31
-continued
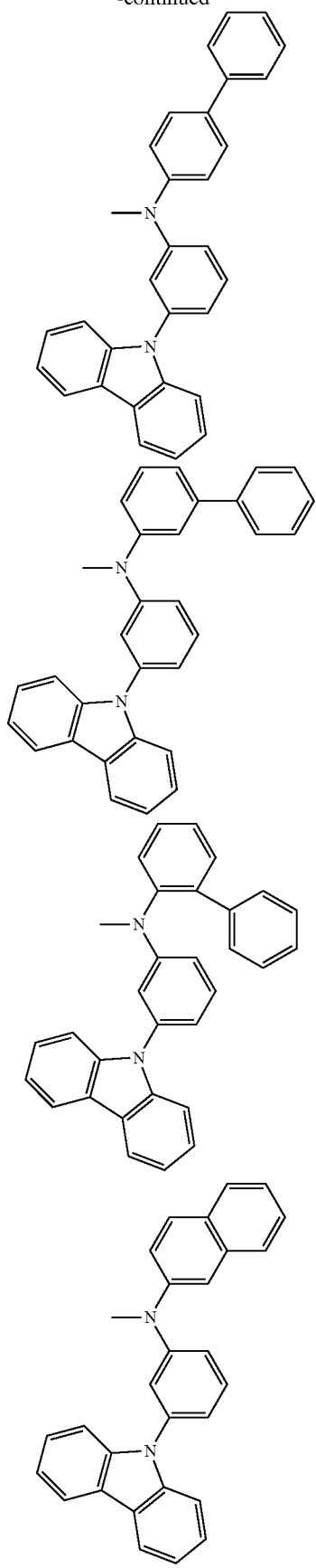
32
-continued
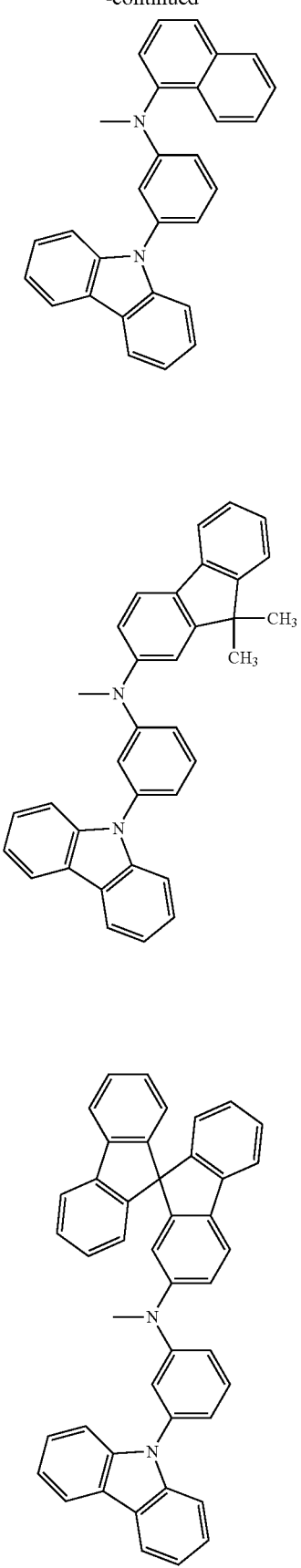

(Am1-5)
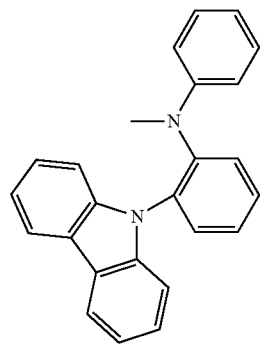
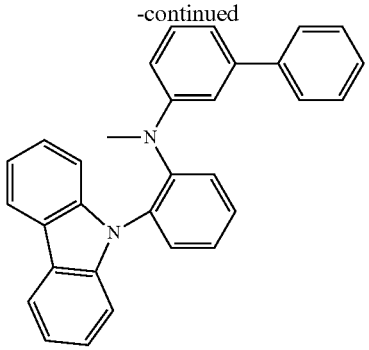
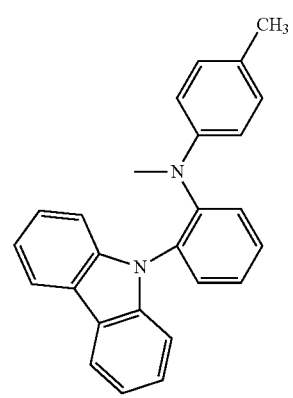
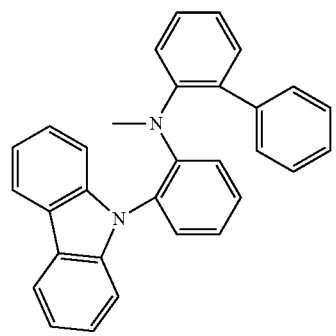
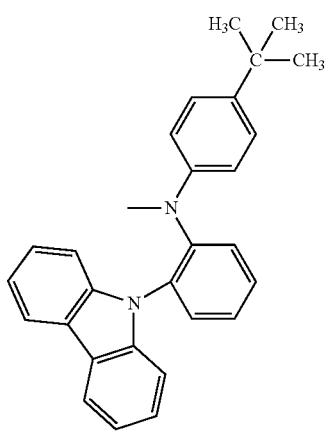
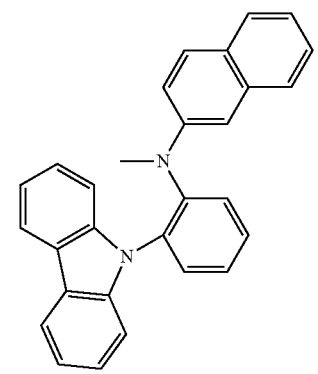
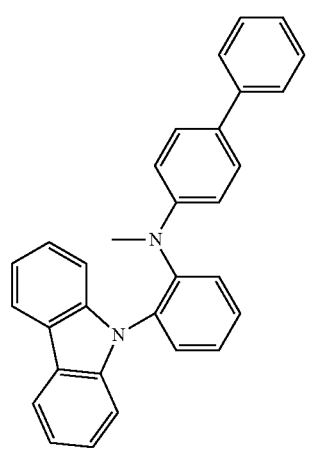
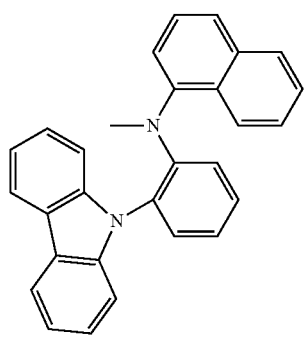

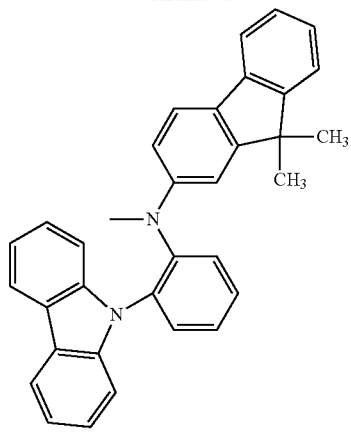
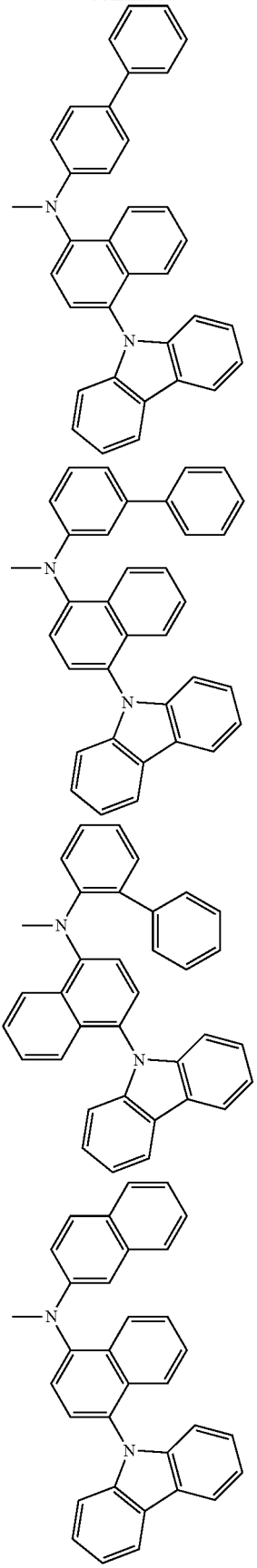
(Am1-6)

-continued
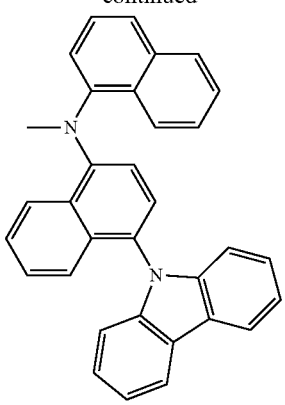
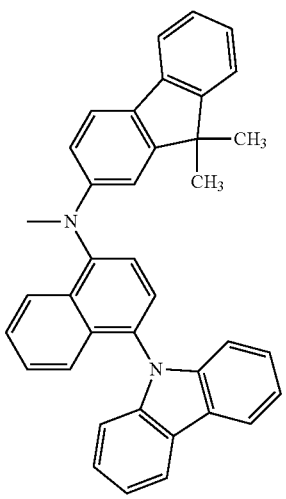
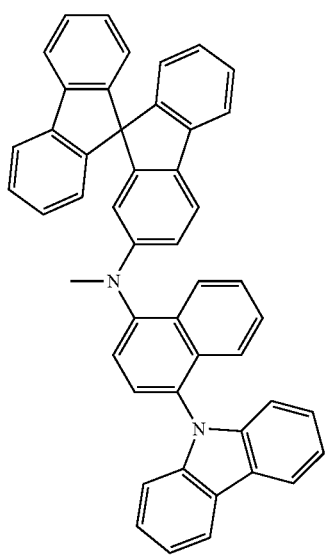
-continued
(Am1-7)
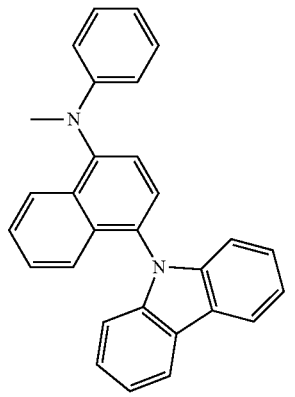
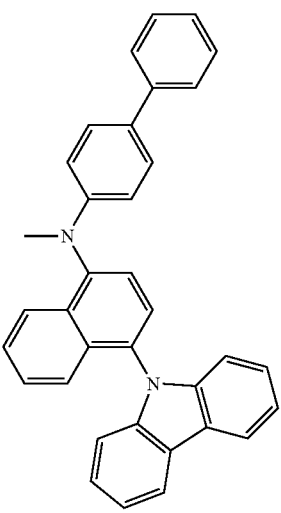
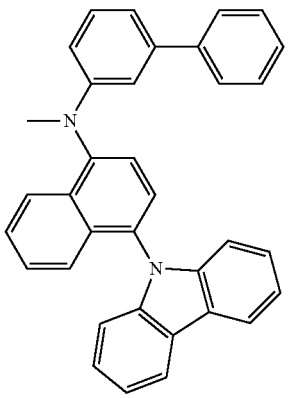

-continued
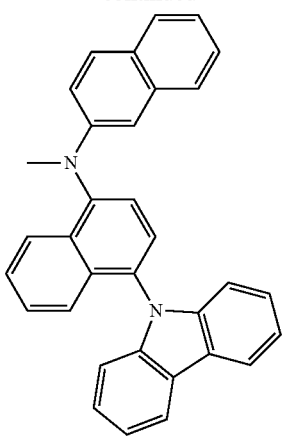
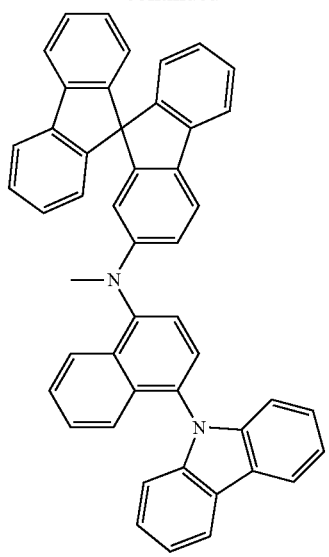
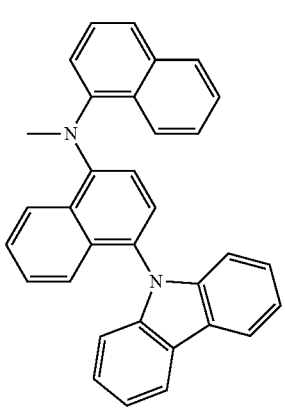
(Am1-8)
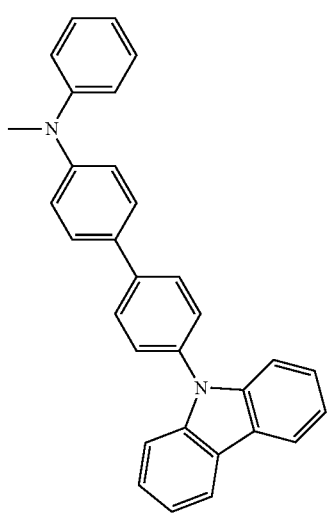
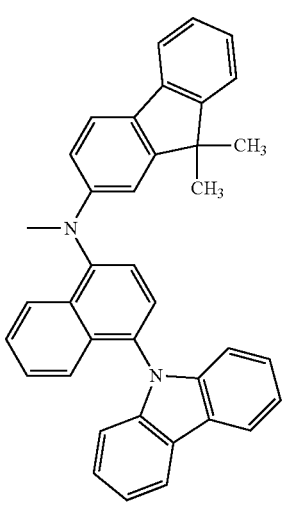
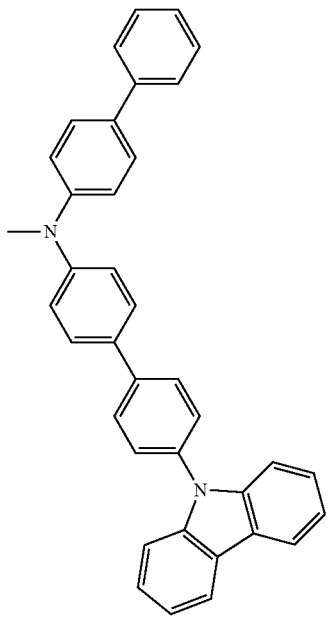

-continued
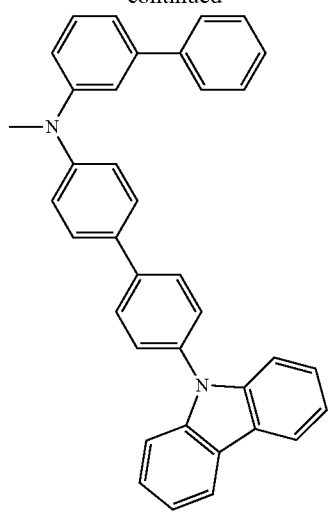
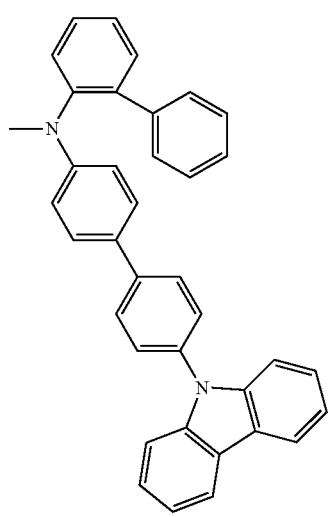
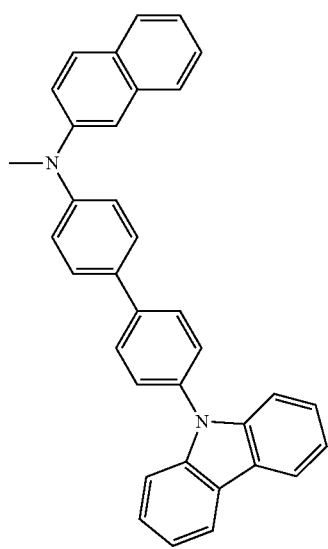
-continued
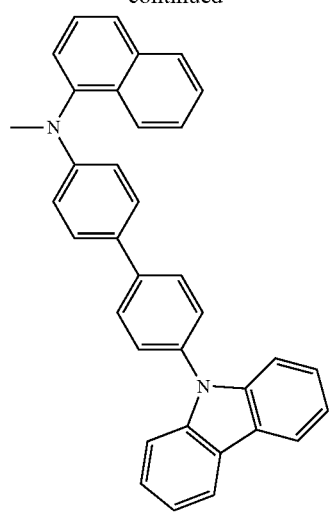
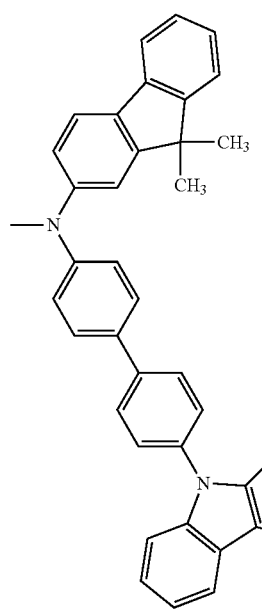
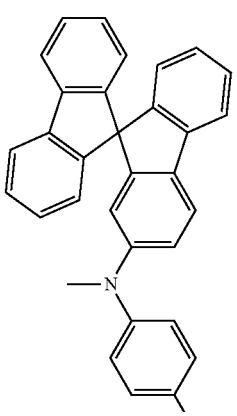

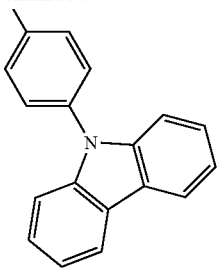
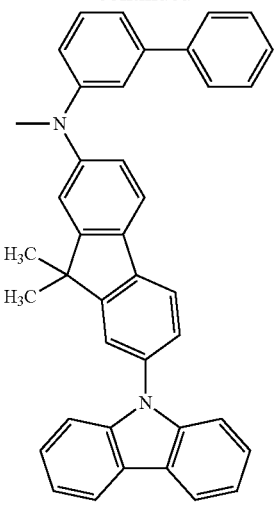
(Am1-9)
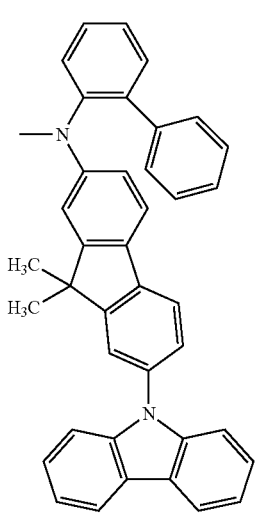
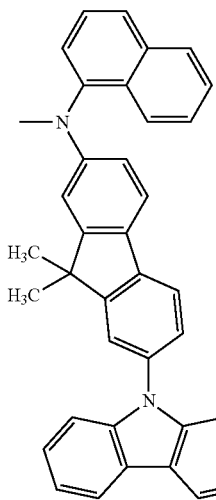

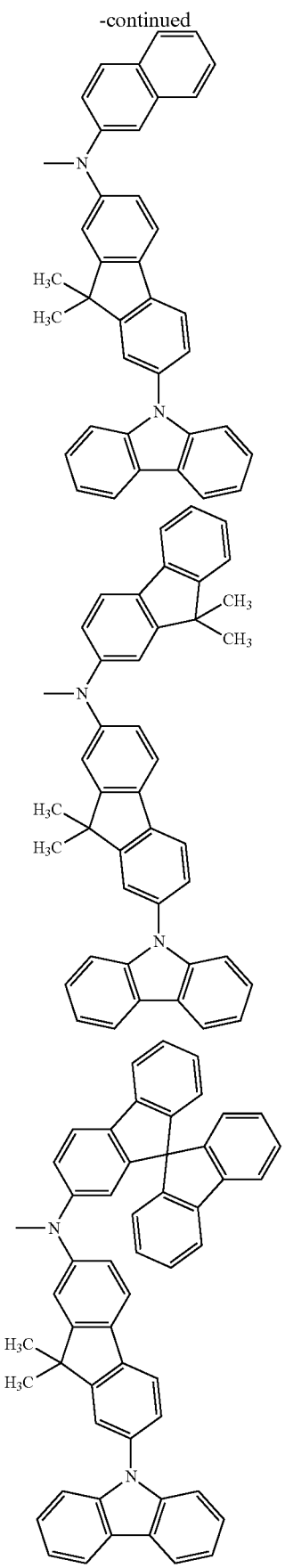
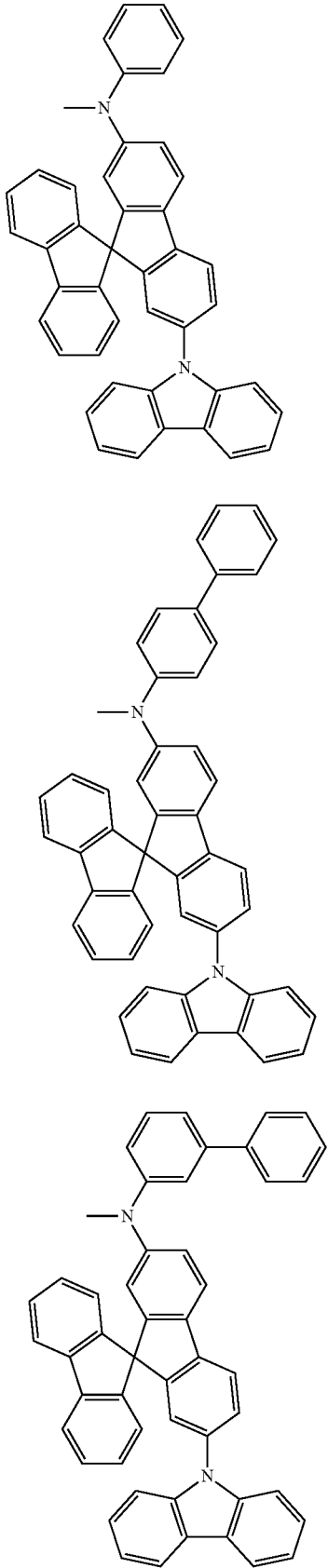
(Am1-10)

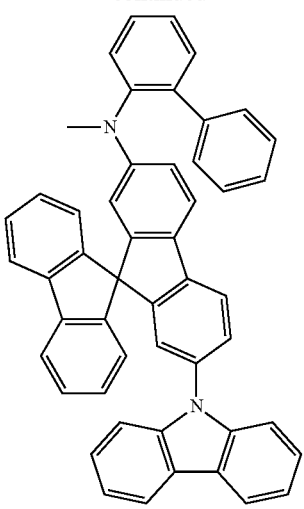
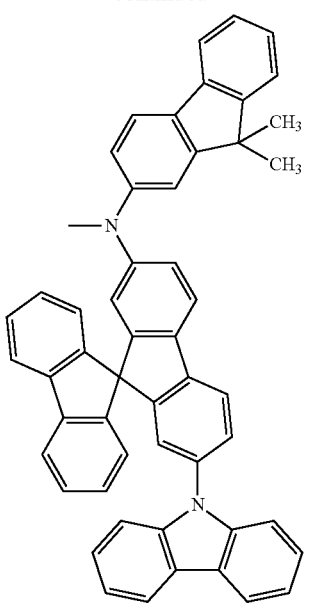
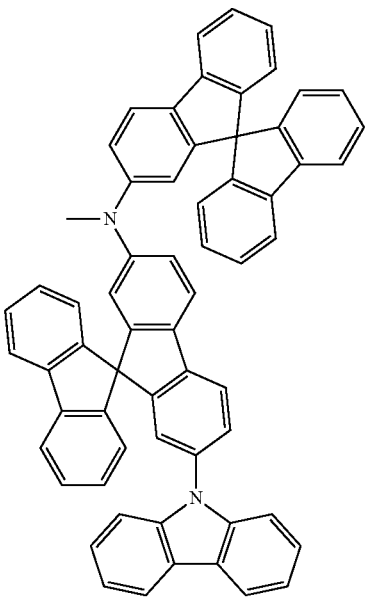
(Am2-1)
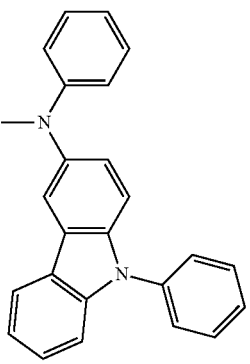

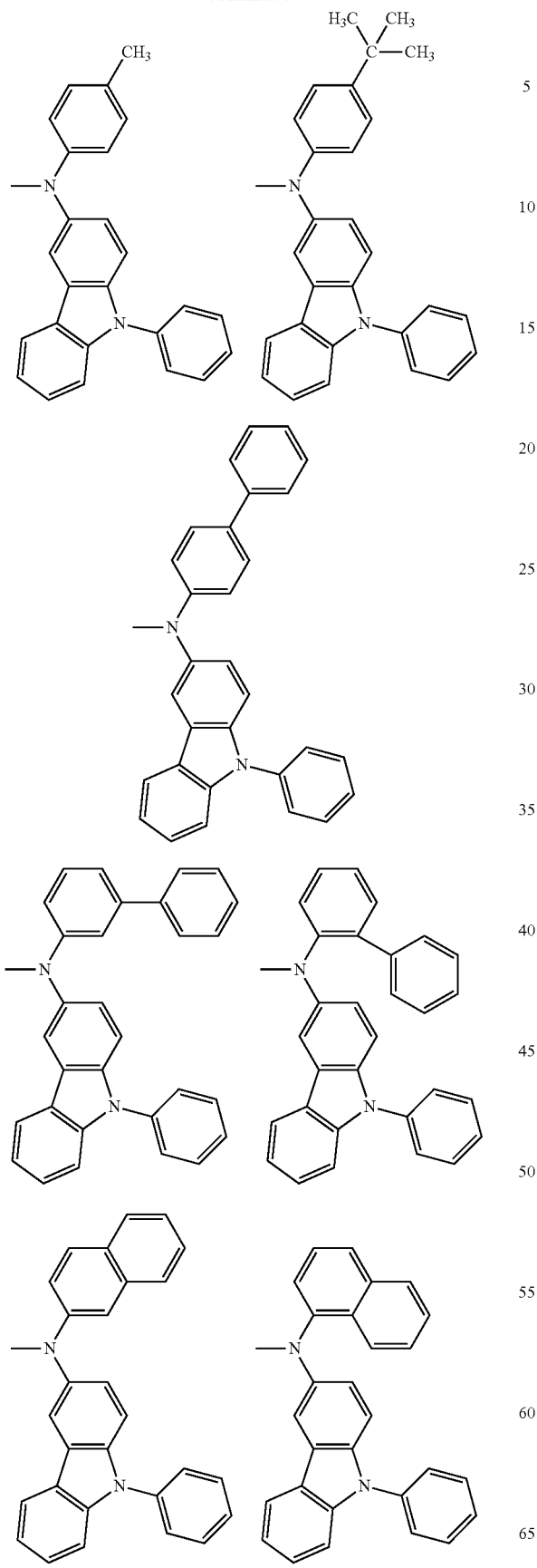
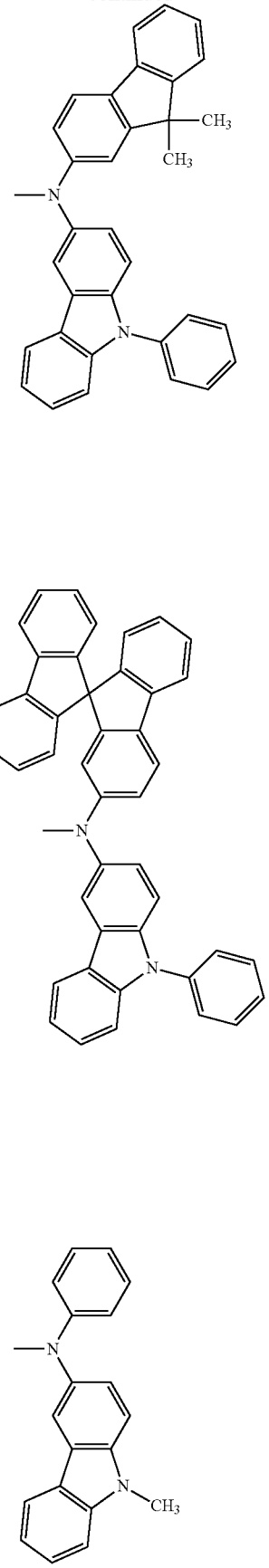
(Am2-2)

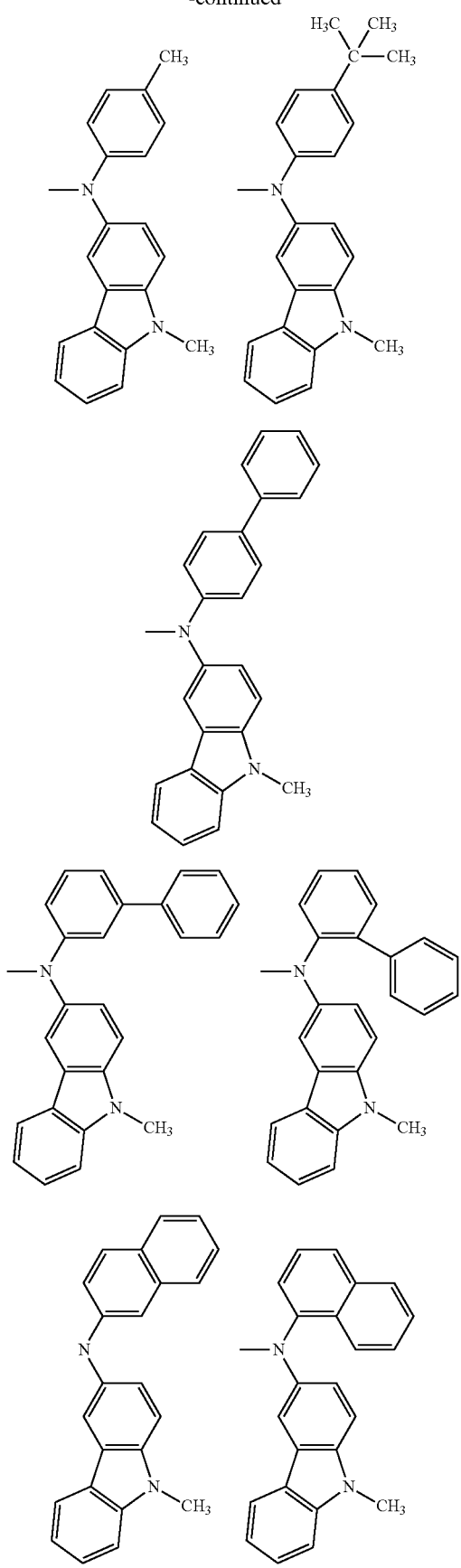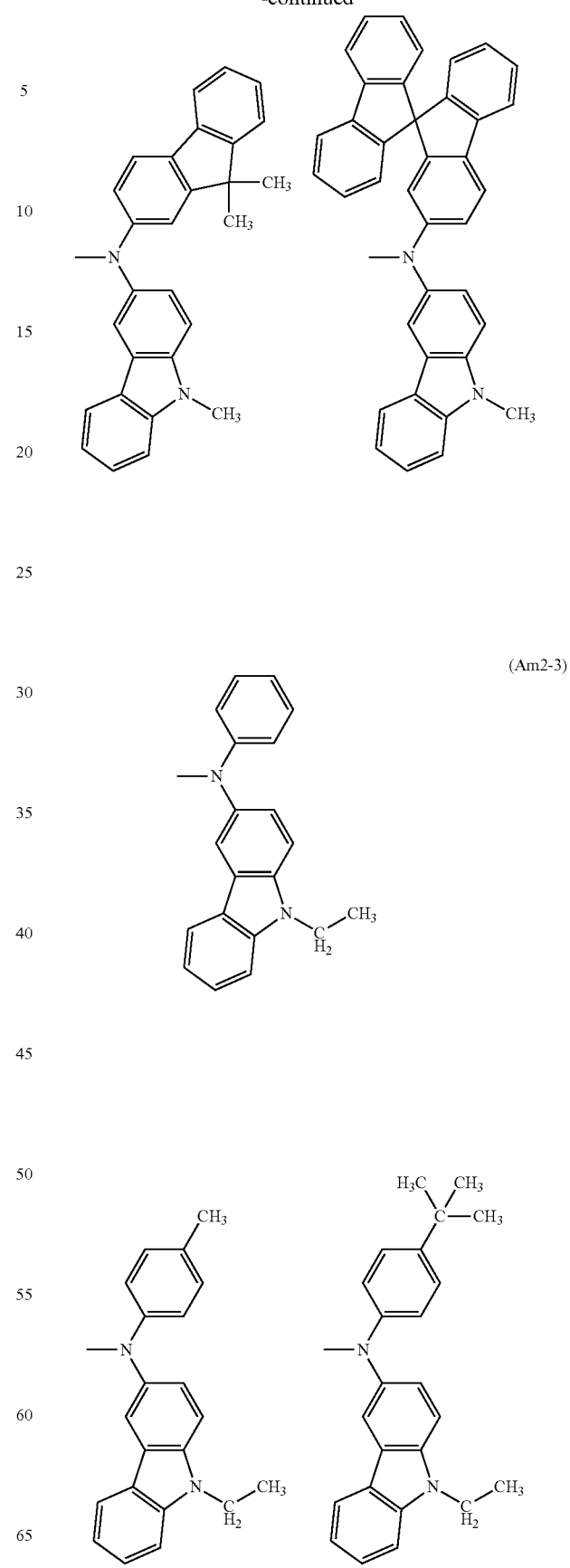

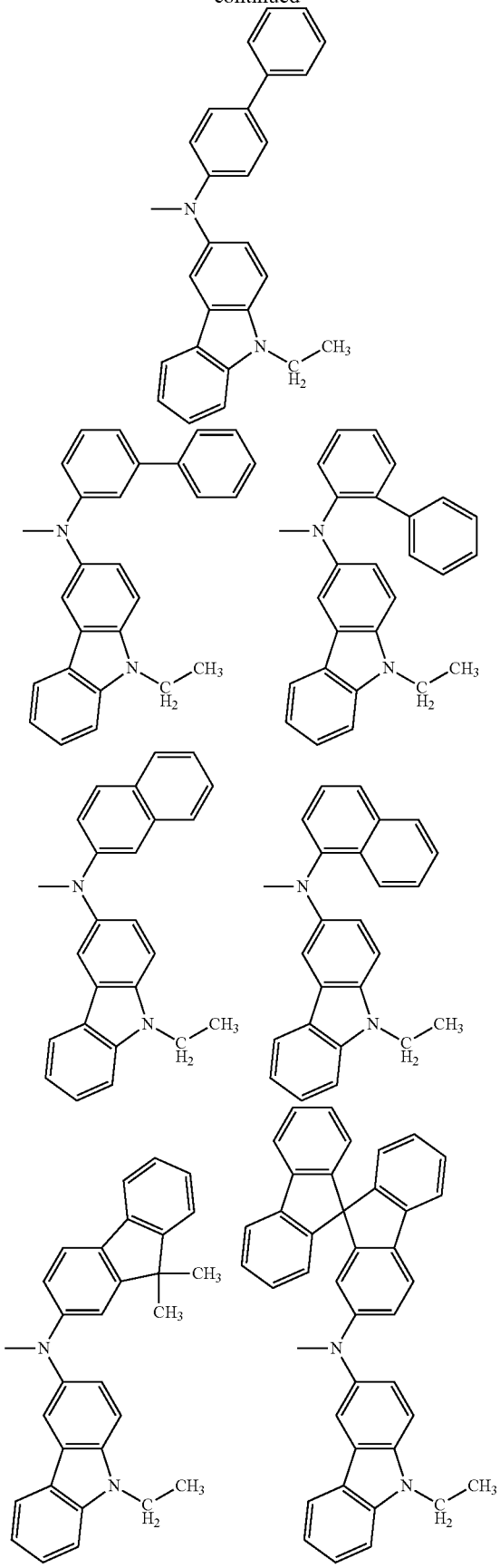
(Am2-4)

55
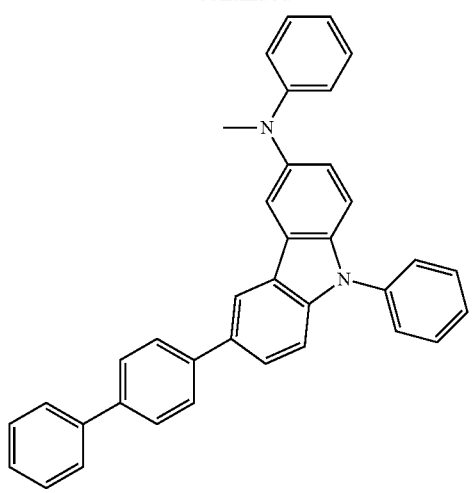
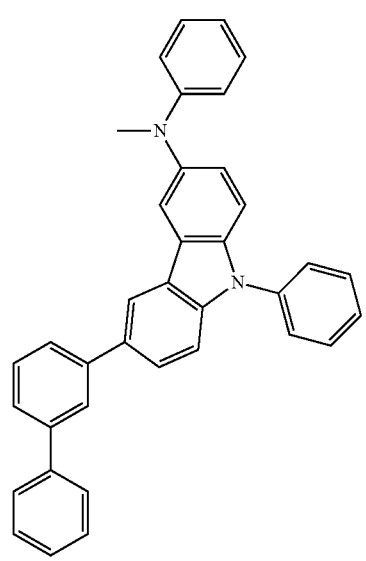
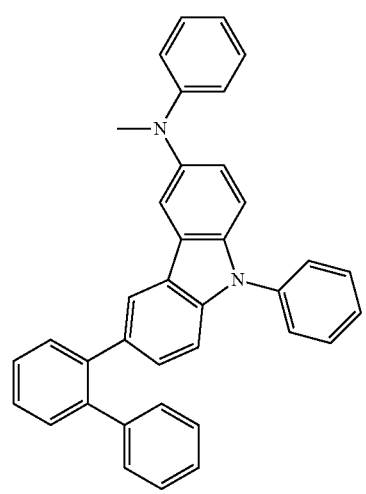
56
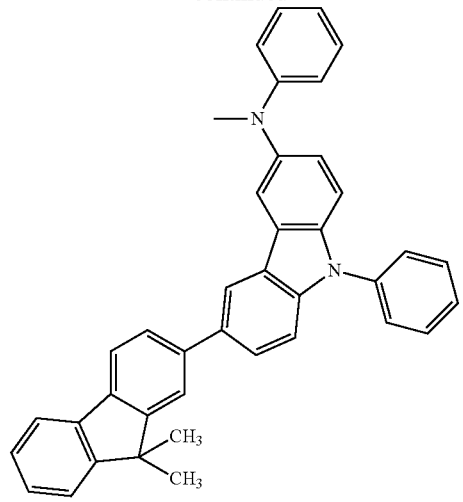
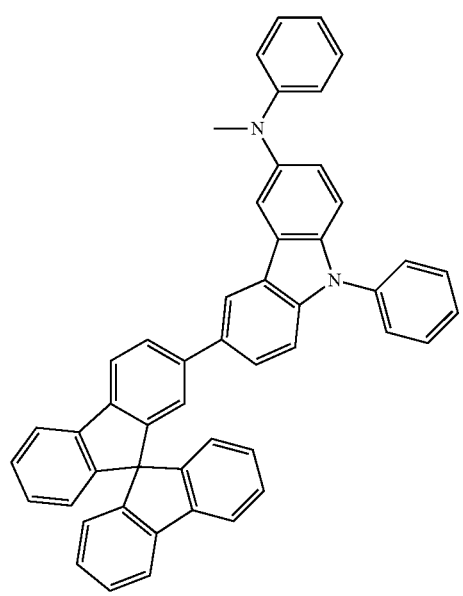
(Am2-5)
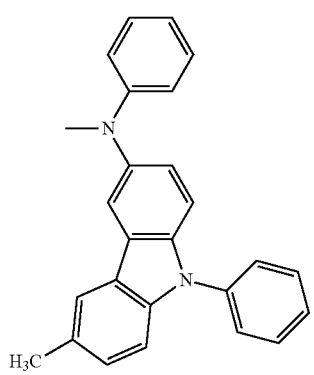

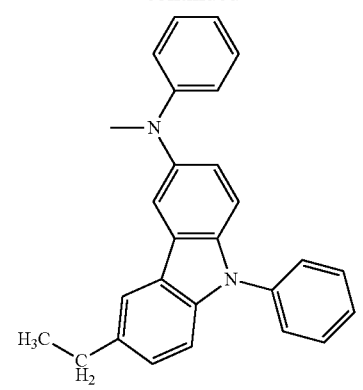
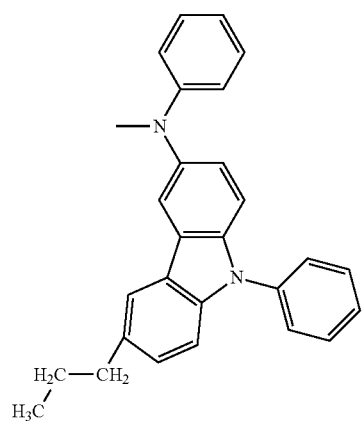
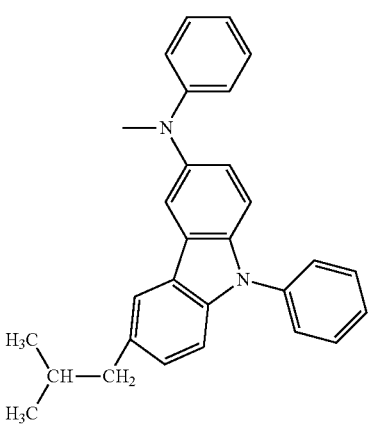
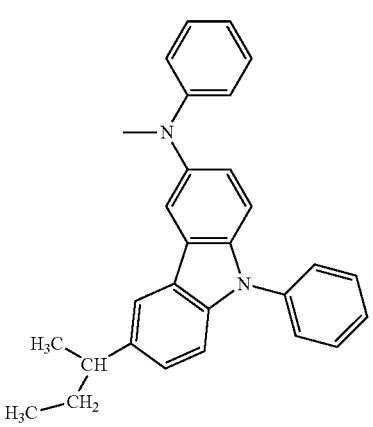
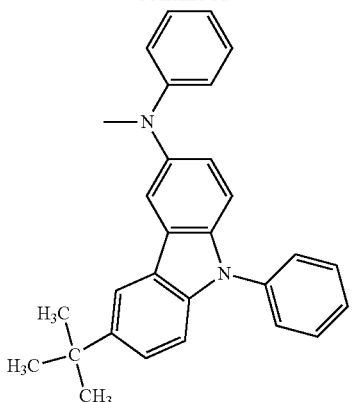
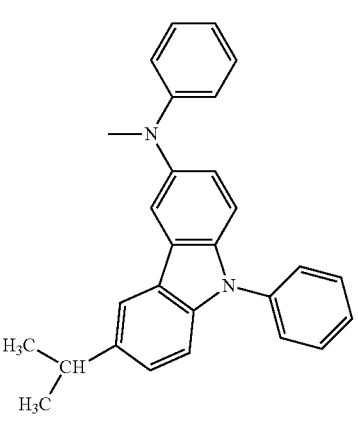
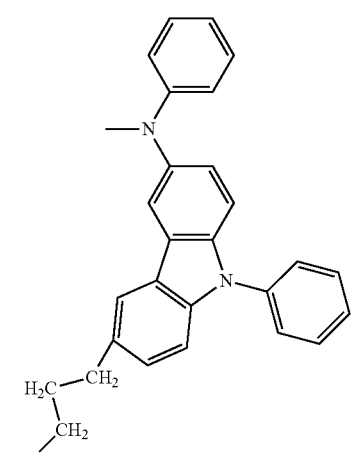
(Am3-1)
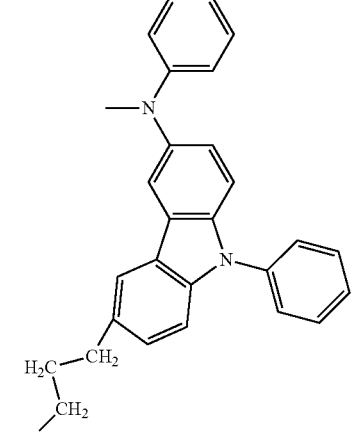

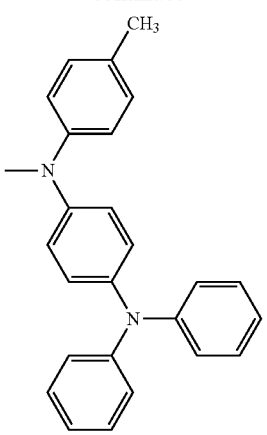
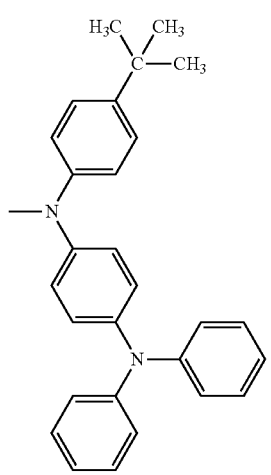
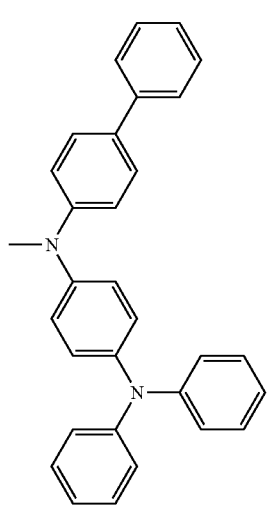
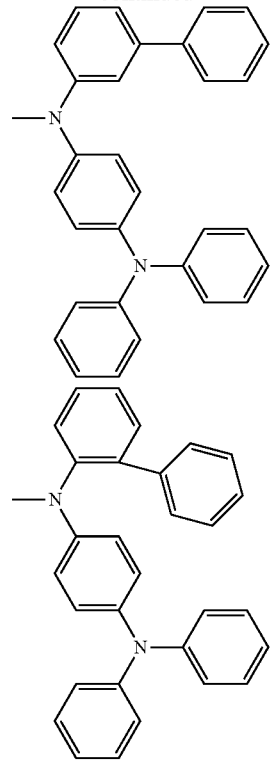
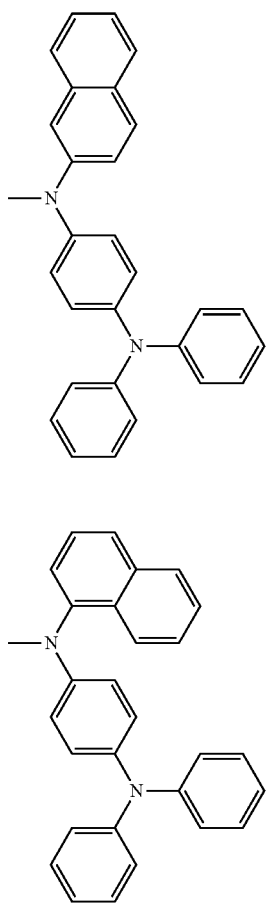

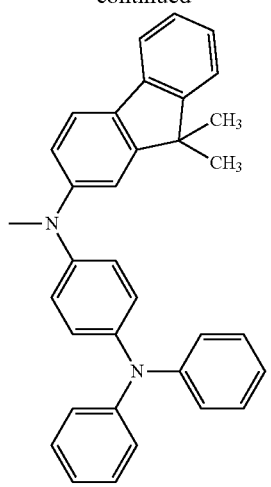
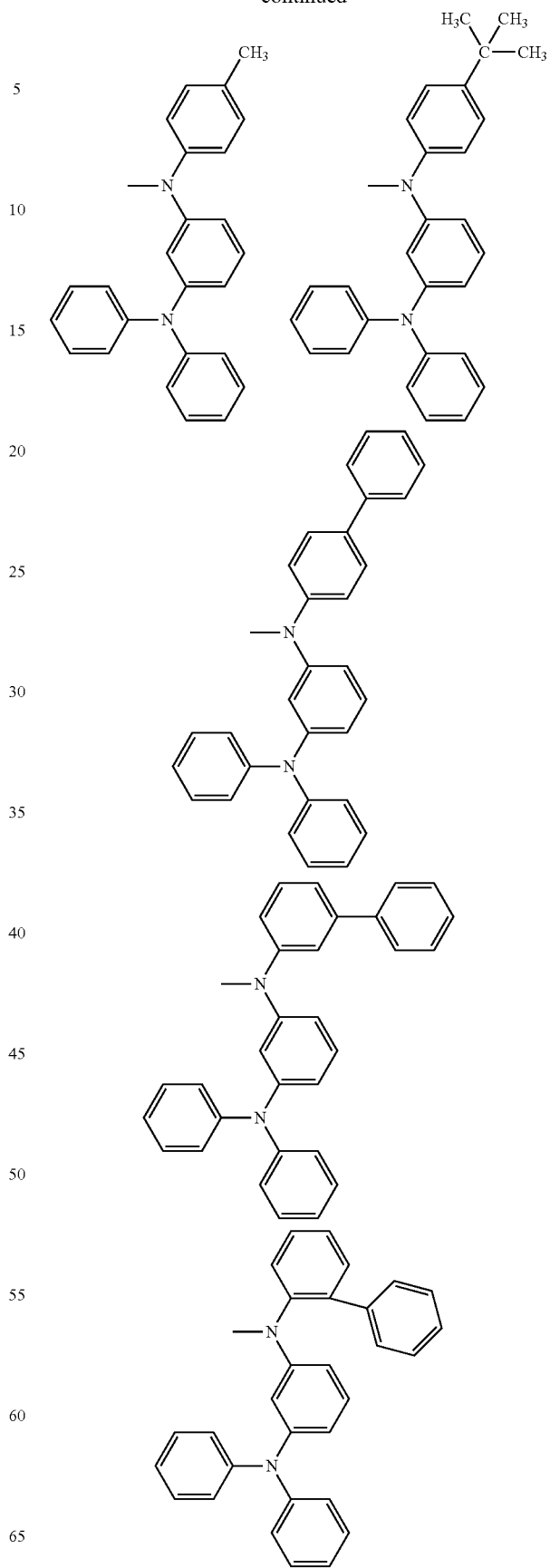
(Am3-2)

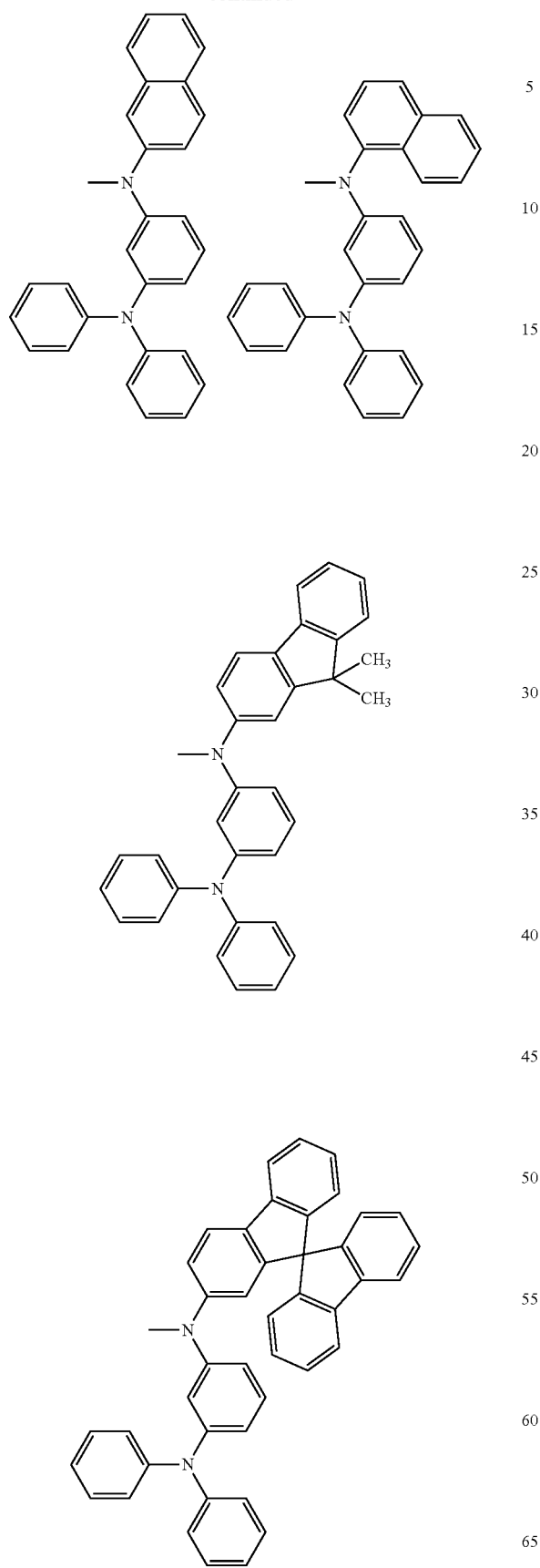
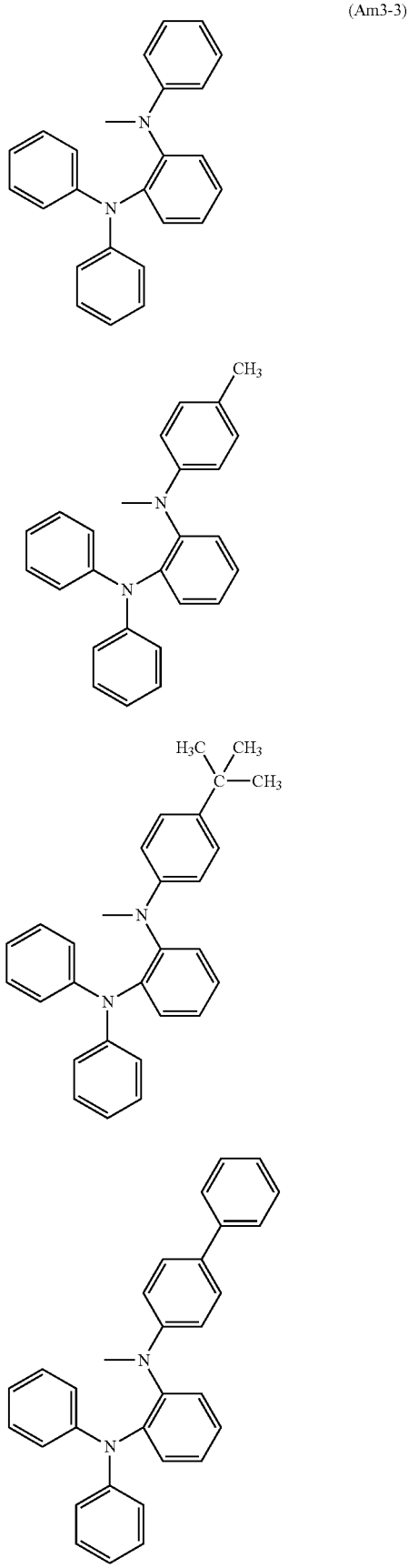
(Am3-3)

-continued
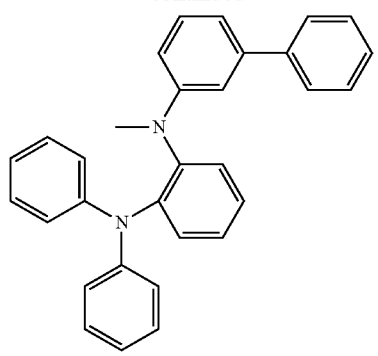
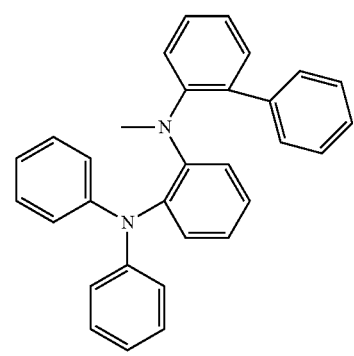
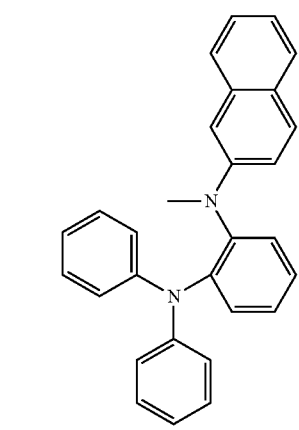
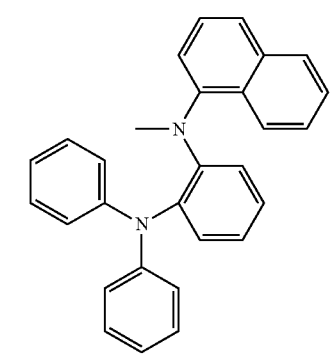
-continued
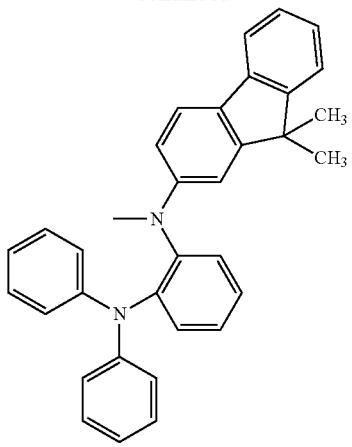
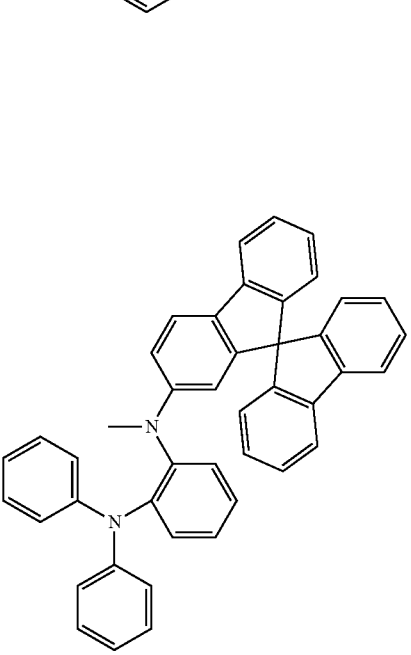
(Am3-4)
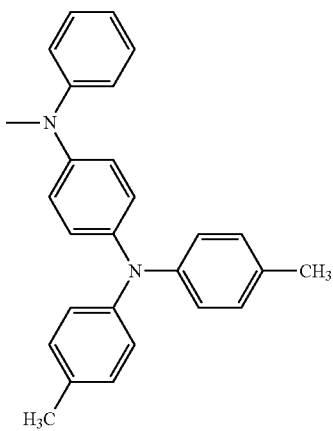

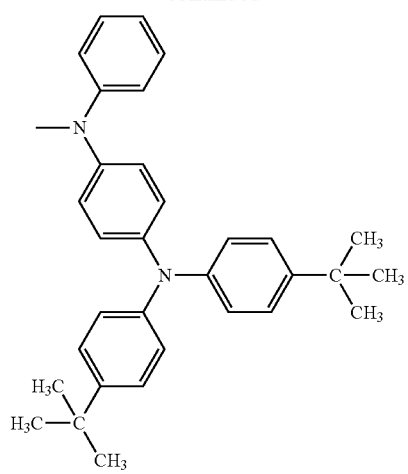
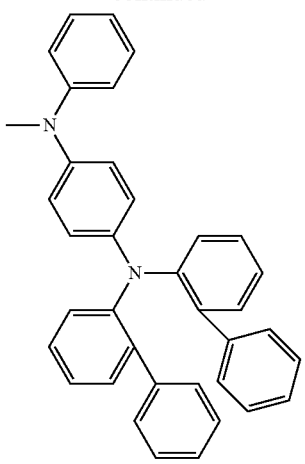
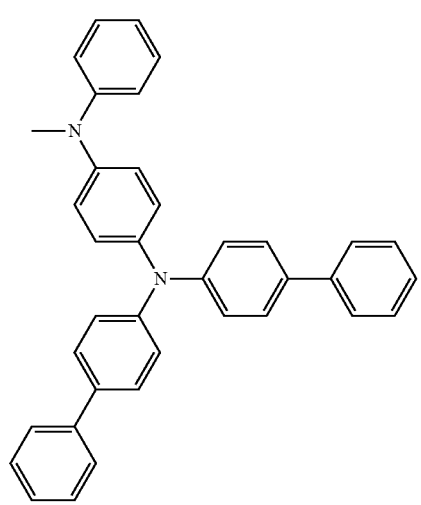
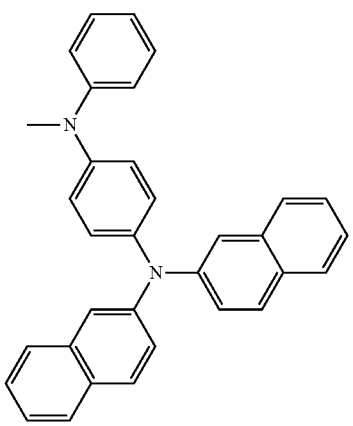
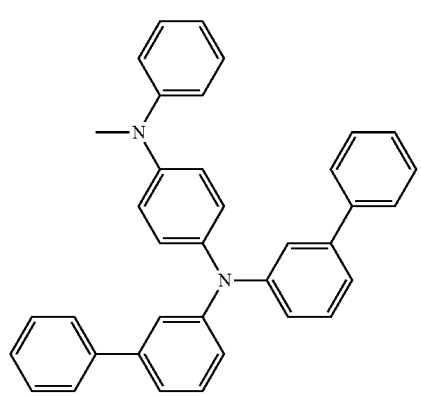
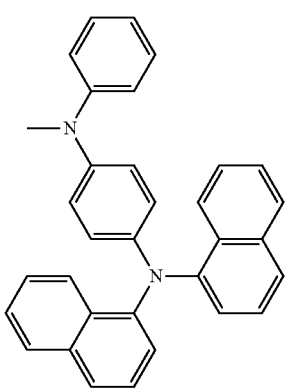

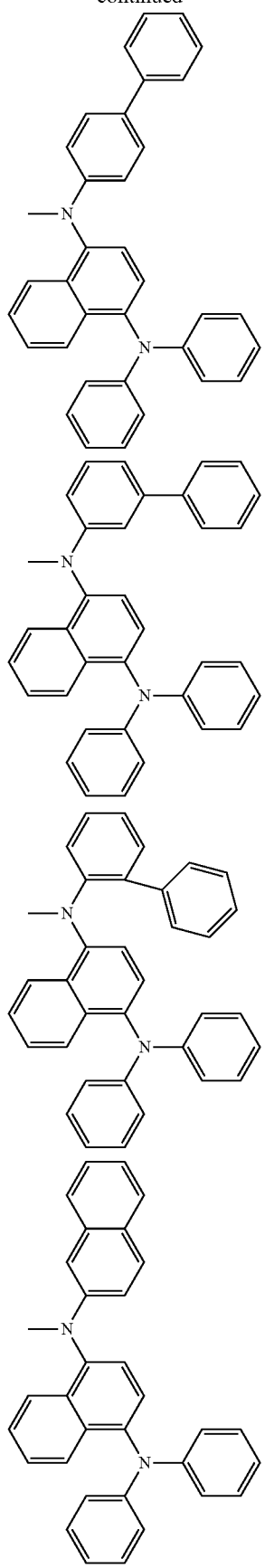

-continued
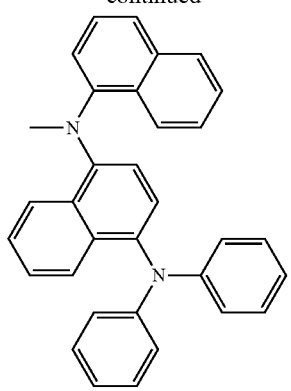
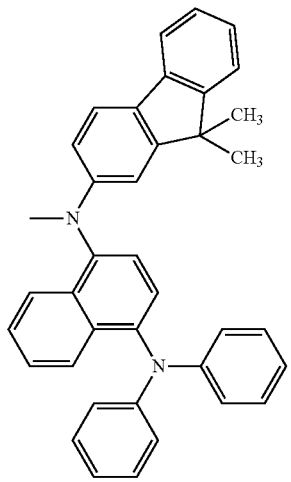
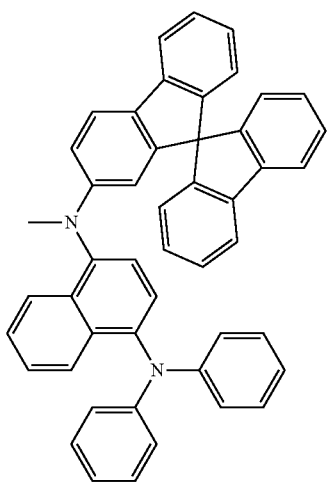
-continued
(Am3-6)
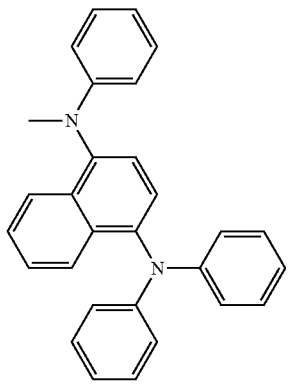
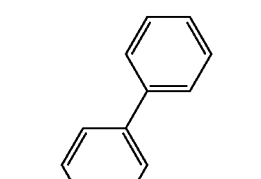
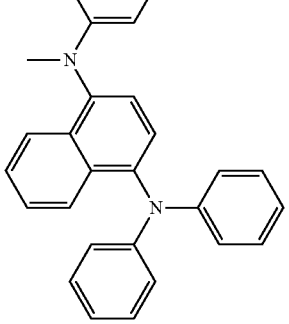
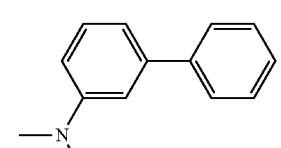
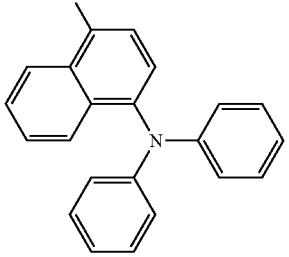
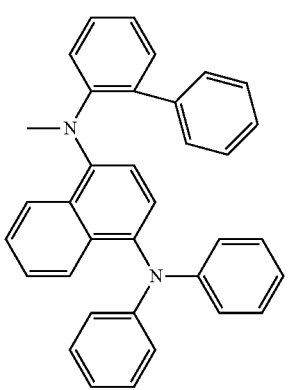

73
-continued
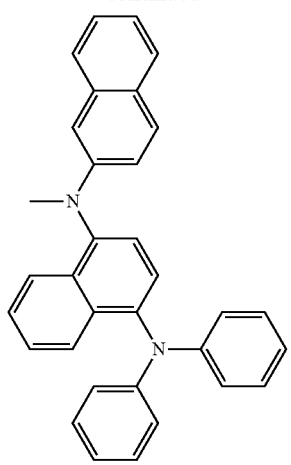
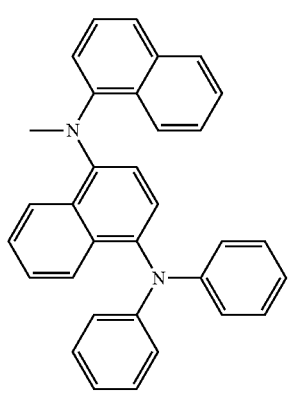
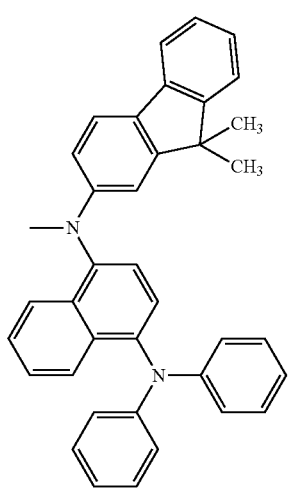
74
-continued
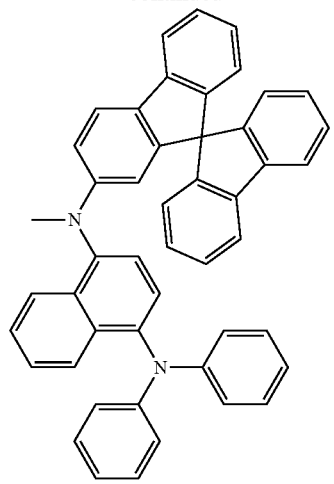
(Am3-7)
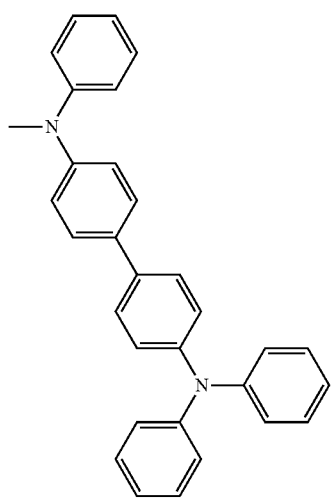
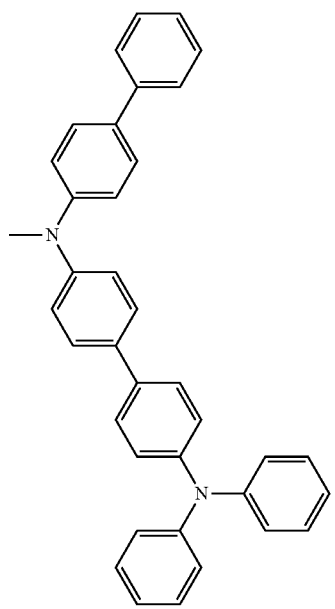

75
-continued
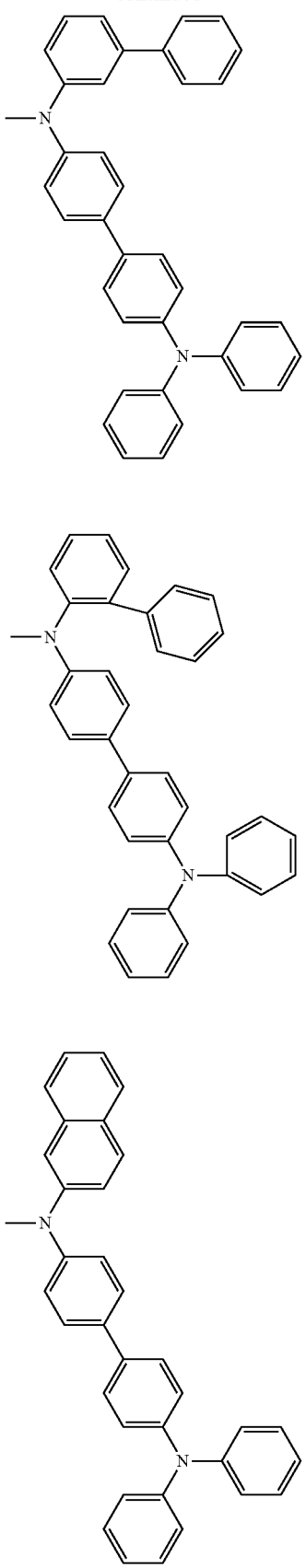
76
-continued
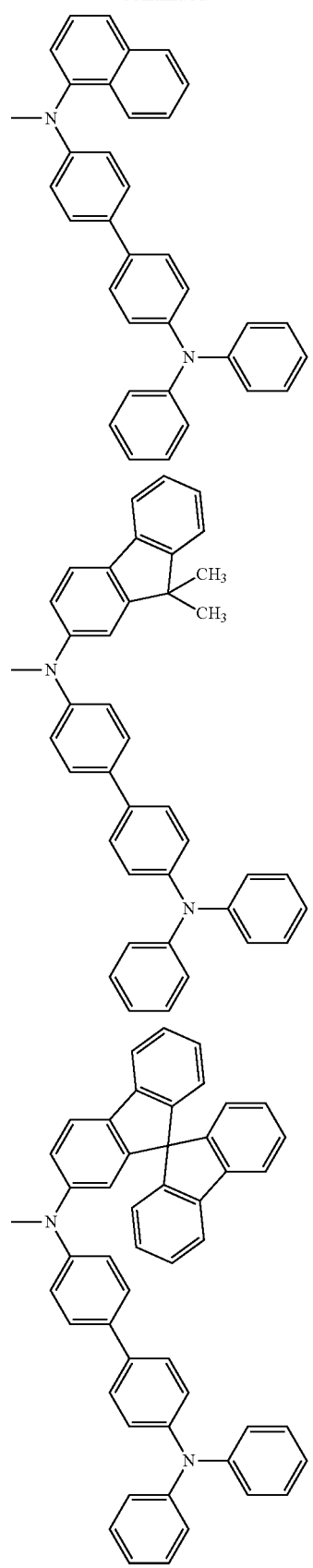

77
-continued
(Am3-8)
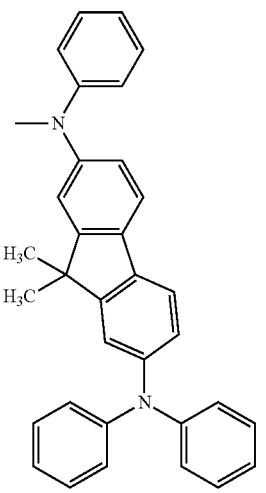
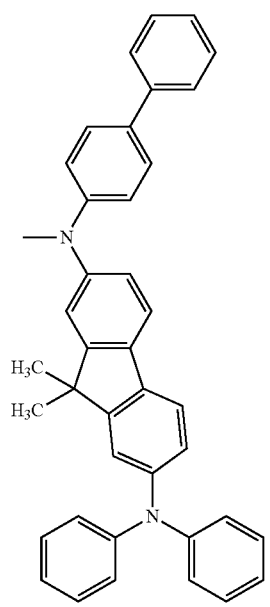
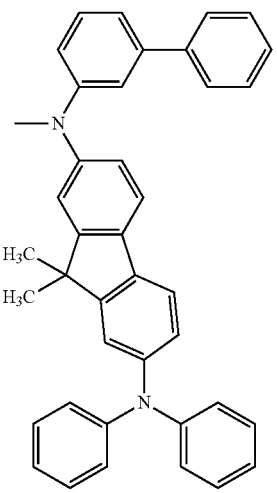
78
-continued
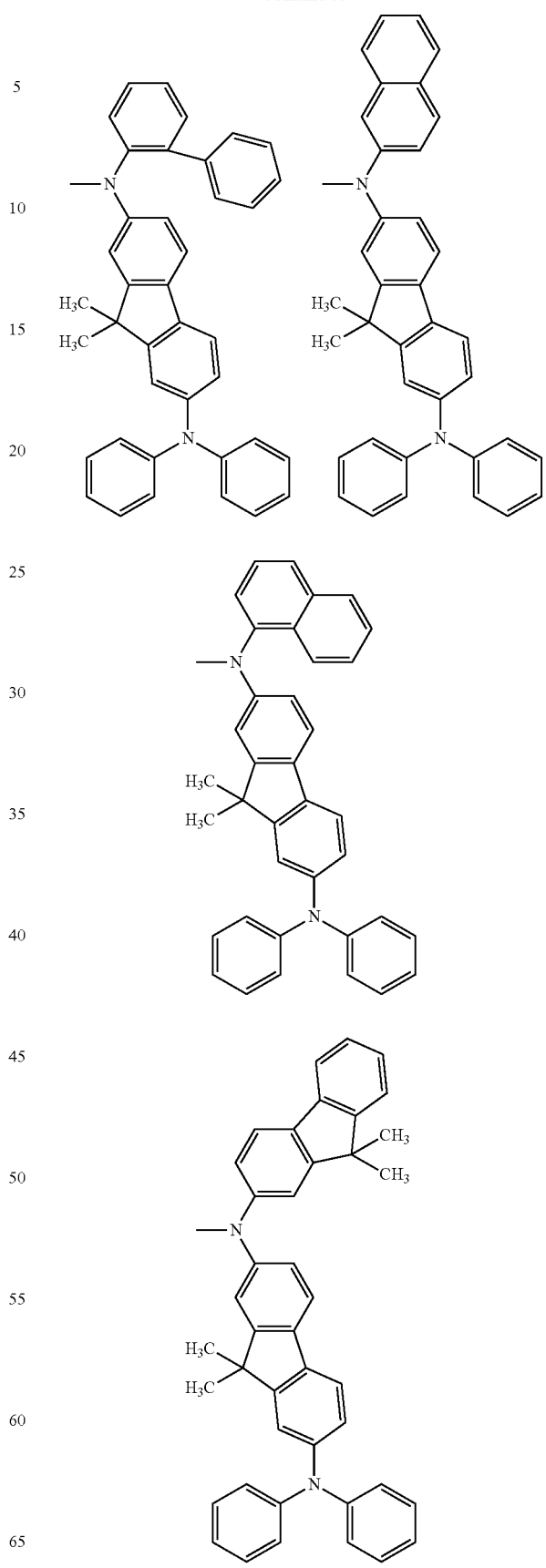

-continued
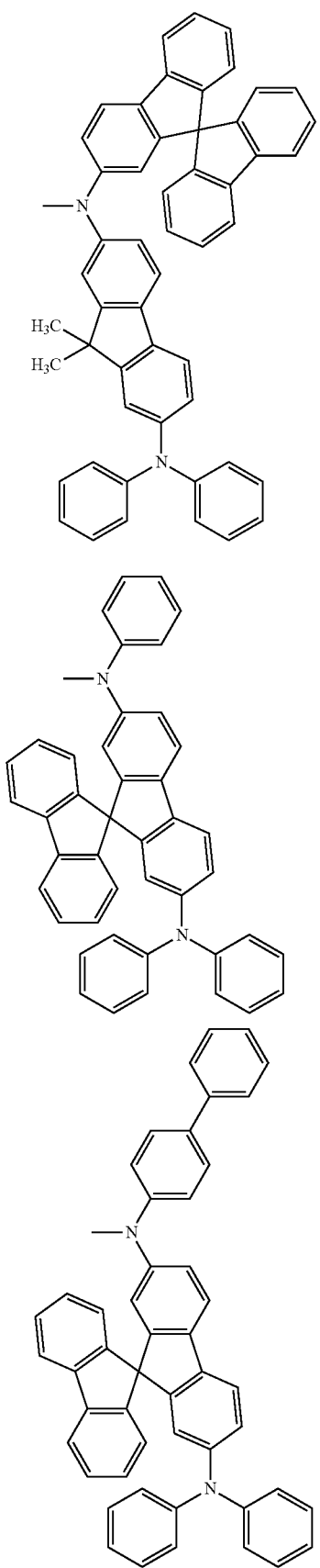
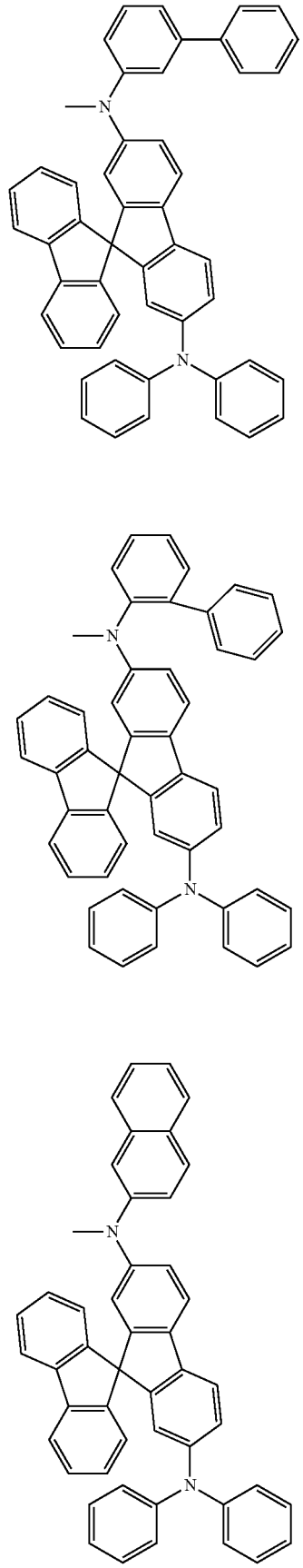
(Am3-9)

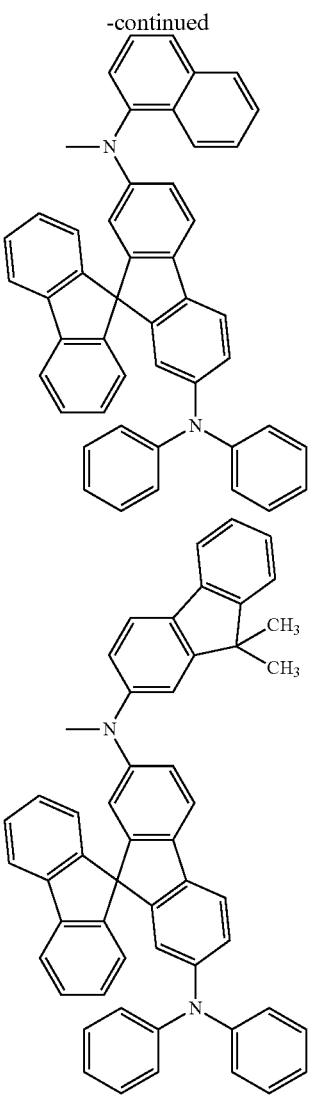

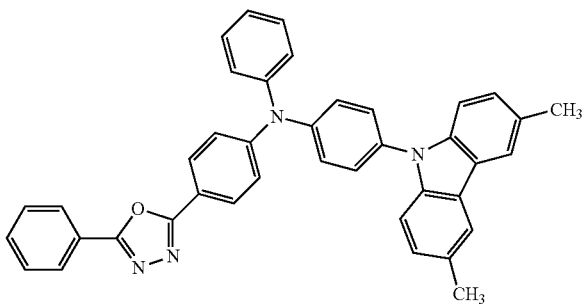

The structural formula group (α), the structural formula group (Ar), the structural formula groups (Am1-1) to (Am1-10), the structural formula groups (Am2-1) to (Am2-5), and the structural formula groups (Am3-1) to (Am3-9) as described above are appropriately combined to form the oxadiazole derivative of the present invention. Hereinafter, specific structural formulas of the oxadiazole derivative of the present invention will be given (the following structural formulas (1) to (140)), but the present invention is not limited thereto.

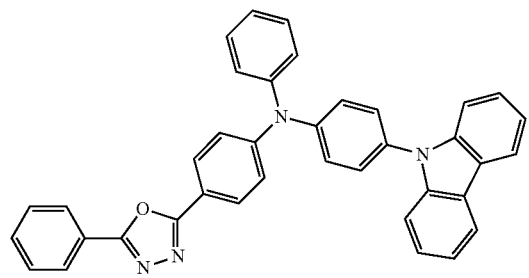

(1)        (2)

-continued
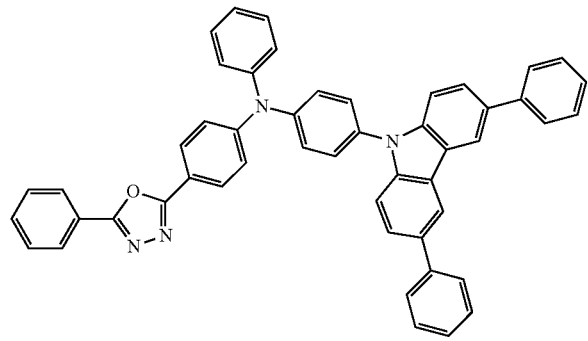
(3)
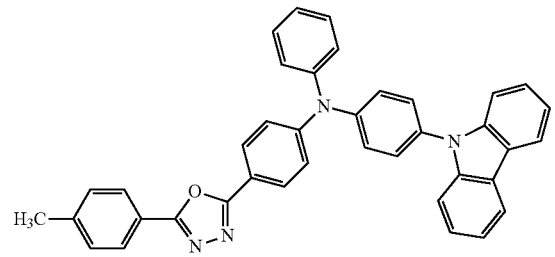
(4)
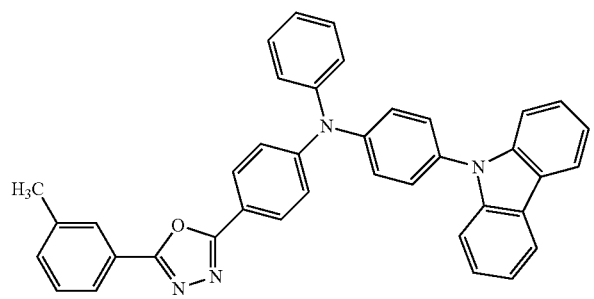
(5)
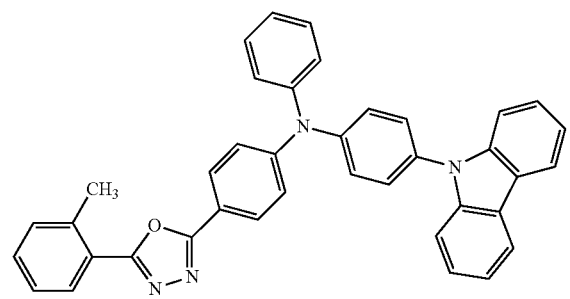
(6)
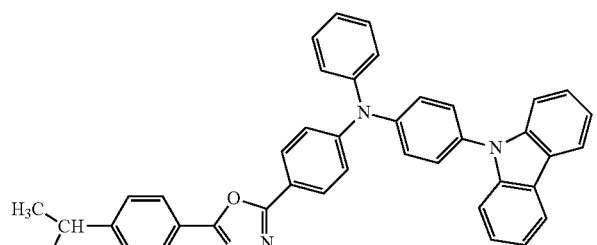
(7)
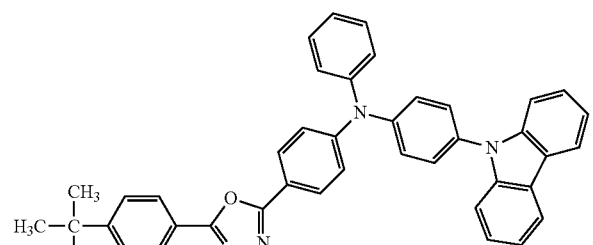
(8)
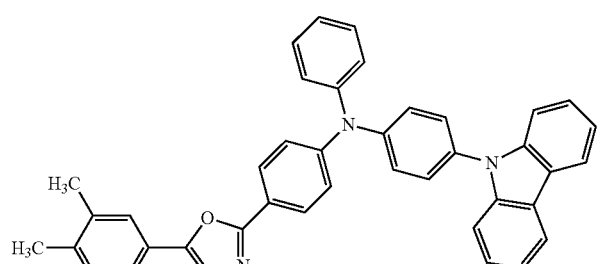
(9)
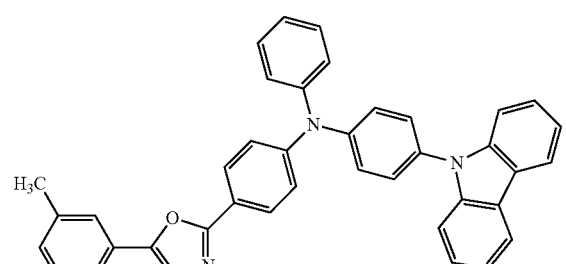
(10)
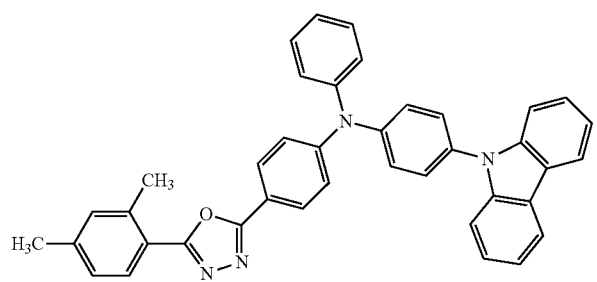
(11)
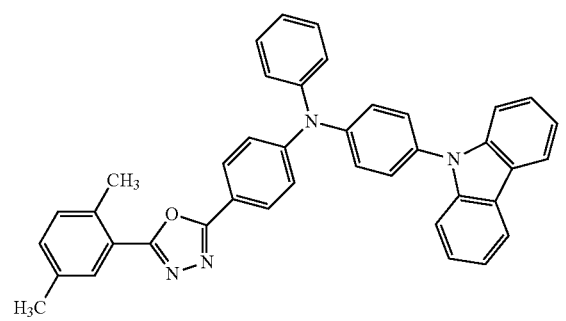
(12)

-continued
(13)
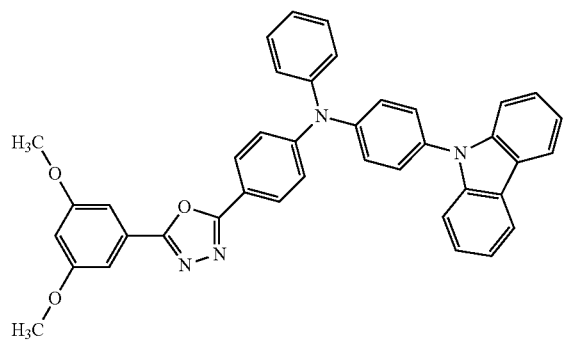
(14)
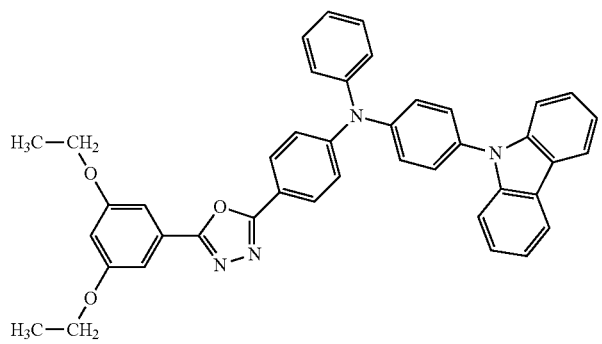
(15)
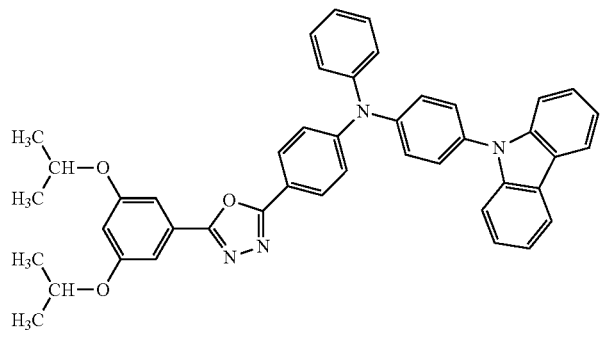
(16)
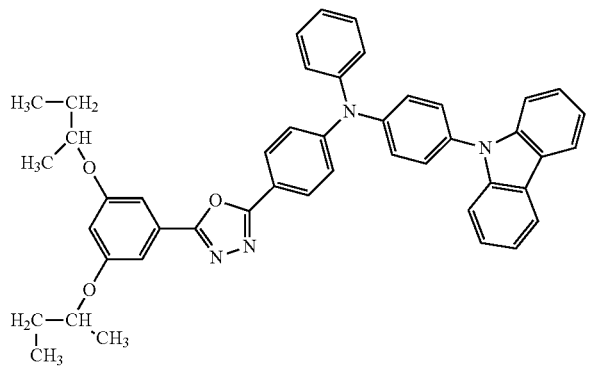
(17)
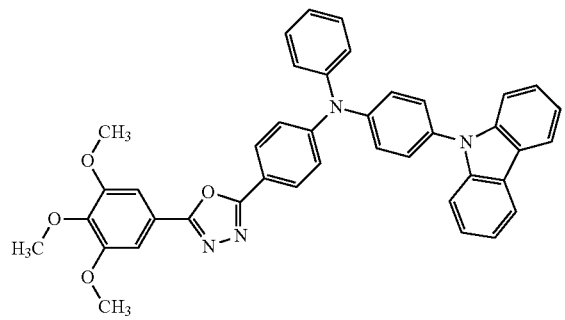
(18)
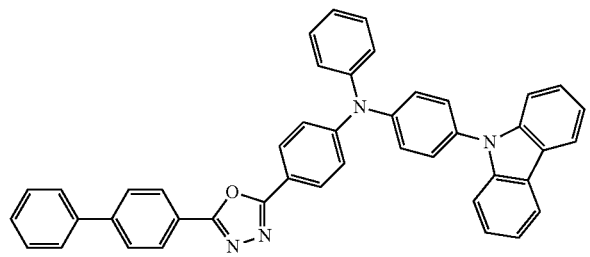
(19)
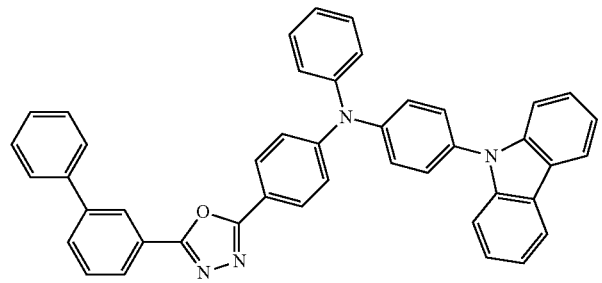
(20)
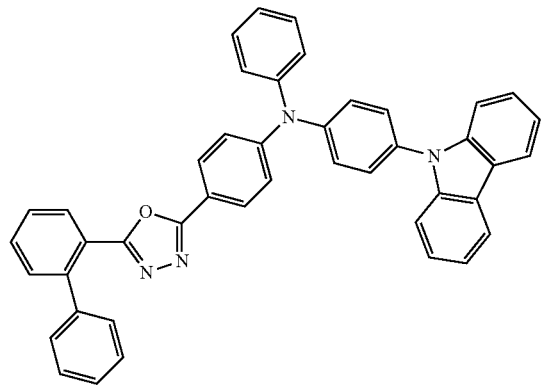

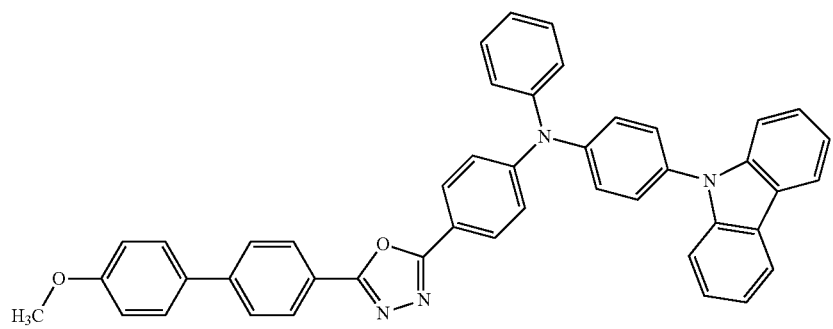
(21)
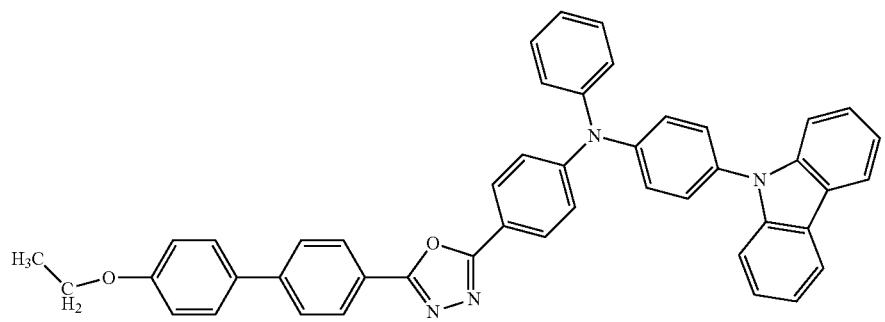
(22)
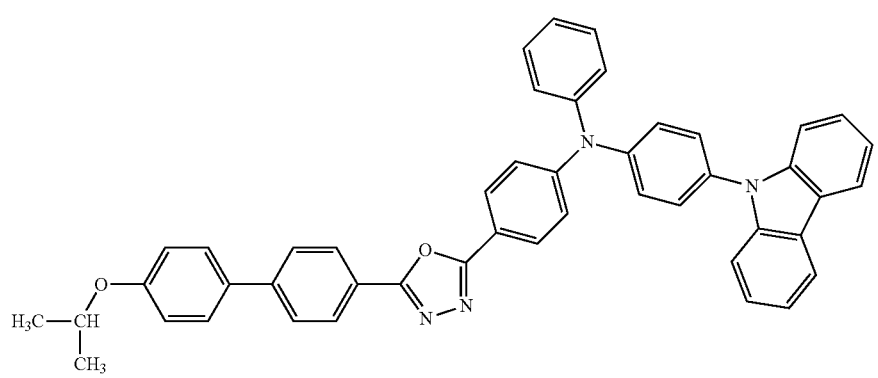
(23)
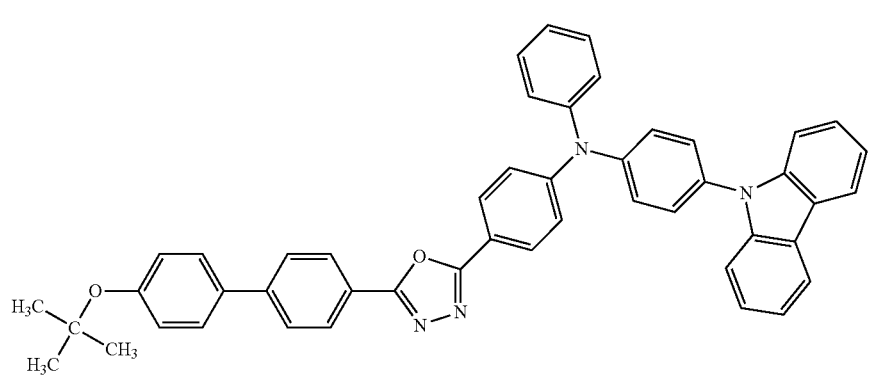
(24)

-continued
(25)
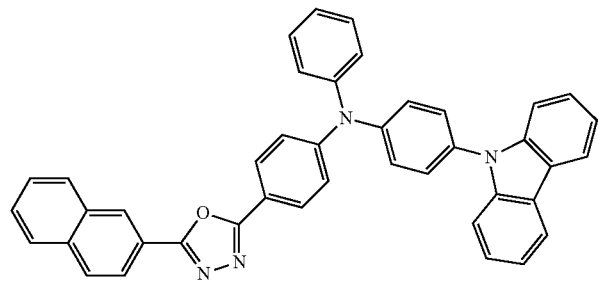
(26)
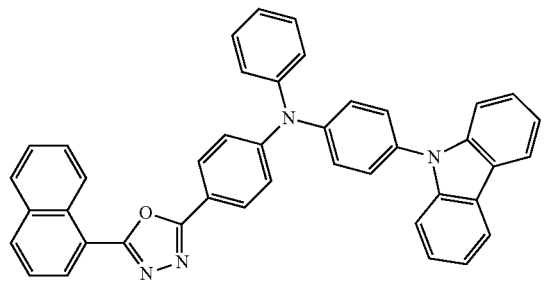
(27)
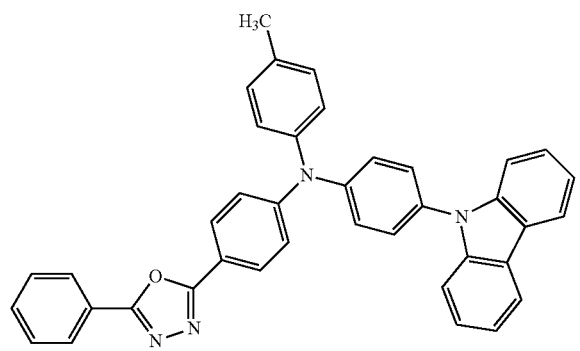
(28)
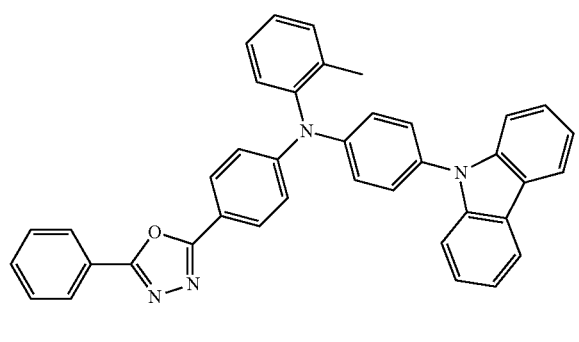
(29)
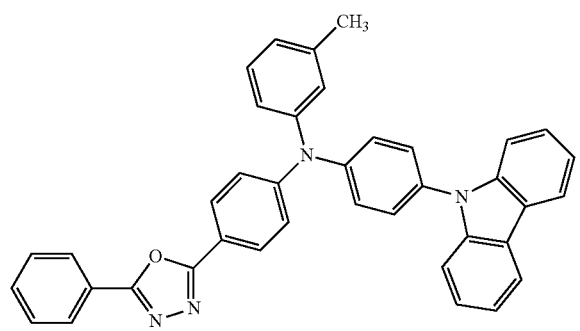
(30)
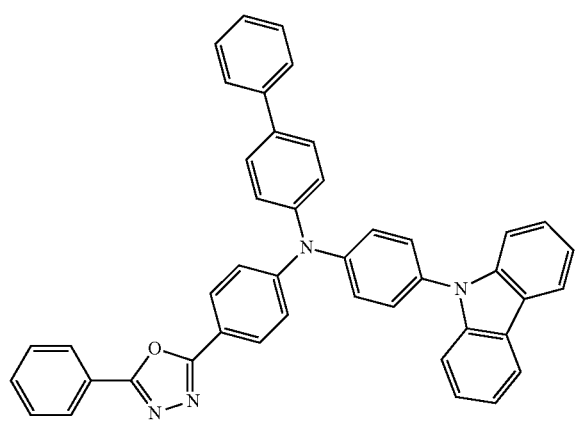
(31)
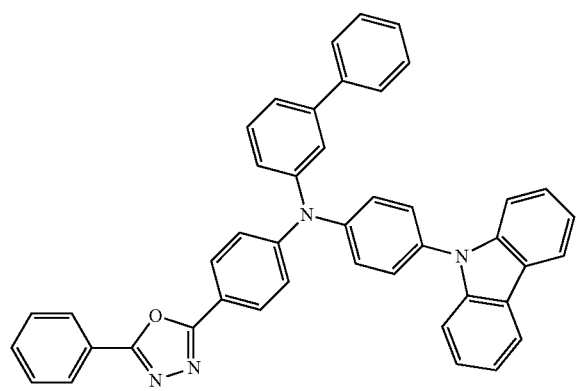
(32)
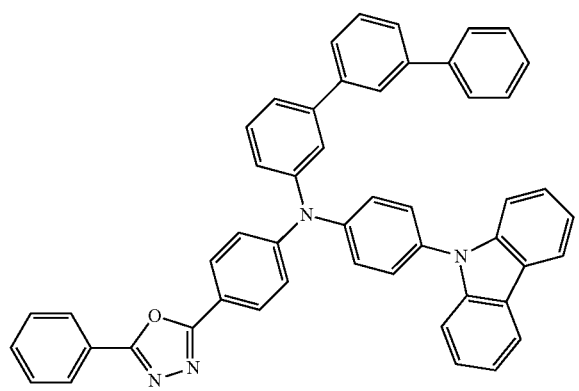

-continued
(33)
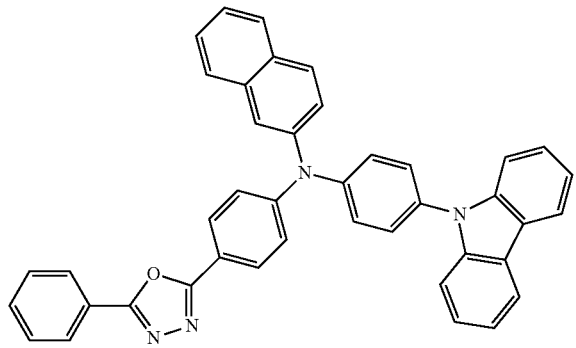
(34)
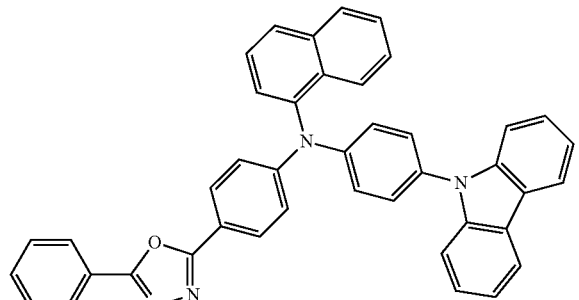
(35)
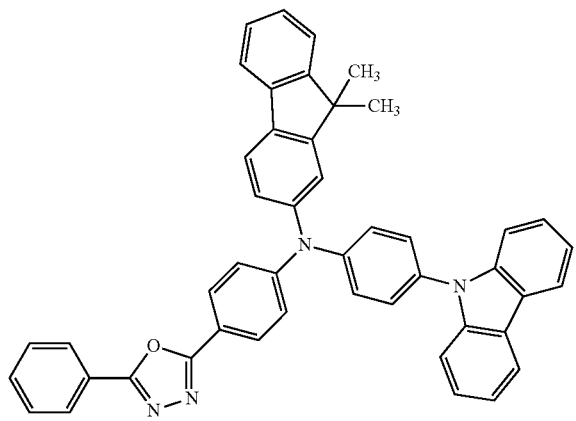
(36)
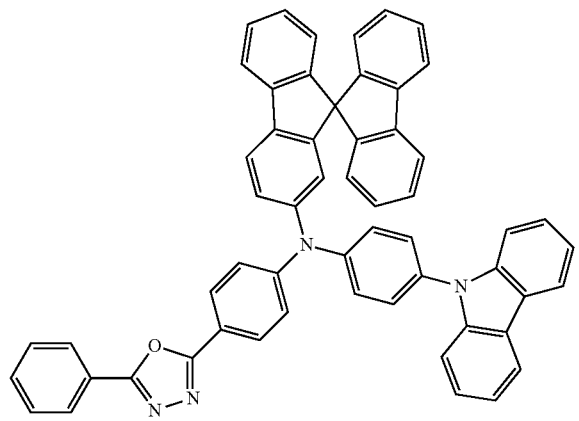
(37)
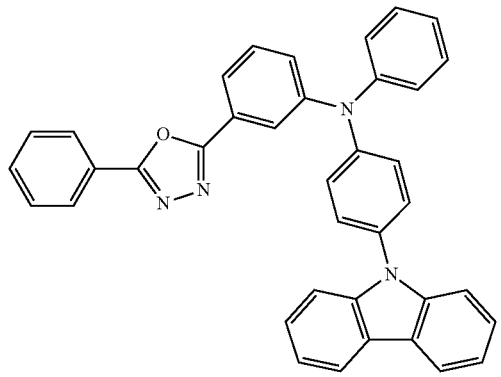
(38)
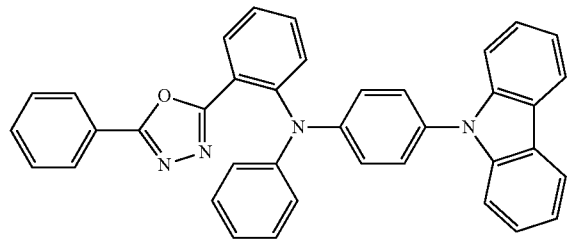
(39)
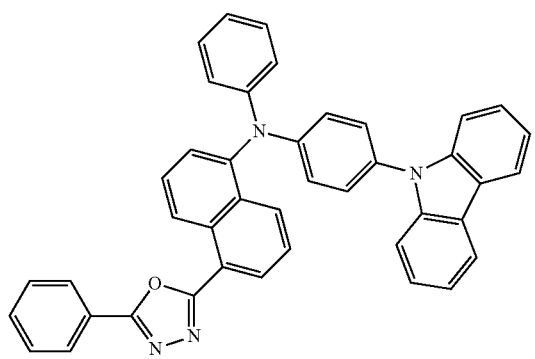
(40)
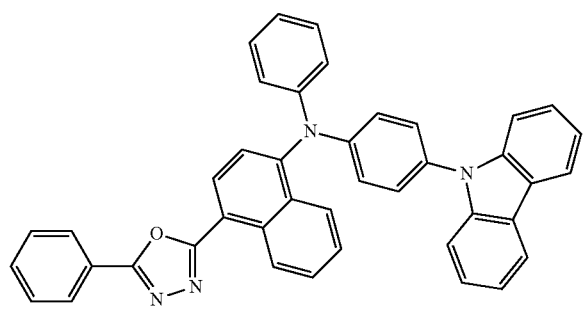

-continued
(41)
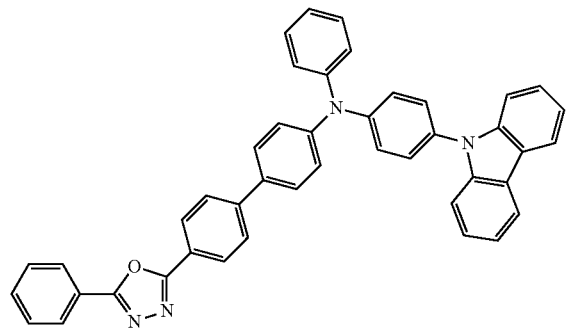
(42)
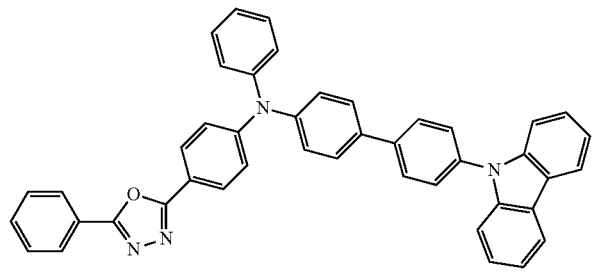
(43)
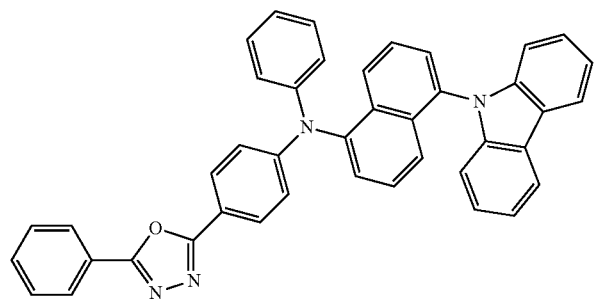
(44)
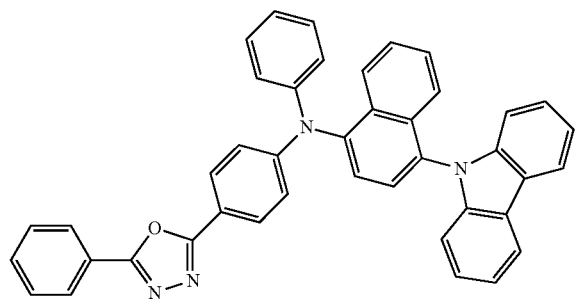
(45)
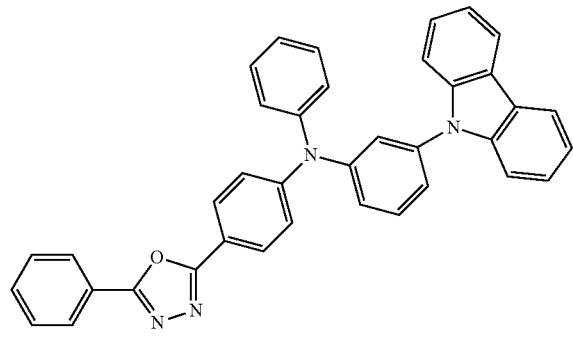
(46)
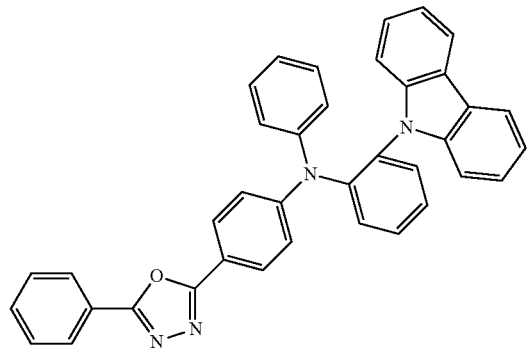
(47)
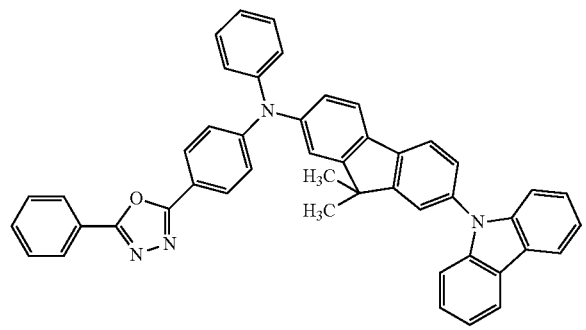
(48)
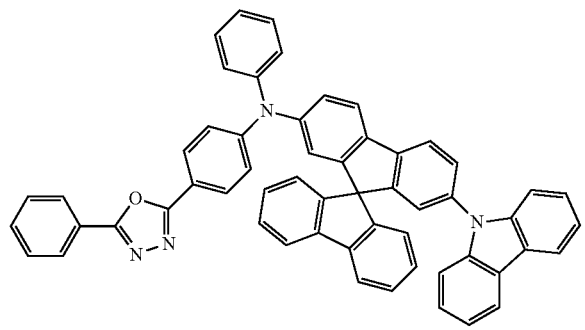

-continued
(49)
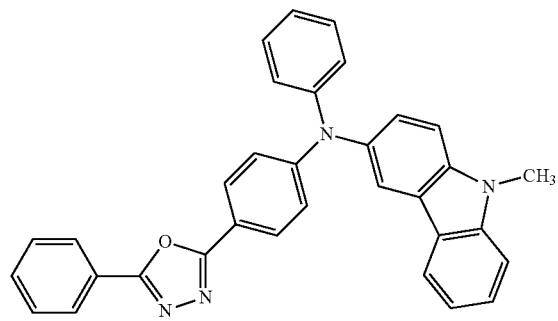
(50)
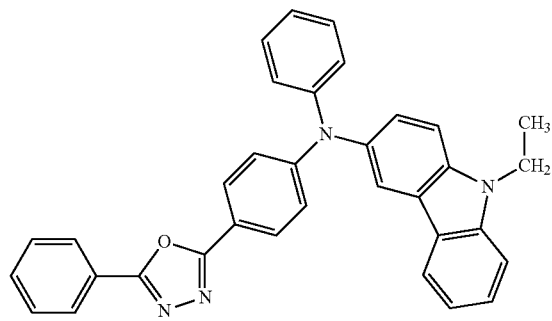
(51)
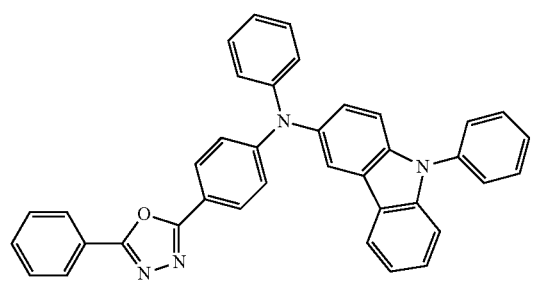
(52)
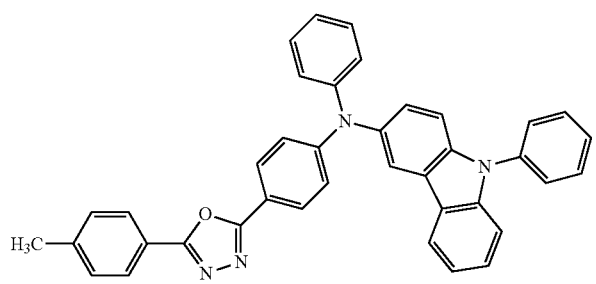
(53)
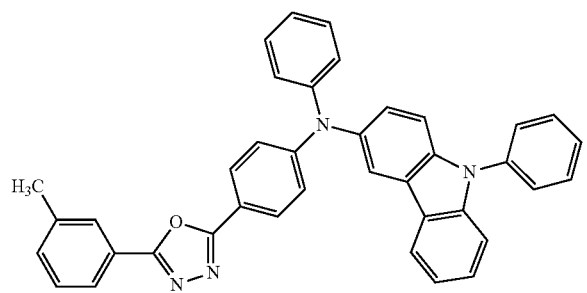
(54)
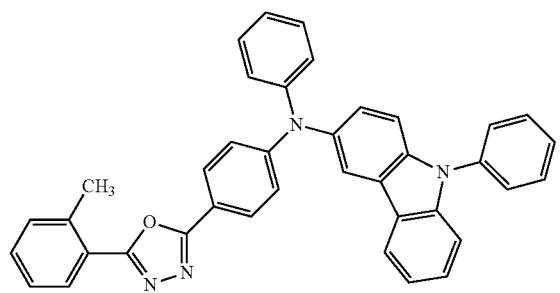
(55)
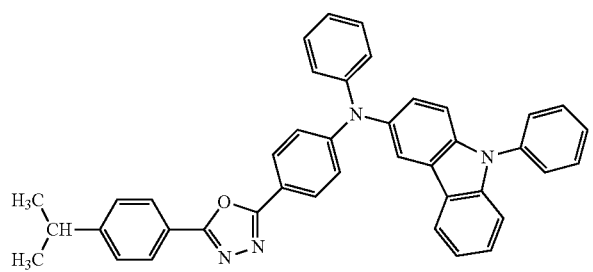
(56)
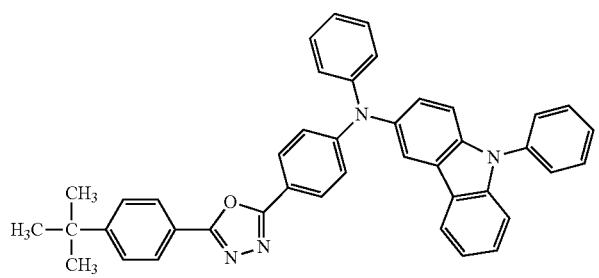
(57)
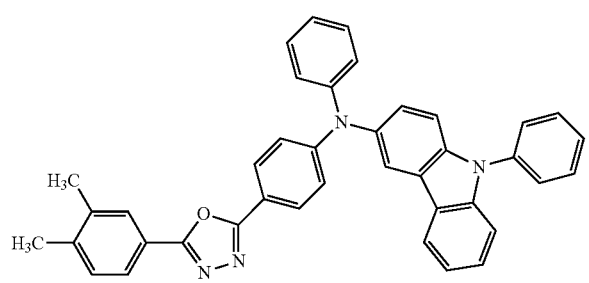
(58)
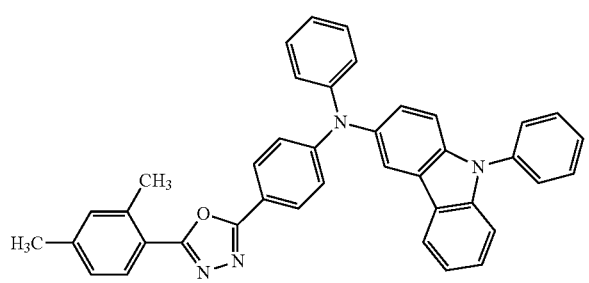

-continued
(59)
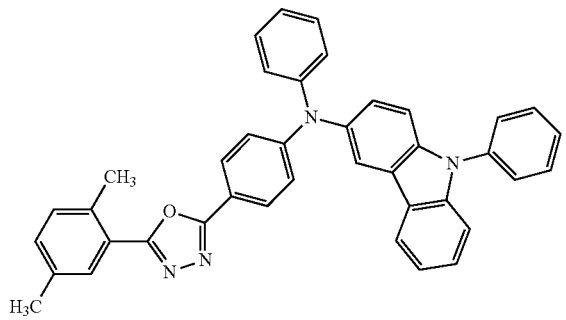
(60)
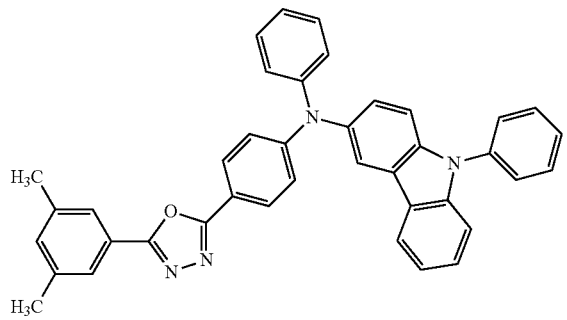
(61)
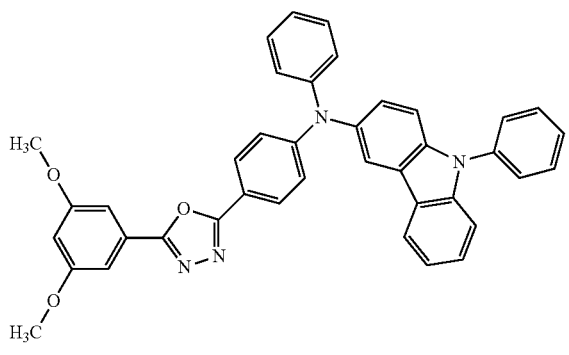
(62)
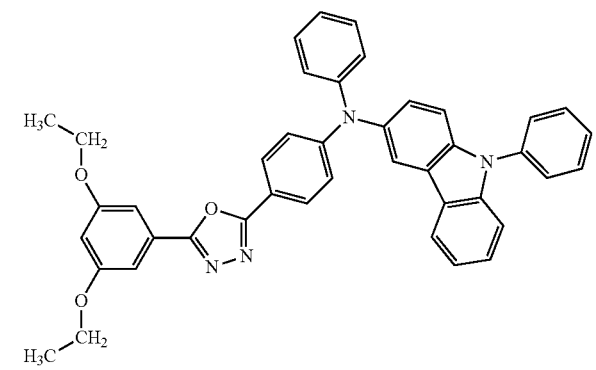
(63)
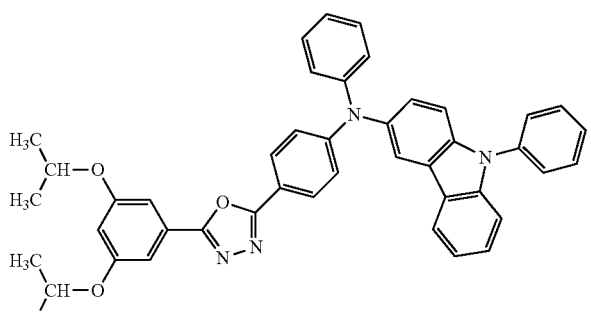
(64)
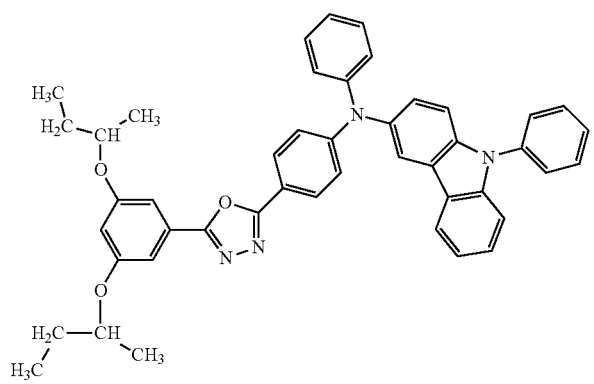
(65)
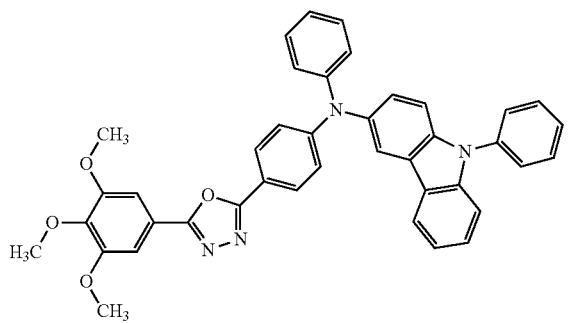
(66)
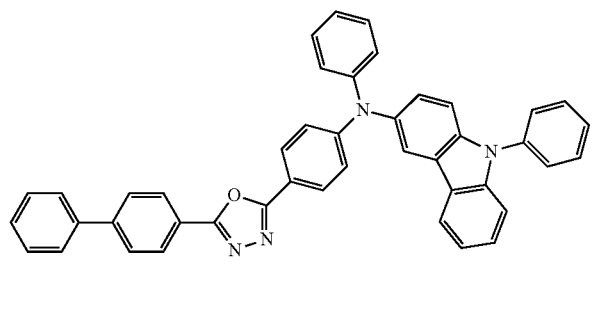

-continued
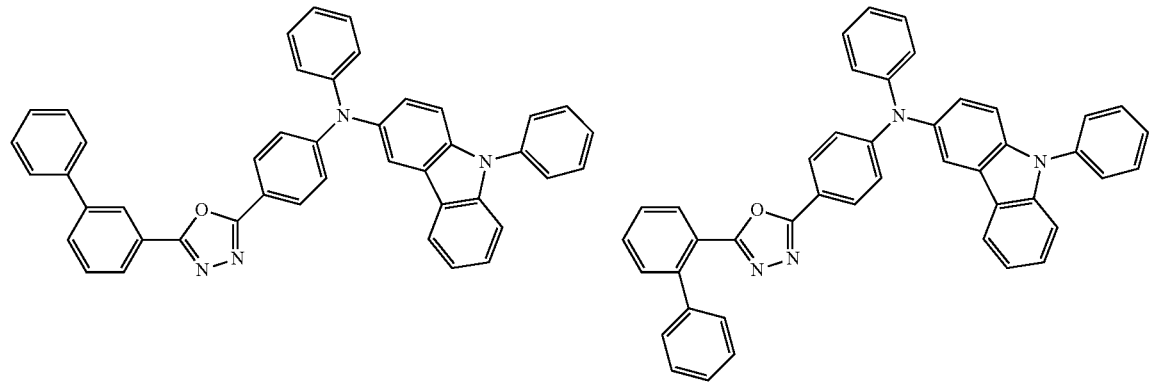
(67)
(68)
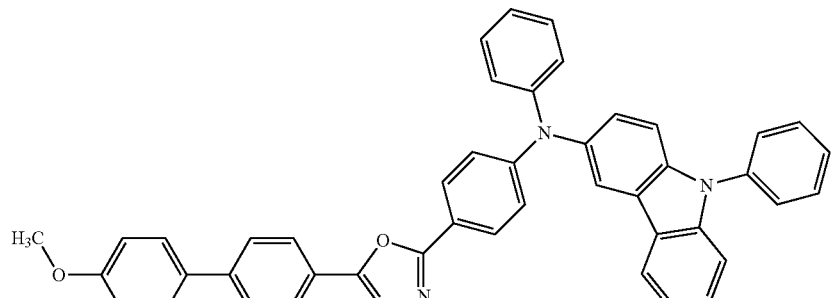
(69)
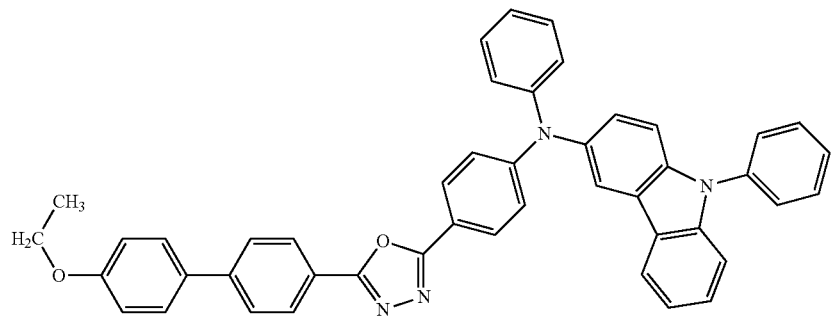
(70)
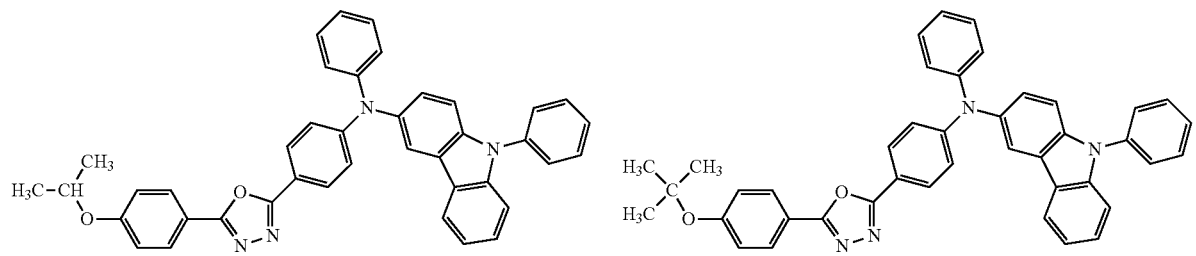
(71)
(72)
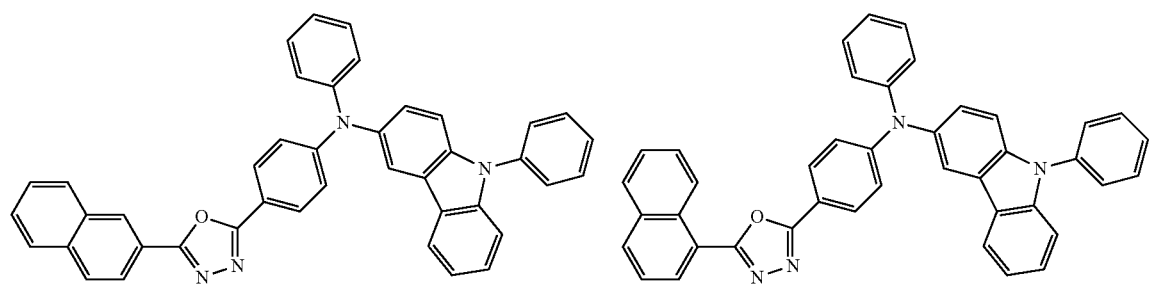
(73)
(74)

-continued
(75)
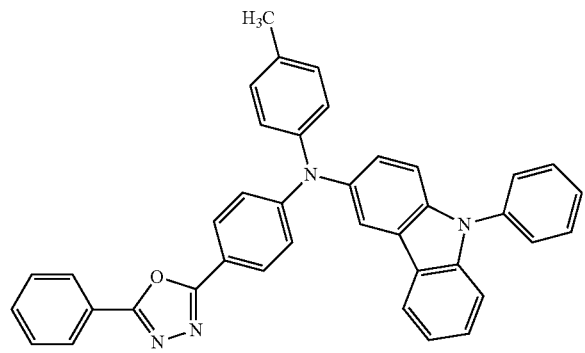
(76)
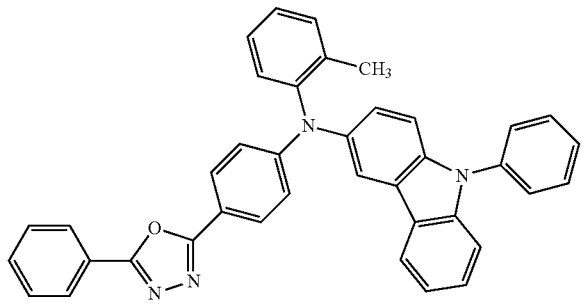
(77)
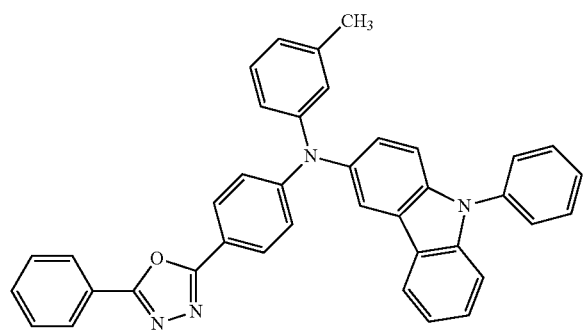
(78)
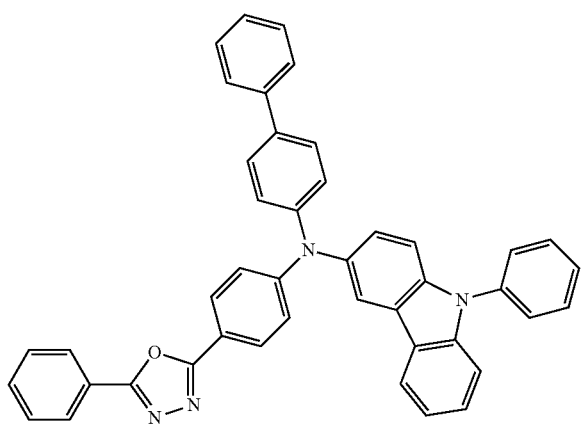
(79)
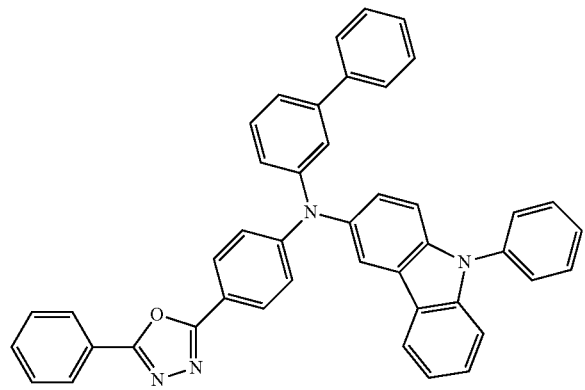
(80)
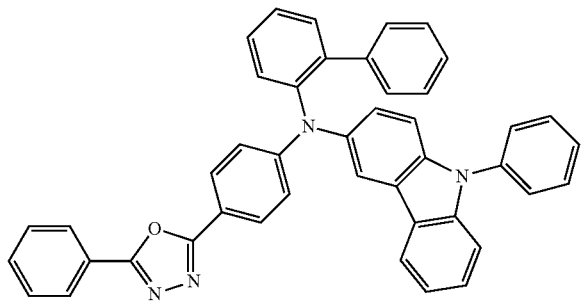
(81)
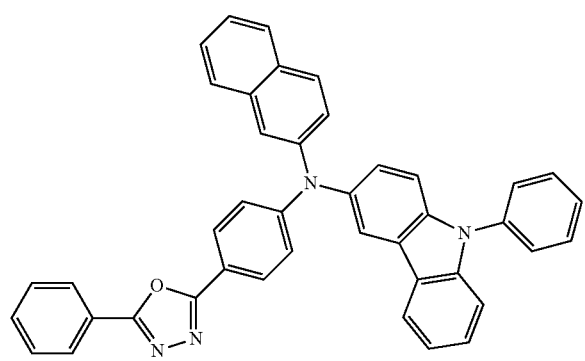
(82)
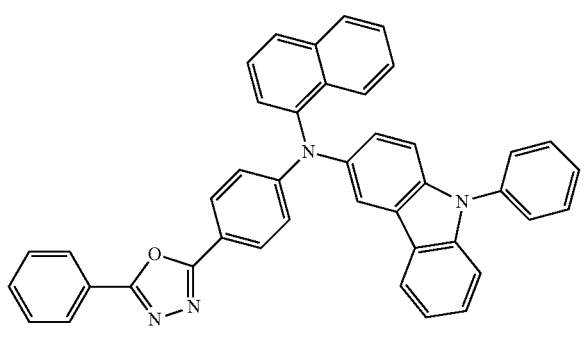

-continued
(83)
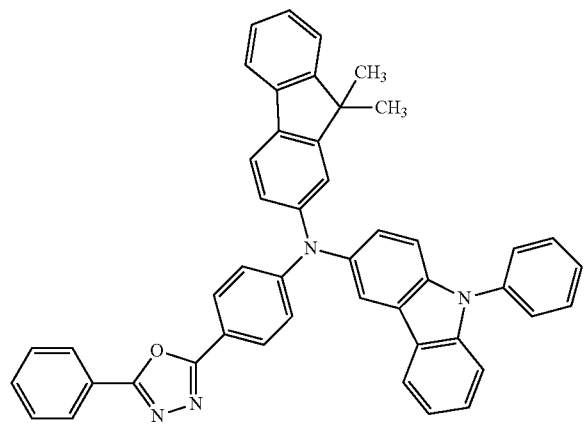
(84)
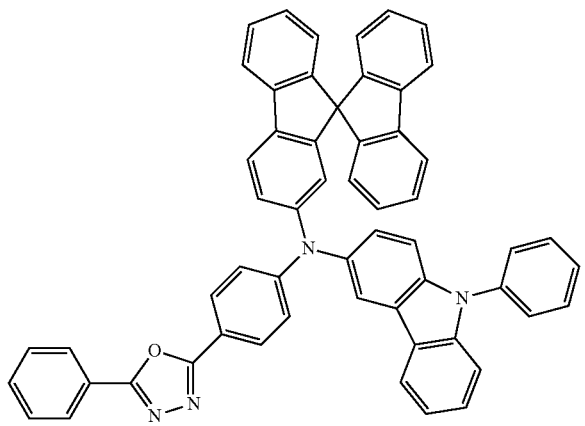
(85)
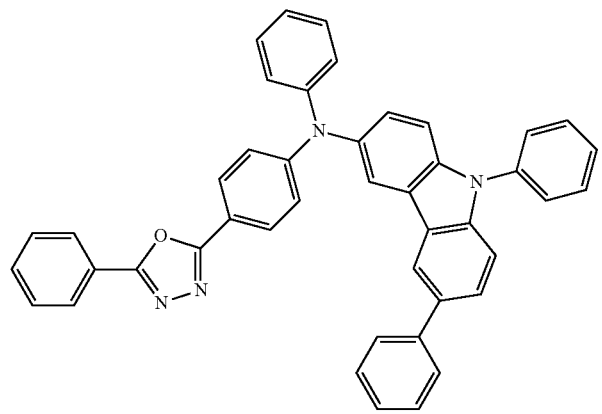
(86)
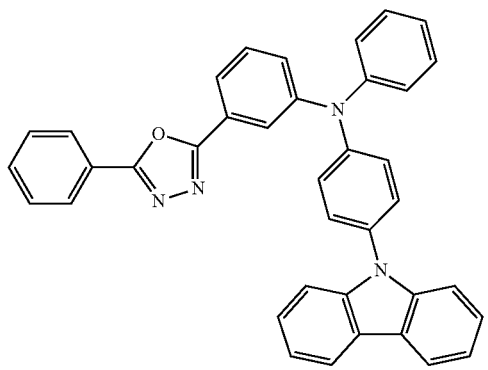
(87)
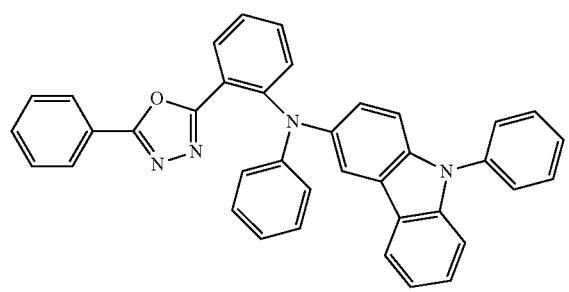
(88)
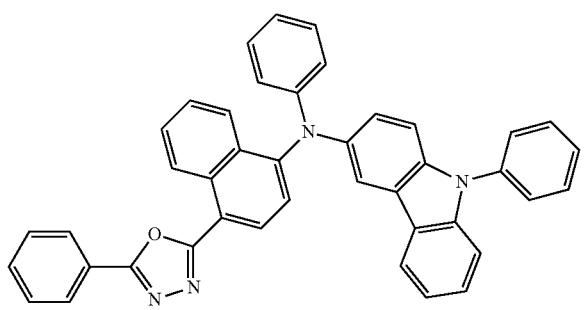
(89)
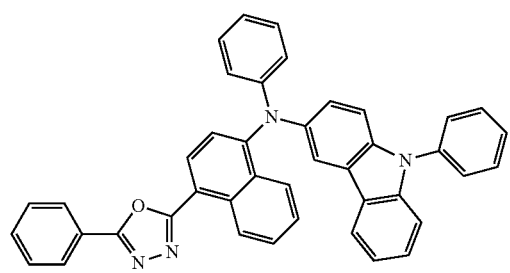
(90)
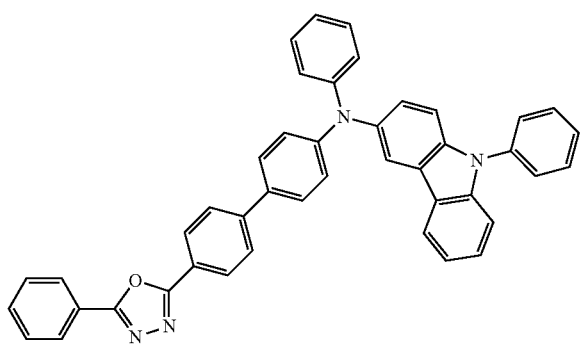

-continued
(91)
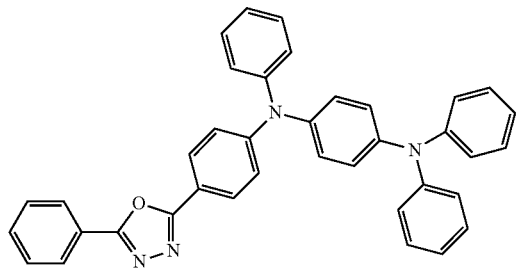
(92)
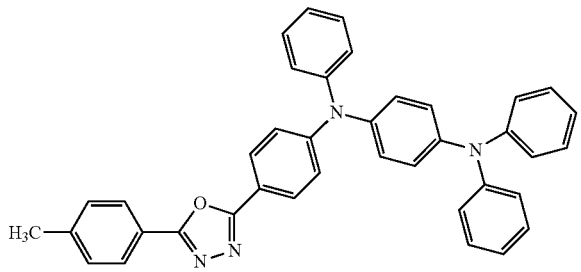
(93)
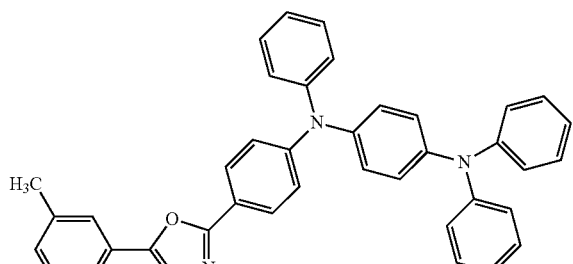
(94)
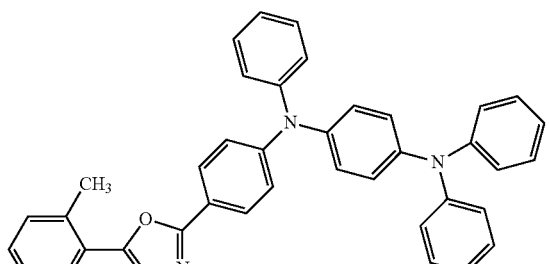
(95)
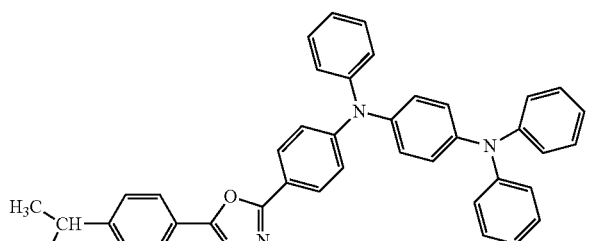
(96)
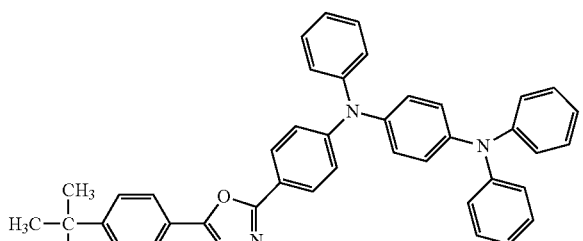
(97)
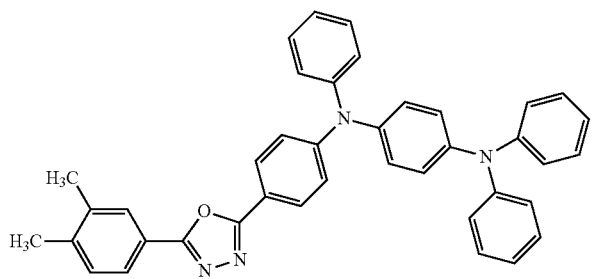
(98)
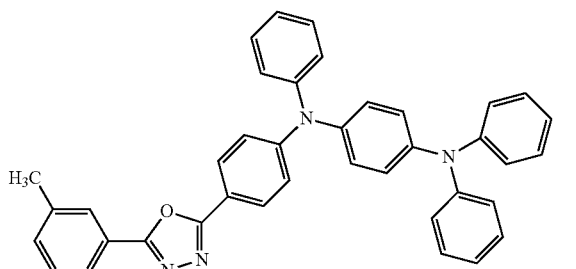
(99)
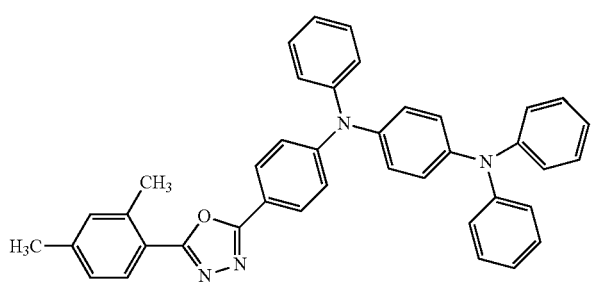
(100)
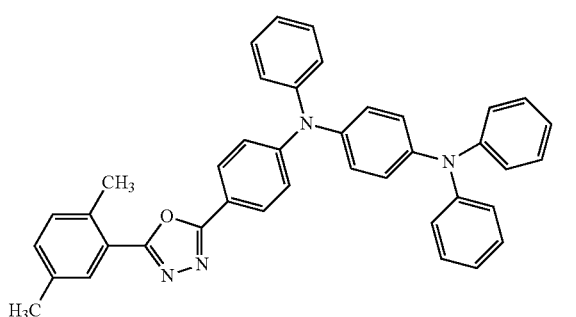

-continued
(101)
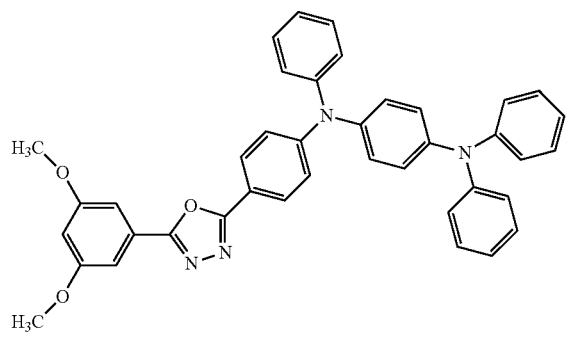
(102)
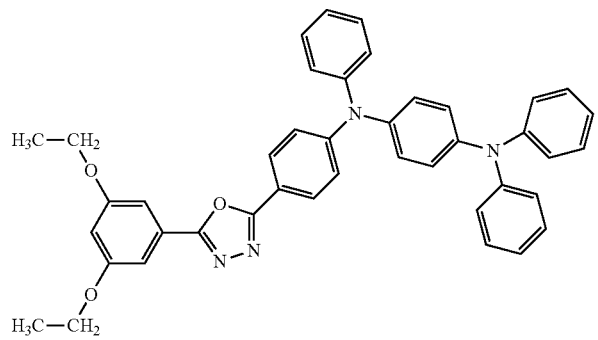
(103)
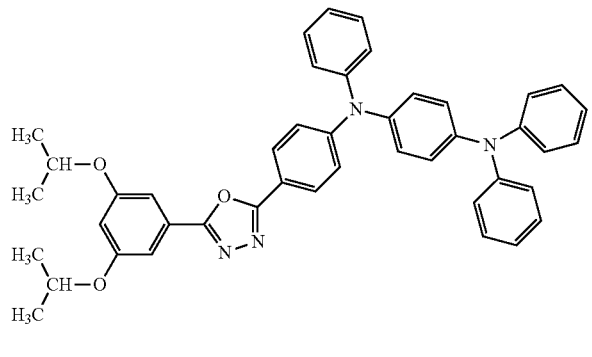
(104)
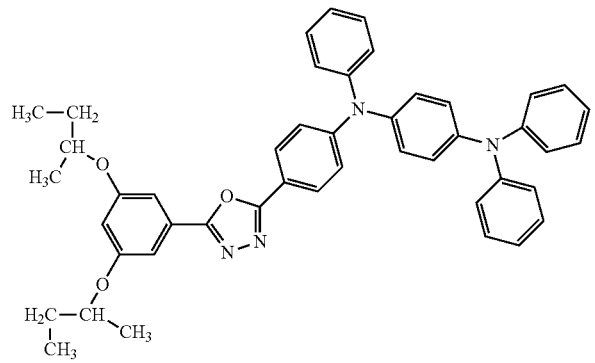
(105)
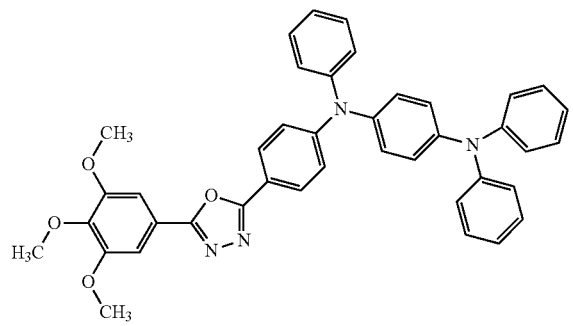
(106)
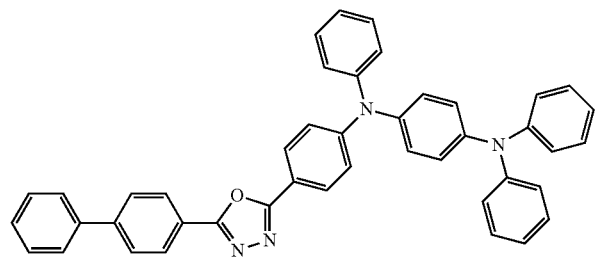
(107)
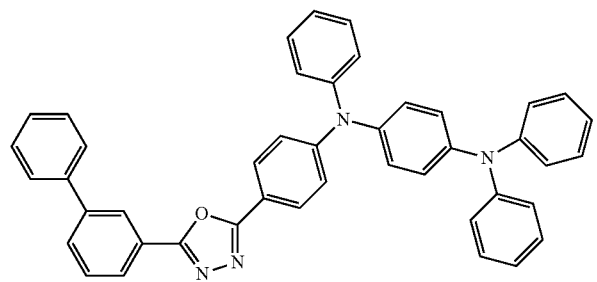
(108)
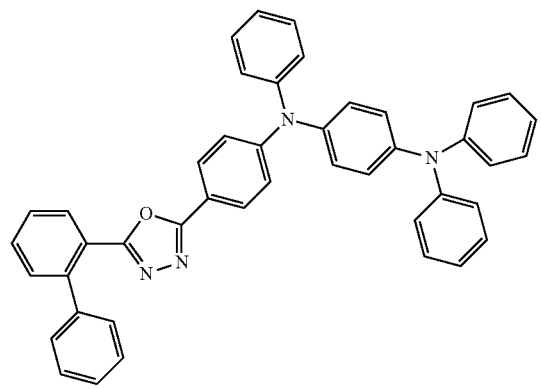

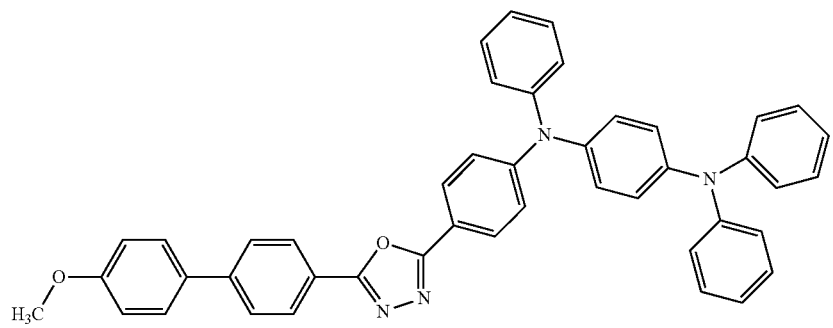
(109)
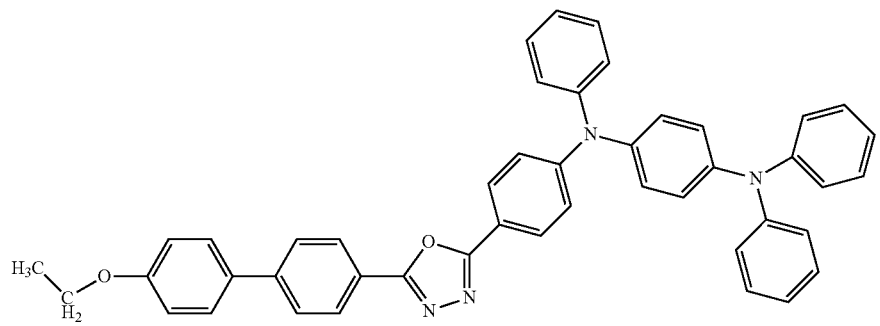
(110)
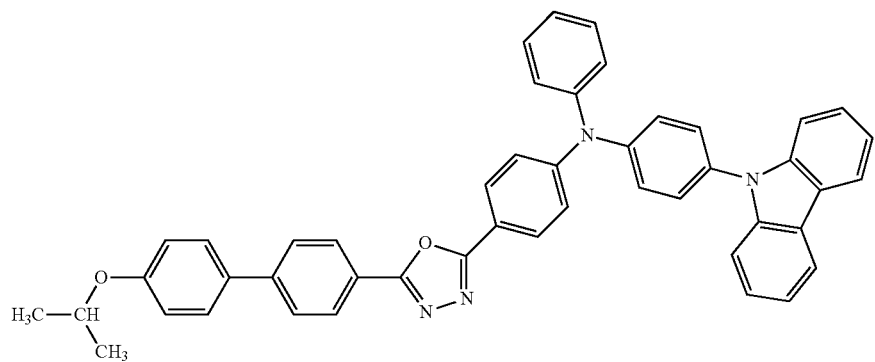
(111)
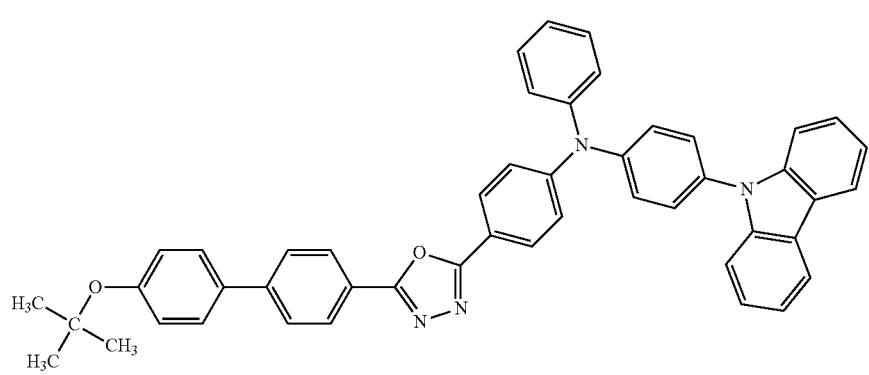
(112)

-continued
(113) (114)
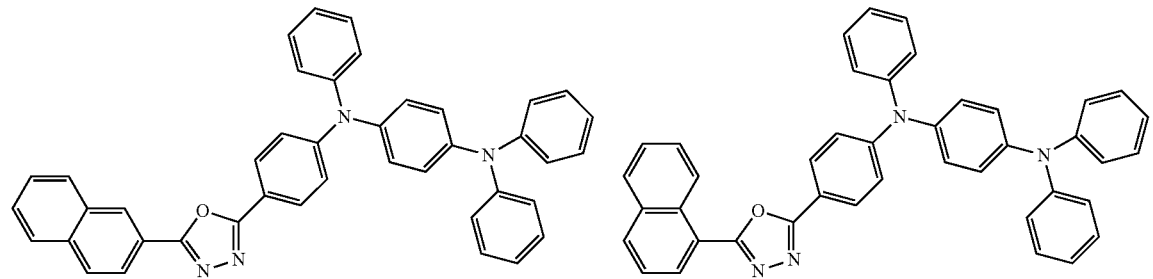
(115) (116)
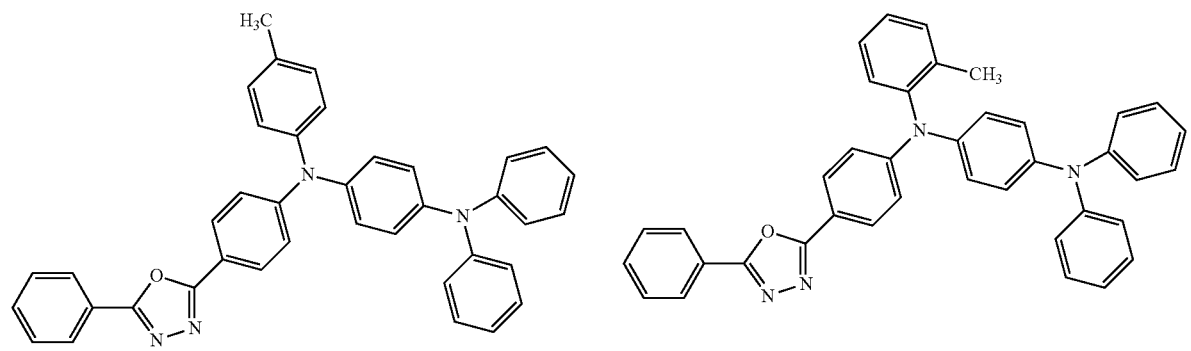
(117) (118)
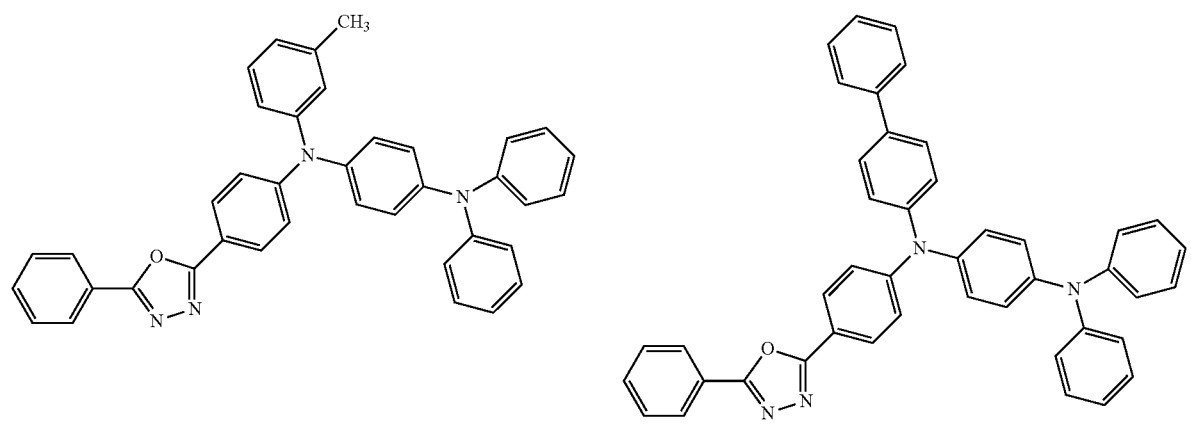
(119) (120)
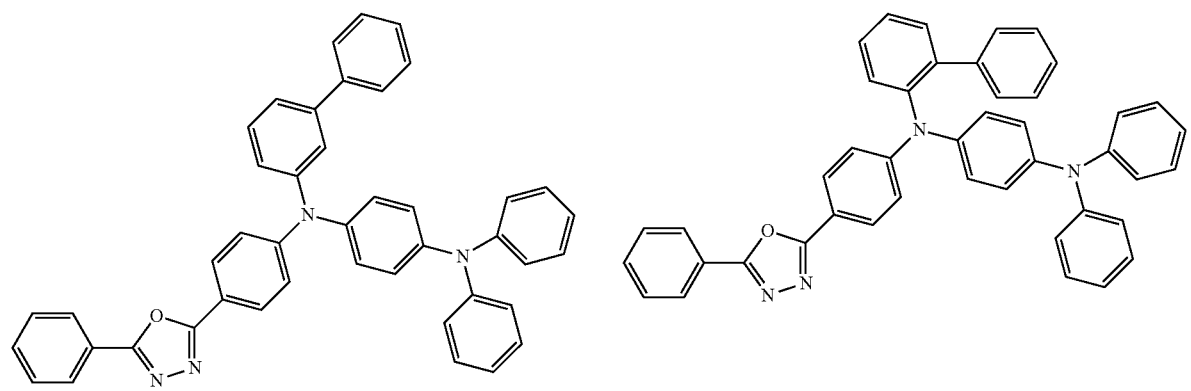

-continued
(121)
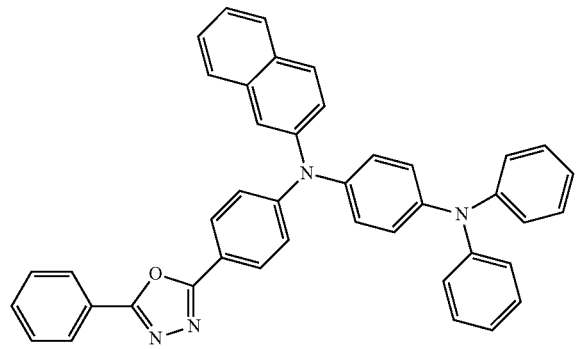
(122)
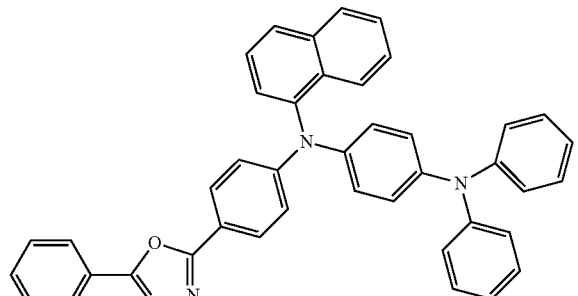
(123)
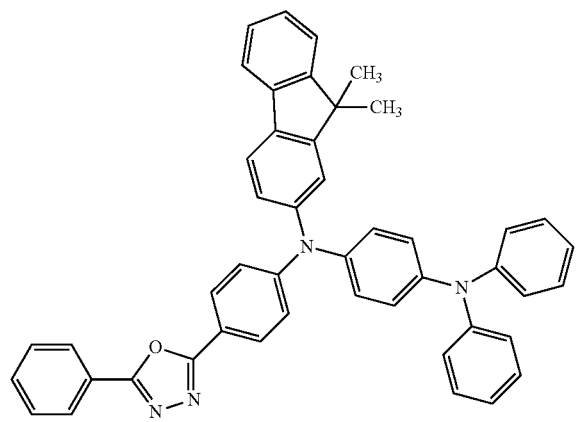
(124)
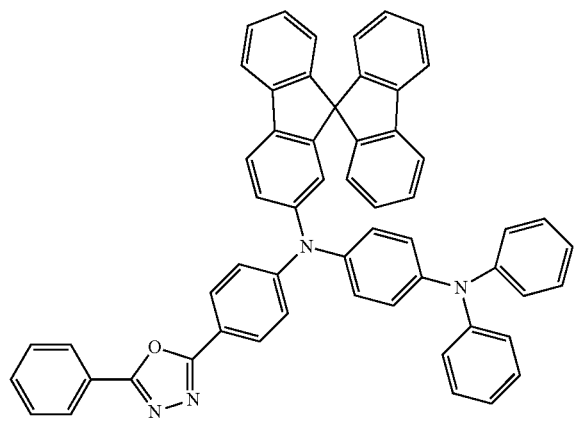
(125)
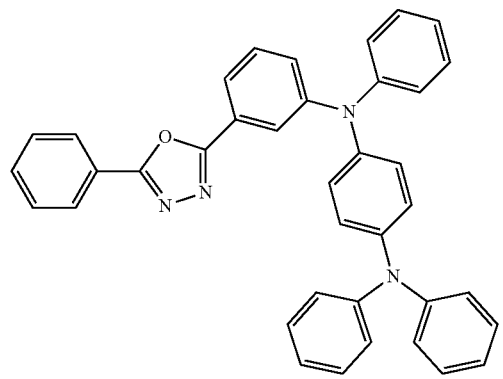
(126)
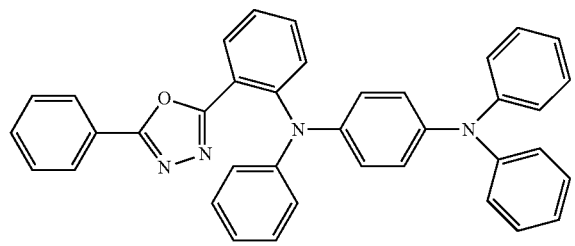
(127)
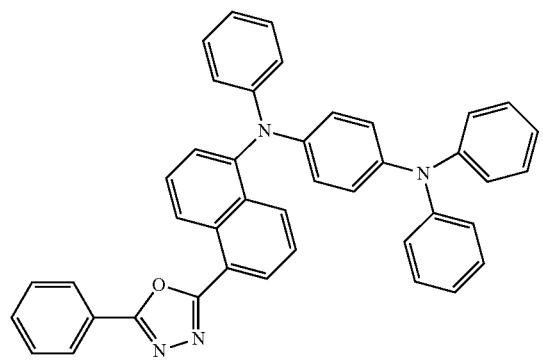
(128)
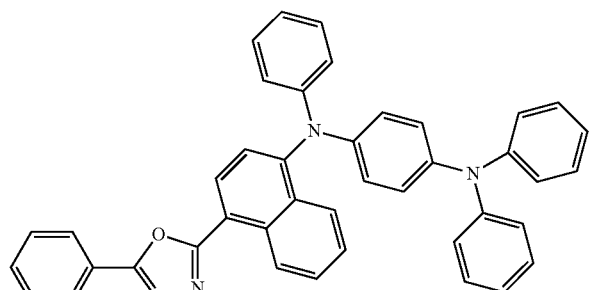

-continued
(129)
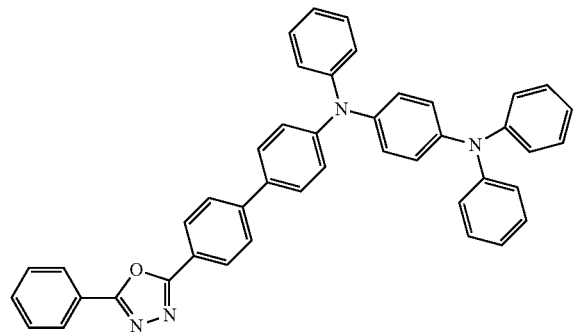
(130)
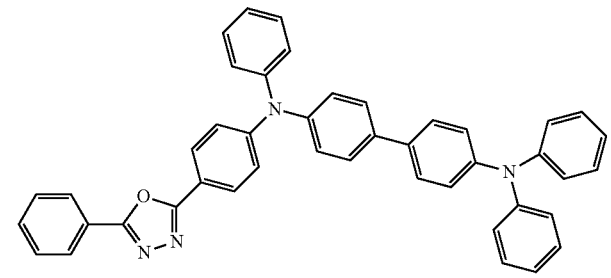
(131)
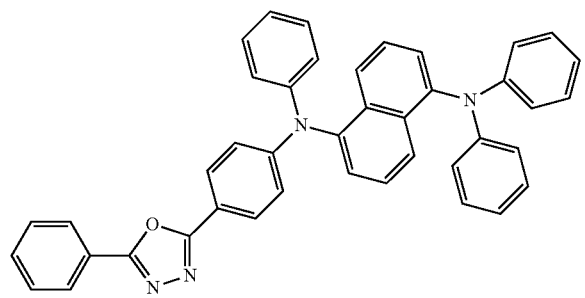
(132)
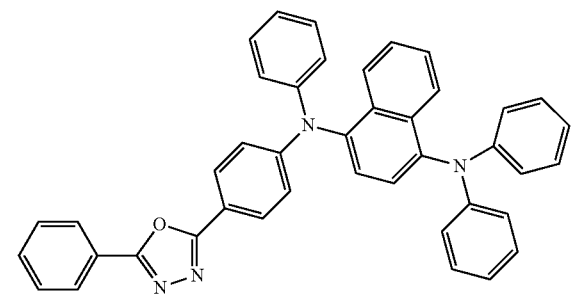
(133)
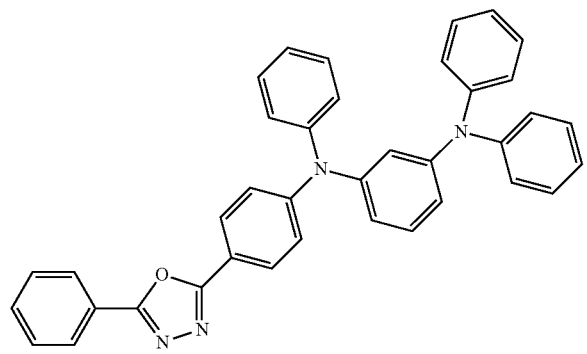
(134)
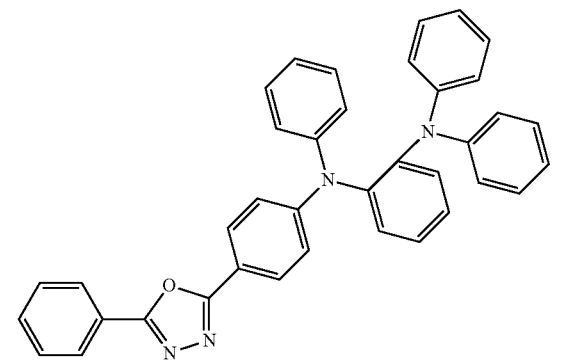
(135)
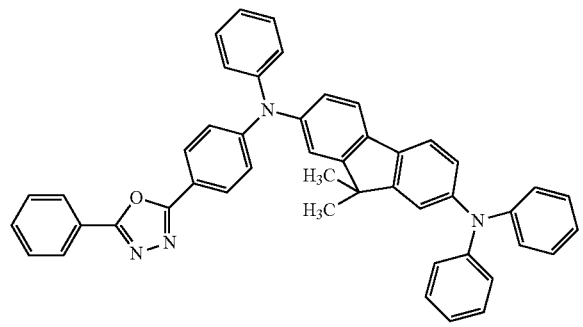
(136)
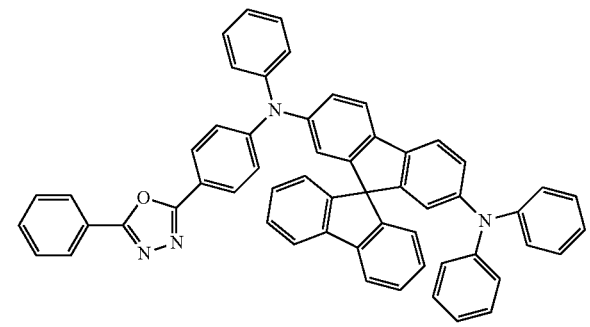

(137)

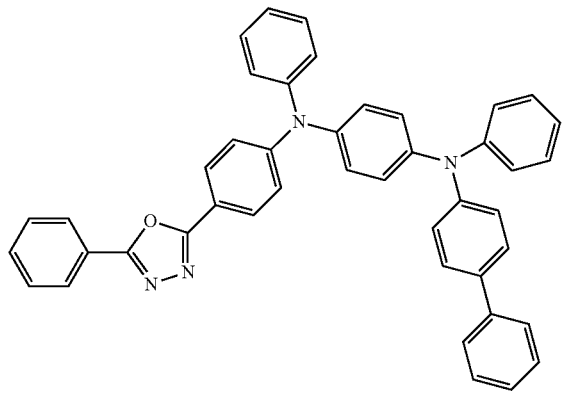

(138)

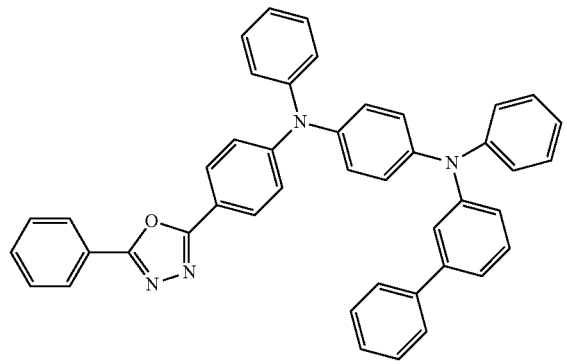

(139)

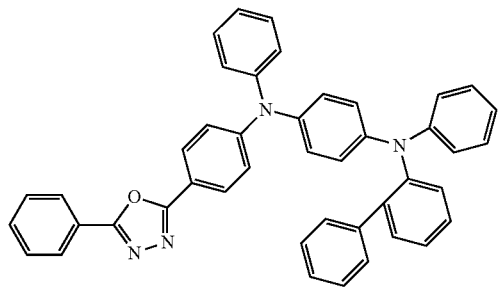

(140)

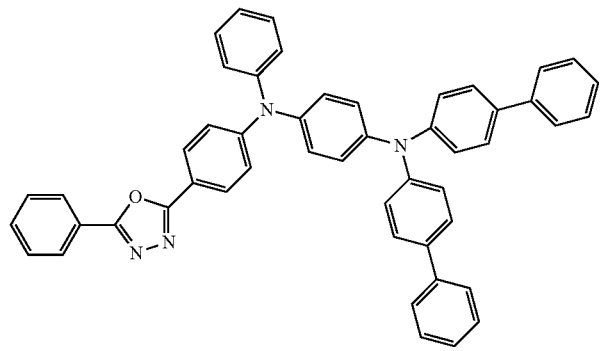

(Embodiment Mode 2)

Embodiment Mode 2 will explain a mode of a light emitting element using the oxadiazole derivative of the present invention explained in Embodiment Mode 1 as a host material of a light emitting layer with reference to FIG. 1.

FIG. 1 is a view showing a light emitting element including a light emitting layer 113 between a first electrode 101 and a second electrode 102. The light emitting layer 113 contains the oxadiazole derivative of the present invention and a light emitting substance. In Embodiment Mode 2, the oxadiazole derivative of the present invention is a host material and the light emitting substance is a guest material in the light emitting layer 113.

By applying voltage to such a light emitting element, a hole injected from the first electrode 101 side and an electron injected from the second electrode 102 side are recombined in the light emitting layer 113; therefore, the light emitting substance is in a excited state. When the light emitting substance in the excited state returns to a ground state, light is emitted. Since the oxadiazole derivative of the present invention is a bipolar substance, the oxadiazole derivative can receive both the hole and the electron efficiently and can transport them to the light emitting substance. Therefore, the light emitting element of the present invention can generate the excited state of the light emitting substance with low driving voltage. In addition, since the oxadiazole derivative of the present invention has high excitation energy, the light emitting substance in the excited state can emit light efficiently without being quenched. Note that, in the light emitting element of Embodiment Mode 2, the first electrode 101 functions as an anode, and the second electrode 102 functions as a cathode.

The light emitting substance (i.e. the guest material) is not particularly limited. However, since the oxadiazole derivative of the present invention has high triplet excitation energy, a phosphorescent compound is preferable as the guest material. Specifically, bis[2-(4',6'-difluorophenyl)pyridinato-N,$C^{2'}$] iridium(III)picolinate (abbreviation: FIrpic), tris(2-phenylpyridinato-N,$C^{2'}$)iridium(III) (abbreviation: Ir(ppy)$_3$), bis(2-phenylpyridinato-N,$C^{2'}$)iridium(III)acetylacetonate (abbreviation: Ir(ppy)$_2$(acac)), bis(2-phenylbenzothiazolato-N,$C^{2'}$)iridium(III)acetylacetonate (abbreviation: Ir(bt)$_2$(acac)), tris(2-phenylquinolinato-N,$C^{2'}$)iridium(III) (abbreviation: Ir(pq)$_3$), bis(2-phenylquinolinato-N,$C^{2'}$)iridium(III) acetylacetonate (abbreviation: Ir(pq)$_2$(acac)), bis[2-(2'-benzo[4,5-α]thienyl)pyridinato-N,$C^{3'}$)iridium(III) acetylacetonate (abbreviation: Ir(btp)$_2$(acac)), bis(1-phenylisoquinolinato-N,$C^{2'}$)iridium(III)acetylacetonate (abbreviation: Ir(pic)$_2$(acac)), (acetylacetonato)bis[2,3-bis(4-fluorophenyl)quinoxalinato]iridium(III) (abbreviation: Ir(Fdpq)$_2$(acac)), 2,3,7,8,12,13,17,18-octaethyl-21H,23H-porphyrinplatinum(II) (abbreviation: PtOEP), or the like can be used.

As the light emitting substance, a fluorescent compound can also be used. Specifically, perylene, 2,5,8,11-tetra(tert-butyl)perylene (abbreviation: TBP), 4,4'-bis[2-(N-ethylcarbazol-3-yl)vinyl]biphenyl (abbreviation: BCzVBi), 5,12-diphenyltetracene, N,N'-dimethylquinacridone (abbreviation: DMQd), N,N'-diphenylquinacridone (abbreviation: DMQd), 4-dicyanomethylene-2-isopropyl-6-[2-(1,1,7,7-tetramethyljulolidin-9-yl)ethenyl]-4H-pyran (abbreviation: DCJT1), rubrene, coumarin 6, coumarin 30, or the like can be used.

A material for the first electrode 101 is not particularly limited. However, when the first electrode 101 functions as an anode as in Embodiment Mode 2, a substance having a high work function is preferably used. Specifically, gold (Au), platinum (Pt), nickel (Ni), tungsten (W), chromium (Cr), molybdenum (Mo), iron (Fe), cobalt (Co), copper (Cu), palladium (Pd), and the like can be used in addition to indium tin oxide (ITO), indium tin oxide containing silicon oxide (ITSO), indium oxide containing 2 to 20 wt % zinc oxide (IZO). Note that the first electrode 101 can be formed by using, for example, a sputtering method, a vapor deposition method, or the like.

A material for the second electrode 102 is not particularly limited. However, when the second electrode 102 functions as a cathode as in Embodiment Mode 2, a substance having a low work function is preferably used. Specifically, alkali metal such as lithium (Li) or cesium (Cs), alkaline earth metal such as magnesium (Mg) or calcium (Ca), rare earth metal such as erbium (Er) or ytterbium (Yb) can be used in addition to aluminum (Al) or indium (In). In addition, alloy such as aluminum-lithium alloy (AlLi) or magnesium-silver alloy (MgAg) can also be used. Note that the second electrode 102 can be formed by using, for example, a sputtering method, a vapor deposition method, or the like.

In order to take out light emission to outside, either the first electrode 101 or the second electrode 102, or both of them are each preferably an electrode formed using a conductive film which transmits visible light such as ITO, or an electrode formed to be several to several tens of nm thick so as to transmit visible light.

As shown in FIG. 1, a hole transporting layer 112 may be provided between the first electrode 101 and the light emitting layer 113. The hole transporting layer has a function of transporting a hole injected from the first electrode 101 to the light emitting layer 113. In such a manner, when the hole transporting layer 112 is provided so that the first electrode 101 and the light emitting layer 113 are apart from each other, light emission is prevented from being quenched due to metal. Note that the hole transporting layer 112 is not always necessary.

A substance for the hole transporting layer 112 is not particularly limited. Typically, an aromatic amine compound such as 4,4'-bis[N-(1-napthyl)-N-phenylamino]biphenyl (abbreviation: NPB), 4,4'-bis[N-(3-methylphenyl)-N-phenylamino]biphenyl (abbreviation: TPD), 4,4'-bis[N-(9,9-dimethylfluoren-2-yl)-N-phenylamino]biphenyl (abbreviation: DFLDPBi), 4,4',4''-tris(N,N-diphenylamino)triphenylamine (abbreviation: TDATA), or 4,4',4''-tris[N-(3-methylphenyl)-N-phenylamino]triphenylamine (abbreviation: m-MTDATA) can be used. In addition, a high molecular compound such as poly(4-vinyltriphenylamine) (abbreviation: PVTPA) can also be used.

Note that the hole transporting layer 112 may have a multilayer structure in which two or more layers are stacked. In addition, the hole transporting layer 112 may also be formed by mixing two or more types of substances.

In addition, as shown in FIG. 1, an electron transporting layer 114 may be provided between the second electrode 102 and the light emitting layer 113. The electron transporting layer has a function of transporting an electron injected from the second electrode 102 to the light emitting layer 113. In such a manner, when the electron transporting layer 114 is provided so that the second electrode 102 and the light emitting layer 113 are apart from each other, light emission is prevented from being quenched due to metal. Note that the electron transporting layer 114 is not always necessary.

A substance for the electron transporting layer 114 is not particularly limited. Typically, a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]quinolinato)beryllium (abbreviation: BeBq$_2$), bis(2-methyl-8-quinolinolato)(4-phenylphenolato)aluminum (abbreviation: BAlq), bis[2-(2-hydroxyphenyl)benzoxazolato]zinc (abbreviation: Zn(BOX)$_2$), or bis[2-(2-hydroxyphenyl)benzothiazolato]zinc (abbreviation: Zn(BTZ)$_2$) can be used. In addition, a heteroaromatic compound such as 2-(4-biphenylyl)-5-(4-tert-buthylphenyl)-1,3,4-oxadiazole (abbreviation: PBD), 1,3-bis[5-(p-tert-buthylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), or 4,4'-bis(5-methylbenzoxazol-2-yl)stilbene (abbreviation: BzOs) can also be used. Further, a high molecular compound such as poly(2,5-pyridine-diyl) (abbreviation: PPy) can also be used.

Note that the electron transporting layer 114 may have a multilayer structure in which two or more layers are stacked. In addition, the electron transporting layer 114 may also be formed by mixing two or more types of substances.

In addition, as shown in FIG. 1, a hole injecting layer 111 may be provided between the first electrode 101 and the hole transporting layer 112. The hole injecting layer has a function of supporting injection of a hole from the electrode functioning as an anode to the hole transporting layer 112. Note that the hole injecting layer 111 is not always necessary.

A substance for the hole injecting layer 111 is not particularly limited. Metal oxide such as vanadium oxide (VOx), niobium oxide (NbOx), tantalum oxide (TaOx), chromium oxide (CrOx), molybdenum oxide (MoOx), tungsten oxide (WOx), manganese oxide (MnOx), rhenium oxide (ReOx), or ruthenium oxide (RuOx) can be used. In addition, a phthalocyanine compound such as phthalocyanine (abbreviation: H$_2$Pc) or copper phthalocyanine (abbreviation: CuPC) can be used. Further, the substance for the hole transporting layer 112 can also be used. Further, a high molecular compound such as a mixture of poly(ethylenedioxythiophene) and poly(styrenesulfonic acid) (abbreviation: PEDOT/PSS) can also be used.

Alternatively, for the hole injecting layer 111, a composite material obtained by mixing an organic compound and an electron acceptor may also be used. Since a hole is generated in the organic compound by the electron acceptor, the composite material is excellent in a hole injecting property and a hole transporting property. In this case, as the organic compound, a material which is excellent in transporting a hole that is generated, specifically, the substance for the hole transporting layer 112 (an aromatic amine compound or the like) as described above is preferably used, for example. As the electron acceptor, a substance having an electron accepting property to the organic compound may be used. Specifically, transition metal oxide is preferable. For example, vanadium oxide (VOx), niobium oxide (NbOx), tantalum oxide (TaOx), chromium oxide (CrOx), molybdenum oxide (MoOx), tungsten oxide (WOx), manganese oxide (MnOx), rhenium oxide (ReOx), ruthenium oxide (RuOx), or the like can be used. In addition, Lewis acid such as iron (III) chloride or aluminum (III) chloride can also be used. Further, an organic compound such as 7,7,8,8-tetracyano-2,3,5,6-tetrafluoroquinodimethane (abbreviation: F4-TCNQ) can also be used.

Note that the hole injecting layer 111 may have a multilayer structure in which two or more layers are stacked. In addition, the hole injecting layer 111 may also be formed by mixing two or more types of substances.

In addition, as shown in FIG. 1, an electron injecting layer 115 may be provided between the second electrode 102 and the electron transporting layer 114. The electron injecting layer has a function of supporting injection of an electron from the electrode functioning as a cathode to the electron transporting layer 114. Note that the electron injecting layer 115 is not always necessary.

A substance for the electron injecting layer 115 is not particularly limited. An alkali metal compound or an alkaline earth metal compound such as lithium fluoride (LiF), cesium fluoride (CsF), calcium fluoride ($CaF_2$), or lithium oxide (LiOx) can be used. In addition, a rare earth metal compound such as erbium fluoride ($ErF_3$) can also be used. In addition, the substance for the electron transporting layer 114 as described above can also be used.

Alternatively, for the electron injecting layer 115, a composite material obtained by mixing an organic compound and an electron donor may also be used. Since an electron is generated in the organic compound by the electron donor, the composite material is excellent in an electron injecting property and an electron transporting property. In this case, as the organic compound, a material which is excellent in transporting an electron that is generated, specifically, the substance for the electron transporting layer 114 (a metal complex, a heteroaromatic compound, or the like) as described above is preferably used, for example. As the electron donor, a substance having an electron donating property to the organic compound may be used. Specifically, alkali metal, alkaline earth metal, or rare earth metal is preferable. For example, lithium, cesium, magnesium, calcium, erbium, ytterbium or the like can be used. In addition, an alkali metal compound or an alkaline earth metal compound such as lithium oxide (LiOx), calcium oxide (CaOx), barium oxide (BaOx); or cesium carbonate ($Cs_2CO_3$) can be used. Further, Lewis acid-base such as magnesium oxide or an organic compound such as tetrathiafulvalene (abbreviation: TTF) can also be used.

In the light emitting element of the present invention as described above, each of the hole injecting layer 111, the hole transporting layer 112, the light emitting layer 113, the electron transporting layer 114, and the electron injecting layer 115 may be formed by using any of a vapor deposition method, an ink-jetting method, a coating method, and the like. In addition, the first electrode 101 or the second electrode 102 may be formed by using any of a sputtering method, a vapor deposition method, an ink-jetting method, a coating method, and the like.

(Embodiment Mode 3)

Figure 2:
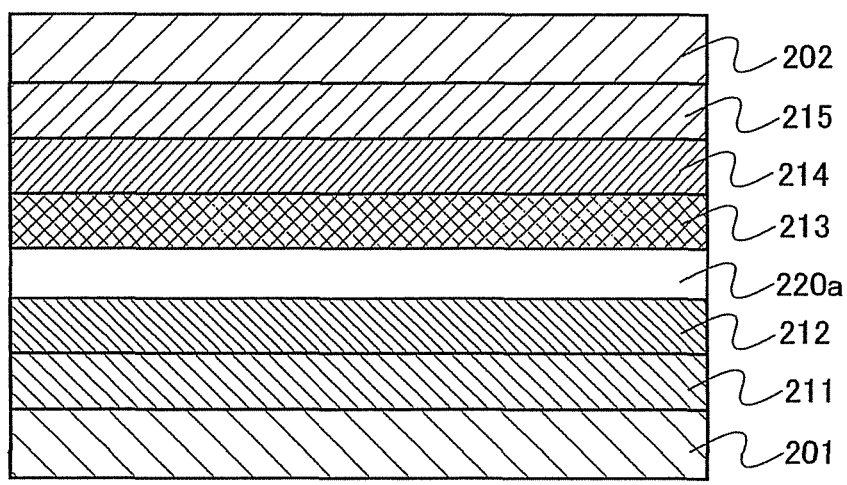
FIG. 2 is a view explaining an element structure of a light emitting element containing an oxadiazole derivative of the present invention.
Figure 3:
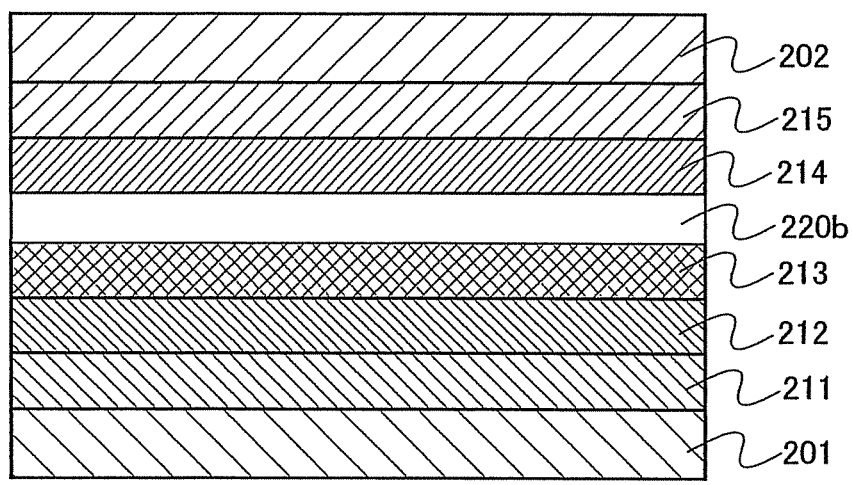
FIG. 3 is a view explaining an element structure of a light emitting element containing an oxadiazole derivative of the present invention.

Embodiment Mode 3 will explain a mode of a light emitting element using the oxadiazole derivative of the present invention as an exciton blocking layer with reference to FIGS. 2 and 3. Note that the exciton blocking layer is a kind of hole transporting layer or electron transporting layer provided so as to be in contact with a light emitting layer and is particularly a layer which has higher excitation energy than that of the light emitting layer and has a function of blocking an exciton in the light emitting layer from moving to another layer.

In a light emitting element shown in FIG. 2, a light emitting layer 213 is provided between a first electrode 201 functioning as an anode and a second electrode 202 functioning as a cathode. Further, an exciton blocking layer 220a containing the oxadiazole derivative of the present invention is provided to be in contact with the anode side of the light emitting layer 213. Therefore, in FIG. 2, the exciton blocking layer 220a is a kind of hole transporting layer.

In addition, in a light emitting element shown in FIG. 3, a light emitting layer 213 is provided between a first electrode 201 functioning as an anode and a second electrode 202 functioning as a cathode. Further, an exciton blocking layer 220b containing the oxadiazole derivative of the present invention is provided to be in contact with the cathode side of the light emitting layer 213. Therefore, in FIG. 3, the exciton blocking layer 220b is a kind of electron transporting layer.

By the structure of FIG. 2 or 3, an exciton generated in the light emitting layer 213 can be efficiently kept in the light emitting layer 213, whereby light emitting efficiency is enhanced. In addition, since the oxadiazole derivative of the present invention is a bipolar substance, as shown in FIGS. 2 and 3, the layer on either the anode side or the cathode side of the light emitting layer can be used as the exciton blocking layer. Accordingly, although not shown in FIGS. 2 and 3, the exciton blocking layers containing the oxadiazole derivative of the present invention can also be provided on both sides of the light emitting layer 213.

Here, the light emitting layer 213 can employ various structures. For example, the light emitting layer 213 may be formed using a host material and a guest material. As a specific example of the host material, 4,4'-di(9-carbazolyl)biphenyl (abbreviation: CBP), 2-tert-butyl-9,10-di(2-naphthyl)anthracene (abbreviation: t-BuDNA), 9-[4-(9-carbazolyl)phenyl]-10-phenylanthracene (abbreviation: CzPA), or the like can be used in addition to NPB, DFLDPBi, $ALq_3$, BAlq, and the like. Further, as a specific example of the guest material, 9-(4-{N-[4-(carbazol-9-yl)phenyl]-N-phenylamino}phenyl)-10-phenylanthracene (abbreviation: YGAPA) or the like can be used in addition to the phosphorescent compound and the fluorescent compound described in Embodiment Mode 2.

Note that the first electrode 201 may have the same structure as that of the first electrode 101 described in Embodiment Mode 2. In addition, the second electrode 202 may have the same structure as that of the second electrode 102 described in Embodiment Mode 2.

Further, in Embodiment Mode 3, as shown in FIGS. 2 and 3, a hole injecting layer 211, a hole transporting layer 212, an electron transporting layer 214, and an electron injecting layer 215 are provided. As for structures of these layers, the structure of each layer described in Embodiment Mode 2 may be employed. Note that these layers are not always necessary and may be appropriately provided depending on the property of the element.

(Embodiment Mode 4)

Figure 4A:
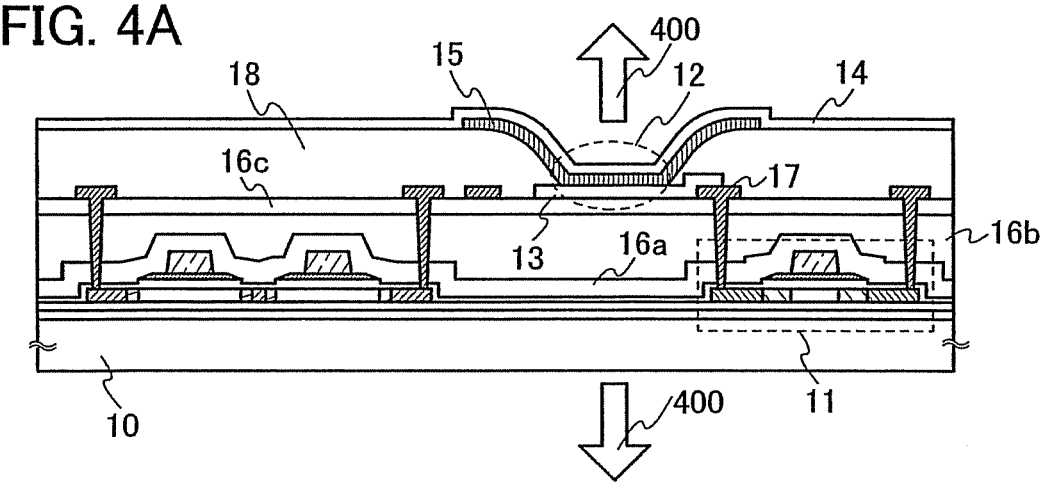
FIGS. 4A to 4C are views each explaining a light emitting device using a light emitting element of the present invention.
Figure 4B:
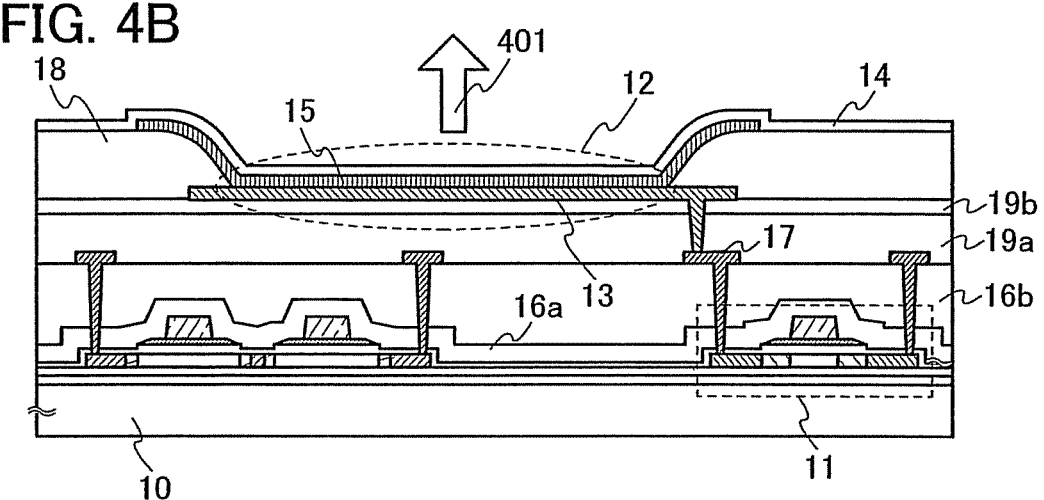
Figure 4C:
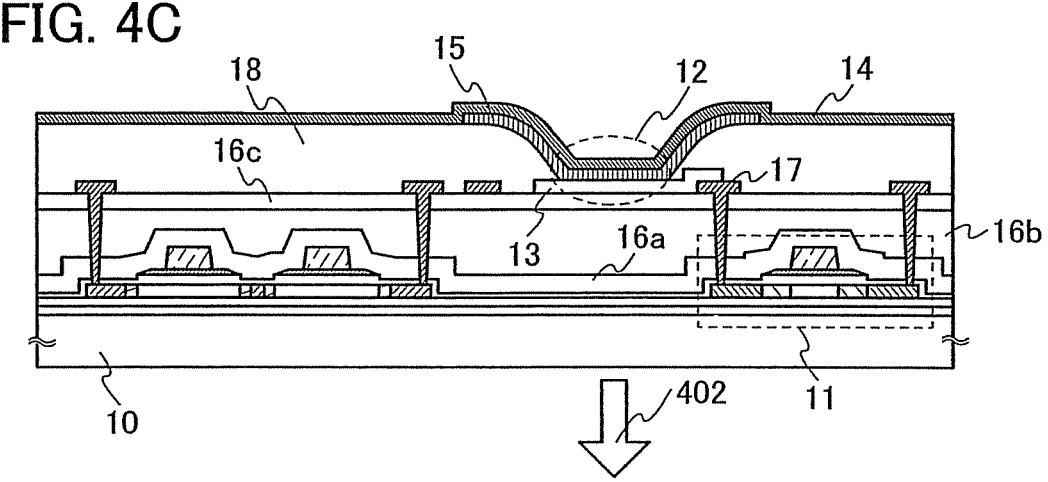

Embodiment Mode 4 will explain a mode of a light emitting device including a light emitting element of the present invention with reference to FIGS. 4A to 4C. FIGS. 4A to 4C are cross-sectional views of the light emitting devices.

In FIGS. 4A to 4C, a portion surrounded by a dotted line in a rectangular shape is a transistor 11 which is provided to drive a light emitting element 12 of the present invention. The light emitting element 12 of the present invention, in which a layer 15 including a light emitting layer is provided between a first electrode 13 and a second electrode 14, contains the oxadiazole derivative of the present invention. Specifically, the light emitting element 12 has the structure as shown in Embodiment Mode 2 or 3. A drain region of the transistor 11 is electrically connected to the first electrode 13 by a wiring 17 going through a first interlayer insulating film 16 (16a, 16b, and 16c). The light emitting element 12 is separated from other adjacently-provided light emitting elements by a partition layer 18. The light emitting device having such a structure is provided over a substrate 10 in Embodiment Mode 4.

Note that the transistors 11 shown in FIGS. 4A to 4C are each a top gate type in which a gate electrode is provided opposite to a substrate, with a semiconductor layer in the center. However, the structure of the transistor 11 is not particularly limited, and for example, a bottom gate type may be used. In the case of a bottom gate type, the transistor 11 may have a structure in which a protective film is formed over the semiconductor layer which forms a channel (a channel protective type) or a structure in which part of the semiconductor layer which forms a channel is concave (a channel etched type).

Alternatively, the semiconductor layer included in the transistor 11 may be either crystalline or amorphous. Further, it may be semi-amorphous or the like.

Note that characteristics of the semi-amorphous semiconductor are as follows. It has an intermediate structure between an amorphous structure and a crystalline structure (including a single crystal and a polycrystal) and a third state which is stable in terms of free energy, and it includes a crystalline region having short-range order and lattice distortion. At least part of a region in the film contains a crystal grain having a diameter of 0.5 to 20 nm. A Raman spectrum derived from an L-O phonon is shifted to a lower wavenumber side than 520 $cm^{-1}$. The diffraction peaks of (III) and (220) to be caused by a Si crystal lattice are observed in X-ray diffraction. At least hydrogen or halogen of 1 atomic % is contained to terminate a dangling bond. The semi-amorphous semiconductor is also referred to as a so-called microcrystalline semiconductor and is formed by performing glow discharge decomposition (plasma CVD) to gas containing silicide. $SiH_4$ is given as the gas containing silicide. In addition, $Si_2H_6$, $SiH_2Cl_2$, $SiHCl_3$, $SiCl_4$, $SiF_4$, or the like can also be used as the gas containing silicide. The gas containing silicide may be diluted with $H_2$, or $H_2$ and one or more rare gas elements of He, Ar, Kr, and Ne. A dilution ratio thereof may range from 2 to 1000 times; pressure, approximately 0.1 to 133 Pa; and a power supply frequency, 1 to 120 MHz, preferably, 13 to 60 MHz. A substrate heating temperature may be less than or equal to 300° C., preferably, 100 to 250° C. The concentration of an atmospheric constituent impurity such as oxygen, nitrogen, or carbon, as an impurity element in the film, is preferably less than or equal to $1\times10^{20}$ atoms/$cm^3$; particularly, the concentration of oxygen is less than or equal to $5\times10^{19}$ atoms/$cm^3$, preferably less than or equal to $1\times10^{19}$ atoms/$cm^3$. Note that mobility of a TFT (thin film transistor) using the semi-amorphous semiconductor is approximately 1 to 10 $cm^2$/Vsec.

As a specific example of the crystalline semiconductor layer, a layer formed of single-crystal or polycrystalline silicon, silicon germanium, or the like can be given. It may be formed by laser crystallization or may be formed by crystallization through a solid phase growth method using, for example, nickel or the like.

When the semiconductor layer is formed using an amorphous substance, for example, amorphous silicon, a light emitting device preferably has a circuit in which the transistor 11 and all other transistors (transistors included in a circuit for driving a light emitting element) are all n-channel transistors. Other than that, the light emitting device may have a circuit including either n-channel transistors or p-channel transistors, or the light emitting device may have a circuit including both types of transistors.

Further, the first interlayer insulating film 16 (16a to 16c) may be a multilayer as shown in FIGS. 4A, 4C, or a single layer. Note that the first interlayer insulating film 16a is formed using an inorganic material such as silicon oxide or silicon nitride; and the first interlayer insulating film 16b is formed using a self-planarizing substance such as acrylic, siloxane (an organic group in which a skeleton structure is formed of a bond of silicon (Si) and oxygen (O) and at least hydrogen is contained as a substituent), or silicon oxide which can be formed by coating. In addition, the first interlayer insulating film 16c is formed using a silicon nitride film containing argon (Ar). Note that the substance forming each layer is not particularly limited, and a substance other than the foregoing substances may also be used. Alternatively, a layer formed using a substance other than the foregoing substances may be further combined. As described above, the first interlayer insulating film 16 (16a to 16c) may be formed using either an inorganic film or an organic film, or both of them.

The partition layer 18 preferably has a shape in which, in the edge, a curvature radius changes continuously. In addition, the partition layer 18 is formed using acrylic, siloxane, resist, silicon oxide, or the like. Note that the partition layer 18 may be formed using either an inorganic film or an organic film, or both of them.

In FIGS. 4A and 4C, only the first interlayer insulating film 16 (16a to 16c) is provided between the transistor 11 and the light emitting element 12. However, as shown in FIG. 4B, a second interlayer insulating film 19 (19a and 19b) may also be provided in addition to the first interlayer insulating film 16 (16a and 16b). In the light emitting device shown in FIG. 4B, the first electrode 13 goes through the second interlayer insulating film 19 and connects to the wiring 17.

The second interlayer insulating film 19 may be a multilayer, like the first interlayer insulating film 16, or a single layer. The second interlayer insulating film 19a is formed using a self-planarizing substance such as acrylic, siloxane (an organic group in which a skeleton structure is formed of a bond of silicon (Si) and oxygen (O) and at least hydrogen is contained as a substituent), or silicon oxide which can be formed by coating. Further, the second interlayer insulating film 19b is formed using a silicon nitride film containing argon (Ar). Note that a substance forming each layer is not particularly limited, and a substance other than the foregoing substances can also be used. Alternatively, a layer formed using a substance other than the foregoing substances may be further combined. As described above, the second interlayer insulating film 19 may be formed using either an inorganic film or an organic film, or both of them.

When both the first electrode 13 and the second electrode 14 are formed using a light transmitting substance in the light emitting element 12, light emissions 400 can be extracted through both the first electrode 13 and the second electrode 14 as indicated by the outlined arrows in FIG. 4A. When only the second electrode 14 is formed using a light-transmitting substance, light emission 401 can be extracted only through the second electrode 14 as indicated by the outlined arrow in FIG. 4B. In this case, it is preferable to form the first electrode 13 using a highly reflective material or provide a film formed using a highly reflective material (reflective film) below the first electrode 13. Further, when only the first electrode 13 is formed using a light-transmitting substance, light emission 402 can be extracted only through the first electrode 13 as indicated by the outlined arrow in FIG. 4C. In this case, it is preferable to form the second electrode 14 using a highly reflective material or provide a reflective film above the second electrode 14.

In the light emitting element 12, the layer 15 may be stacked so as to operate the light emitting element 12 when voltage is applied so that potential of the second electrode 14 becomes higher than that of the first electrode 13, or the layer 15 may be stacked so as to operate the light emitting element 12 when voltage is applied so that potential of the second electrode 14 becomes lower than that of the first electrode 13. In the former case, the transistor 11 is an n-channel transistor, and in the latter case, the transistor 11 is a p-channel transistor.

As described above, Embodiment Mode 4 describes the active type light emitting device which controls driving of the light emitting element by the transistor. In addition, a passive type light emitting device, which drives a light emitting element without particularly providing an element for driving such as a transistor, may also be employed.

In the light emitting device shown in Embodiment Mode 4, the light emitting element of the present invention is used; therefore, light emitting efficiency is high and driving voltage is low. Therefore, there is a feature that power consumption is low.

(Embodiment Mode 5)

A light emitting device using the light emitting element of the present invention can display a favorable image. Therefore, electronic devices that are capable of providing an excellent image can be obtained by applying the light emitting device of the present invention to a display portion of the electronic devices. In addition, the light emitting device including the light emitting element of the present invention can be driven with low power consumption because it has high light emitting efficiency and low driving voltage. Therefore, electronic devices with low power consumption can be obtained by applying the light emitting device of the present invention to the display portion of the electronic devices, and for example, a telephone set that has long battery standing time, and the like can be obtained. The following will show examples of the electronic devices provided with the light emitting device to which the light emitting element of the present invention is applied.

Figure 5A:
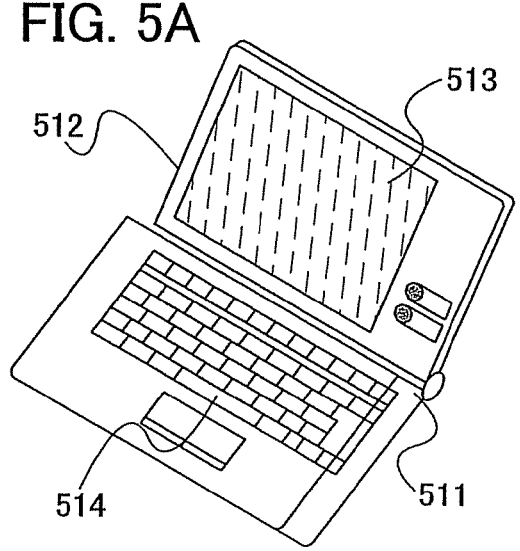
FIGS. 5A to 5C are views each explaining an electronic device using a light emitting device of the present invention.

FIG. 5A is a computer manufactured by employing the present invention, which includes a main body 511, a frame body 512, a display portion 513, a keyboard 514, and the like. The computer can be completed by incorporating the light emitting device including the light emitting element of the present invention thereinto as a display portion.

Figure 5B:
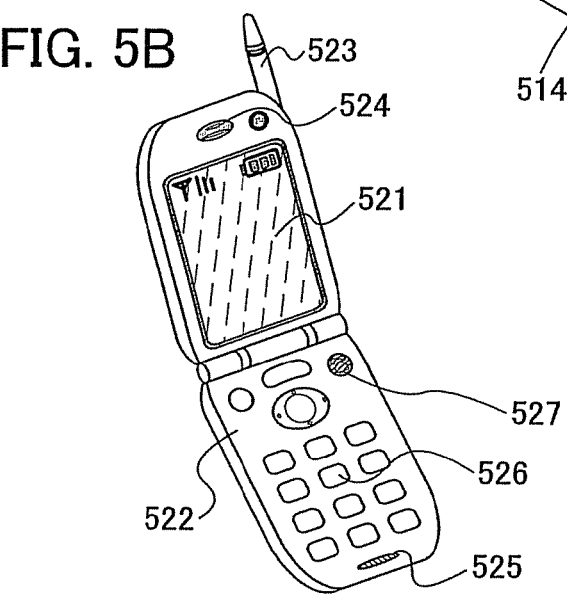

FIG. 5B is a telephone set manufactured by employing the present invention, in which a main body 522 includes a display portion 521, an audio output portion 524, an audio input portion 525, operation switches 526 and 527, an antenna 523, and the like. The telephone set can be completed by incorporating the light emitting device including the light emitting element of the present invention thereinto as a display portion.

Figure 5C:
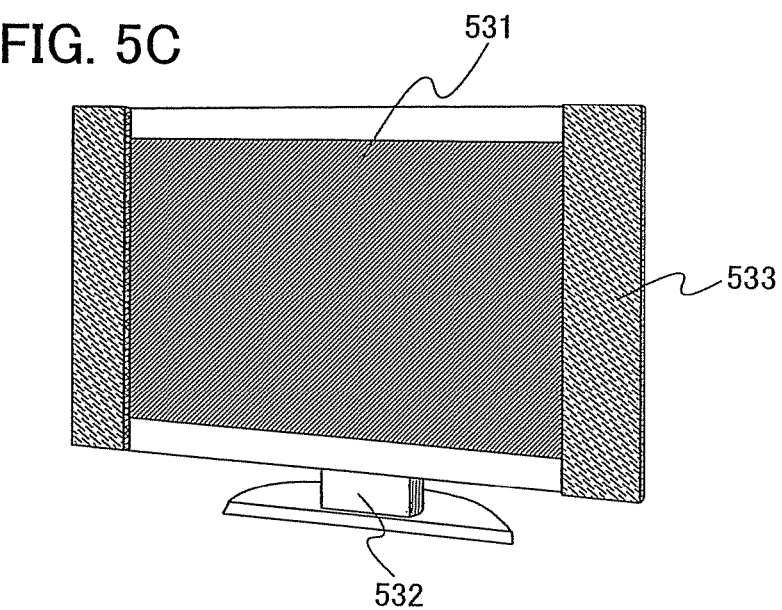

FIG. 5C is a television set manufactured by employing the present invention, which includes a display portion 531, a frame body 532, a speaker 533, and the like. The television set can be completed by incorporating the light emitting device including the light emitting element of the present invention thereinto as a display portion.

As described above, the light emitting device of the present invention is extremely suitable to be used as the display portion of various kinds of electronic devices.

Although the computer and the like are described in Embodiment Mode 5, the light emitting device including the light emitting element of the present invention may also be mounted on a navigation system, lighting equipment, or the like.

[Embodiment 1]

SYNTHESIS EXAMPLE 1

Synthesis Example 1 will specifically show a synthesis example of 2-(4-{N-[4-(carbazol-9-yl)phenyl]-N-phenylamino}phenyl)-5-phenyl-1,3,4-oxadiazole (abbreviation: YGAO11) that is the oxadiazole derivative of the present invention represented by the structural formula (1) of Embodiment Mode 1.

Step 1: Synthesis of 2-(4-bromophenyl)-5-phenyl-1,3,4-oxadiazole (abbreviation: O11Br)

In Step 1, O11Br was synthesized according to (i) to (iii) shown below.

(i) Synthesis of 4-bromobenzohydrazide

First, 3.0 g (13.9 mmol) of methyl-4-bromobenzoate was put in a 100-mL three-neck flask, 10 mL of ethanol was added therein, and the mixture was stirred. Thereafter, 4.0 mL of hydrazine monohydrate was added therein, and the mixture was heated and stirred at 78° C. for 5 hours. The obtained solid was washed with water and collected by suction filtration; thus, 2.0 g of a white solid of 4-bromobenzohydrazide that was an object was obtained (yield: 67%).

(ii) Synthesis of 1-benzoyl-2-(4-bromobenzoyl)hydrazine

Subsequently, 2.0 g (13.9 mmol) of the 4-bromobenzohydrazide obtained in (i) above was put in a 300-mL three-neck flask, 7 mL of N-methyl-2-pyrrolidone (abbreviation: NMP) was added therein, and the mixture was stirred. Thereafter, a mixture of 2.5 mL of N-methyl-2-pyrrolidone and 2.5 mL (21.5 mmol) of benzoyl chloride was dripped through a 50-mL dropping funnel, and the mixture was stirred at 80° C. for 3 hours. The obtained solid was washed with water and a sodium carbonate aqueous solution in this order and collected by suction filtration. Then, the solid was recrystallized with acetone; thus, 3.6 g of a white solid of 1-benzoyl-2-(4-bromobenzoyl)hydrazine that was an object was obtained (yield: 80%).

(iii) Synthesis of O11Br

Further, 15 g (47 mmol) of the 1-benzoyl-2-(4-bromobenzoyl)hydrazine obtained by the method shown in (ii) above was put in a 200-mL three-neck flask, 100 mL of phosphoryl chloride was added therein, and the mixture was heated and stirred at 100° C. for 5 hours. After the reaction, the solid obtained by completely distilling off phosphoryl chloride was washed with water and a sodium carbonate aqueous solution in this order and collected by suction filtration. Then, the solid was recrystallized with methanol; thus, 13 g of a white solid of O11Br that was an object of Step 1 was obtained (yield: 89%). A synthesis scheme of Step 1 described above is shown in the following scheme (a-1).

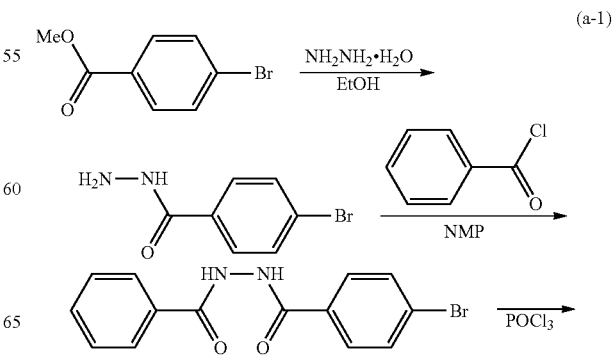

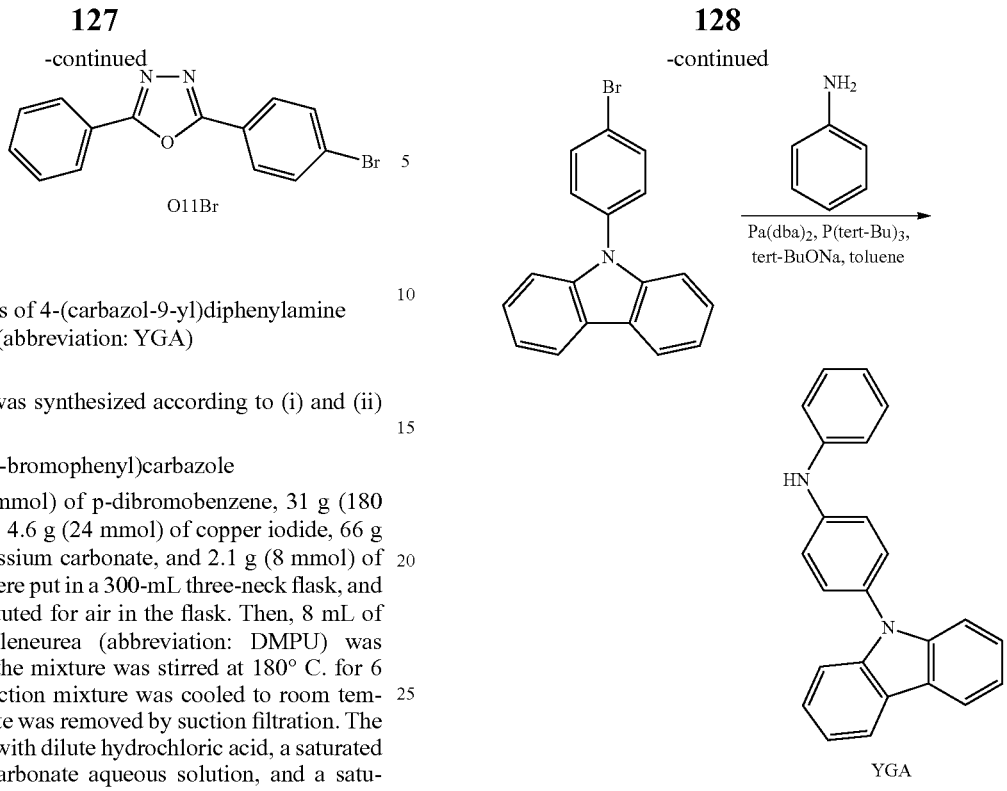

O11Br

Step 2: Synthesis of 4-(carbazol-9-yl)diphenylamine (abbreviation: YGA)

In Step 2, YGA was synthesized according to (i) and (ii) shown below.

(i) Synthesis of 9-(4-bromophenyl)carbazole

First, 56 g (240 mmol) of p-dibromobenzene, 31 g (180 mmol) of carbazole, 4.6 g (24 mmol) of copper iodide, 66 g (480 mmol) of potassium carbonate, and 2.1 g (8 mmol) of 18-crown-6-ether were put in a 300-mL three-neck flask, and nitrogen was substituted for air in the flask. Then, 8 mL of N,N'-dimethylpropyleneurea (abbreviation: DMPU) was added therein, and the mixture was stirred at 180° C. for 6 hours. After the reaction mixture was cooled to room temperature, a precipitate was removed by suction filtration. The filtrate was washed with dilute hydrochloric acid, a saturated sodium hydrogen-carbonate aqueous solution, and a saturated saline solution in this order and dried with magnesium sulfate. After being dried, the solution was filtered naturally and concentrated, and an obtained oily substance was purified by silica gel column chromatography (hexane:ethyl acetate=9:1) and recrystallized with chloroform and hexane; thus, 21 g of a light brown plate-shaped crystal of 9-(4-bromophenyl)carbazole that was an object was obtained (yield: 35%).

(ii) Synthesis of YGA

Subsequently, 5.4 g (17 mmol) of the 9-(4-bromophenyl) carbazole that was obtained in (i) above, 1.8 mL (20 mmol) of aniline, 0.1 g (0.2 mmol) of bis(dibenzylideneacetone)palladium(0), and 3.9 g (40 mmol) of sodium-tert-butoxide were put in a 200-mL three-neck flask, and nitrogen was substituted for air in the flask. Then, 0.1 mL of a 10% hexane solution of tri(tert-butyl)phosphine and 50 mL of toluene were added therein, and the mixture was stirred at 80° C. for 6 hours. After the reaction mixture was filtered through Florisil, Celite, and alumina, the filtrate was washed with water and a saturated saline solution and dried with magnesium sulfate. After being dried, the solution was filtered naturally and concentrated, and an obtained oily substance was purified by silica gel column chromatography (hexane:ethyl acetate=9:1); thus, 4.1 g of YGA that was an object of Step 2 was obtained (yield: 73%). The synthesis scheme of Step 2 as described above is shown in the following scheme (b-1).

(b-1)

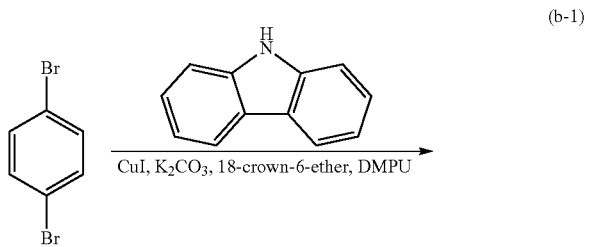

Step 3: Synthesis of 2-(4-{N-[4-(carbazol-9-yl)phenyl]-N-phenylamino}phenyl)-5-phenyl-1,3,4-oxadiazole (abbreviation: YGAO11)

3.0 g (10.0 mmol) of O11Br obtained in Step 1, 3.4 g (10.0 mmol) of YGA obtained in Step 2, and 1.9 g (19.9 mmol) of sodium-tert-butoxide were put in a 100-mL three-neck flask, and nitrogen was substituted for air in the flask. Then, 45 mL of toluene, 0.3 mL of a 10% hexane solution of tri(tert-butyl) phosphine, 0.3 g (0.6 mmol) of bis(dibenzylideneacetone) palladium(0) were added therein, and the mixture was heated and stirred for at 120° C. 5 hours. After the reaction, the mixture was filtered through Celite, and the filtrate was washed with water and dried with magnesium sulfate. After being dried, the solution was filtrated, and the filtrate was concentrated. An obtained solid was dissolved in toluene and purified by silica gel column chromatography. Purification by column chromatography was performed by using toluene as a developing solvent and then using a mixed solvent of toluene: ethyl acetate=1:1 as a developing solvent. The purified solid was recrystallized with chloroform and hexane; thus, 4.7 g of a light yellow solid YGAO11 that was an object of Synthesis Example 1 was obtained (yield: 85%). The synthesis scheme of Step 3 as described above is shown in the following scheme (c-1).

(c-1)

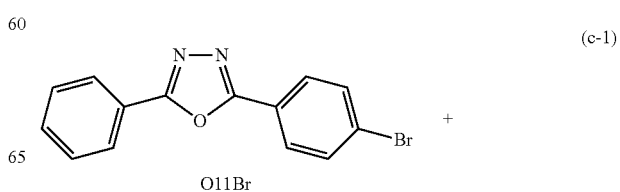

O11Br

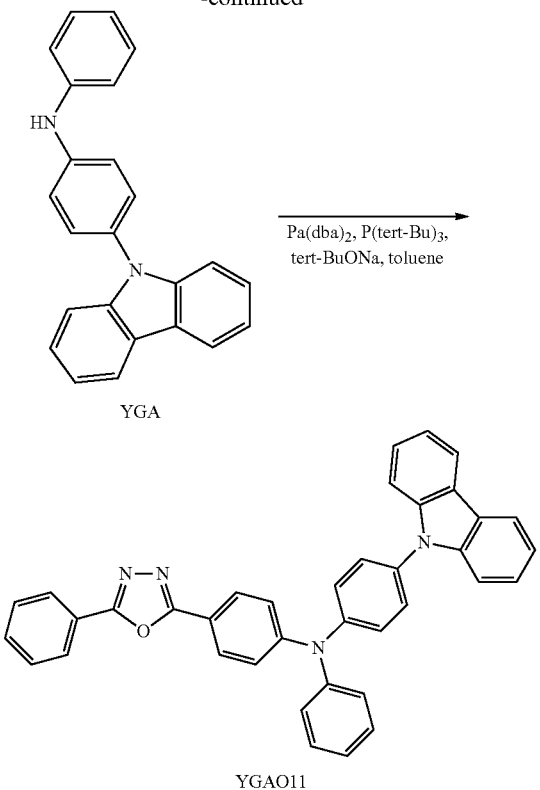

YGA

YGAO11

Figure 6A:
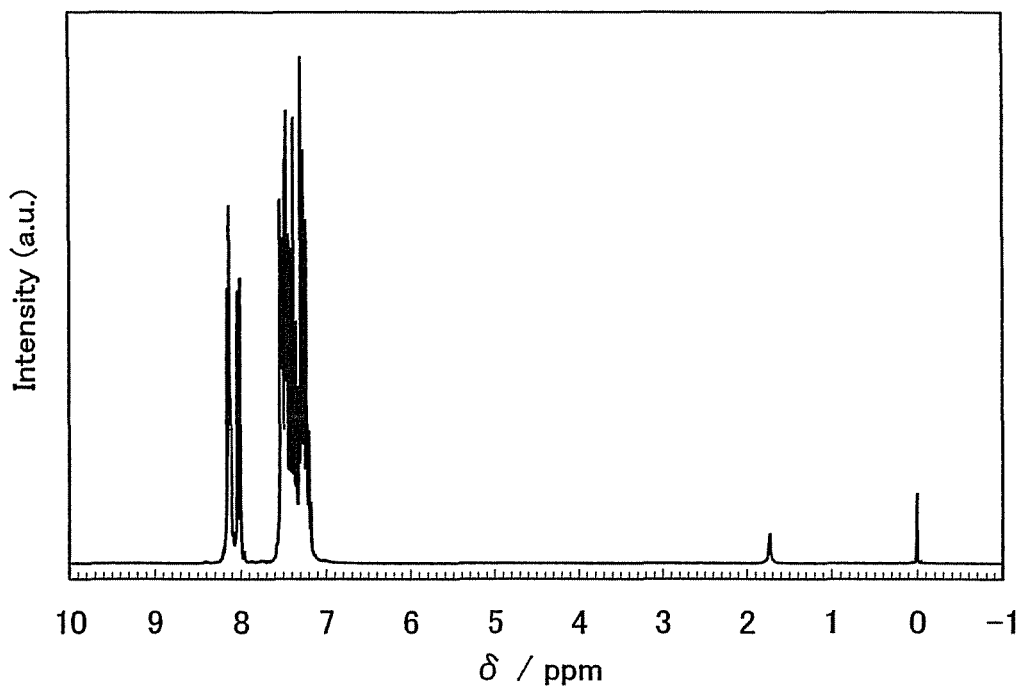
FIGS. 6A and 6B are diagrams each showing an $^1$H-NMR chart of an oxadiazole derivative YGAO11 of the present invention.
Figure 6B:
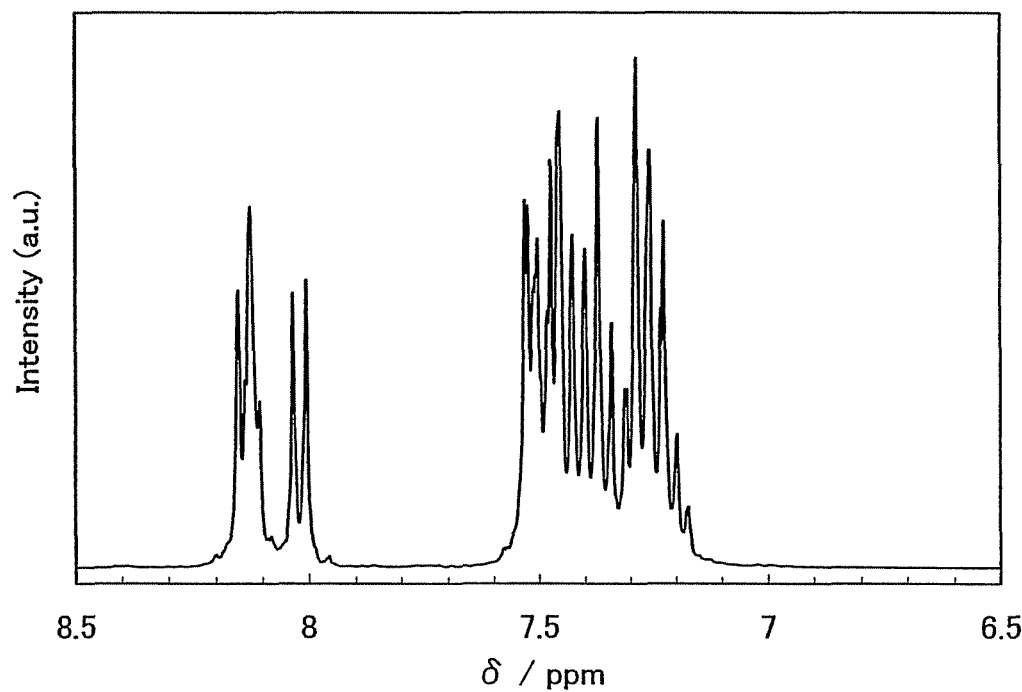

The following shows a result of analyzing YGAO11 that was obtained by nuclear magnetic resonance spectroscopy ($^1$H-NMR). FIG. 6A shows an $^1$H-NMR chart and FIG. 6B shows an enlarged chart thereof. Accordingly, it was found that the oxadiazole derivative YGAO11 of the present invention represented by the structural formula (I) was obtained in Synthesis Example 1.

$^1$H-NMR (CDCl$_3$, 300 MHz,): δ=7.14-7.53 (m, 19H), δ=8.03 (d, J=8.7, 2H), δ=8.11-8.15 (m, 4H)

In addition, sublimation purification of the obtained YGAO11 was performed by a train sublimation method. Under a reduced pressure of 7 Pa, sublimation purification was performed at 265° C. for 12 hours, setting the flow rate of argon to be 3 mL/min. When sublimation purification was performed on 4.5 g of YGAO11, the yield was 3.4 g and 76%.

Figure 7A:
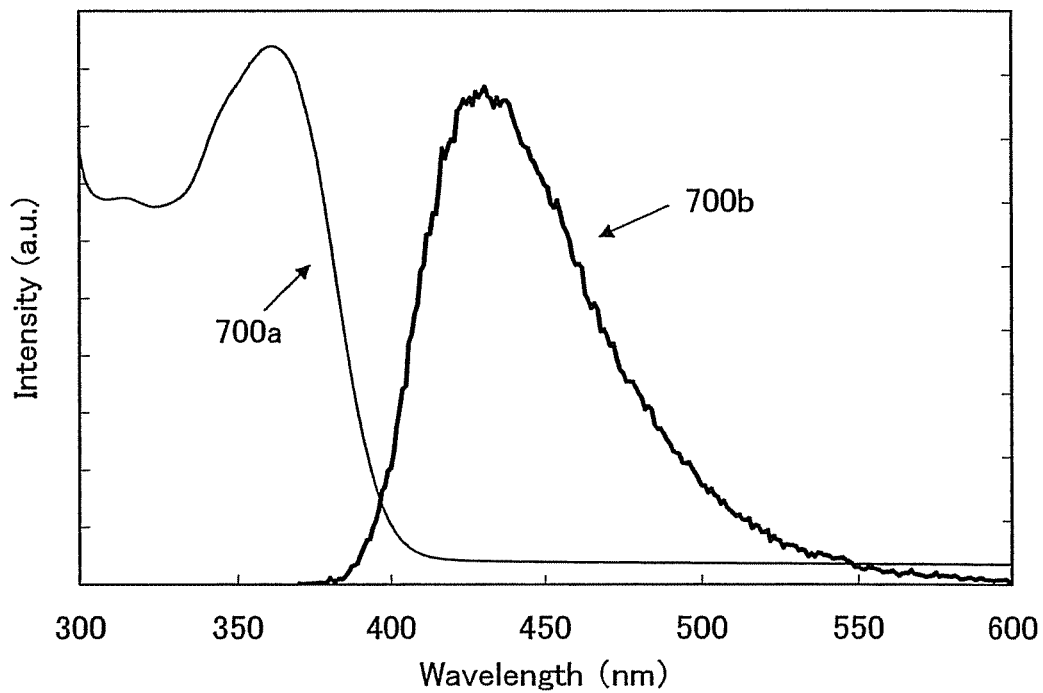
FIGS. 7A and 7B are diagrams each showing an ultraviolet/visible absorption spectrum and an emission spectrum of an oxadiazole derivative YGAO11 of the present invention.
Figure 7B:
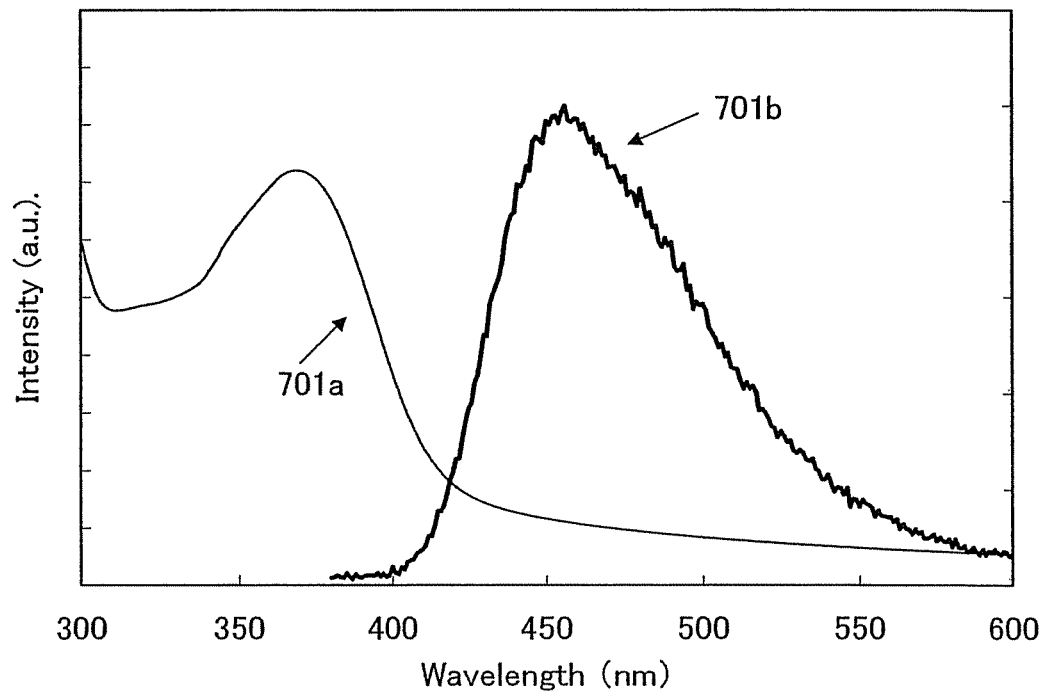

Next, the absorption spectrum and the emission spectrum of YGAO11 were measured. The absorption spectrum was measured using an ultraviolet-visible spectrophotometer (V-550, by JASCO Corporation) and the emission spectrum was measured using a spectrofluorometer (FS920, by Hamamatsu Photonics K.K.). The measurement was performed at room temperature for a toluene solution and a deposited film. FIG. 7A shows the measurement result for the toluene solution and FIG. 7B shows the measurement result for the deposited film. The horizontal axis indicates the wavelength and the vertical axis indicates the intensity of the absorption and light emission.

As shown in FIG. 7A, the oxadiazole derivative YGAO11 of the present invention has an absorption peak at 362 nm with the toluene solution. A reference numeral 700*a* is an absorption spectrum. In addition, the emission spectrum 700*b* has a peak at 431 nm. Note that the emission spectrum was measured through excitation of YGAO11 at a wavelength of 362 nm.

In addition, as shown in FIG. 7B, the deposited film of the oxadiazole derivative YGAO11 of the present invention has an absorption peak at 369 nm. A reference numeral 701*a* is an absorption spectrum. In addition, the emission spectrum 701*b* has a peak at 456 nm. Note that the emission spectrum was measured through excitation of YGAO11 at a wavelength of 369 nm.

Data on the absorption spectrum in FIG. 7B was used to obtain the absorption edge by a Tauc plot. Further, the energy of the absorption edge was used as an energy gap to find that an energy gap of YGAO11 was 3.06 eV. Accordingly, it was found that the oxadiazole derivative YGAO11 of the present invention has high excitation energy.

In addition, when the ionizing potential of YGAO11 in a thin film state was measured with a photoelectron spectrometer (AC-2, by RIKEN KEIKI CO., LTD.) in the air, the ionizing potential was 5.49 eV. As a result, it was found that the HOMO level was −5.49 eV. Further, when the LUMO level was calculated from the value of the energy gap and the HOMO level obtained as described above, the LUMO level was −2.43 eV.

Further, the optimal molecular structure of YGAO11 in the ground state was calculated using the B3LYP/6-311 (d, p) of the density functional theory (DFT). The accuracy of calculation of the DFT is higher than that of a Hartree-Fock (HF) method which does not consider electron correlation. In addition, calculation costs for the DFT are lower than that of a method of perturbation (MP) which has the same level of accuracy of calculation as that of the DFT. Therefore, the DFT was employed for this calculation. The calculation was performed using a high performance computer (HPC) (Altix3700 DX, by SGI Japan, Ltd.). When singlet excitation energy (energy gap) of YGAO11 was calculated using the B3LYP/6-311 (d, p) of a time-dependent density functional theory (TDDFT) in the molecular structure optimized by the DFT, the singlet excitation energy was 3.18 eV. In addition, when triplet excitation energy of YGAO11 was calculated, it was 2.53 eV. According to the above results, it is understood that the oxadiazole derivative of the present invention is a substance having high excitation energy, in particular, a substance having high triplet excitation energy.

Further, the glass transition point was measured with a differential scanning calorimeter (Pyris 1 DSC, by Perki-nElmer Inc.). After a sample was heated to 330° C. at 40° C./min, it was cooled to room temperature at 40° C./min. After that, the temperature was raised to 330° C. at 10° C./min, the sample was cooled to room temperature at 40° C./min, and the glass transition point was measured. As a result, it was found that the glass transition point (Tg) of YGAO11 was 99° C.

Subsequently, an oxidation property and a reduction property of YGAO11 were examined by cyclic voltammetry (CV). An electrochemical analyzer (ALS model 600A, by BAS Inc.) was used as a measuring device. The solution for the CV measurement was prepared by using dehydrated dimethylformamide (DMF) as a solvent, dissolving a supporting electrolyte of tetra-n-butylammonium perchlorate (n-Bu$_4$NClO$_4$) to a concentration of 100 mM, and dissolving YGAO11, the object of measurement, to a concentration of 1 mM. A platinum electrode (PTE platinum electrode, by BAS Inc.) was used as a working electrode, another platinum electrode (Pt counter electrode (5 cm) for VC-3, by BAS Inc.) was used as an auxiliary electrode, and an Ag/Ag$^+$ electrode (RE5 non-aqueous solvent reference electrode, by BAS Inc.) was used as a reference electrode.

The oxidation property was measured by first scanning potential of the working electrode with respect to the reference electrode from −0.11 to 0.90 V and then continuously scanning the potential from 0.90 to −0.11 V. In addition, the reduction property was measured by first scanning potential of the working electrode with respect to the reference electrode from −0.07 to −2.60 V and then continuously scanning the potential from −2.60 to −0.07 V. The scanning speed of the CV measurement was set to be 0.1 V/s.

Figure 8A:
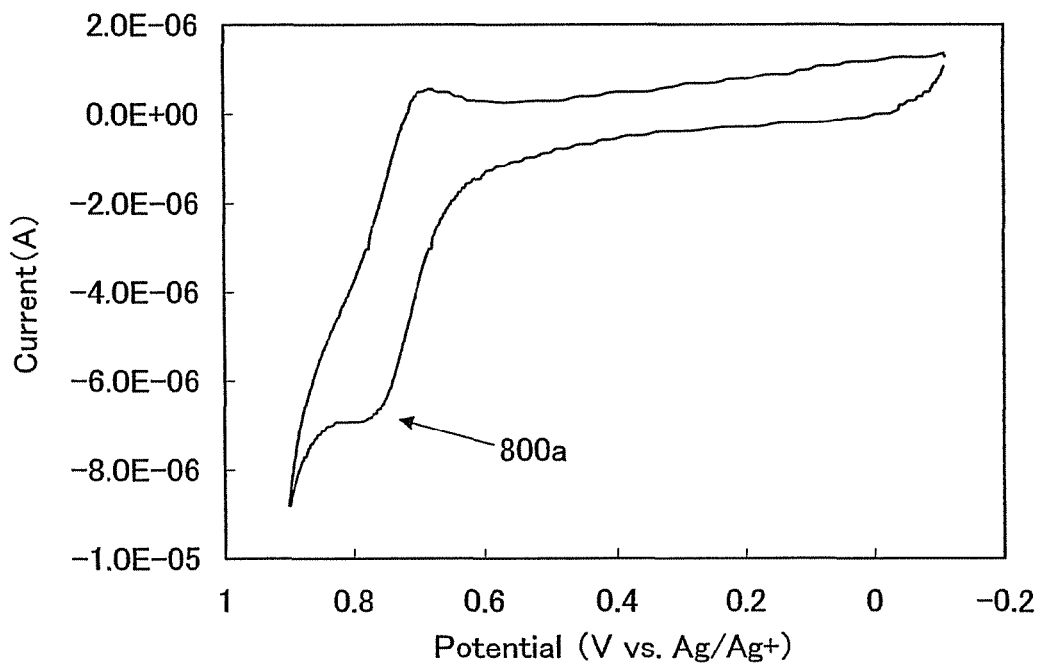
FIGS. 8A and 8B are diagrams each showing a CV curve of an oxadiazole derivative YGAO11 of the present invention.
Figure 8B:
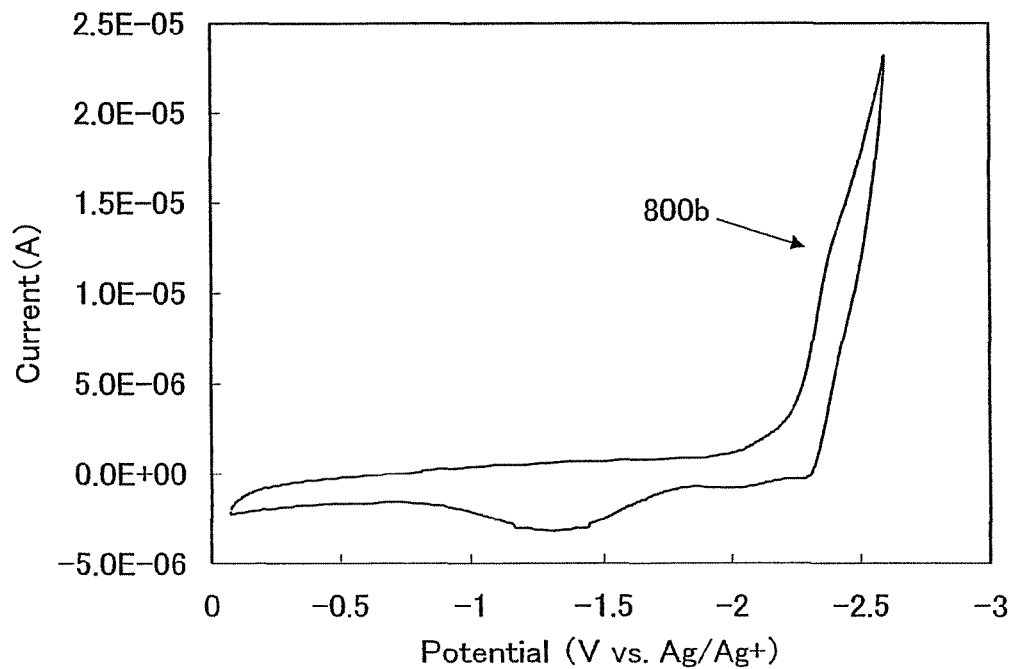

FIG. 8A shows a CV curve for the oxidation property of YGAO11, and FIG. 8B shows a CV curve for the reduction property. In FIGS. 8A and 8B, the horizontal axis indicates the potential of the working electrode with respect to the reference electrode, and the vertical axis indicates a value of current which flows between the working electrode and the auxiliary electrode. As shown in FIGS. 8A and 8B, both the oxidation peak 800a and the reduction peak 800b of YGAO11 were clearly observed. Specifically, a current which shows oxidation was observed in the vicinity of 0.87 V (vs. Ag/Ag$^+$ electrode), and a current which shows reduction was observed in the vicinity of −2.40 V (vs. Ag/Ag$^+$ electrode). Accordingly, it was found that YGAO11 is a substance which can easily receive both a hole and an electron.

SYNTHESIS EXAMPLE 2

Synthesis Example 2 will specifically show a synthesis example of 2-phenyl-5-{(4-[N-phenyl-N-(9-phenylcarbazol-3-yl)amino]phenyl-1,3,4-oxadiazole (abbreviation: PCAO11) that is the oxadiazole derivative of the present invention represented by the structural formula (51) of Embodiment Mode 1.

Step 1: Synthesis of 2-(4-bromophenyl)-5-phenyl-1,3,4-oxadiazole (abbreviation: O11Br)

This synthesis is described in Step 1 of Synthesis Example 1 and will thus be omitted here.

Step 2: Synthesis of N-phenyl-(9-phenylcarbazol-3-yl)amine (abbreviation: PCA

In Step 2, PCA was synthesized according to (i) and (ii) shown below.
(i) Synthesis of 3-bromo-9-phenylcarbazole First, 24.3 g (100 mmol) of N-phenylcarbazole was dissolved in 600 mL of glacial acetic acid, 17.8 g (100 mmol) of N-bromosuccinimide was slowly added therein, and the mixture was stirred at room temperature for 18 hours. This reaction solution was dripped to 1 L of ice water while being stirred, and a white solid which was precipitated was washed with water three times. The obtained solid was dissolved in 150 mL of diethyl ether and washed with a saturated sodium hydrogen-carbonate aqueous solution and water. After being washed, an organic layer was dried with magnesium sulfate. After filtration, the filtrate was concentrated. Thereafter, approximately 50 mL of methanol was added to an obtained solid, and the solid was irradiated with ultrasonic waves to be uniformly dissolved. This solution was left at rest, and a white precipitate was obtained. This precipitate was collected by filtration and dried; thus, 28.4 g of a white powder of 3-bromo-9-phenylcarbazole that was an object was obtained (yield: 88%).
(ii) Synthesis of PCA Subsequently, under nitrogen, 110 mL of dehydrated xylene and 7.0 g (75 mmol) of aniline were added to a mixture of 19 g (60 mmol) of the 3-bromo-9-phenylcarbazole obtained in (i) above, 340 mg (0.6 mmol) of bis(dibenzylideneacetone)palladium(0), 1.6 g (3.0 mmol) of 1,1-bis(diphenylphosphino)ferrocene (DPPF), and 13 g (180 mmol) of sodium-tert-butoxide. This mixture was heated and stirred in a nitrogen atmosphere at 90° C. for 7.5 hours. After the reaction was terminated, approximately 500 mL of toluene, which was heated to 50° C., was added to an obtained suspension, and this suspension was filtered through Florisil, alumina, and Celite. The thus obtained filtrate was concentrated, and hexane and ethyl acetate were added to a solid which was precipitated, and irradiation with ultrasonic waves was performed. The thus obtained suspension was filtered, and the residue was dried; thus, 15 g of a cream-colored powder of PCA that was an object of Step 2 was obtained (yield: 75%). The synthesis scheme of Step 2 as described above is shown in the following scheme (b-2).

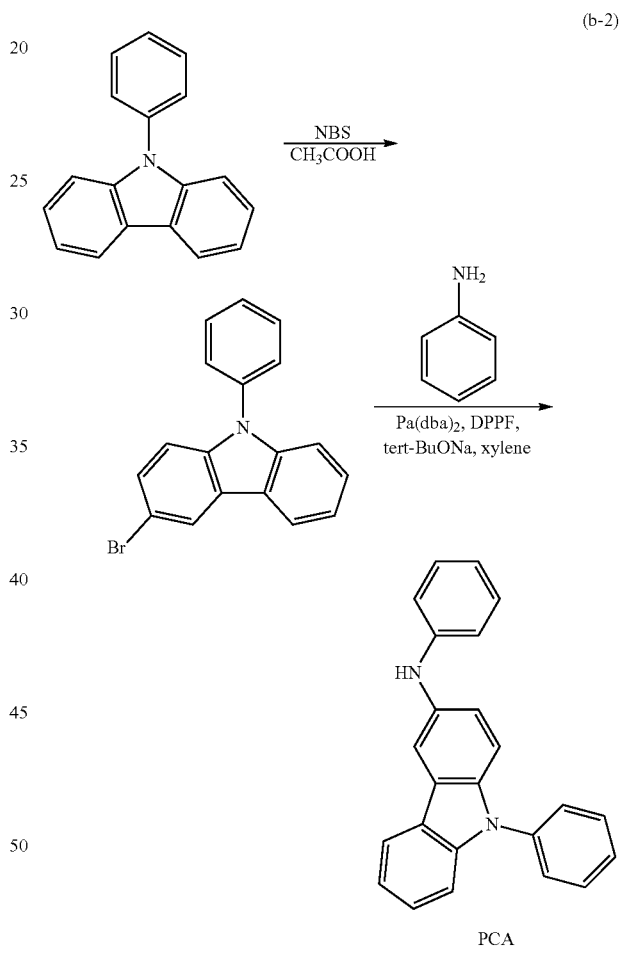

Step 3: Synthesis of 2-phenyl-5-{4-[N-phenyl-N-(9-phenylcarbazol-3-yl)amino]phenyl}-1,3,4-oxadiazole (abbreviation: PCAO11)

First, 1.0 g (3.3 mmol) of O11Br obtained in Step 1, 1.1 g (3.3 mmol) of PCA obtained in Step 2, and 0.6 g (6.7 mmol) of sodium-tert-butoxide were put in a 100-mL three-neck flask, and nitrogen was substituted for air in the flask. Then, 15 mL of toluene and 0.1 mL of a 10% hexane solution of tri-tert-butylphosphine were added therein, and nitrogen was further substituted for air in the flask. 0.1 g (0.2 mmol) of bis(dibenzylideneacetone)palladium(0) was added therein, and the mixture was stirred at 80° C. for 5 hours. After the reaction was terminated, an obtained solid was dissolved in chloroform and washed with water, and then filtered through Celite, and the filtrate was further washed with water. An obtained organic layer was dried with magnesium sulfate and filtered, and the filtrate was concentrated. An obtained solid was dissolved in toluene and purified by silica gel column chromatography. Purification by column chromatography was performed by using toluene as a developing solvent and then using a mixed solvent of toluene:ethyl acetate=1:1 as a developing solvent. The purified solid was recrystallized with chloroform and hexane; thus, 0.99 g of a yellow solid PCAO11 that was an object of Synthesis Example 2 was obtained (yield: 54%). The synthesis scheme of Step 3 as described above is shown in the following scheme (c-2).

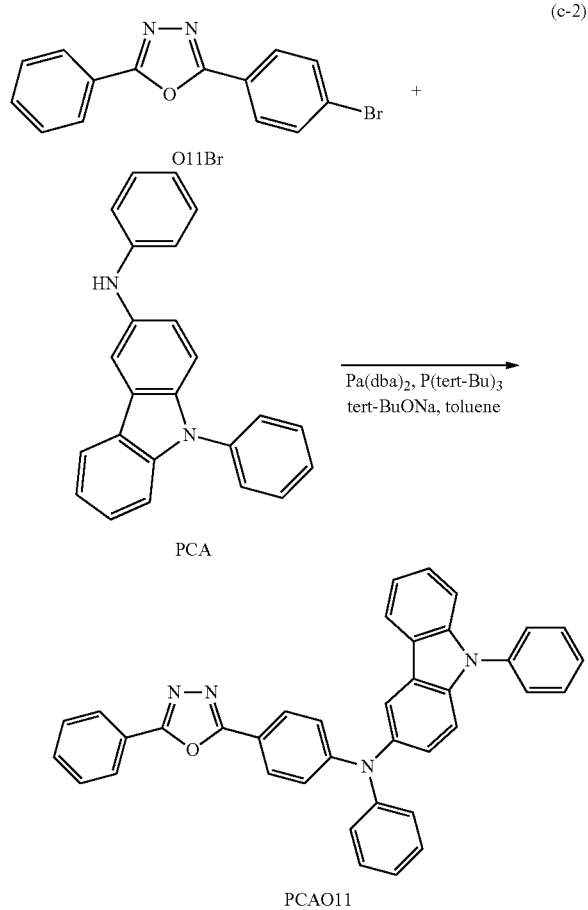

Figure 9A:
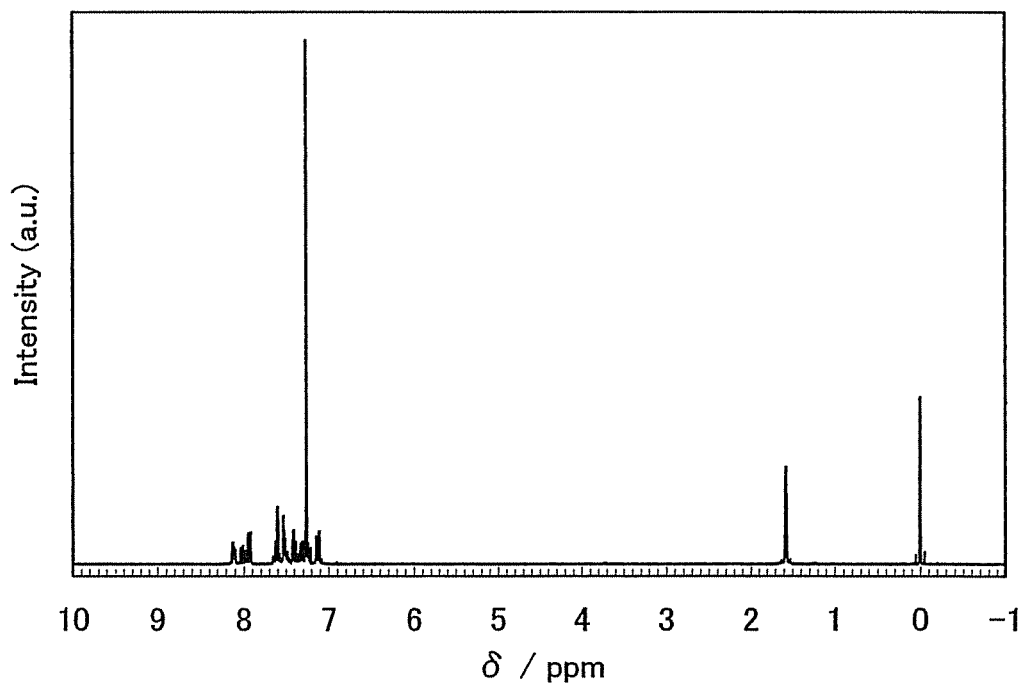
FIGS. 9A and 9B are diagrams each showing an $^1$H-NMR chart of an oxadiazole derivative PCAO11 of the present invention.
Figure 9B:
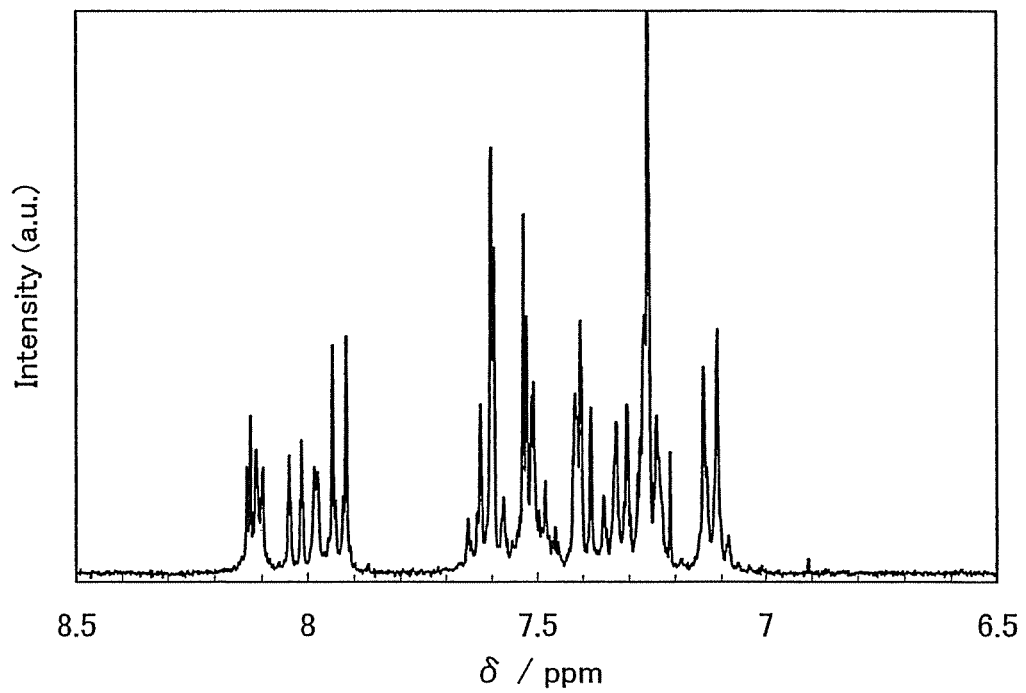

The following shows a result of analyzing PCAO11 that was obtained in Step 3 by nuclear magnetic resonance spectroscopy ($^1$H-NMR). FIG. 9A shows an $^1$H-NMR chart and FIG. 9B shows an enlarged chart thereof. Accordingly, it was found that the oxadiazole derivative PCAO11 of the present invention represented by the structural formula (51) was obtained in Synthesis Example 2.

$^1$H-NMR (CDCl$_3$, 300 MHz,): δ=7.11-7.65 (m, 20H), δ=7.93 (d, J=9.0, 2H), δ=8.03-7.98 (m, 2H), δ=8.12 (m, 2H)

In addition, sublimation purification of the obtained PCAO11 was performed by a train sublimation method. Under a reduced pressure of 7 Pa, sublimation purification was performed at 270° C. for 12 hours, setting the flow rate of argon to be 3 mL/min. When sublimation purification was performed on 0.99 g of PCAO11, the yield was 0.71 g and 72%.

Figure 10A:
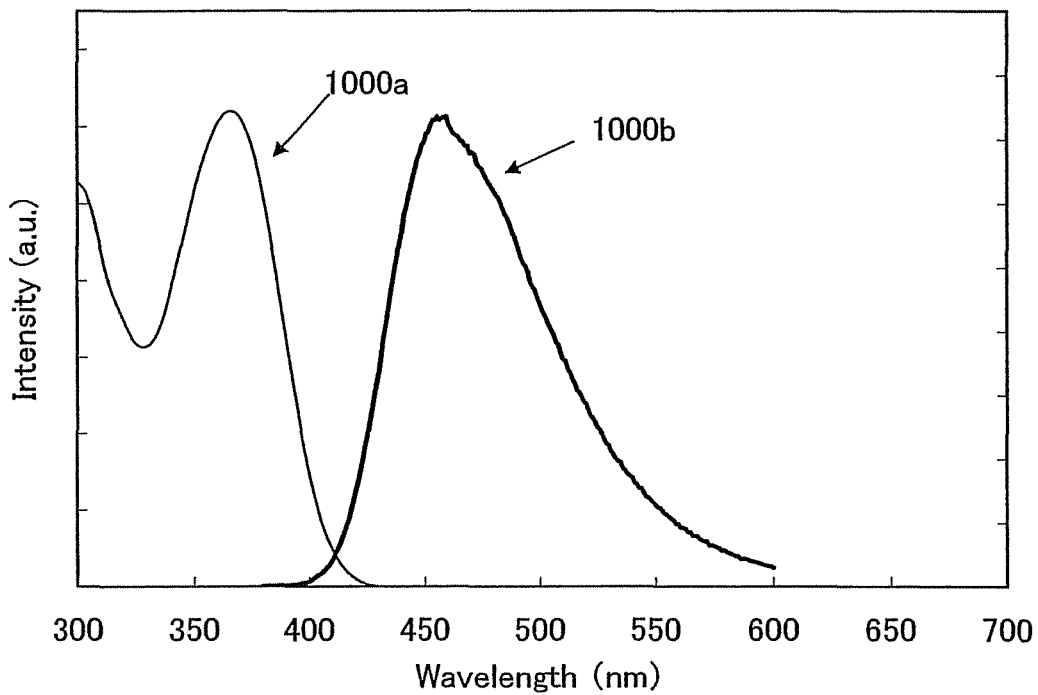
FIGS. 10A and 10B are diagrams each showing an ultraviolet/visible absorption spectrum and an emission spectrum of an oxadiazole derivative PCAO11 of the present invention.
Figure 10B:
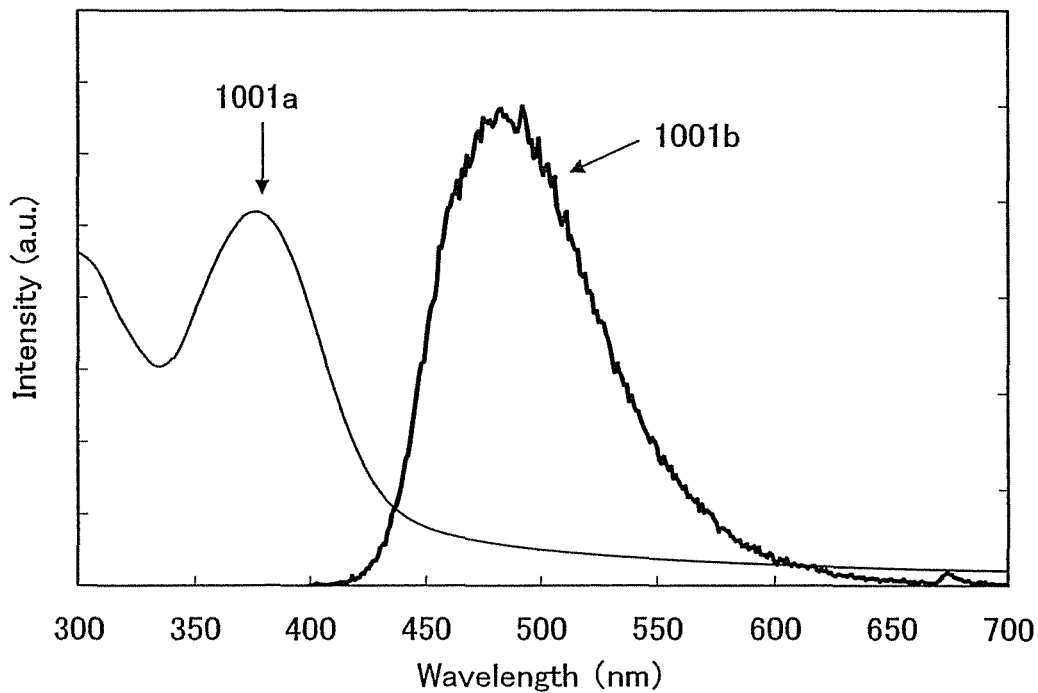

Next, the absorption spectrum and the emission spectrum of PCAO11 were measured. The absorption spectrum was measured using an ultraviolet-visible spectrophotometer (V-550, by JASCO Corporation) and the emission spectrum was measured using a spectrofluorometer (FS920, by Hamamatsu Photonics K.K.). The measurement was performed at room temperature for a toluene solution and a deposited film. FIG. 10A shows a measurement result for the toluene solution and FIG. 10B shows a measurement result for the deposited film. The horizontal axis indicates the wavelength and the vertical axis indicates the intensity of the absorption and light emission.

As shown in FIG. 10A, the oxadiazole derivative PCAO11 of the present invention has an absorption peak at 366 nm with the toluene solution. A reference numeral 1000*a* is an absorption spectrum. In addition, the emission spectrum 1000*b* has a peak at 456 nm. Note that the emission spectrum was measured through excitation of PCAO11 at a wavelength of 366 nm.

In addition, as shown in FIG. 10B, the deposited film of the oxadiazole derivative PCAO11 of the present invention has an absorption peak at 377 nm. A reference numeral 1001*a* is an absorption spectrum. In addition, the emission spectrum 1001*b* has a peak at 483 nm. Note that the emission spectrum was measured through excitation of PCAO11 at a wavelength of 356 nm.

Data on the absorption spectrum in FIG. 10B was used to obtain the absorption edge by a Tauc plot. Further, the energy of the absorption edge was used as an energy gap to find that an energy gap of PCAO11 was 2.97 eV. Accordingly, it was found that the oxadiazole derivative PCAO11 of the present invention has high excitation energy.

In addition, when the ionizing potential of PCAO11 in a thin film state was measured with a photoelectron spectrometer (AC-2, by RIKEN KEIKI CO., LTD.) in the air, the ionizing potential was 5.30 eV. As a result, it was found that the HOMO level was −5.30 eV. Further, when the LUMO level was calculated from the value of the energy gap and the HOMO level obtained as described above, the LUMO level was −2.33 eV.

Further, the optimal molecular structure of PCAO11 in the ground state was calculated using the B3LYP/6-311 (d, p) of the density functional theory (DFT). The accuracy of calculation of the DFT is higher than that of a Hartree-Fock (HF) method which does not consider electron correlation. In addition, calculation costs of the DFT are lower than that of a method of perturbation (MP) which has the same level of accuracy of calculation as that of the DFT. Therefore, the DFT was employed in this calculation. The calculation was performed using a high performance computer (HPC) (Altix3700 DX, by SGI Japan, Ltd.). In addition, when singlet excitation energy (energy gap) of PCAO11 was calculated using the B3LYP/6-311 (d, p) of a time-dependent density functional theory (TDDFT) in the molecular structure optimized by the DFT, the singlet excitation energy was 3.11 eV. In addition, when triplet excitation energy of PCAO11 was calculated, it was 2.50 eV. According to the above results, it is understood that the oxadiazole derivative of the present invention is a substance having high excitation energy, in particular, a substance having high triplet excitation energy.

Further, the glass transition point was measured by a differential scanning calorimeter (DSC Pyris 1, by PerkinElmer, Inc.). After a sample was heated to 280° C. at 40° C./min, it was cooled to room temperature at 40° C./min. After that, the temperature was raised to 280° C. at 10° C./min, the sample was cooled to room temperature at 40° C./min, and the glass transition point was measured. As a result, it was found that the glass transition point (Tg) of PCAO11 was 103° C.

Subsequently, an oxidation property and a reduction property of PCAO11 were examined by cyclic voltammetry (CV). The measurement device, and the solution and the concentration for the CV measurement were the same as those of Synthesis Example 1.

The oxidation property was measured by first scanning potential of the working electrode with respect to the reference electrode from −0.22 to 0.80 V and then continuously scanning the potential from 0.80 to −0.22 V. In addition, the reduction property was measured by scanning potential of the working electrode with respect to the reference electrode from −0.60 to −2.70 V and continuously scanning the potential from −2.70 to −0.60 V. The scanning speed of the CV measurement was set to be 0.1 V/s.

Figure 11A:
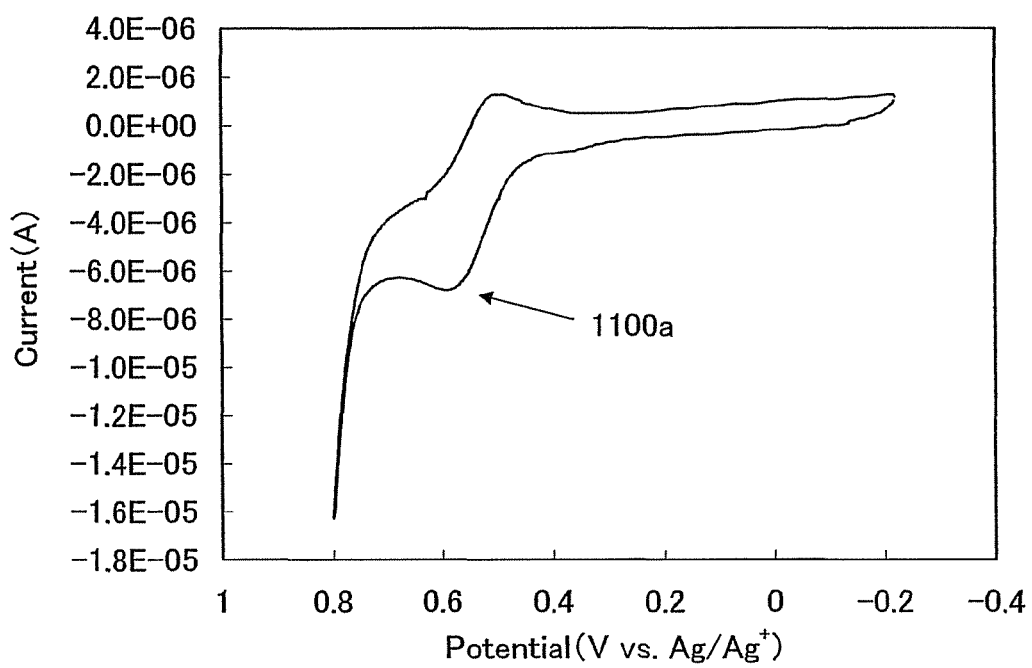
FIGS. 11A and 11B are diagrams each showing a CV curve of an oxadiazole derivative PCAO11 of the present invention.
Figure 11B:
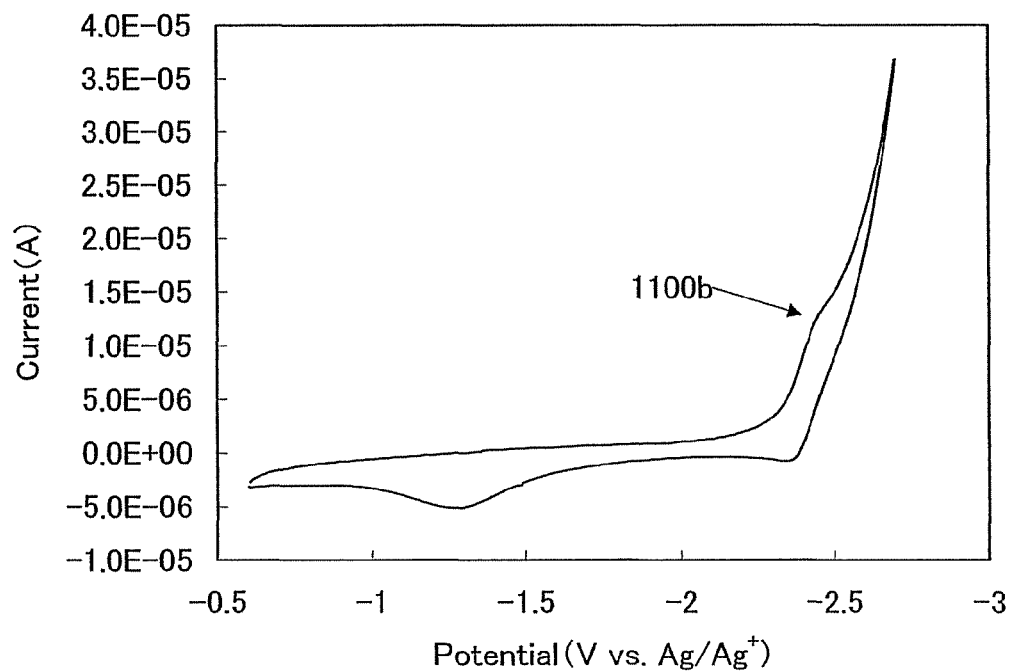

FIG. 11A shows a CV curve for the oxidation property of PCAO11, and FIG. 11B shows a CV curve for the reduction property. In FIGS. 11A and 11B, the horizontal axis indicates potential of the working electrode with respect to the reference electrode, and the vertical axis indicates a value of current which flows between the working electrode and the auxiliary electrode. As shown in FIGS. 11A and 11B, both the oxidation peak 1100a and the reduction peak 1100a of PCAO11 were clearly observed. Accordingly, it was found that PCAO11 was a substance which can easily receive both a hole and an electron.

SYNTHESIS EXAMPLE 3

Synthesis Example 3 will specifically show a synthesis example of 2-{4-[N-(4-diphenylaminophenyl)-N-phenylamino]phenyl}-5-phenyl-1,3,4-oxadiazole (abbreviation: DPAO11) that is the oxadiazole derivative of the present invention represented by the structural formula (91) of Embodiment Mode 1.

Step 1: Synthesis of
2-(4-bromophenyl)-5-phenyl-1,3,4-oxadiazole
(abbreviation: O11Br)

This synthesis is described in Step 1 of Synthesis Example 1 and will thus be omitted here.

Step 2: Synthesis of
N,N,N'-triphenyl-1,4-phenylenediamine
(abbreviation: DPA

In Step 2, DPA was synthesized according to (i) and (ii) shown below.

(i) Synthesis of 4-bromotriphenylamine

First, 25 g (100 mmol) of triphenylamine, 18 g (100 mmol) of N-bromosuccinimide, and 400 mL of ethyl acetate were put in a 1000-mL Erlenmeyer flask, and the mixture was stirred at room temperature in the air for 18 hours. After the reaction was terminated, the mixture was washed with a saturated sodium carbonate aqueous solution twice to obtain an organic layer and a water layer. Then, the water layer was extracted twice with ethyl acetate, and the extract was combined with the organic layer and washed with a saturated saline solution. The solution was dried with magnesium sulfate and filtered naturally, and the filtrate was concentrated. An obtained colorless solid was recrystallized with ethyl acetate-hexane; thus, 22 g of a colorless powdered solid of 4-bromotriphenylamine was obtained (yield: 66%).

(ii) Synthesis of N,N,N'-triphenyl-1,4-phenylenediamine (abbreviation: DPA)

Subsequently, 0.56 g (6 mmol) of the 4-bromotriphenylamine obtained in (i) above, 0.35 g (0.6 mmol) of bis(dibenzylideneacetone)palladium(0), and 0.58 g (6 mmol) of sodium-tert-butoxide were put in a 100-mL three-neck flask, 5 mL of toluene was added therein, and nitrogen was substituted for air in the flask. Then, 0.56 g (6 mmol) of aniline and 0.37 mL (1.8 mmol) of a 10% hexane solution of tri-tert-butylphosphine were added therein, and the mixture was heated and stirred at 80° C. for 5 hours. After the reaction, the reaction was terminated by adding a saturated saline solution, and a water layer was extracted with approximately 100 mL of ethyl acetate. The extract was dried with magnesium sulfate and filtered. The filtrate was concentrated and purified by silica gel column chromatography of ethyl acetate:hexane=1:20; thus, 0.24 g of a light yellow powdered solid DPA that was an object of Step 2 was obtained (yield: 42%). The synthesis scheme of Step 2 as described above is shown in the following scheme (b-3).

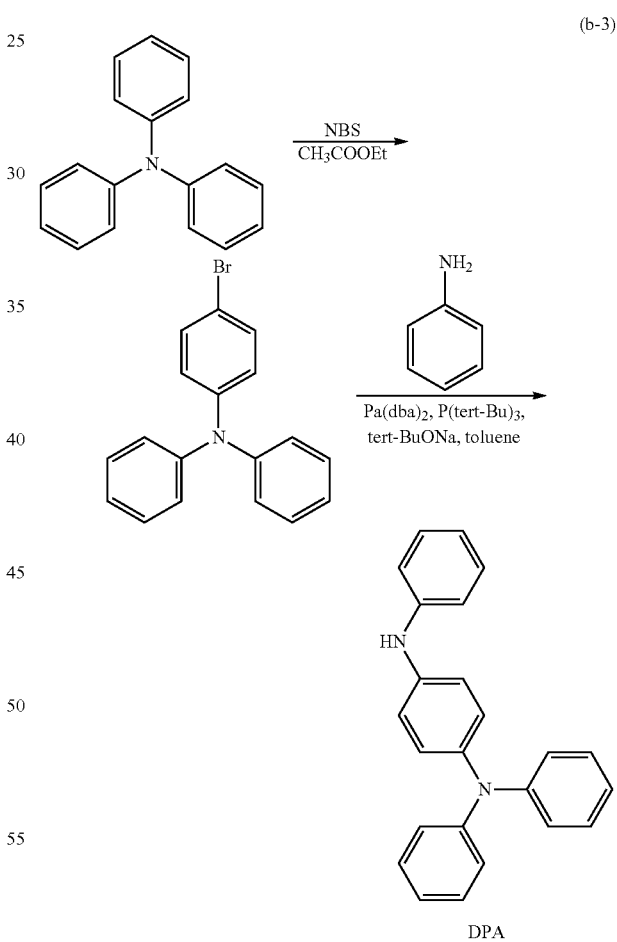

(b-3)

Step 3: Synthesis of 2-{4-[N-(4-diphenylaminophenyl)-N-phenylamino]phenyl}-5-phenyl-1,3,4-oxadiazole (abbreviation: DPAO11)

0.61 g (2.0 mmol) of O11Br obtained in Step 1, 0.67 g (2.0 mmol) of DPA obtained by the method shown in Step 2, 1.0 g (10.4 mmol) of sodium-tert-butoxide, and 0.014 g (0.02 mmol) of bis(dibenzylideneacetone)palladium(0) were put in a 50-mL three-neck flask, and nitrogen was substituted for air in the flask. Then, 7 mL of toluene and 0.1 mL of a 10% hexane solution of tri-tert-butylphosphine were added therein, and the mixture was heated and stirred at 80° C. for 8 hours. After the reaction was terminated, an obtained solid was dissolved in chloroform, washed with water and a saturated saline solution in this order, and filtered through Celite. The filtrate was concentrated, and an obtained solid was dissolved in toluene and purified by silica gel column chromatography. Purification by column chromatography was performed by using toluene as a developing solvent and then using a mixed solvent of toluene:ethyl acetate=1:1 as a developing solvent. The purified solid was recrystallized with chloroform and hexane; thus, 0.65 g of a yellow solid DPAO11 that was an object of Synthesis Example 3 was obtained (yield: 58%). The synthesis scheme of Step 3 as described above is shown in the following scheme (c-3).

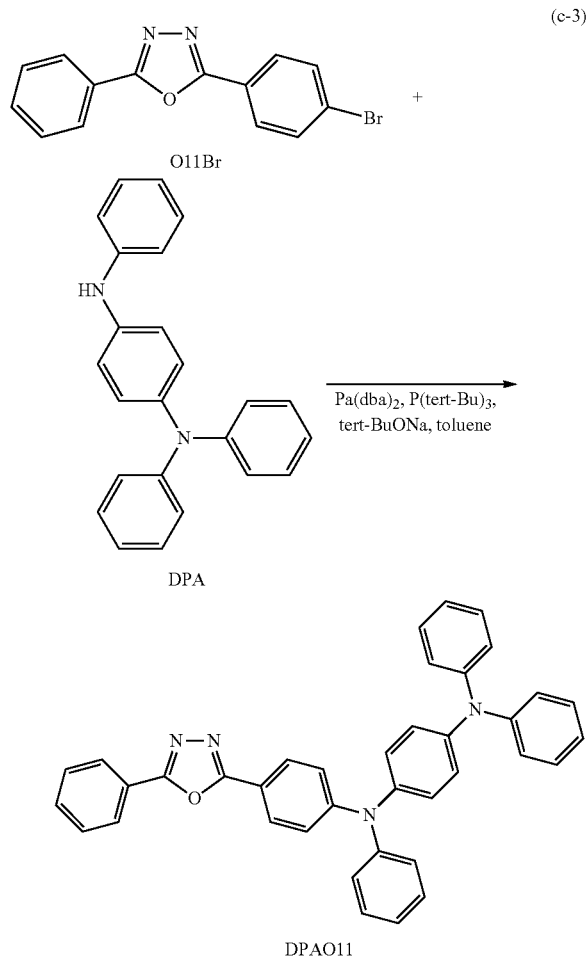

Figure 12A:
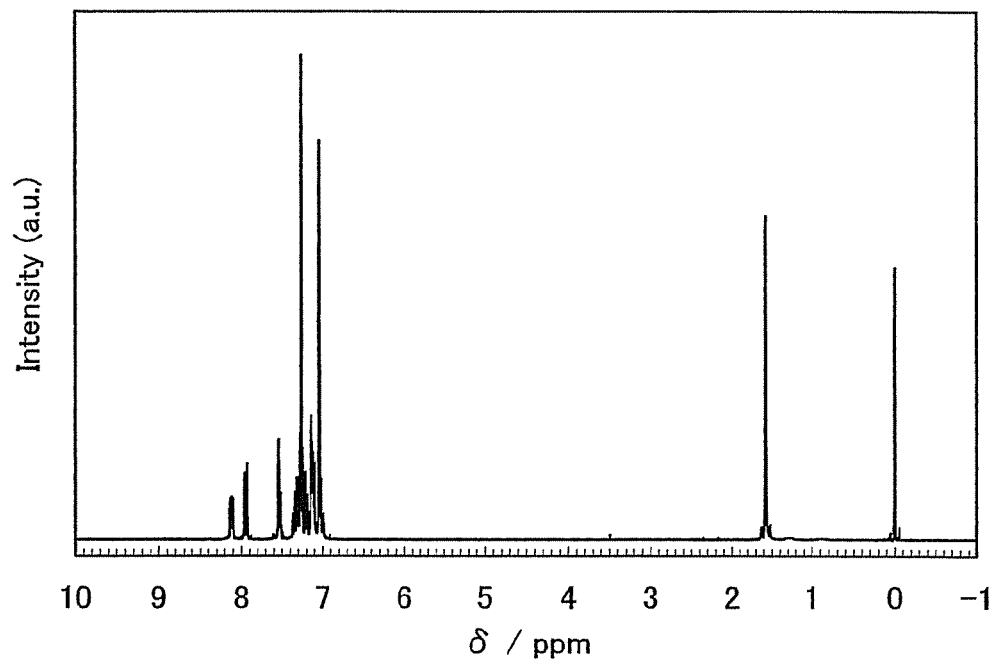
FIGS. 12A and 12B are diagrams each showing an $^1$H-NMR chart of an oxadiazole derivative DPAO11 of the present invention.
Figure 12B:
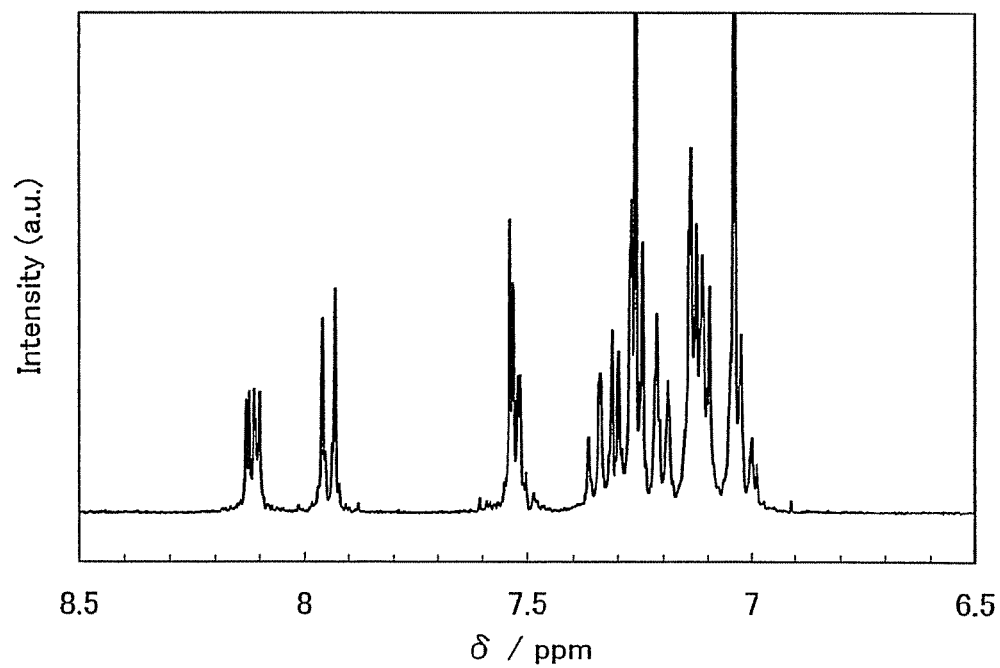

The following shows a result of analyzing DPAO11 that was obtained in Step 3 by nuclear magnetic resonance spectroscopy ($^1$H-NMR). FIG. 12A shows an $^1$H-NMR chart and FIG. 12B shows an enlarged chart thereof. Accordingly, it was found that the oxadiazole derivative DPAO11 of the present invention represented by the structural formula (91) was obtained in Synthesis Example 3.

$^1$H-NMR (CDCl$_3$, 300 MHz,): δ=7.00-7.37 (m, 21H), δ=7.52 (m, 3H), δ=7.95 (d, J=9.0, 2H), δ=8.10-8.13 (m, 2H)

Figure 13A:
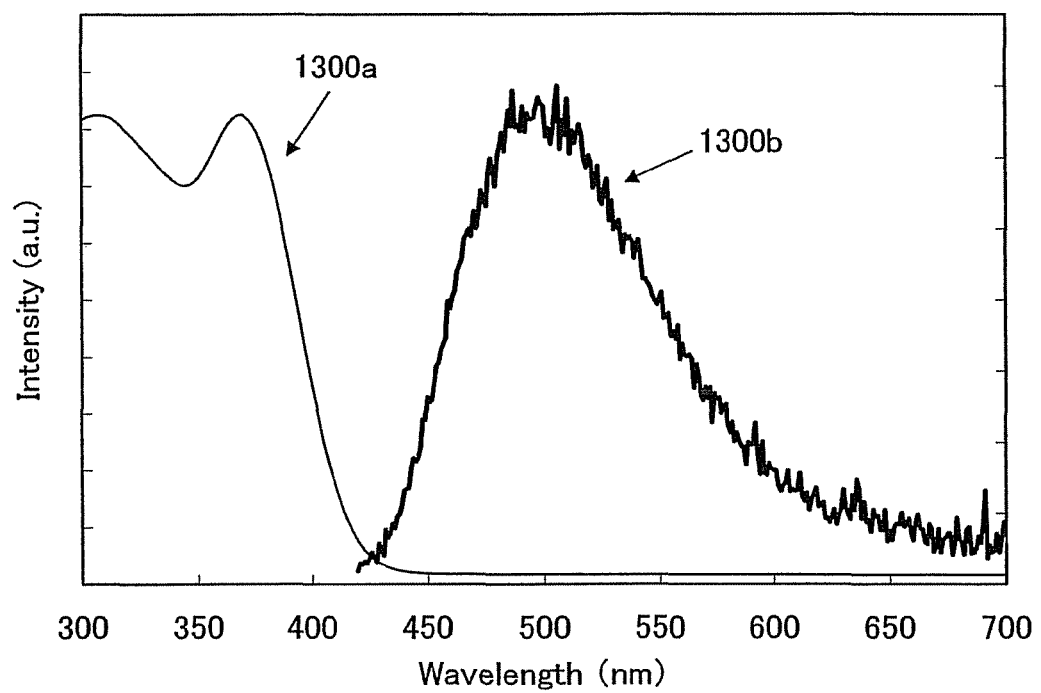
FIGS. 13A and 13B are diagrams each showing an ultraviolet/visible absorption spectrum and an emission spectrum of an oxadiazole derivative DPAO11 of the present invention.
Figure 13B:
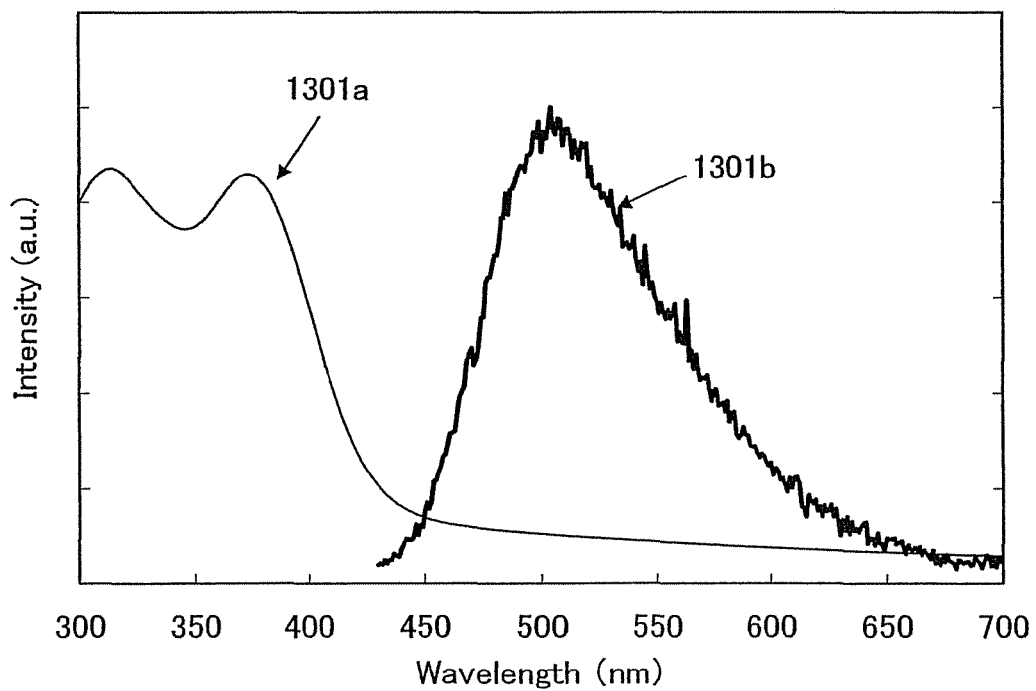

Next, the absorption spectrum and the emission spectrum of DPAO11 were measured. The absorption spectrum was measured using an ultraviolet-visible spectrophotometer (V-550, by JASCO Corporation) and the emission spectrum was measured using a spectrofluorometer (FS920, by Hamamatsu Photonics K.K.). The measurement was performed at room temperature for a toluene solution and a deposited film. FIG. 13A shows a measurement result for the toluene solution and FIG. 13B shows a measurement result for the deposited film. The horizontal axis indicates the wavelength and the vertical axis indicates the intensity of the absorption and light emission.

As shown in FIG. 13A, the oxadiazole derivative DPAO11 of the present invention has an absorption peak at 369 nm with the toluene solution. A reference numeral 1300a is an absorption spectrum. In addition, the emission spectrum 1300b has a peak at 498 nm. Note that the emission spectrum was measured through excitation of DPAO11 at a wavelength of 369 nm.

In addition, as shown in FIG. 13B, the deposited film of the oxadiazole derivative DPAO11 of the present invention has an absorption peak at 373 nm. A reference numeral 1301a is an absorption spectrum. In addition, the emission spectrum 1301b has a peak at 504 nm. Note that the emission spectrum was measured through excitation of DPAO11 at a wavelength of 373 nm.

Data on the absorption spectrum in FIG. 13B was used to obtain the absorption edge by a Tauc plot. Further, the energy of the absorption edge was used as an energy gap to find that an energy gap of DPAO11 was 2.99 eV. Accordingly, it was found that the oxadiazole derivative DPAO11 of the present invention has high excitation energy.

In addition, when the ionizing potential of DPAO11 in a thin film state was measured with a photoelectron spectrometer (AC-2, by RIKEN KEIKI CO., LTD.) in the air, the ionizing potential was 5.41 eV. As a result, it was found that the HOMO level was −5.41 eV. Further, when the LUMO level was calculated from the value of the energy gap and the HOMO level obtained as described above, the LUMO level was −2.42 eV.

Further, the glass transition point was measured with a differential scanning calorimeter (DSC Pyris 1, by PerkinElmer Inc.). After a sample was heated to 280° C. at 40° C./min, it was cooled to room temperature at 40° C./min. After that, the temperature was raised to 280° C. at 10° C./min, the sample was cooled to room temperature at 40° C./min, and the glass transition point was measured. As a result, it was found that the glass transition point (Tg) of DPAO11 was 72° C.

Subsequently, an oxidation property and a reduction property of DPAO11 were examined by cyclic voltammetry (CV). The measurement device, and the solution and the concentration for the CV measurement were the same as those of Synthesis Example 1.

The oxidation property was measured by first scanning potential of the working electrode with respect to the reference electrode from −0.35 to 0.60 V and then continuously scanning the potential from 0.60 to −0.35 V. In addition, the reduction property was measured by first scanning potential of the working electrode with respect to the reference electrode from −0.32 to −2.60 V and then continuously scanning the potential from −2.60 to −0.32 V. The scanning speed of the CV measurement was set to be 0.1 V/s.

Figure 14A:
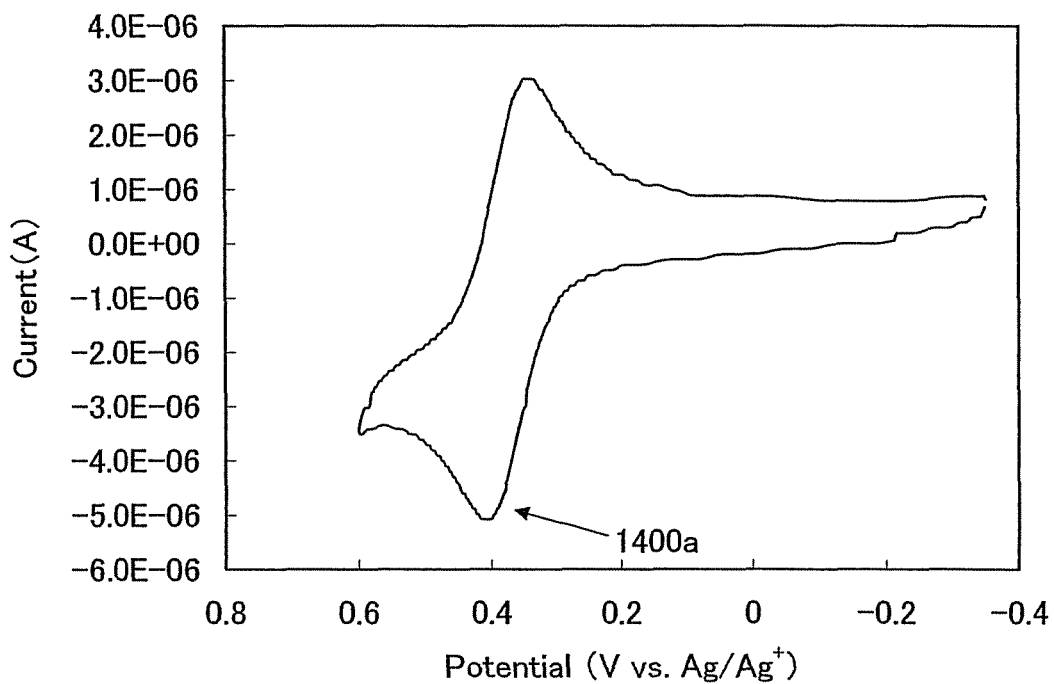
FIGS. 14A and 14B are diagrams each showing a CV curve of an oxadiazole derivative DPAO11 of the present invention.
Figure 14B:
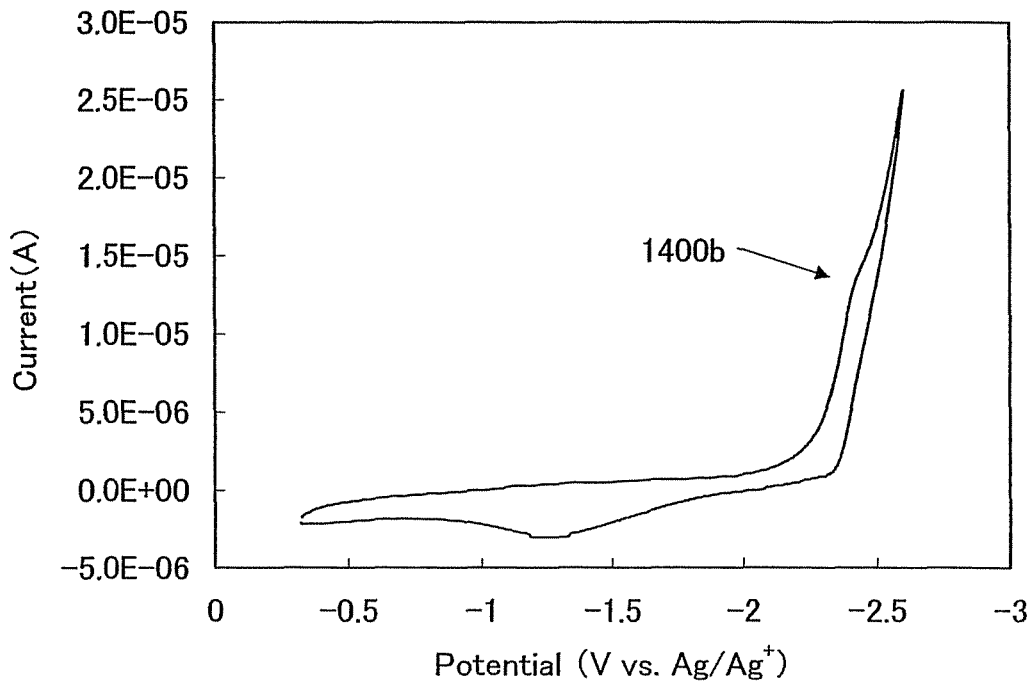

FIG. 14A shows a CV curve for the oxidation property of DPAO11, and FIG. 14B shows a CV curve for the reduction property. In FIGS. 14A and 14B, the horizontal axis indicates potential of the working electrode with respect to the reference electrode, and the vertical axis indicates a value of current which flows between the working electrode and the auxiliary electrode. As shown in FIGS. 14A and 14B, both the oxidation peak 1400a and the reduction peak 1400b of DPAO11 were clearly observed. Accordingly, it was found that DPAO11 was a substance which can easily receive both a hole and an electron.

[Embodiment 2]

Embodiment 2 will specifically show an example of a light emitting element using the oxadiazole derivative YGAO11 of the present invention synthesized in Synthesis Example 1 of Embodiment 1 as a host material of a light emitting layer and a green phosphorescent compound as a guest material. FIG. 1 shows an element structure.

<<Manufacturing of a Light Emitting Element of Embodiment 2>>

A glass substrate with a thickness of 110 nm, over which indium tin oxide containing silicon oxide (ITSO) is formed, is prepared. The periphery of the ITSO surface was covered with an insulating film so that a surface of 2 mm×2 mm was exposed. Note that ITSO is a first electrode 101 which functions as an anode of a light emitting element. As pretreatment for forming a light emitting element over the substrate, the surface of the substrate was cleaned with a porous resin brush, baked at 200° C. for 1 hour, and subjected to UV ozone treatment for 370 seconds.

Subsequently, the substrate was fixed to a holder provided in a vacuum deposition apparatus so that the surface provided with ITSO faced downward.

After pressure in the vacuum deposition apparatus was reduced to $10^{-4}$ Pa, NPB represented by the following structural formula (i) and molybdenum oxide (VI) were codeposited so as to meet NPB:molybdenum oxide (VI)=4:1 (mass ratio), whereby a hole injecting layer 111 was formed. A thickness thereof was set to be 50 nm. Note that a codeposition method is a deposition method in which a plurality of different substances are concurrently evaporated from different evaporation sources, respectively. Next, NPB was deposited to be 10 nm thick, whereby a hole transporting layer 112 was formed. Further, over the hole transporting layer 112, the oxadiazole derivative YGAO11 of the present invention and Ir(ppy)$_2$(acac) represented by the following structural formula (II) were codeposited so as to meet YGAO11:Ir(ppy)$_2$(acac)=1:0.08 (mass ratio), whereby a light emitting layer 113 was formed. A thickness thereof was set to be 30 nm. Then, BCP represented by the following structural formula (III) was deposited to be 10 nm thick, whereby an electron transporting layer 114 was formed. Further, over the electron transporting layer 114, Alq$_3$ represented by the following structural formula (Iv) and lithium (Li) were codeposited so as to meet Alq$_3$:Li=1:0.01 (mass ratio), whereby an electron injecting layer 115 was formed. A thickness thereof was set to be 30 nm. Finally, aluminum was formed to be 200 nm thick as a second electrode 102 which functions as a cathode, whereby a light emitting element of the present invention was obtained. Note that, in the above deposition process, all deposition was performed by a resistance heating method.

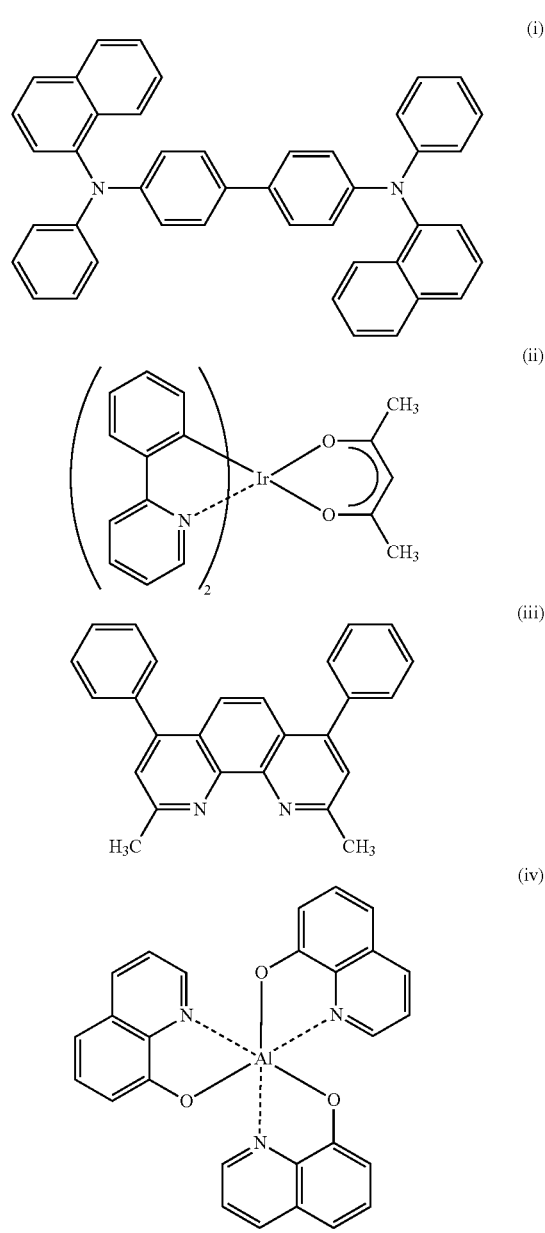

<<Manufacturing of a Light Emitting Element of Comparative Example 1>>

For comparison, similarly to Embodiment 2, a light emitting element of Comparative Example 1 was manufactured using CBP represented by the following structural formula (v) instead of the oxadiazole derivative YGAO11 of the present invention. In other words, a light emitting layer 113 of the light emitting element of Comparative Example 1 was formed by codeposition so that CBP:Ir(ppy)$_2$(acac)=1:0.08 (mass ratio) was met. Note that CBP is a known compound which is widely used as a host material of a phosphorescent compound.

(v)

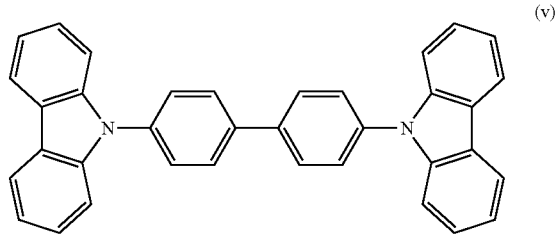 [SMILES: c1ccc2c(c1)c1ccccc1n2-c1ccc(-c2ccc(-n3c4ccccc4c4ccccc43)cc2)cc1]

<<Operation Characteristics of Light Emitting Elements of Embodiment 2 and Comparative Example 1>>

After the light-emitting elements of Embodiment 2 and Comparative Example 1 obtained as described above were sealed in a glove box with a nitrogen atmosphere so as not to expose the light-emitting elements to the air, operation characteristics of these light-emitting elements were measured. Note that the measurements were performed at room temperature (an atmosphere kept at 25° C.).

Figure 15A:
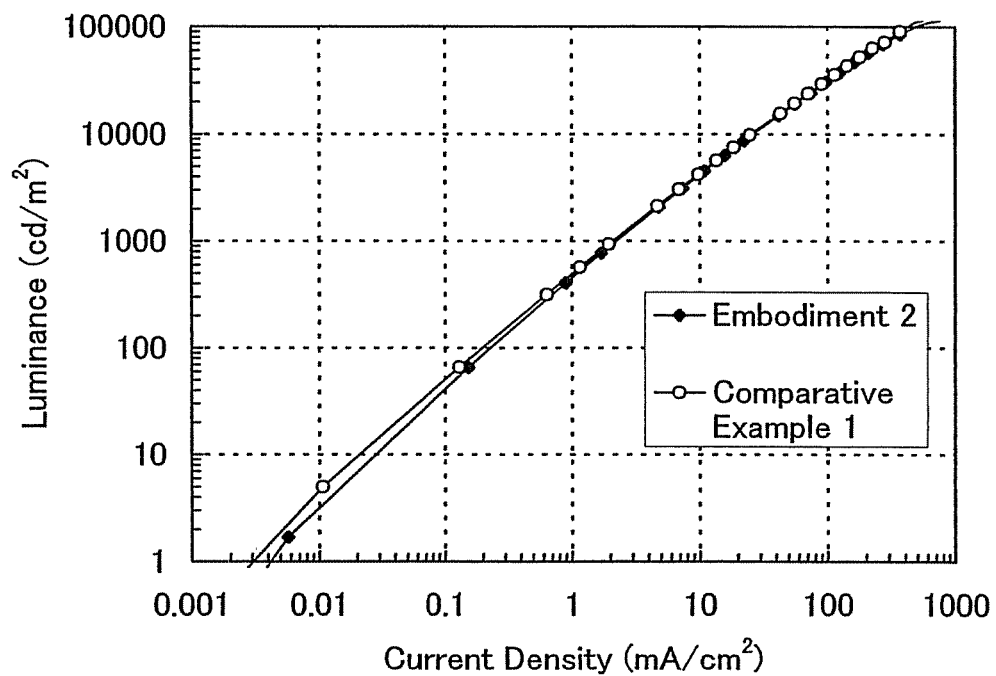
FIGS. 15A and 15B are diagrams each showing operation characteristics of light emitting elements of Embodiment 2 and Comparative Example 1.
Figure 15B:
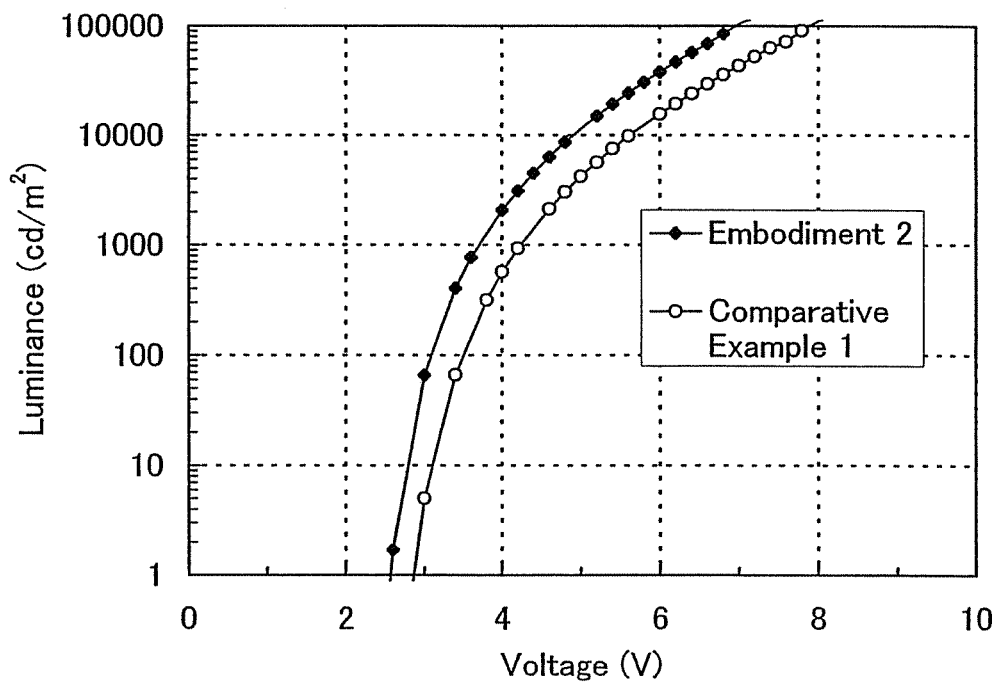
Figure 16:
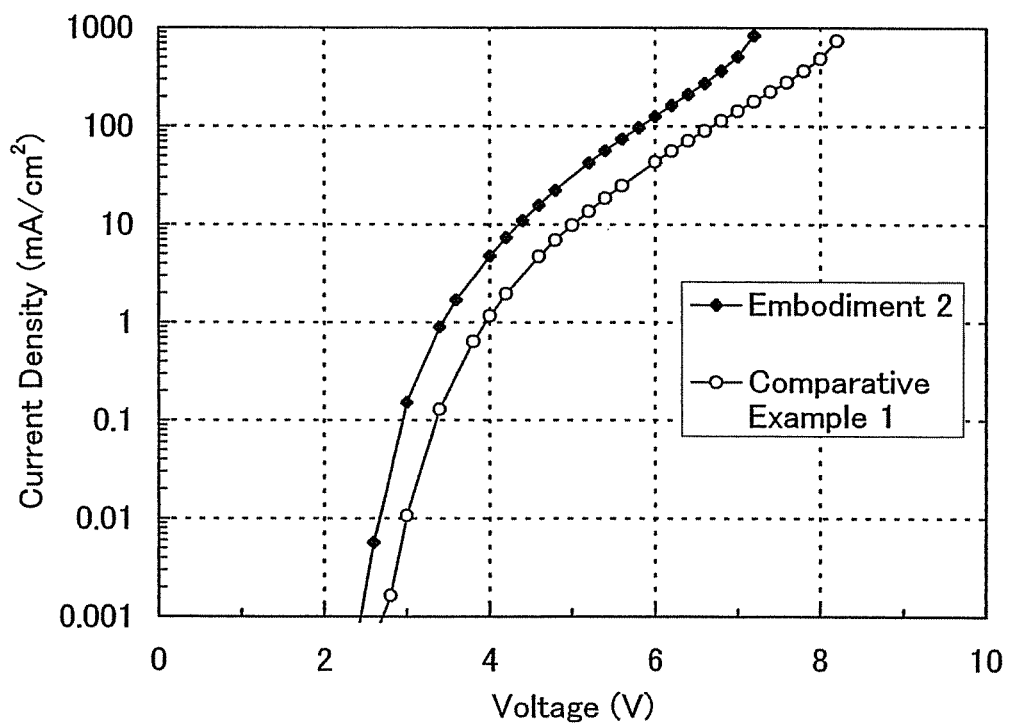
FIG. 16 is a diagram showing operation characteristics of light emitting elements of Embodiment 2 and Comparative Example 1.
Figure 28:
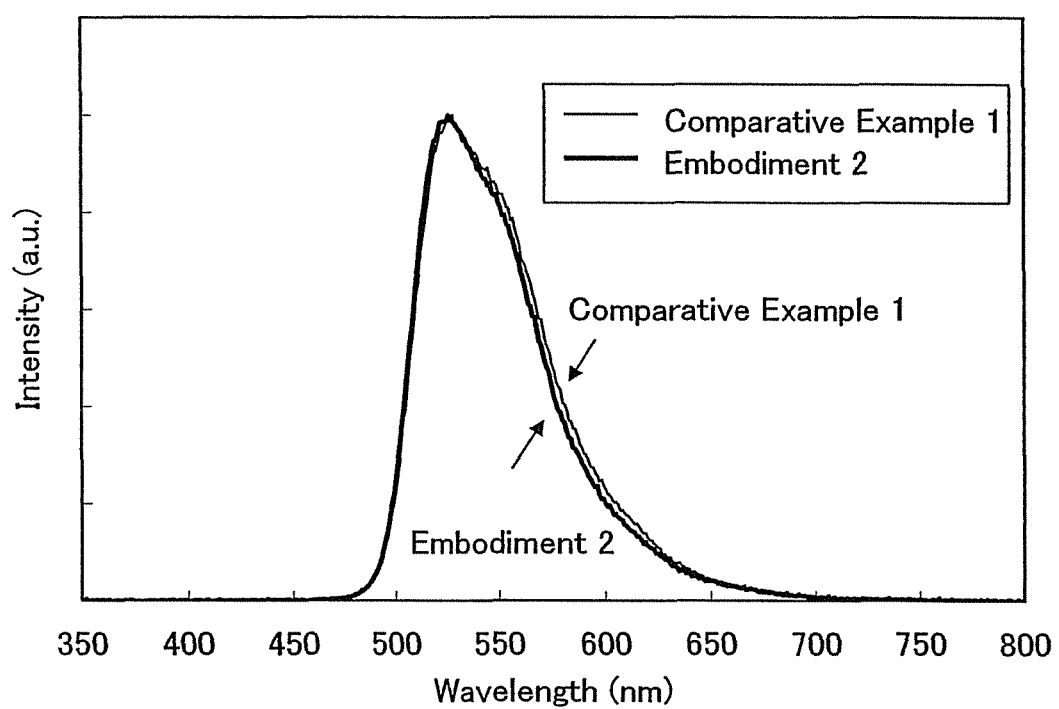
FIG. 28 is a diagram showing an emission spectrum of light emitting elements of Embodiment 2 and Comparative Example 1.

FIGS. 15A and 15B show current density-luminance characteristics and voltage-luminance characteristics of the light-emitting elements of Embodiment 2 and Comparative Example 1, respectively. According to FIGS. 15A and 15B, it is found that current density-luminance characteristics are equivalent, but as for the voltage-luminance characteristics, the light emitting element of Embodiment 2 is superior. For example, when comparison was made when a voltage of 4.0 V was applied, current flowed at a current density of 4.76 mA/cm$^2$ and light was emitted at a luminance of 2080 cd/m$^2$ in the light emitting element of Embodiment 2, whereas current flowed at a current density of 1.16 mA/cm$^2$ only and light was emitted at a luminance of 568 cd/m$^2$ in the light emitting element of Comparative Example 1. Therefore, it was found that the driving voltage of the light emitting element of Embodiment 2 was lower than that of the light emitting element of Comparative Example 1. FIG. 16 shows voltage-current density characteristics of the light emitting elements of Embodiment 2 and Comparative Example 1. According to this diagram, it is found that current flows more easily in the oxadiazole derivative of the present invention than in CBP, which is thought to lead reduction in driving voltage. Further, FIG. 28 shows the emission spectra of the light emitting elements of Embodiment 2 and Comparative Example 1 when a current of 1 mA is applied. When a voltage of 4.0 V was applied, the CIE chromaticity coordinates of the light emitting element of Embodiment 2 were (x, y)=(0.32, 0.65), the CIE chromaticity coordinates of the light emitting element of Comparative Example 1 were (x, y)=(0.33, 0.64), and emission of green light from 1$r$(ppy)$_2$(acac) which was a guest material was obtained in either case.

Figure 17A:
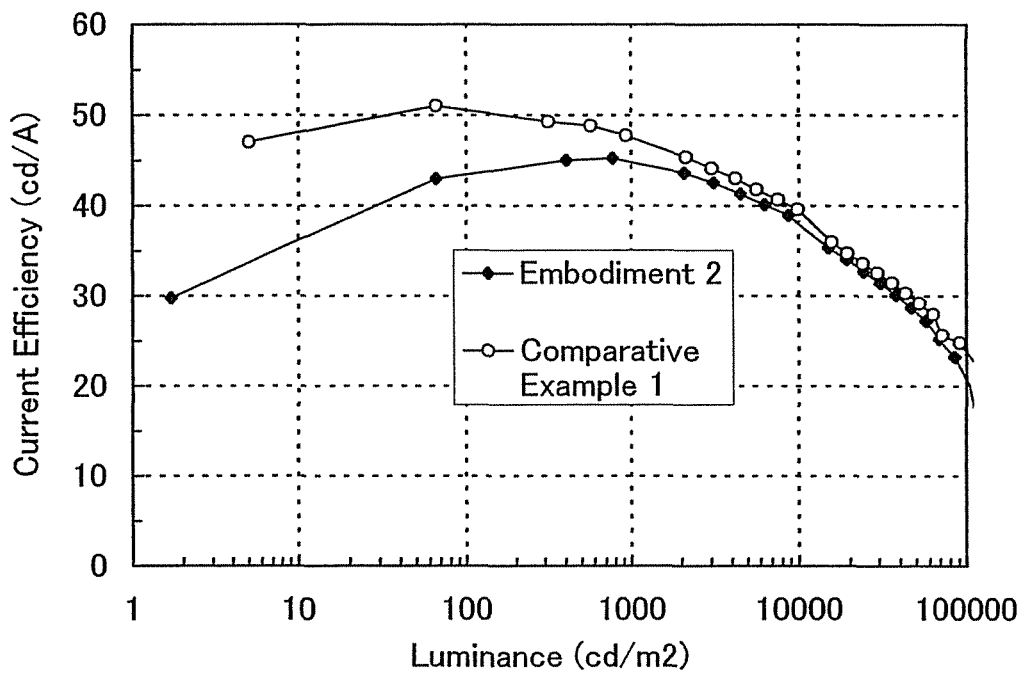
FIGS. 17A and 17B are diagrams each showing operation characteristics of light emitting elements of Embodiment 2 and Comparative Example 1.
Figure 17B:
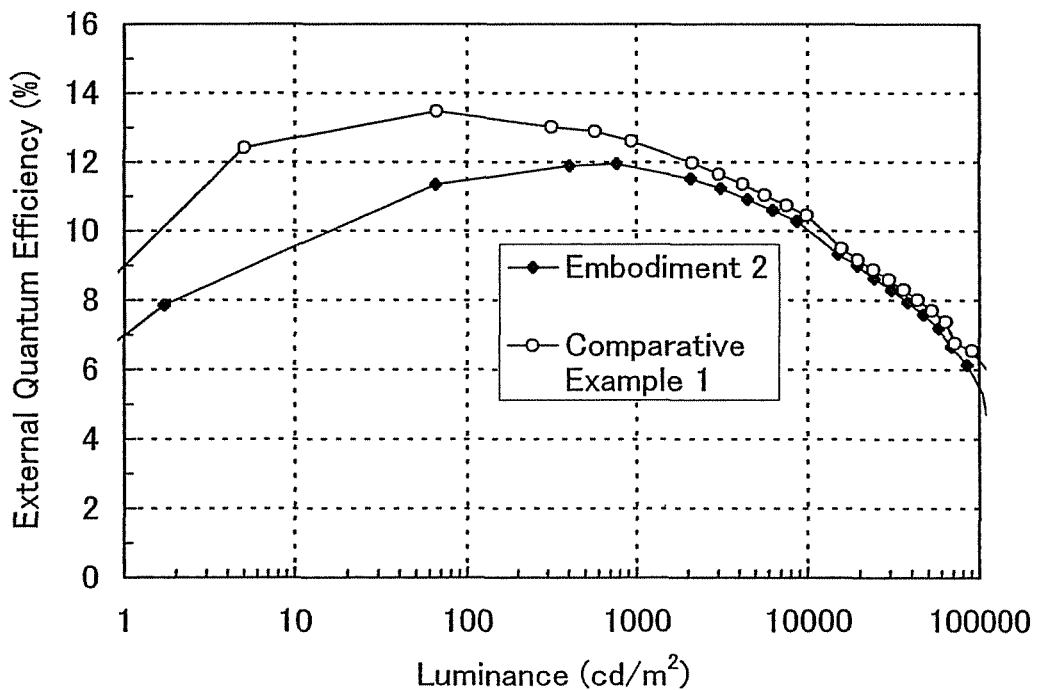

In addition, FIG. 17A shows luminance-current efficiency characteristics for these light emitting elements. In FIG. 17B, the vertical axis of FIG. 17A was converted to external quantum efficiency. According to FIGS. 17A and 17B, it is found that the light emitting element of Embodiment 2 has high current efficiency over 40 cd/A at 1000 cd/m$^2$. In addition, external quantum efficiency of the light emitting element of Embodiment 2 at 1000 cd/m$^2$ was 12%. Further, the power efficiency of the light emitting element of Embodiment 2 at 1000 cd/m$^2$ was 391 m/W, which is high power efficiency.

As described above, when the oxadiazole derivative of the present invention is used as a host material of the light emitting layer and the phosphorescent compound is used as a guest material to manufacture the light emitting element, it is possible to reduce driving voltage as well as obtain high light emitting efficiency. Therefore, by implementing the present invention, a light emitting element with low power consumption can be obtained.

[Embodiment 3]

Embodiment 3 will specifically show an example of a light emitting element using the oxadiazole derivative YGAO11 of the present invention synthesized in Synthesis Example 1 of Embodiment 1 as a host material of a light emitting layer and a red phosphorescent compound as a guest material. FIG. 1 shows an element structure.

First, a glass substrate with a thickness of 110 nm, over which indium tin oxide containing silicon oxide (ITSO) is formed, is prepared. The periphery of the ITSO surface was covered with an insulating film so that a surface of 2 mm×2 mm was exposed. Note that ITSO is a first electrode 101 which functions as an anode of a light emitting element. As pretreatment for forming a light emitting element over the substrate, the surface of the substrate was cleaned with a porous resin brush, baked at 200° C. for 1 hour, and subjected to UV ozone treatment for 370 seconds.

Subsequently, the substrate was fixed to a holder provided in a vacuum deposition apparatus so that the surface provided with ITSO faced downward.

After pressure in the vacuum deposition apparatus was reduced to 10$^{-4}$ Pa, NPB and molybdenum oxide (VI) were codeposited so as to meet NPB:molybdenum oxide (VI)=4:1 (mass ratio), whereby a hole injecting layer 111 was formed. A thickness thereof was set to be 50 nm. Next, NPB was deposited to be 10 nm thick, whereby a hole transporting layer 112 was formed. Further, over the hole transporting layer 112, the oxadiazole derivative YGAO11 of the present invention and Ir(Fdpq)$_2$(acac) represented by the following structural formula (vi) were codeposited so as to meet YGAO11: Ir(Fdpq)$_2$(acac)=1:0.05 (mass ratio), whereby a light emitting layer 113 was formed. A thickness thereof was set to be 30 nm. Then, BAlq represented by the following structural formula (vii) was deposited to be 10 nm thick, whereby an electron transporting layer 114 was formed. Further, over the electron transporting layer 114, Alq$_3$ and lithium (Li) were codeposited so as to meet Alq$_3$:Li=1:0.01 (mass ratio), whereby an electron injecting layer 115 was formed. A thickness thereof was set to be 50 nm. Finally, aluminum was formed to be 200 nm thick as a second electrode 102 which functions as a cathode, whereby a light emitting element of the present invention was obtained. Note that, in the above deposition process, all deposition was performed by a resistance heating method.

(vi)

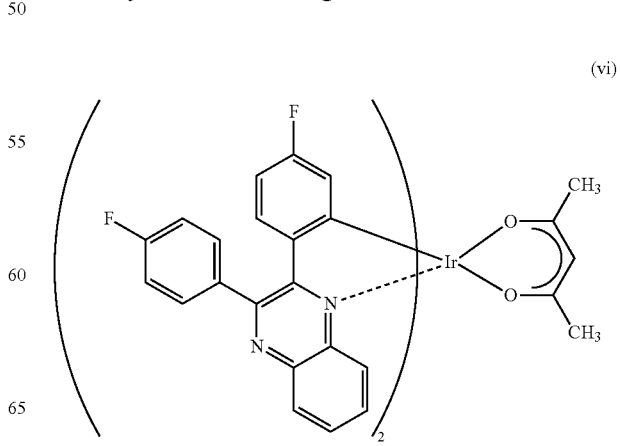

-continued

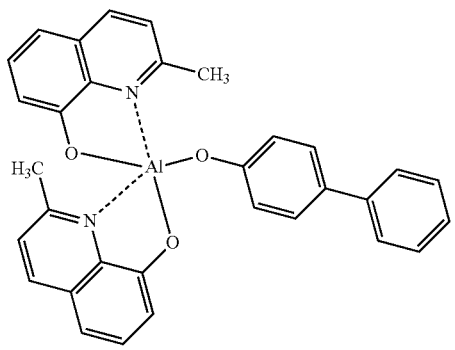

(vii)

After the light-emitting element was sealed in a glove box with a nitrogen atmosphere so as not to expose the light emitting element to the air, operation characteristics of the light emitting element were measured. Note that the measurement was performed at room temperature (an atmosphere kept at 25° C.).

Figure 18A:
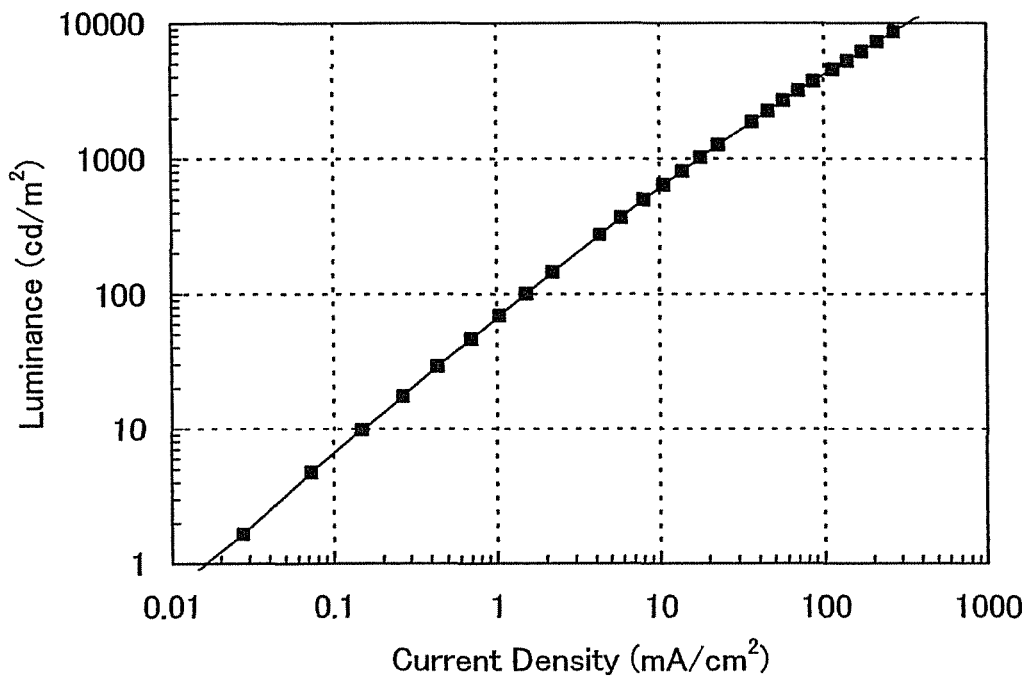
FIGS. 18A and 18B are diagrams each showing operation characteristics of a light emitting element of Embodiment 3.
Figure 18B:
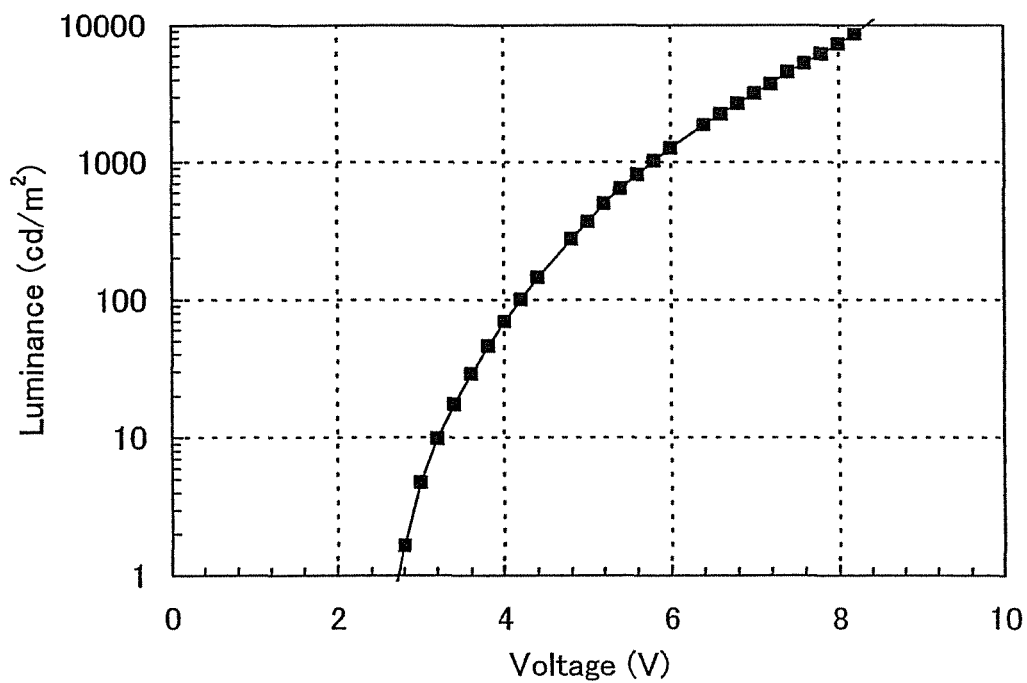

FIGS. 18A and 18B show current density-luminance characteristics and voltage-luminance characteristics of the light emitting element, respectively. When a voltage of 5.8 V was applied, current flowed at a current density of 18.0 mA/cm$^2$ and light was emitted at a luminance of 1020 cd/m$^2$ in the light emitting element of Embodiment 3. Therefore, it was found that the light emitting element of the present invention operates with low voltage. When a voltage of 5.8 V was applied, the CIE chromaticity coordinates of the light emitting element of Embodiment 3 were (x, y)=(0.71, 0.29) and emission of dark red light from 1r(Fdpq)$_2$(acac) which was a guest material was obtained.

Figure 19A:
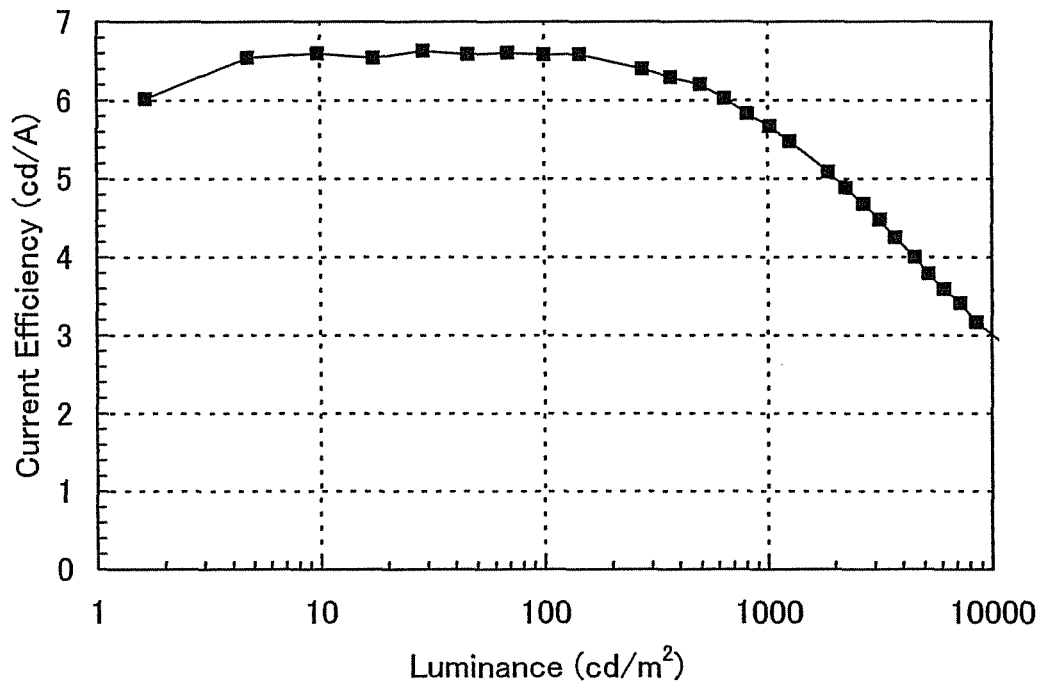
FIGS. 19A and 19B are diagrams each showing operation characteristics of a light emitting element of Embodiment 3.
Figure 19B:
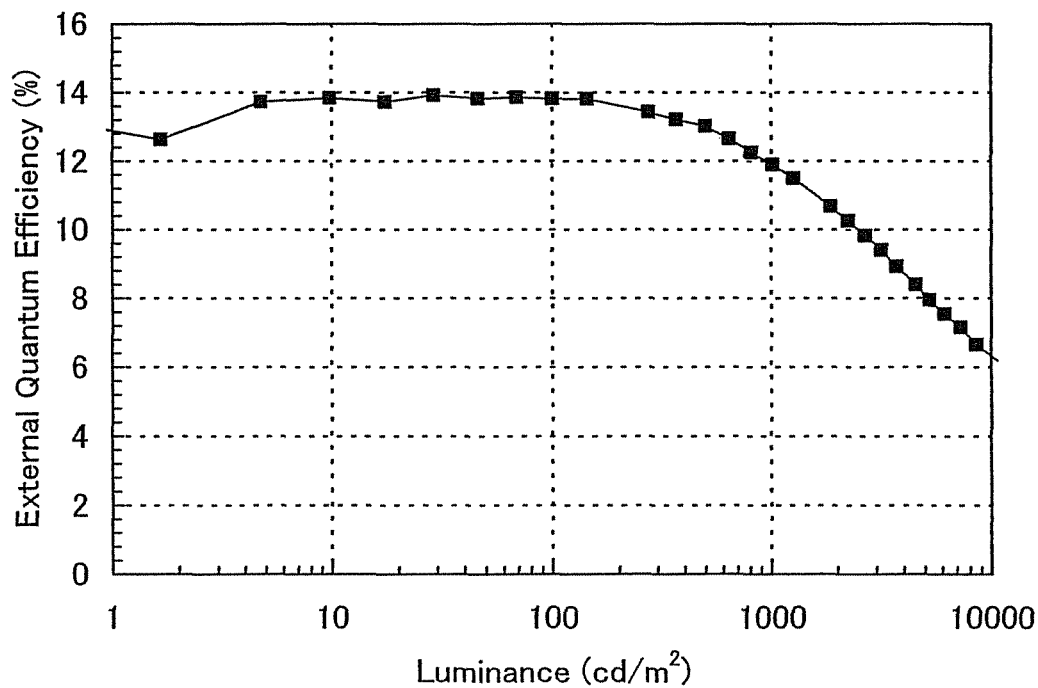

In addition, FIG. 19A shows luminance-current efficiency characteristics of the light emitting element. In FIG. 19B, the vertical axis of FIG. 19A was converted to external quantum efficiency. According to FIGS. 19A and 19B, although the light emitting element of Embodiment 3 exhibits emission of dark red light with low luminosity, the maximum light emitting efficiency was 6.63 cd/A which is extremely high light emitting efficiency. In addition, the external quantum efficiency at that time was 13.9%.

As described above, when the oxadiazole derivative of the present invention is used as a host material of the light emitting layer and the phosphorescent compound is used as a guest material to manufacture the light emitting element, it is possible to obtain a light emitting element with high light emitting efficiency and low driving voltage. Therefore, by implementing the present invention, a light emitting element with low power consumption can be obtained.

[Embodiment 4]

In Embodiment 4, a light emitting element was manufactured in a manner similar to that of Embodiment 3 except that Alq was used instead of BAlq for the electron transporting layer 114.

After the light-emitting element was sealed in a glove box with a nitrogen atmosphere so as not to expose the light-emitting element to the air, operation characteristics of the light-emitting element were measured. Note that the measurement was performed at room temperature (an atmosphere kept at 25° C.).

Figure 20A:
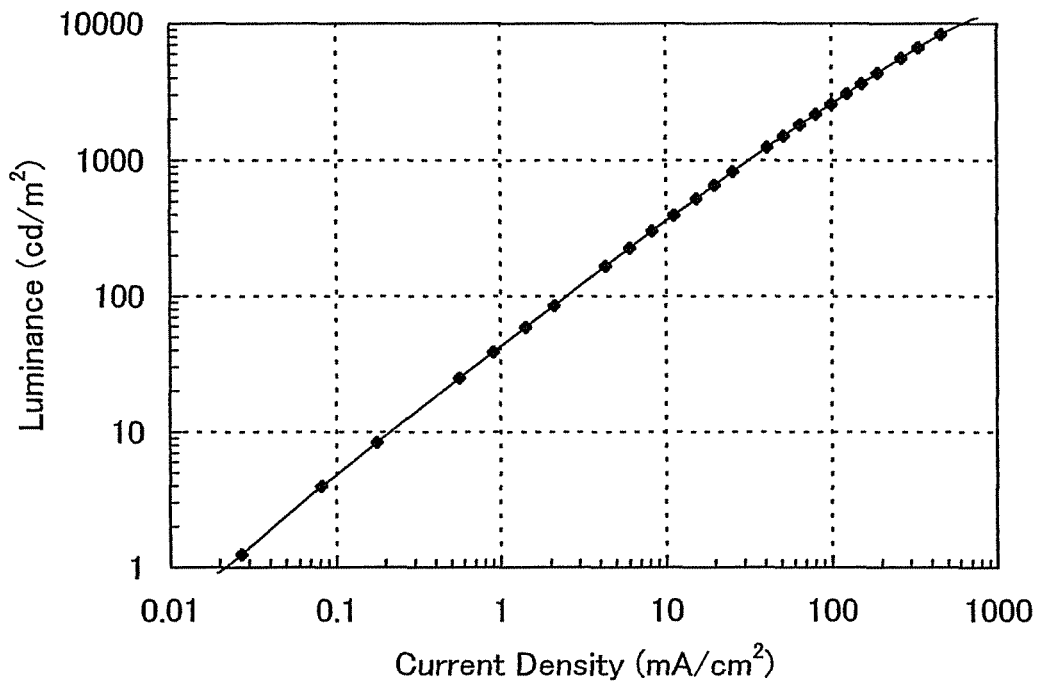
FIGS. 20A and 20B are diagrams each showing operation characteristics of a light emitting element of Embodiment 4.
Figure 20B:
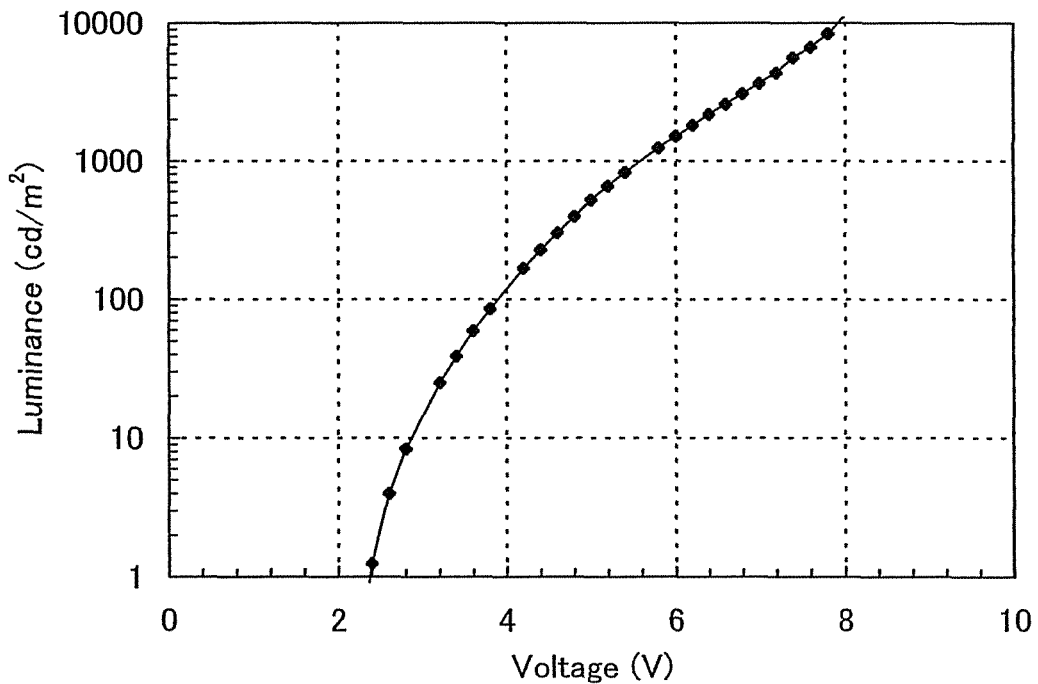

FIGS. 20A and 20B show current density-luminance characteristics and voltage-luminance characteristics of the light-emitting element, respectively. When a voltage of 5.4 V was applied, current flowed at a current density of 25.7 mA/cm$^2$ and light was emitted at a luminance of 824 cd/m$^2$ in the light emitting element of Embodiment 4. Therefore, it was found that the light emitting element of the present invention operates with low voltage. When a voltage of 5.4 V was applied, the CIE chromaticity coordinates of the light emitting element of Embodiment 4 were (x, y)=(0.70, 0.30) and emission of dark red light from Ir(Fdpq)$_2$(acac) which was a guest material was obtained.

Figure 21A:
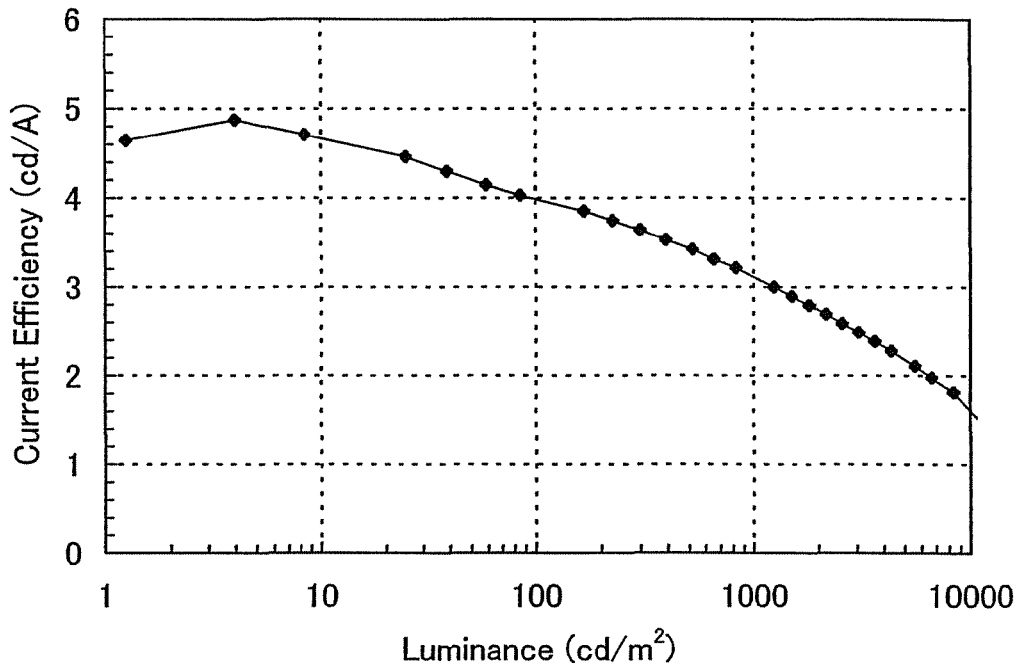
FIGS. 21A and 21B are diagrams each showing operation characteristics of a light emitting element of Embodiment 4.
Figure 21B:
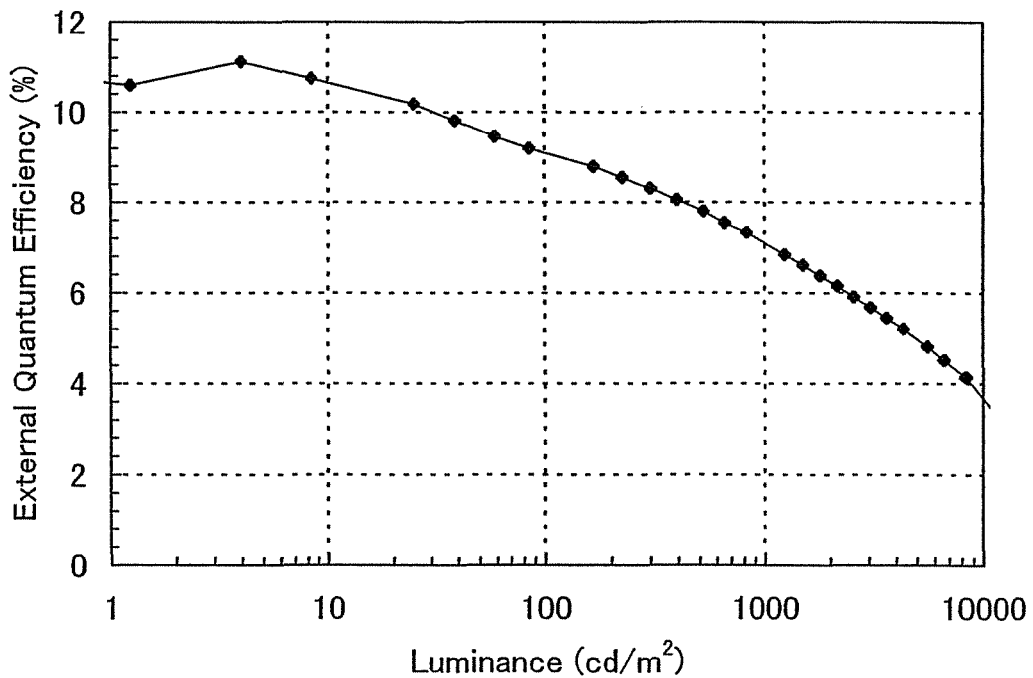

In addition, FIG. 21A shows luminance-current efficiency characteristics of the light emitting element. In FIG. 21B, the vertical axis of FIG. 21A was converted to external quantum efficiency. According to FIGS. 21A and 21B, although the light emitting element of Embodiment 4 exhibits emission of dark red light with low luminosity, the maximum light emitting efficiency was 4.87 cd/A which is extremely high light emitting efficiency. In addition, the external quantum efficiency at that time was 11.3%.

As described above, when the oxadiazole derivative of the present invention is used as a host material of the light emitting layer and the phosphorescent compound is used as a guest material to manufacture the light emitting element, it is possible to obtain a light emitting element with high light emitting efficiency and low driving voltage. Therefore, by implementing the present invention, a light emitting element with low power consumption can be obtained.

[Embodiment 5]

Embodiment 5 will specifically show an example of a light emitting element using the oxadiazole derivative DPAO11 of the present invention synthesized in Synthesis Example 3 of Embodiment 1 as a host material of a light emitting layer and a red phosphorescent compound as a guest material. FIG. 1 shows an element structure.

First, a glass substrate with a thickness of 110 nm, over which indium tin oxide containing silicon oxide (ITSO) is formed, is prepared. The periphery of the ITSO surface was covered with an insulating film so that a surface of 2 mm×2 mm was exposed. Note that ITSO is a first electrode 101 which functions as an anode of a light emitting element. As pretreatment for forming a light emitting element over the substrate, the surface of the substrate was cleaned with a porous resin brush, baked at 200° C. for 1 hour, and subjected to UV ozone treatment for 370 seconds.

Subsequently, the substrate was fixed to a holder provided in a vacuum deposition apparatus so that the surface provided with ITSO faced downward.

After pressure in the vacuum deposition apparatus was reduced to 10$^{-4}$ Pa, NPB and molybdenum oxide (VI) were codeposited so as to meet NPB:molybdenum oxide (VI)=4:1 (mass ratio), whereby a hole injecting layer 111 was formed. A thickness thereof was set to be 50 nm. Next, NPB was deposited to be 10 nm thick, whereby a hole transporting layer 112 was formed. Further, over the hole transporting layer 112, the oxadiazole derivative DPAO11 of the present invention and Ir(Fdpq)$_2$(acac) were codeposited so as to meet DPAO11: Ir(Fdpq)$_2$(acac)=1:0.10 (mass ratio), whereby a light emitting layer 113 was formed. A thickness thereof was set to be 30 nm. Then, BCP was deposited to be 10 nm thick, whereby an electron transporting layer 114 was formed. Further, over the electron transporting layer 114, Alq$_3$ and lithium (Li) were codeposited so as to meet Alg$_3$:Li=1:0.01 (mass ratio), whereby an electron injecting layer 115 was formed. A thickness thereof was set to be 50 nm. Finally, aluminum was formed to be 200 nm thick as a second electrode 102 which functions as a cathode, whereby a light emitting element of the present invention was obtained. Note that, in the above desposition process, all deposition was performed by a resistance heating method.

After the light emitting element was sealed in a glove box with a nitrogen atmosphere so as not to expose the light emitting element to the air, operation characteristics of the light emitting element were measured. Note that the measurement was performed at room temperature (an atmosphere kept at 25° C.).

Figure 22A:
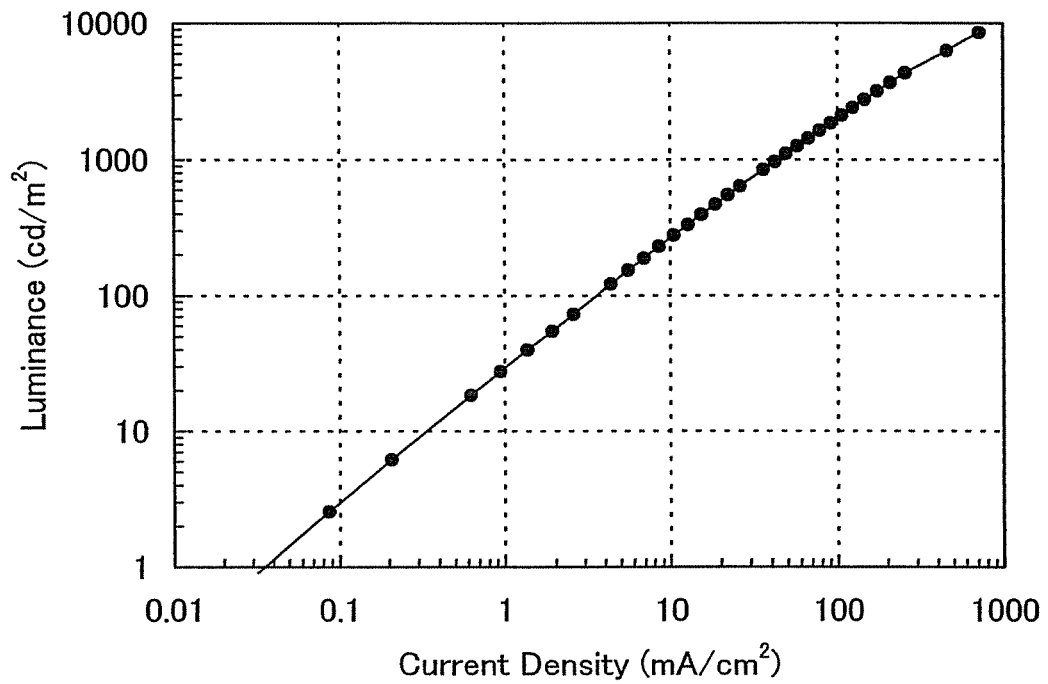
FIGS. 22A and 22B are diagrams each showing operation characteristics of a light emitting element of Embodiment 5.
Figure 22B:
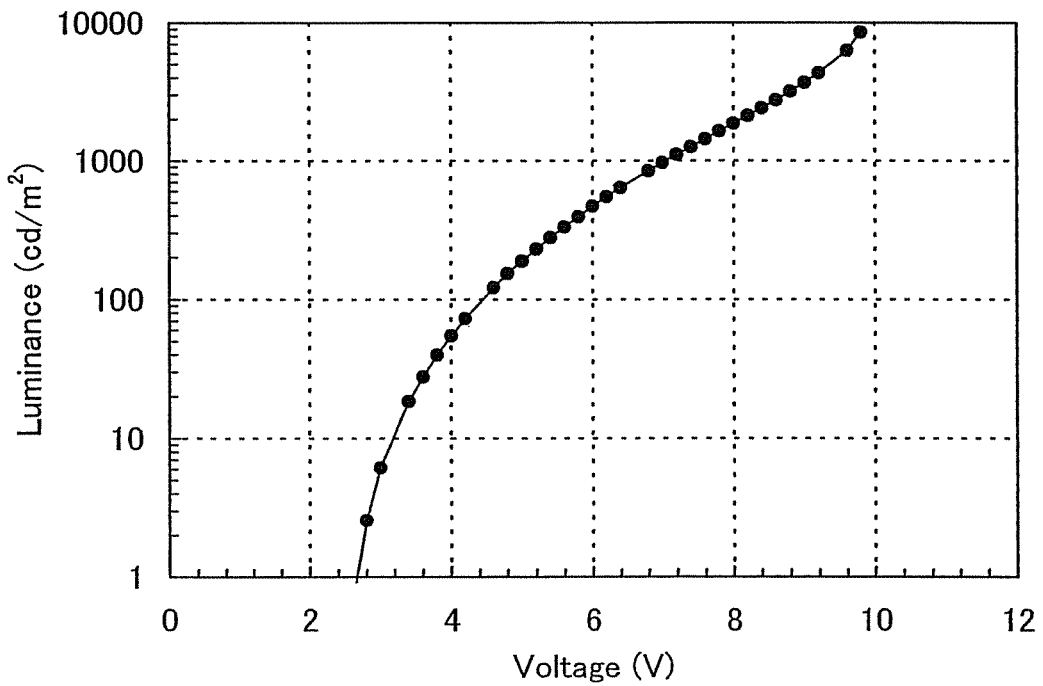

FIGS. 22A and 22B show current density-luminance characteristics and voltage-luminance characteristics of the light-emitting element, respectively. When a voltage of 7.0 V was applied, current flowed at a current density of 42.1 mA/cm$^2$ and light was emitted at a luminance of 965 cd/m$^2$ in the light emitting element of Embodiment 5. Therefore, it was found that the light emitting element of the present invention operates with low voltage. When a voltage of 7.0 V was applied, the CIE chromaticity coordinates of the light emitting element of Embodiment 5 were (x, y)=(0.70, 0.29) and emission of dark red light from Ir(Fdpq)$_2$(acac) which was a guest material was obtained.

Figure 23A:
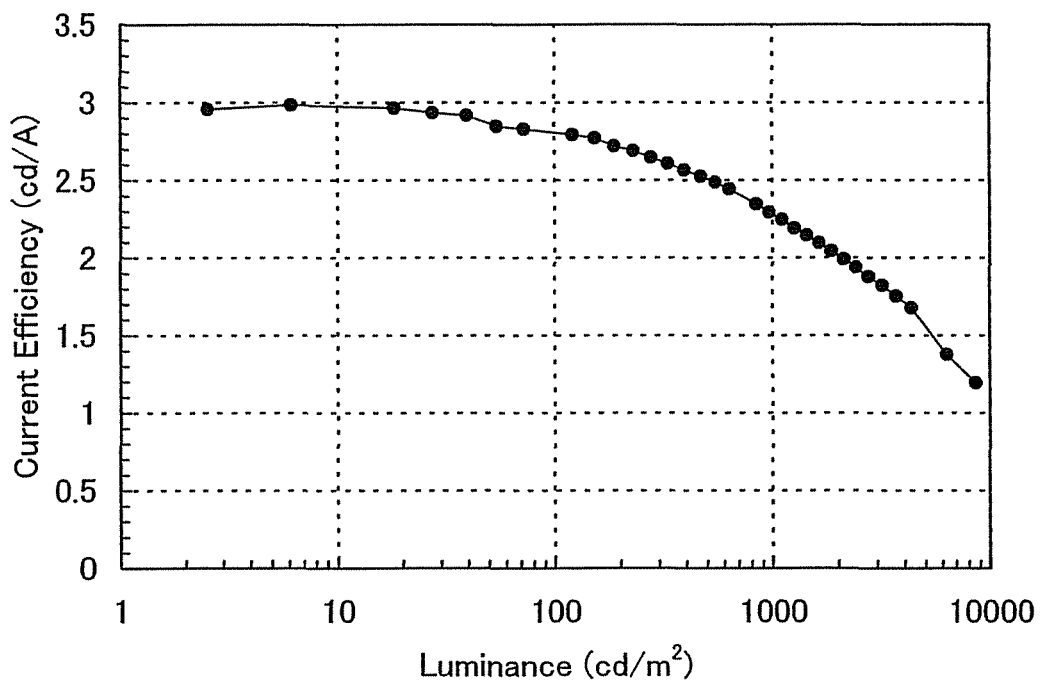
FIGS. 23A and 23B are diagrams each showing operation characteristics of a light emitting element of Embodiment 5.
Figure 23B:
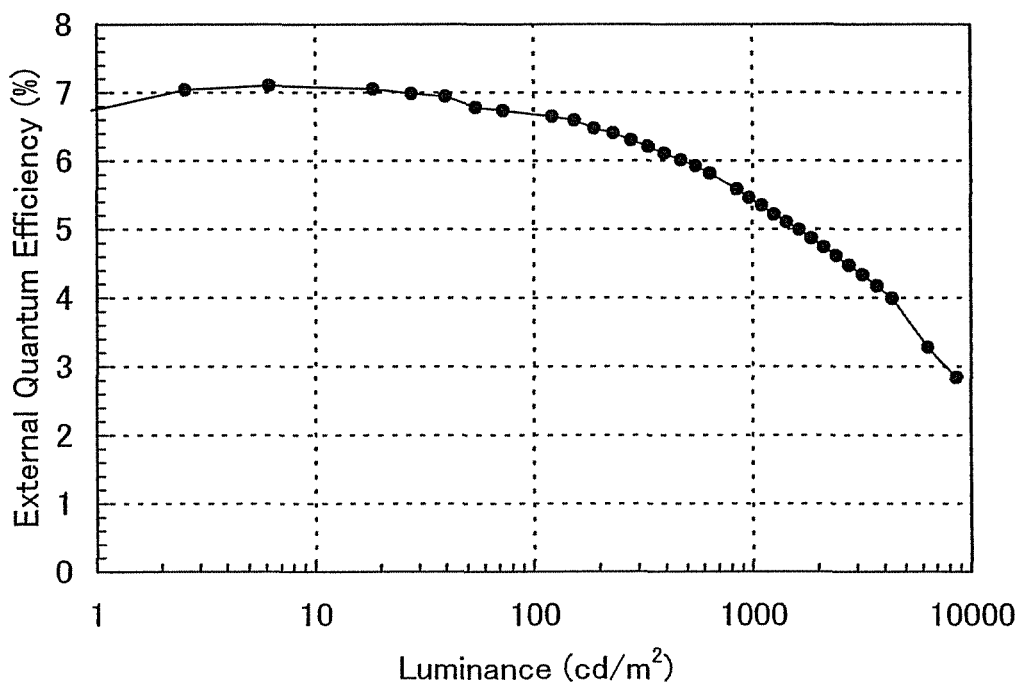

In addition, FIG. 23A shows luminance-current efficiency characteristics of the light emitting element. In FIG. 23B, the vertical axis of FIG. 23A was converted to external quantum efficiency. According to FIGS. 23A and 23B, although the light emitting element of Embodiment 5 exhibits emission of dark red light with low luminosity, the maximum light emitting efficiency was 2.99 cd/A which is extremely high light emitting efficiency. In addition, the external quantum efficiency at that time was 7.10%.

As described above, when the oxadiazole derivative of the present invention is used as a host material of the light emitting layer and the phosphorescent compound is used as a guest material to manufacture the light emitting element, it is possible to obtain a light emitting element with high light emitting efficiency and low driving voltage. Therefore, by implementing the present invention, a light emitting element with low power consumption can be obtained.

[Embodiment 6]

Embodiment 6 will specifically show an example of a blue light emitting element using the oxadiazole derivative YGAO11 of the present invention synthesized in Synthesis Example 1 of Embodiment 1 as an exciton blocking layer. FIG. 2 shows an element structure.

<<Manufacturing of a Light Emitting Element of Embodiment 6>>

First, a glass substrate with a thickness of 110 nm, over which indium tin oxide containing silicon oxide (ITSO) is formed, is prepared. The periphery of the ITSO surface was covered with an insulating film so that a surface of 2 mm×2 mm was exposed. Note that ITSO is a first electrode 201 which functions as an anode of a light emitting element. As pretreatment for forming a light emitting element over the substrate, the surface of the substrate was cleaned with a porous resin brush, baked at 200° C. for 1 hour, and subjected to UV ozone treatment for 370 seconds.

Subsequently, the substrate was fixed to a holder provided in a vacuum deposition apparatus so that the surface provided with ITSO faced downward.

After pressure in the vacuum deposition apparatus was reduced to 10$^{-4}$ Pa, NPB and molybdenum oxide (VI) were codeposited so as to meet NPB:molybdenum oxide (VI)=4:1 (mass ratio), whereby a hole injecting layer 211 was formed. A thickness thereof was set to be 50 nm. Next, NPB was deposited to be 10 nm thick, whereby a hole transporting layer 212 was formed. Further, over the hole transporting layer 212, the oxadiazole derivative YGAO11 of the present invention was deposited to be 2 nm thick, whereby an exciton blocking layer 220a was formed. In addition, CzPA represented by the following structural formula (viii) and YGAPA represented by the following structural formula (ix) were codeposited so as to meet CzPA:YGAPA=1:0.04 (mass ratio), whereby a light emitting layer 213 was formed. A thickness thereof was set to be 30 nm. Then, Alq$_3$ was deposited to be 10 nm thick, whereby an electron transporting layer 214 was formed. Further, over the electron transporting layer 214, Alq$_3$ and lithium (Li) were codeposited so as to meet Alq$_3$:Li=1:0.01 (mass ratio), whereby an electron injecting layer 215 was formed. A thickness thereof was set to be 20 nm. Finally, aluminum was formed to be 200 nm thick as a second electrode 202 which functions as a cathode, whereby a light emitting element of the present invention was obtained. Note that, in the above deposition process, all deposition was performed by a resistance heating method.

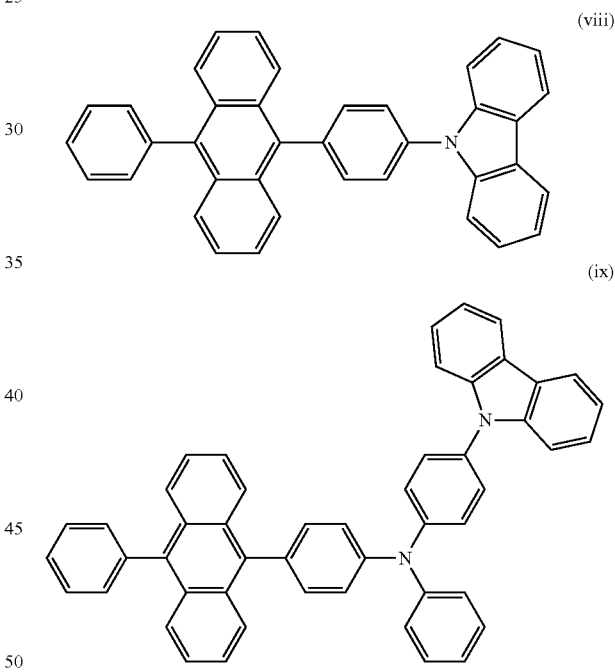

<<Manufacturing of a Light Emitting Element of Comparative Example 2>>

For comparison, a light emitting element of Comparative Example 2 was manufactured in a manner similar to that of Embodiment 6 except that the exciton blocking layer 220a in the light emitting element of Embodiment 6 was not provided.

<<Operation Characteristics of Light Emitting Elements of Embodiment 6 and Comparative Example 2>>

After the light-emitting elements of Embodiment 6 and Comparative Example 2 obtained as described above were sealed in a glove box with a nitrogen atmosphere so as not to expose the light-emitting elements to the air, operation characteristics of the light-emitting elements were measured.

Note that the measurements were performed at room temperature (an atmosphere kept at 25° C.).

Figure 24A:
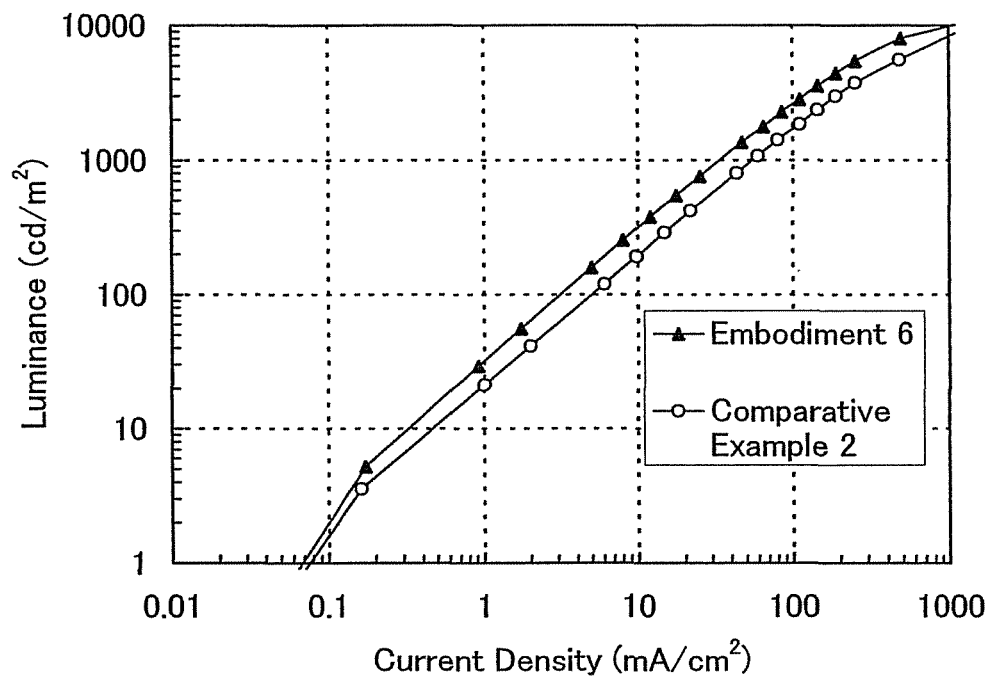
FIGS. 24A and 24B are diagrams each showing operation characteristics of light emitting elements of Embodiment 6 and Comparative Example 2.
Figure 24B:
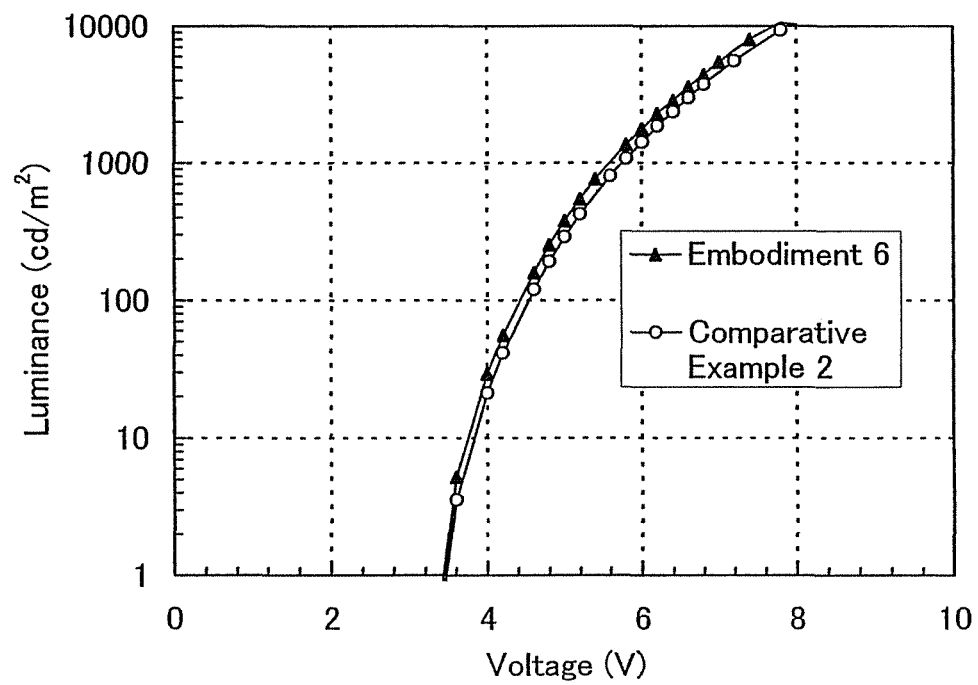
Figure 25:
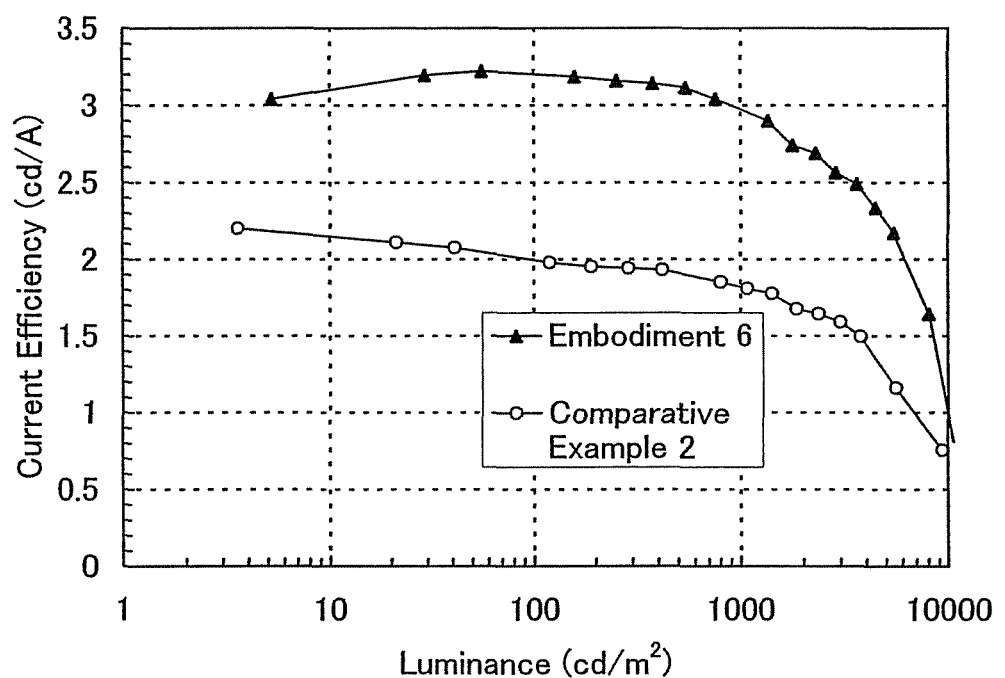
FIG. 25 is a diagram showing operation characteristics of light emitting elements of Embodiment 6 and Comparative Example 2.

FIGS. 24A and 24B show current density-luminance characteristics and voltage-luminance characteristics of the light emitting elements of Embodiment 6 and Comparative Example 2, respectively. According to FIGS. 24A and 24B, it is found that the voltage-luminance characteristics are equivalent, but as for the current density-luminance characteristics, the light emitting element of Embodiment 6 is superior. In other words, as shown in luminance-current efficiency characteristics of FIG. 25, current efficiency is higher in the light emitting element of Embodiment 6. When a voltage of 5.2 V was applied (luminance of the light emitting element of Embodiment 6 was 546 cd/m$^2$ and luminance of the light emitting element of Comparative Example 2 was 421 cd/m$^2$), the CIE chromaticity coordinates of the light emitting element of Embodiment 6 were (x, y)=(0.15, 0.13), the CIE chromaticity coordinates of the light emitting element of Comparative Example 2 were (x, y)=(0.15, 0.14), and emission of blue light from YGAPA which was a guest material was obtained in either case.

As described above, when the oxadiazole derivative of the present invention is used as an exciton blocking layer, it is possible to obtain a light emitting element with high light emitting efficiency. Therefore, by implementing the present invention, a light emitting element with low power consumption can be obtained.

[Embodiment 7]

This embodiment will explain a synthesis method of 9-(4-{N-[4-(9-carbazolyl)phenyl]-N-phenylamino}phenyl)-10-phenylanthracene (abbreviation: YGAPA) represented by the structural formula (201) used for the light emitting element manufactured in other embodiments.

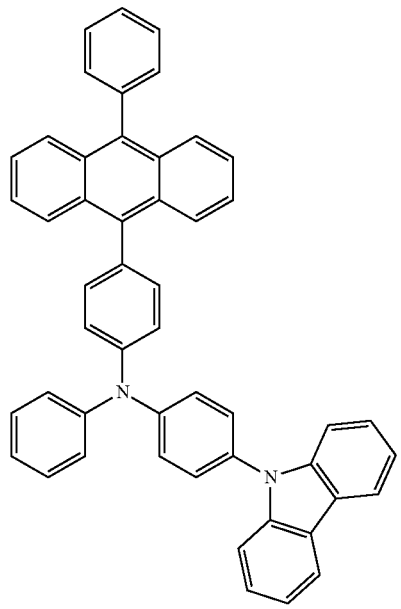

(201)

[Step 1]

A synthesis method of 9-phenyl-10-(4-bromophenyl)anthracene (abbreviation: PA) will be explained.

(i) Synthesis of 9-phenylanthracene

The following shows a synthesis scheme (f-1) of 9-phenylanthracene.

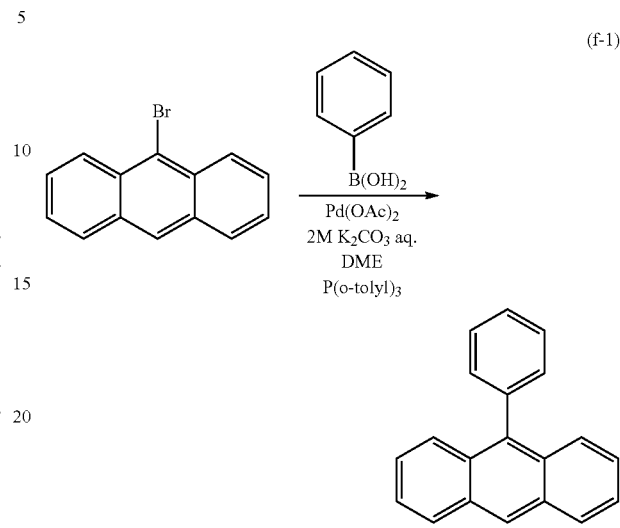

(f-1)

5.4 g (21.1 mmol) of 9-bromoanthracene, 2.6 g (21.1 mmol) of phenylboronic acid, 60 mg (0.21 mmol) of palladium acetate (Pd(OAc)$_2$), 10 mL (20 mmol) of a potassium carbonate (K$_2$CO$_3$) aqueous solution (2 mol/L), 263 mg (0.84 mmol) of tri(o-tolyl)phosphine (P(o-tolyl)$_3$), and 20 mL of 1,2-dimethoxyethane (abbreviation: DME) were mixed and stirred at 80° C. for 9 hours. After the reaction, the precipitated solid was collected by suction filtration, dissolved in toluene, and filtered through Florisil, Celite, and alumina. The filtrate was washed with water and a saturated saline solution and then dried with magnesium sulfate. After the solution was filtered naturally and the filtrate was concentrated, 21.5 g of a light brown solid of 9-phenylanthracene that was an object was obtained (yield: 85%).

(ii) Synthesis of 10-bromo-9-phenylanthracene

The following shows a synthesis scheme (f-2) of 10-bromo-9-phenylanthracene.

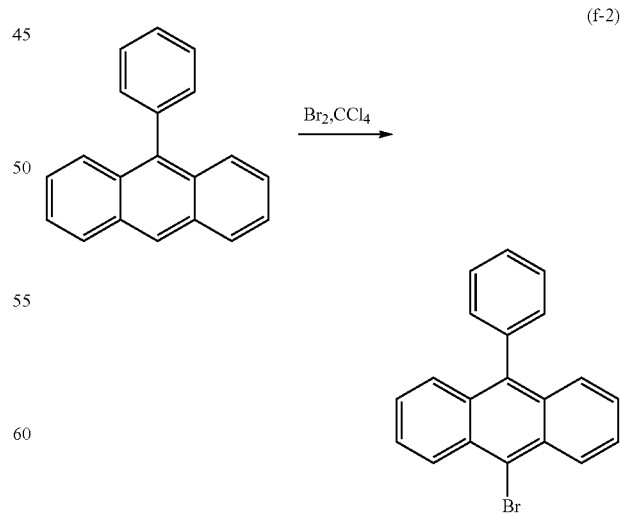

(f-2)

After 6.0 g (23.7 mmol) of 9-phenylanthracene was dissolved in 80 mL of carbon tetrachloride, a solution of 3.80 g (21.1 mmol) of bromine dissolved in 10 mL of carbon tetrachloride was dripped through a dropping funnel into the reaction solution. After the dripping, the solution was stirred at room temperature for one hour. After the reaction, a sodium thiosulfate aqueous solution was added to stop the reaction. An organic layer was washed with a sodium hydroxide (NaOH) aqueous solution and a saturated saline solution and dried with magnesium sulfate. After the solution was filtered naturally, the filtrate was concentrated, dissolved in toluene, and filtered through Florisil, Celite, and alumina. When the filtrate was concentrated and recrystallized with dichloromethane and hexane, 7.0 g of a light yellow solid of 10-bromo-9-phenylanthracene that was an object was obtained (yield: 89%).

(iii) Synthesis of 9-iodo-10-phenylanthracene

The following shows a synthesis scheme (f-3) of 9-iodo-10-phenylanthracene.

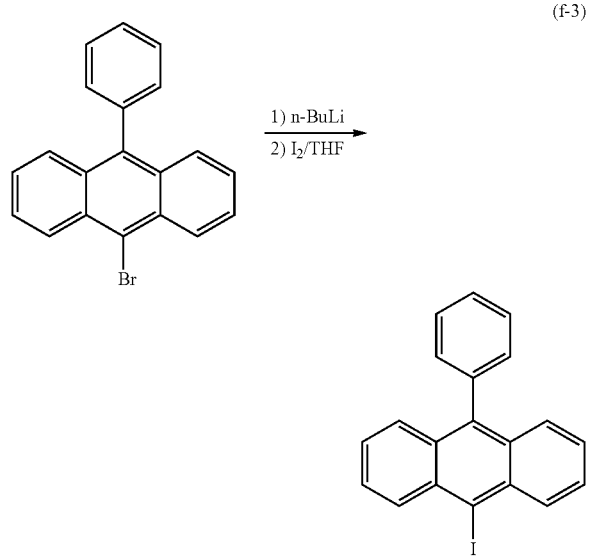

After 3.33 g (10 mmol) of 9-bromo-10-phenylanthracene was dissolved in 80 mL of tetrahydrofuran (abbreviation: THF) and cooled to −78° C., 7.5 mL (12.0 mmol) of n-BuLi (1.6 mol/L) was dripped through a dropping funnel into the reaction solution, and the mixture was stirred for one hour. Subsequently, a solution of 5 g (20.0 mmol) of iodine dissolved in 20 mL of THF was dripped, and the solution was stirred further at −78° C. for 2 hours. After the reaction, a sodium thiosulfate aqueous solution was added to stop the reaction. An organic layer was washed with a sodium thiosulfate aqueous solution and a saturated saline solution and dried with magnesium sulfate. After the solution was filtered naturally, the filtrate was concentrated and recrystallized with ethanol; thus, 3.1 g of a light yellow solid of 9-iodo-10-phenylanthracene that was an object was obtained (yield: 83%).

(iv) Synthesis of 9-phenyl-10-(4-bromophenyl)anthracene (abbreviation: PA)

The following shows a synthesis scheme (f-4) 9-phenyl-10-(4-bromophenyl)anthracene (abbreviation: PA).

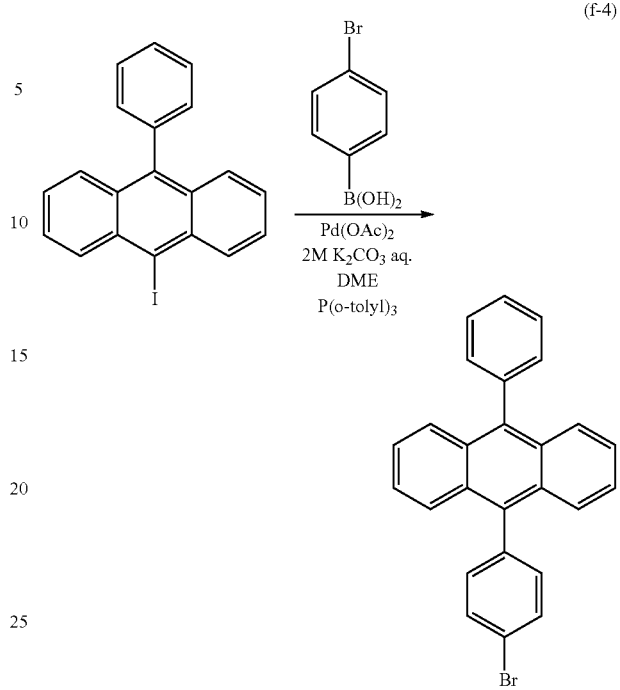

1.0 g (2.63 mmol) of 9-iodo-10-phenylanthracene, 542 mg (2.70 mmol) of p-bromophenylboronic acid, 46 mg (0.03 mmol) of tetrakis(triphenylphosphine)palladium (0) (Pd (PPh$_3$)$_4$), 3 mL (6 mmol) of a potassium carbonate (K$_2$CO$_3$) aqueous solution (2 mol/L), and 10 mL of toluene were stirred at 80° C. for 9 hours. After the reaction, toluene was added therein, and the mixture was filtered through Florisil, Celite, and alumina. The filtrate was washed with water and a saturated saline solution and then dried with magnesium sulfate. After the solution was filtered naturally, the filtrate was concentrated and recrystallized with chloroform and hexane; thus, 562 mg of a light brown solid of 9-phenyl-10-(4-bromophenyl)anthracene that was an object was obtained (yield: 45%).

[Step 2]

A synthesis method of 9-(4-{N-[4-(9-carbazolyl)phenyl]-N-phenylamino}phenyl)-10-phenylanthracene (abbreviation: YGAPA) will be explained. The following shows a synthesis scheme (f-5) of 9-(4-{N-[4-(9-carbazolyl)phenyl]-N-phenylamino}phenyl)-10-phenylanthracene (abbreviation: YGAPA).

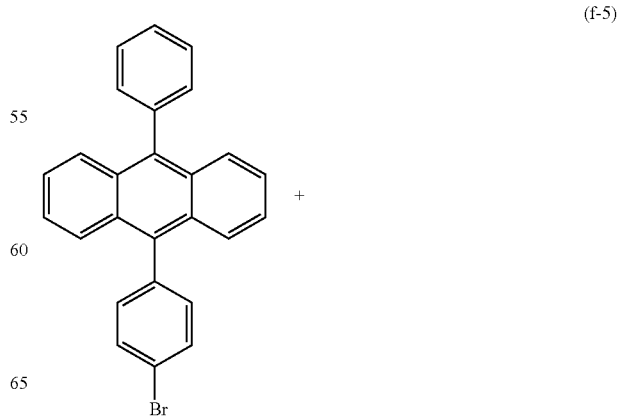

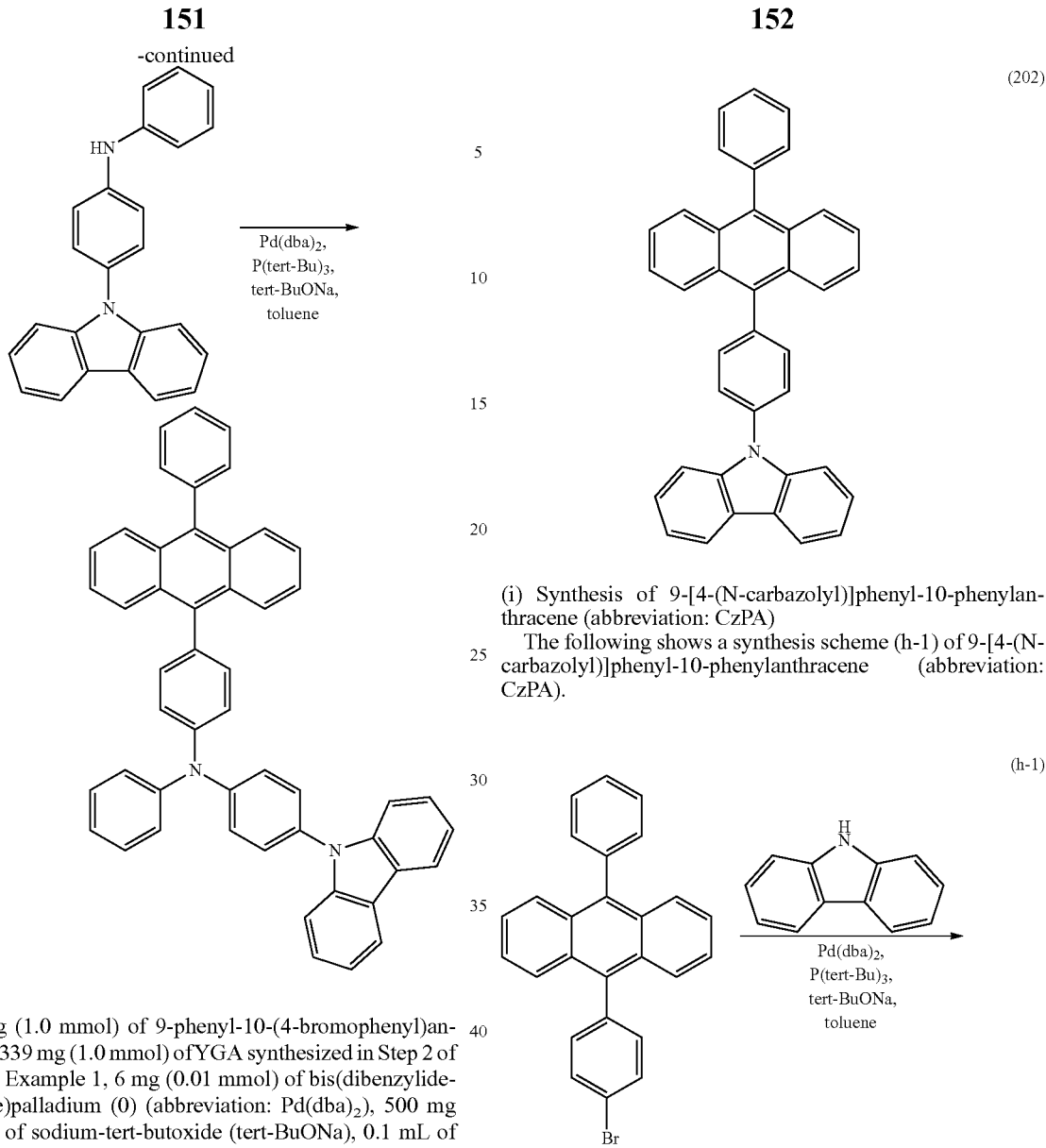

Figure 26A:
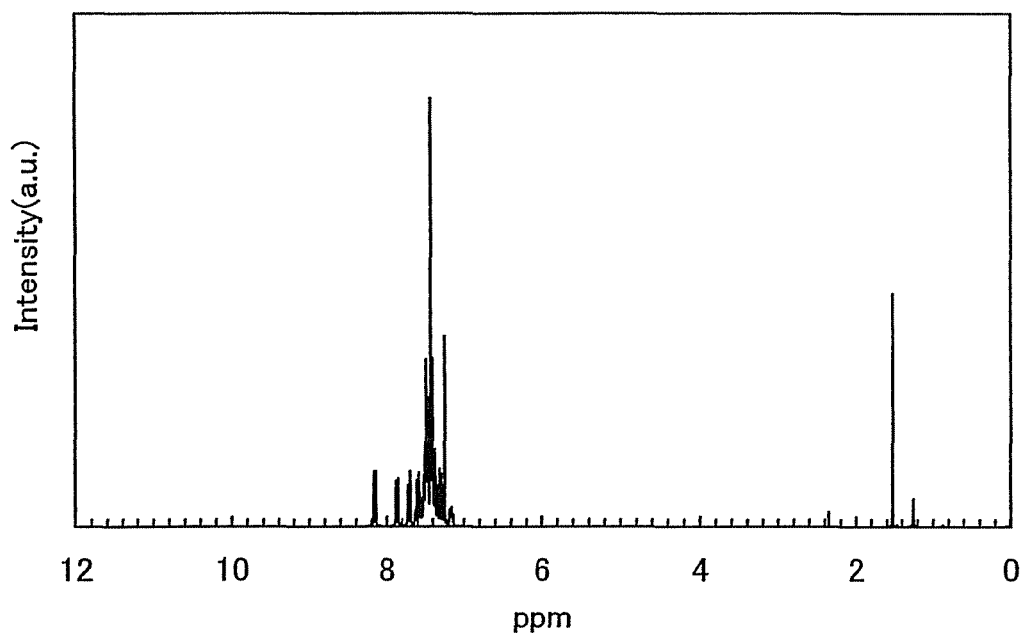
FIGS. 26A and 26B are diagrams each showing an $^1$H-NMR chart of 9-(4-{N-[4-(9-carbazolyl)phenyl]-N-phenylamino}phenyl)-10-phenylanthracene.
Figure 26B:
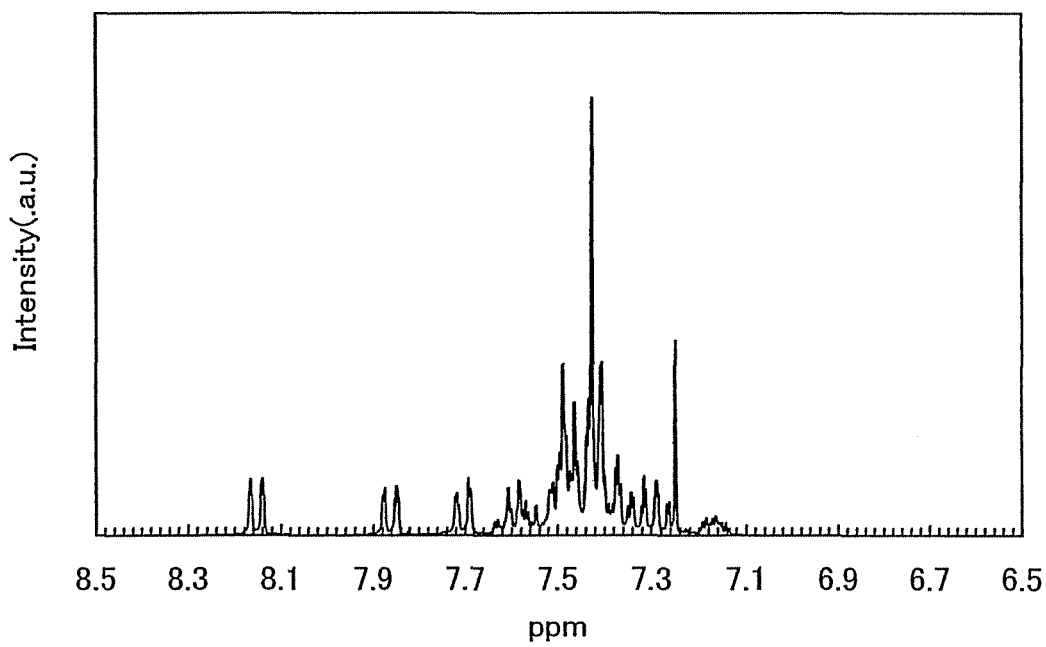

409 mg (1.0 mmol) of 9-phenyl-10-(4-bromophenyl)anthracene, 339 mg (1.0 mmol) of YGA synthesized in Step 2 of Synthesis Example 1, 6 mg (0.01 mmol) of bis(dibenzylideneacetone)palladium (0) (abbreviation: Pd(dba)$_2$), 500 mg (5.2 mol) of sodium-tert-butoxide (tert-BuONa), 0.1 mL of tri(tert-butyl)phosphine (P(tert)-Bu)$_3$), and 10 mL of toluene were stirred at 80° C. for four hours. After the reaction, the solution was washed with water, a water layer was extracted with toluene, and the water layer as well as an organic layer was washed with a saturated saline solution and then dried with magnesium sulfate. After the solution was filtered naturally and concentrated, an obtained oily substance was purified by silica gel column chromatography (hexane:toluene=7:3) and recrystallized with dichloromethane and hexane. Then, 534 mg of a yellow powdered solid of YGAPA that was an object was obtained (yield: 81%). When this compound was measured by nuclear magnetic resonance spectrometry (NMR), it was confirmed that the compound was 9-(4-{N-[4-(9-carbazolyl)phenyl]-N-phenylamino}phenyl)-10-phenylanthracene (abbreviation: YGAPA). FIGS. 26A and 26B show $^1$H-NMR charts of YGAPA.

[Embodiment 8]

This embodiment will explain a synthesis method of 9-[4-(N-carbazolyl)]phenyl-10-phenylanthracene (abbreviation: CzPA) represented by the structural formula (202) used for the light emitting element manufactured in other embodiments.

(i) Synthesis of 9-[4-(N-carbazolyl)]phenyl-10-phenylanthracene (abbreviation: CzPA)

The following shows a synthesis scheme (h-1) of 9-[4-(N-carbazolyl)]phenyl-10-phenylanthracene (abbreviation: CzPA).

A mixture of 1.3 g (3.2 mmol) of 9-phenyl-10-(4-bromophenyl)anthracene, 578 mg (3.5 mmol) of carbazole, 50 mg (0.017 mmol) of bis(dibenzylideneacetone)palladium (0), 1.0 mg (0.010 mmol) of t-butoxysodium, 0.1 mL of tri(t-butylphosphine), and 30 mL of toluene was heated and refluxed at 110° C. for 10 hours. After the reaction, the solution was washed with water, a water layer was extracted with toluene, and the water layer as well as an organic layer was washed with a saturated saline solution and then dried with magnesium sulfate. After the solution was filtered naturally and concentrated, an obtained oily substance was purified by silica gel column chromatography (hexane:toluene=7:3) and recrystallized with dichloromethane and hexane. Then, 1.5 g of 9-[4-(N-carbazolyl)]phenyl-10-phenylanthracene (abbreviation: CzPA) that was an object was obtained (yield: 93%). When 5.50 g of the obtained CzPA was sublimed and purified for 20 hours under the conditions of a temperature of 270° C., in argon air (flow rate: 3.0 mL/min), and a pressure of 6.7 Pa, 3.98 g of CzPa was collected at a yield of 72%.

The NMR data of the obtained CzPa is shown below.

$^1$H-NMR (300 MHz, CDCl$_3$): δ=8.22 (d, J=7.8 Hz, 2H), δ=7.86-7.82 (m, 3H), and δ=7.61-7.36 (m, 20H).

Figure 27:
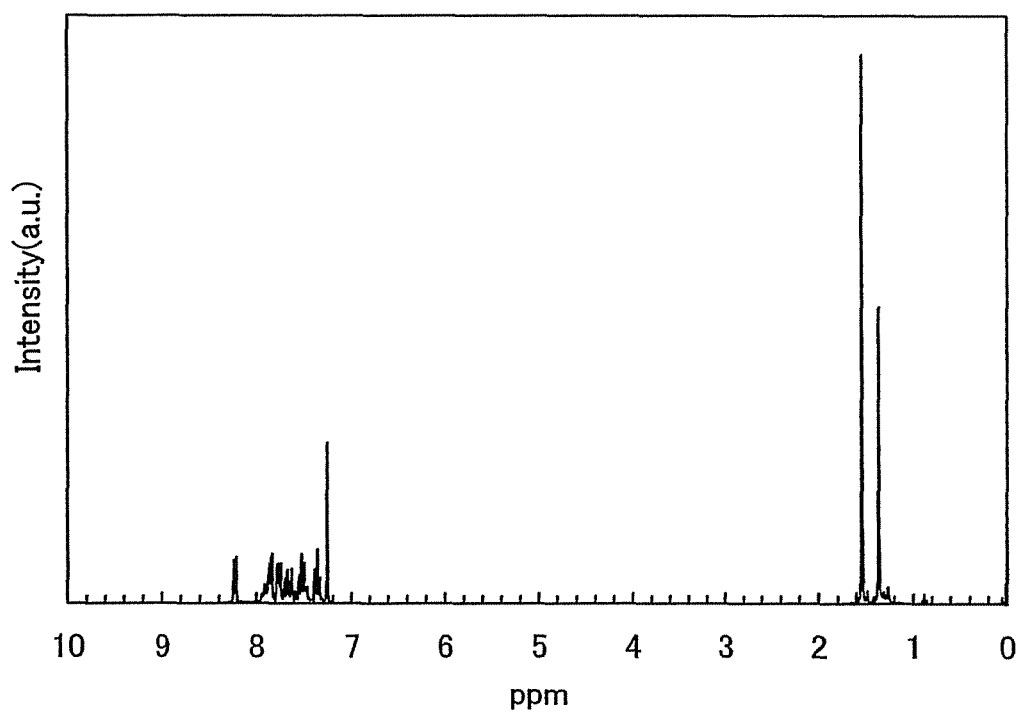
FIG. 27 is a diagram showing an $^1$H-NMR chart of 9-[4-(N-carbazolyl)]phenyl-10-phenylanthracene.

In addition, FIG. 27 shows an $^1$H-NMR chart.

[Embodiment 9]

SYNTHESIS EXAMPLE 4

Synthesis Example 4 will specifically show a synthesis example of 2-(3-{N-[4-(carbazol-9-yl)phenyl]-N-phenylamino}phenyl)-5-phenyl-1,3,4-oxadiazole (abbreviation: mYGAO11) that is the oxadiazole derivative of the present invention represented by the structural formula (68) of Embodiment Mode 1.

(86)

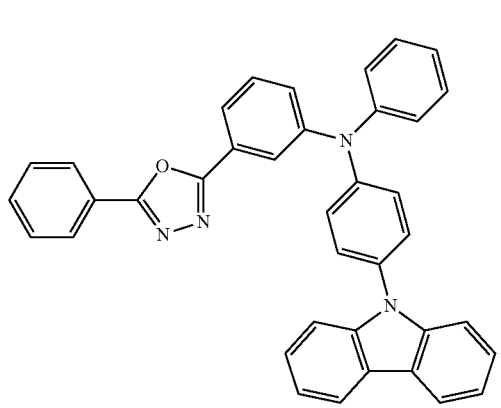

Step 1: Synthesis of
2-(3-bromophenyl)-5-phenyl-1,3,4-oxadiazole
(abbreviation: mO11Br)

In Step 1, mO11Br was synthesized according to (i) to (iii) shown below.

(i) Synthesis of 3-bromobenzoylhydrazine

First, 10 g (44 mmol) of ethyl-3-bromobenzoate was put in a 200-mL three-neck flask, 50 mL of ethanol was added therein, and the mixture was stirred. Thereafter, 12 mL of hydrazine monohydrate was added therein, and the mixture was stirred at 78° C. for 5 hours so as to be reacted. After the reaction, water was added to the reaction solution, and a solid was precipitated. The precipitated solid was collected by suction filtration. The obtained solid was put in approximately 500 mL of water, washed, and again collected by suction filtration; thus, 8.1 g of a white solid that was an object was obtained (yield: 86%).

(ii) Synthesis of 1-benzoyl-2-(3-bromobenzoyl)hydrazine

Subsequently, 5.0 g (23 mmol) of 3-bromobenzohydrazine obtained in (i) above was put in a 300-mL three-neck flask, 10 mL of N-methyl-2-pyrrolidone was added therein, and the mixture was stirred. Thereafter, a mixed solution of 10 mL of N-methyl-2-pyrrolidone and 3.2 mL (28 mmol) of benzoyl chloride was dripped to the above mixture through a 50-mL dropping funnel. After the dripping, the mixture was heated and stirred at 80° C. for 3 hours so as to be reacted. After the reaction, water was added to the reaction solution, and a solid was precipitated. The precipitated solid was collected by suction filtration to obtain another solid. The obtained solid was washed with approximately 1 L of water and collected by suction filtration. The collected solid was washed with methanol and collected by suction filtration; thus, 7.1 g of a white solid that was an object was obtained (yield: 96%).

(iii) Synthesis of mO11Br

Further, 7.1 g (22 mmol) of 1-benzoyl-2-(3-bromobenzoyl)hydrazine obtained by the method shown in (ii) above was put in a 300-mL three-neck flask, 100 mL of phosphoryl chloride was added therein, and the mixture was heated and stirred at 100° C. for 5 hours so as to be reacted. After the reaction, a solid was obtained by completely distilling off the phosphoryl chloride in the flask. The obtained solid was washed with water and a sodium carbonate aqueous solution in this order and collected by suction filtration. Then, the collected solid was recrystallized with methanol; thus, 4.9 g of a white solid that was an object was obtained (yield: 73%). A synthesis scheme of Step 1 described above is shown in the following scheme (a-4).

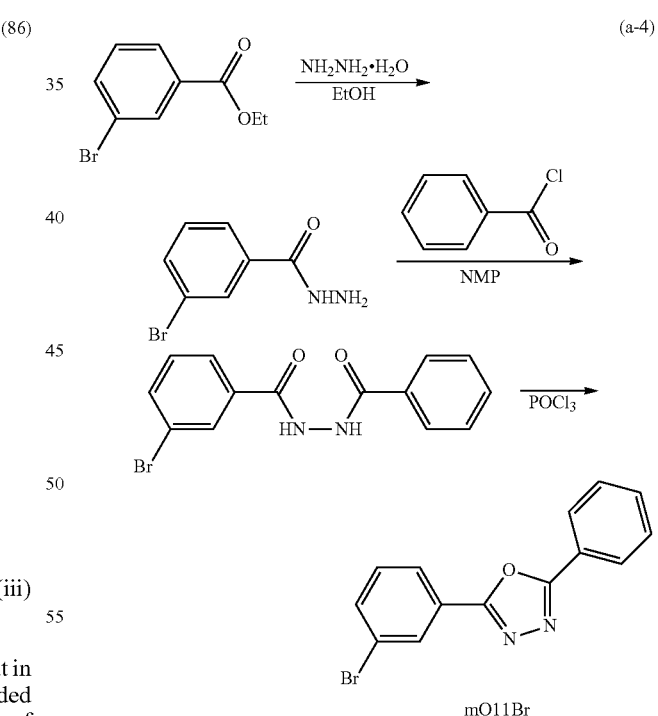

(a-4)

Step 2: Synthesis of 2-(3-{N-[4-(carbazol-9-yl)phenyl]-N-phenylamino}phenyl)-5-phenyl-1,3,4-oxadiazole (abbreviation: mYGAO11)

2.0 g (6.6 mmol) of 2-(3-bromophenyl)-5-phenyl-1,3,4-oxadiazole (abbreviation: mO11Br) obtained in Step 1, 2.2 g (6.6 mmol) of 4-(carbazol-9-yl)diphenylamine (abbreviation: YGA) obtained in Step 2 of Synthesis Example 1, 1.3 g (13 mmol) of sodium-tert-butoxide, and 0.1 g (0.2 mmol) of bis(dibenzylideneacetone)palladium(0) were put in a 100-mL three-neck flask, and nitrogen was substituted for air in the flask. Then, 40 mL of toluene and 0.1 mL of a 10% hexane solution of tri(tert-butyl)phosphine were added to the mixture, and the mixture was heated and stirred at 80° C. for 5 hours. After the reaction, toluene was added to the reaction mixture, and the suspension was collected by suction filtration through Celite. The obtained filtrate was washed with water, a saturated sodium hydrogen-carbonate aqueous solution, and a saturated saline solution in this order. An organic layer and a water layer were separated, and the organic layer was dried with magnesium sulfate. The mixture was collected by suction filtration, the magnesium sulfate was removed, and the filtrate was concentrated to obtain a solid. The obtained solid was dissolved in toluene and purified by silica gel column chromatography. Purification by column chromatography was performed by using toluene as a developing solvent and then using a mixed solvent of toluene:ethyl acetate=1:4 as a developing solvent. An obtained fraction was concentrated to obtain a solid. The obtained solid was recrystallized with a mixed solvent of chloroform and hexane; thus, 2.6 g of a white solid that was an object was obtained (yield: 71%). The synthesis scheme of Step 3 as described above is shown in the following scheme (c-4).

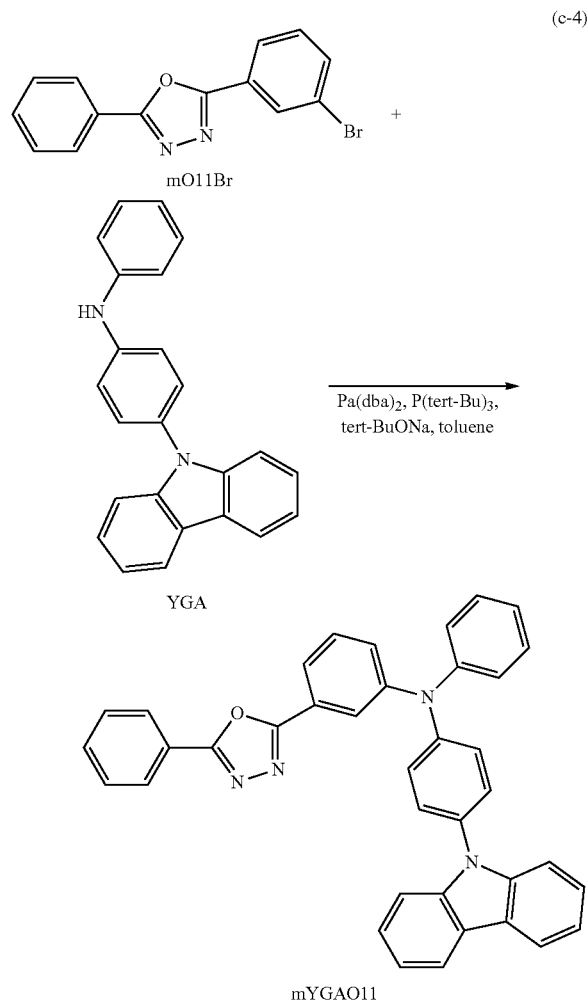

Figure 29A:
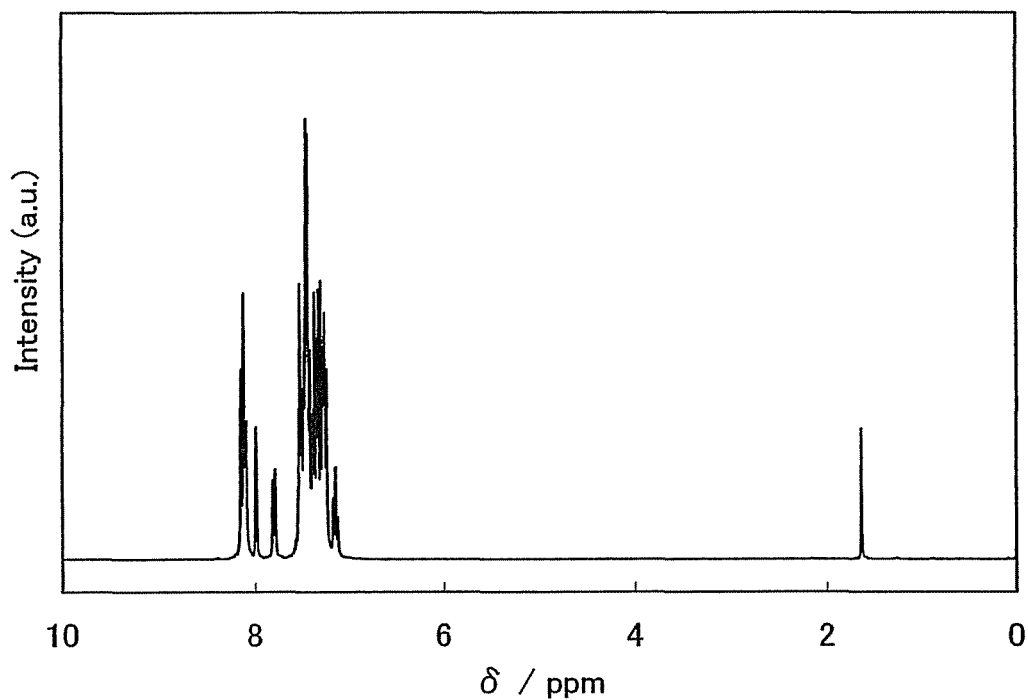
FIGS. 29A and 29B are diagrams each showing an $^1$H-NMR chart of an oxadiazole derivative mYGAO11 of the present invention.
Figure 29B:
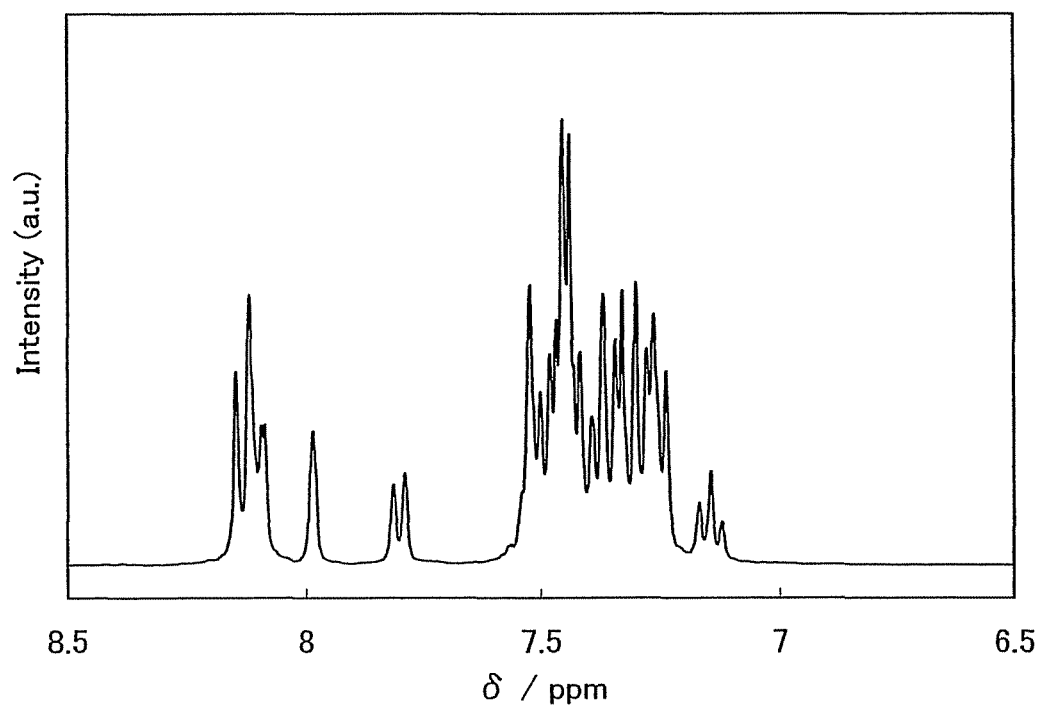

The following shows a result of analyzing mYGAO11 that was obtained by nuclear magnetic resonance spectroscopy ($^1$H-NMR). FIG. 29A shows an $^1$H-NMR chart and FIG. 29B shows an enlarged chart thereof. Accordingly, it was found that the oxadiazole derivative mYGAO11 of the present invention represented by the structural formula (68) was obtained in Synthesis Example 4.

$^1$H-NMR (CDCl$_3$, 300 MHz,): δ=7.11-7.19 (m, 1H), δ=7.20-7.55 (m, 19H), 7.80 (d, J=7.3 Hz, 1H), 7.98 (s, 1H), 8.07-8.19 (m, 4H)

In addition, sublimation purification of the obtained white solid was performed by a train sublimation method. Under a reduced pressure of 7.0 Pa, sublimation purification was performed by heating a material at 272° C. for 3 hours, setting the flow rate of argon to be 3.0 mL/min. When sublimation purification was performed on 1.6 g of mYGAO11, the yield was 1.0 g and 63%.

Figure 30:
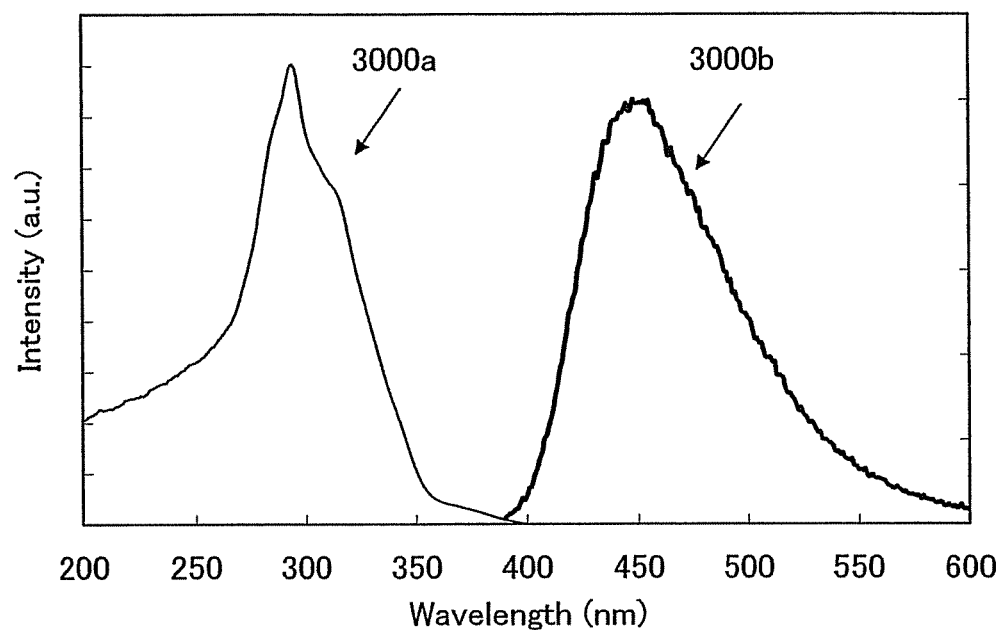
FIG. 30 is a diagram showing an ultraviolet/visible absorption spectrum and an emission spectrum of an oxadiazole derivative mYGAO11 of the present invention.

Next, the absorption spectrum 3000a and the emission spectrum 3000b of mYGAO11, were measured. The absorption spectrum was measured using an ultraviolet-visible spectrophotometer (V-550, by JASCO Corporation) and the emission spectrum was measured using a spectrofluorometer (FS920, by Hamamatsu Photonics K.K.). The measurement was performed at room temperature for a toluene solution. FIG. 30 shows a measurement result for the toluene solution. The horizontal axis indicates the wavelength and the vertical axis indicates the intensity of the absorption and light emission.

As shown in FIG. 30, the oxadiazole derivative mYGAO11 of the present invention has an absorption peak at 293 nm with the toluene solution. In addition, the emission spectrum has a peak at 448 nm. Note that the emission spectrum was measured through excitation of mYGAO11 at a wavelength of 314 nm.

[Embodiment 10]

Embodiment 10 will specifically show an example of a light emitting element using the oxadiazole derivative mYGAO11 of the present invention synthesized in Synthesis Example 4 of Embodiment 9 as a host material of a light emitting layer and a red phosphorescent compound as a guest material. FIG. 1 shows an element structure.

First, a glass substrate with a thickness of 110 nm, over which indium tin oxide containing silicon oxide (ITSO) is formed, is prepared. The periphery of the ITSO surface was covered with an insulating film so that a surface of 2 mm×2 mm was exposed. Note that ITSO is a first electrode 101 which functions as an anode of a light emitting element. As pretreatment for forming a light emitting element over the substrate, the surface of the substrate was cleaned with a porous resin brush, baked at 200° C. for 1 hour, and subjected to UV ozone treatment for 370 seconds.

Subsequently, the substrate was fixed to a holder provided in a vacuum deposition apparatus so that the surface provided with ITSO faced downward.

After pressure in the vacuum deposition apparatus was reduced to 10$^{-4}$ Pa, NPB and molybdenum oxide (VI) were codeposited so as to meet NPB:molybdenum oxide (VI)=4:1 (mass ratio), whereby a hole injecting layer 111 was formed. A thickness thereof was set to be 50 nm. Next, NPB was deposited to be 10 nm thick, whereby a hole transporting layer 112 was formed. Further, over the hole transporting layer 112, the oxadiazole derivative mYGAO11 of the present invention and Ir(Fdpq)$_2$(acac) represented by the following structural formula (vi) were codeposited so as to meet mYGAO11: Ir(Fdpq)$_2$(acac)=1:0.06 (mass ratio), whereby a light emitting layer 113 was formed. A thickness thereof was set to be 30 mm. Then, BAlq represented by the following structural formula (vii) was deposited to be 10 nm thick, whereby an electron transporting layer 114 was formed. Further, over the electron transporting layer 114, Alq$_3$ and lithium (Li) were codeposited so as to meet Alq$_3$:Li=1:0.01 (mass ratio), whereby an electron injecting layer 115 was formed. A thickness thereof was set to be 50 nm. Finally, aluminum was formed to be 200 nm thick as a second electrode 102 which functions as a cathode, whereby a light emitting element of the present invention was obtained. Note that, in the above deposition process, all deposition was performed by a resistance heating method.

After this light-emitting element was sealed in a glove box with a nitrogen atmosphere so as not to expose the light-emitting element to the air, operation characteristics of the light-emitting element were measured. Note that the measurements were performed at room temperature (an atmosphere kept at 25° C.).

Figure 31A:
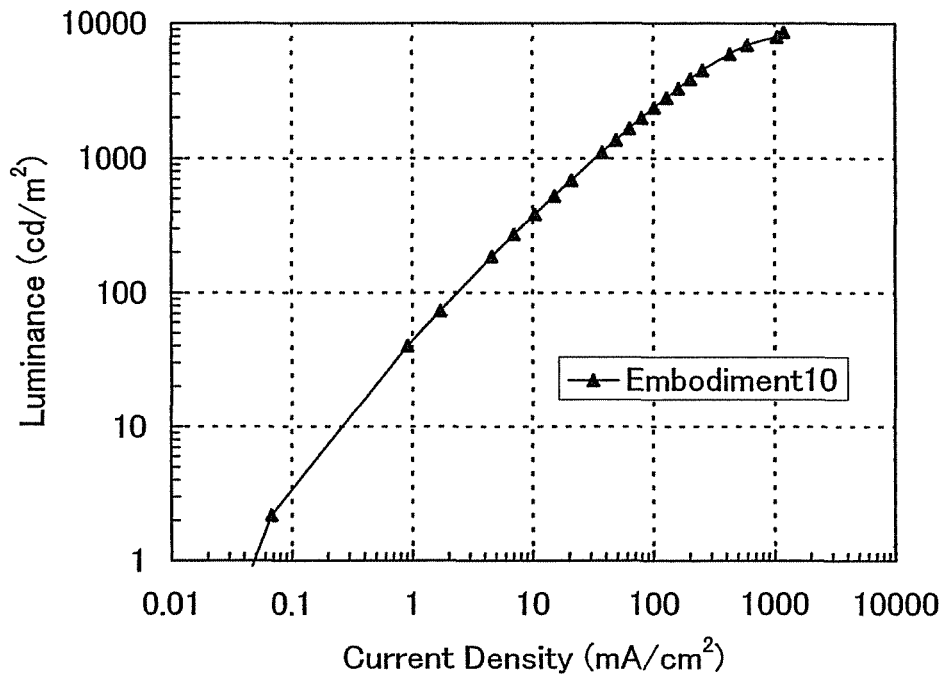
FIGS. 31A and 31B are diagrams each showing operation characteristics of a light emitting element of Embodiment 10.
Figure 31B:
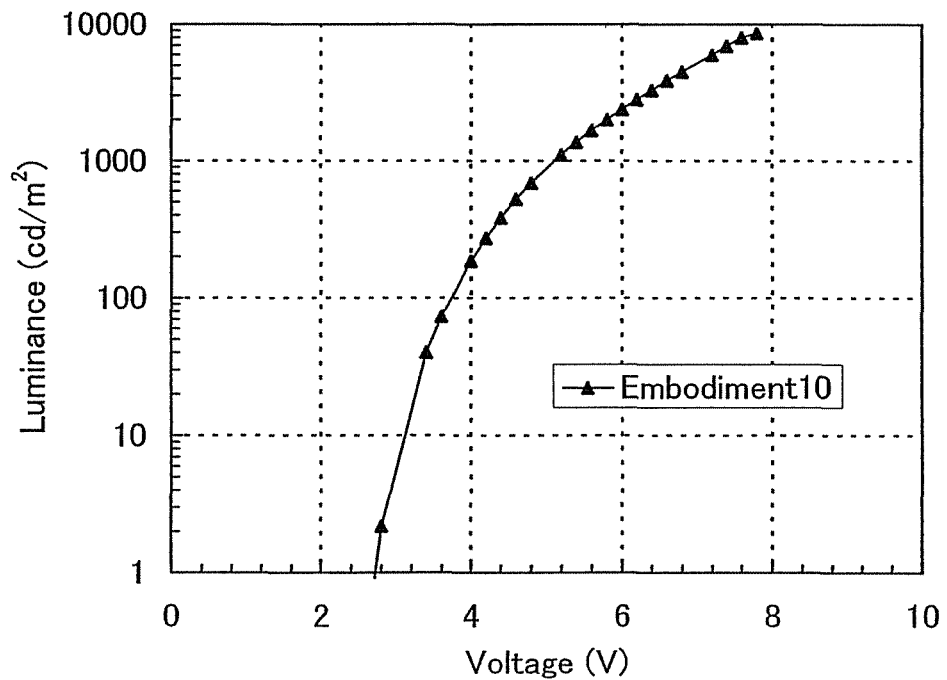

FIGS. 31A and 31B show current density-luminance characteristics and voltage-luminance characteristics of the light-emitting element, respectively. When a voltage of 5.2 V was applied, current flowed at a current density of 37.5 mA/cm$^2$ and light was emitted at a luminance of 1110 cd/m$^2$ in the light emitting element of Embodiment 10. Therefore, it was found that the light emitting element of the present invention operates with low voltage. In addition, when a voltage of 5.2 V was applied, the CIE chromaticity coordinates of the light emitting element of Embodiment 10 were (x, y)=(0.70, 0.30), and emission of dark red light from Ir(Fdpq)$_2$(acac) which was a guest material was obtained.

Figure 32:
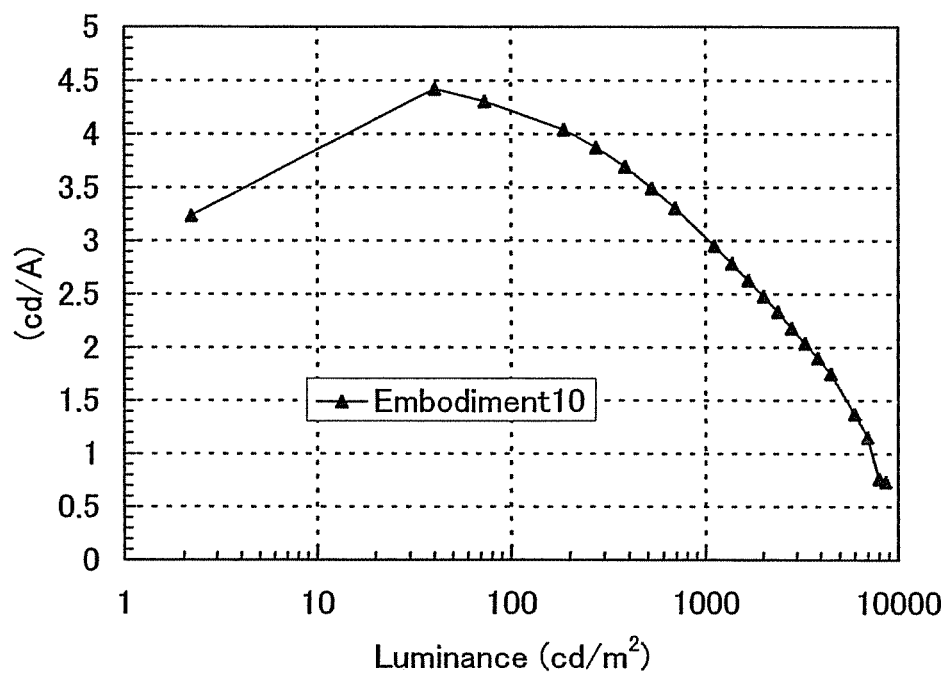
FIG. 32 is a diagram showing operation characteristics of a light emitting element of Embodiment 10.

In addition, FIG. 32 shows luminance-current efficiency characteristics of the light emitting element. According to FIG. 32, although the light emitting element of Embodiment 10 exhibits emission of dark red light with low luminosity, the maximum light emitting efficiency was 4.42 cd/A which is high light emitting efficiency. In addition, the external quantum efficiency at that time was 8.1%.

Figure 33:
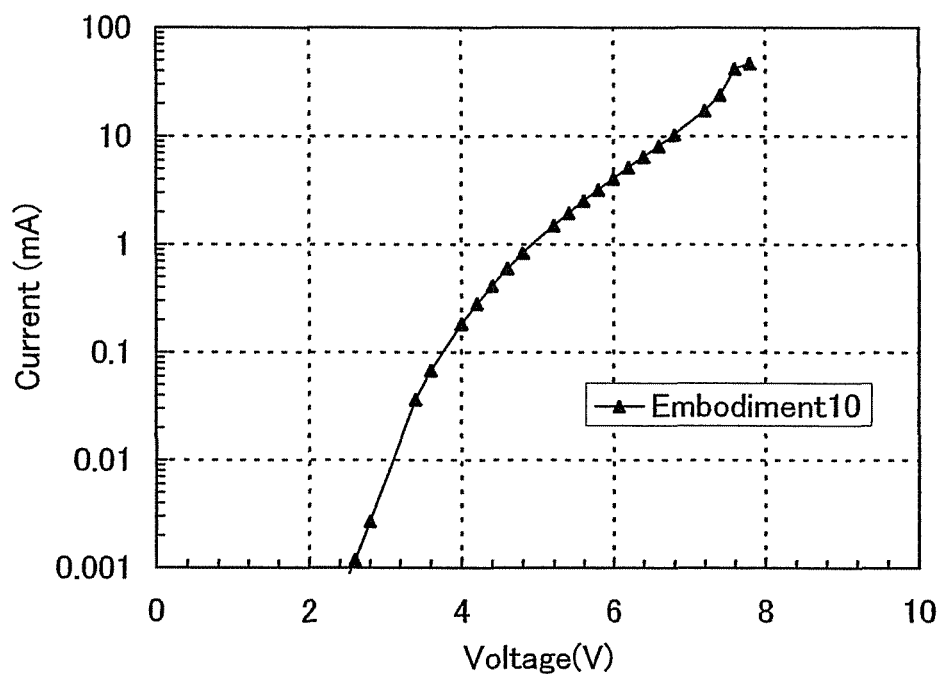
FIG. 33 is a diagram showing operation characteristics of a light emitting element of Embodiment 10.

In addition, FIG. 33 shows voltage-current characteristics of this light emitting element. According to this diagram, it is found that current flows easily in the oxadiazole derivative of the present invention, which is thought to lead reduction in driving voltage.

As described above, when the oxadiazole derivative of the present invention is used as a host material of the light emitting layer and the phosphorescent compound is used as a guest material to manufacture the light emitting element, it is possible to obtain a light emitting element with high light emitting efficiency and low driving voltage. Therefore, by implementing the present invention, a light emitting element with low power consumption can be obtained.

This application is based on Japanese Patent Application serial No. 2005-378843 filed in Japan Patent Office on Dec. 28, 2005, the entire contents of which are hereby incorporated by reference.

The invention claimed is:

1. An oxadiazole derivative represented by a general formula (G2),

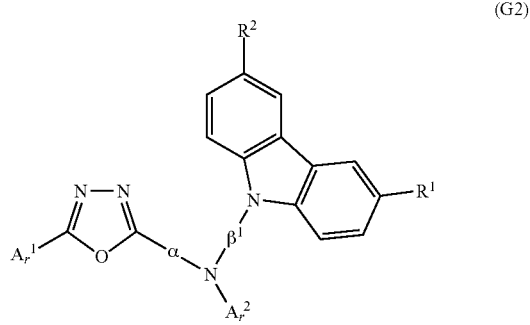

(G2)

wherein each of α and β$^1$ represents an arylene group having 6 to 25 carbon atoms; each of A$_r^1$ and A$_r^2$ represents an aryl group having 6 to 25 carbon atoms; and each of R$^1$ and R$^2$ represents hydrogen, an alkyl group having 1 to 4 carbon atoms, or an aryl group having 6 to 25 carbon atoms.

2. An oxadiazole derivative represented by a general formula (G3),

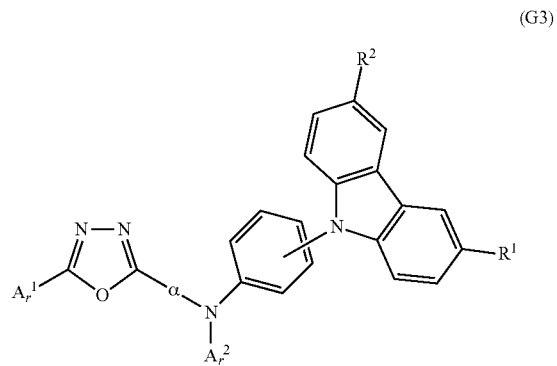

(G3)

wherein α represents an arylene group having 6 to 25 carbon atoms; each of A$_r^1$ and A$_r^2$ represents an aryl group having 6 to 25 carbon atoms; and each of R$^1$ and R$^2$ represents hydrogen, an alkyl group having 1 to 4 carbon atoms, or an aryl group having 6 to 25 carbon atoms.

3. An oxadiazole derivative represented by a general formula (G4),

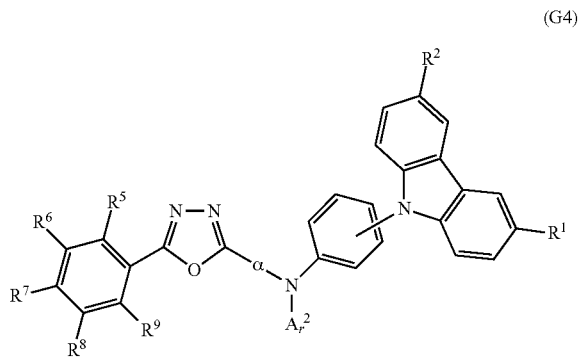

(G4)

wherein α represents an arylene group having 6 to 25 carbon atoms; $A_r^2$ represents an aryl group having 6 to 25 carbon atoms; each of $R^1$ and $R^2$ represents hydrogen, an alkyl group having 1 to 4 carbon atoms, or an aryl group having 6 to 25 carbon atoms; and each of $R^5$ to $R^9$ represents hydrogen, an alkyl group having 1 to 4 carbon atoms, an alkoxy group having 1 to 4 carbon atoms, or a phenyl group.

4. The oxadiazole derivative according to claim 3, wherein the α is any of a 1,2-phenylene group, a 1,3-phenylene group, or a 1,4-phenylene group.

5. An oxadiazole derivative represented by a general formula (G5),

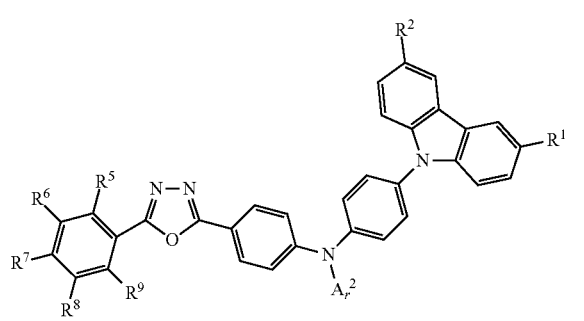

(G5)

wherein $A_r^2$ represents an aryl group having 6 to 25 carbon atoms; each of $R^1$ and $R^2$ represents hydrogen, an alkyl group having 1 to 4 carbon atoms, or an aryl group having 6 to 25 carbon atoms; and each of $R^5$ to $R^9$ represents hydrogen, an alkyl group having 1 to 4 carbon atoms, an alkoxy group having 1 to 4 carbon atoms, or a phenyl group.

6. An oxadiazole derivative represented by a general formula (G6),

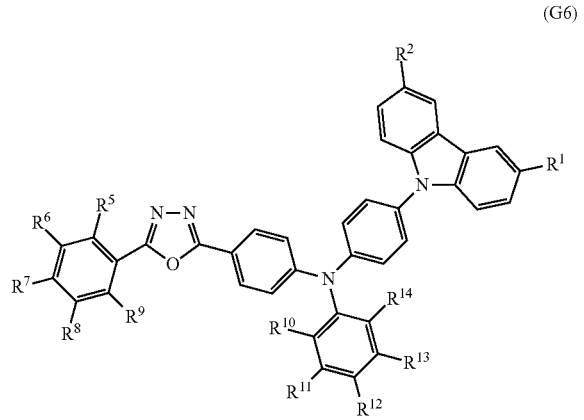

(G6)

wherein each of $R^1$ and $R^2$ represents hydrogen, an alkyl group having 1 to 4 carbon atoms, or an aryl group having 6 to 25 carbon atoms; each of $R^5$ to $R^9$ represents hydrogen, an alkyl group having 1 to 4 carbon atoms, an alkoxy group having 1 to 4 carbon atoms, or a phenyl group; and each of $R^{10}$ to $R^{14}$ represents hydrogen, an alkyl group having 1 to 4 carbon atoms, or a phenyl group.

7. An oxadiazole derivative represented by a general formula (G7),

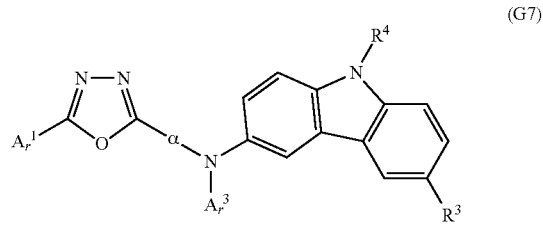

(G7)

wherein α represents an arylene group having 6 to 25 carbon atoms; each of $Ar^1$ and $Ar^3$ represents an aryl group having 6 to 25 carbon atoms; $R^3$ represents hydrogen, an alkyl group having 1 to 4 carbon atoms, or an aryl group having 6 to 25 carbon atoms; and $R^4$ represents an aryl group having 6 to 25 carbon atoms.

8. An oxadiazole derivative represented by a general formula (G8),

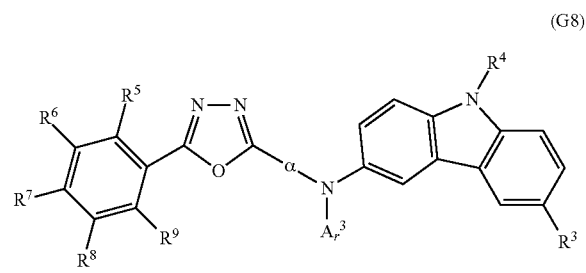

(G8)

wherein α represents an arylene group having 6 to 25 carbon atoms; $Ar^3$ represents an aryl group having 6 to 25 carbon atoms; $R^3$ represents hydrogen, an alkyl group having 1 to 4 carbon atoms, or an aryl group having 6 to 25 carbon atoms; $R^4$ represents an aryl group having 6 to 25 carbon atoms; and each of $R^5$ to $R^9$ represents hydrogen, an alkyl group having 1 to 4 carbon atoms, an alkoxy group having 1 to 4 carbon atoms, or a phenyl group.

9. The oxadiazole derivative according to claim 8, wherein the α is any of a 1,2-phenylene group, a 1,3-phenylene group, or a 1,4-phenylene group.

10. An oxadiazole derivative represented by a general formula (G9),

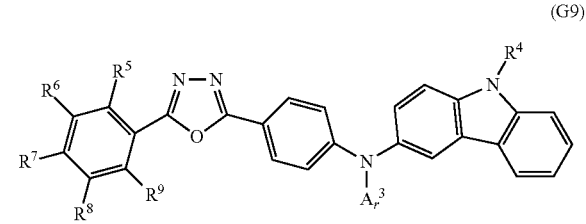

(G9)

wherein $Ar^3$ represents an aryl group having 6 to 25 carbon atoms; $R^4$ represents an aryl group having 6 to 25 carbon atoms; and each of $R^5$ to $R^9$ represents hydrogen, an alkyl group having 1 to 4 carbon atoms, an alkoxy group having 1 to 4 carbon atoms, or a phenyl group.

11. An oxadiazole derivative represented by a general formula (G10),

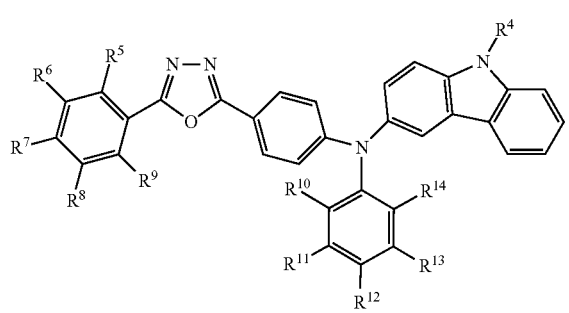

wherein $R^4$ represents an aryl group having 6 to 25 carbon atoms; each of $R^5$ to $R^9$ represents hydrogen, an alkyl group having 1 to 4 carbon atoms, an alkoxy group having 1 to 4 carbon atoms, or a phenyl group; and each of $R^{10}$ to $R^{14}$ represents hydrogen, an alkyl group having 1 to 4 carbon atoms, or a phenyl group.

12. A light emitting element comprising the oxadiazole derivative according to claim 1.

13. A light emitting element comprising a light emitting layer including a light emitting substance and the oxadiazole derivative according to claim 1.

14. The light emitting element according to claim 13, wherein the light emitting substance is a phosphorescent compound.

15. A light emitting element, wherein a layer containing the oxadiazole derivative according to claim 1 is provided to be in contact with a light emitting layer.

16. A light emitting device comprising the light emitting element according to claim 12.

17. An electronic device comprising the light emitting device according to claim 16.

18. A light emitting element comprising the oxadiazole derivative according to claim 7.

19. A light emitting element comprising a light emitting layer including a light emitting substance and the oxadiazole derivative according to claim 7.

20. The light emitting element according to claim 19, wherein the light emitting substance is a phosphorescent compound.

21. A light emitting element, wherein a layer containing the oxadiazole derivative according to claim 7 is provided to be in contact with a light emitting layer.

22. A light emitting device comprising the light emitting element according to claim 18.

23. An electronic device comprising the light emitting device according to claim 22.

* * * * *

UNITED STATES PATENT AND TRADEMARK OFFICE
CERTIFICATE OF CORRECTION

PATENT NO.         : 8,686,159 B2
APPLICATION NO.    : 13/780737
DATED              : April 1, 2014
INVENTOR(S)        : Hiroko Murata et al.

It is certified that error appears in the above-identified patent and that said Letters Patent is hereby corrected as shown below:

In the Specification:

Column 2, Line 11; Change "material; and" to --material, and--.

Column 17, Line 58; Change "(Am1>" to --(Am1')>--.

Column 17, Line 62; Change "21 <c. Synthesis" to --<<c. Synthesis--.

Column 18, Line 6; Change "(Am2), or and (Am3);" to --(Am2), or (Am3);--.

Column 19, Line 1; Change "α" to --a--.

Column 19, Line 66; Change "cc" to --α--.

Column 27, Lines 40 to 60;

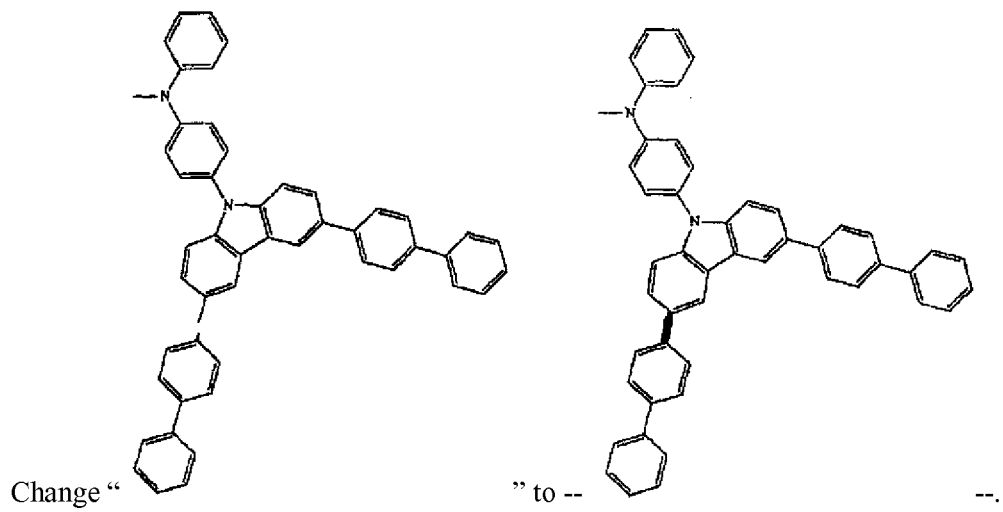

Signed and Sealed this
Ninth Day of September, 2014

Michelle K. Lee
*Deputy Director of the United States Patent and Trademark Office*

CERTIFICATE OF CORRECTION (continued)
U.S. Pat. No. 8,686,159 B2

In the Specification:

Column 29, Lines 45 to 67 and Column 30, Lines 1 to 5;

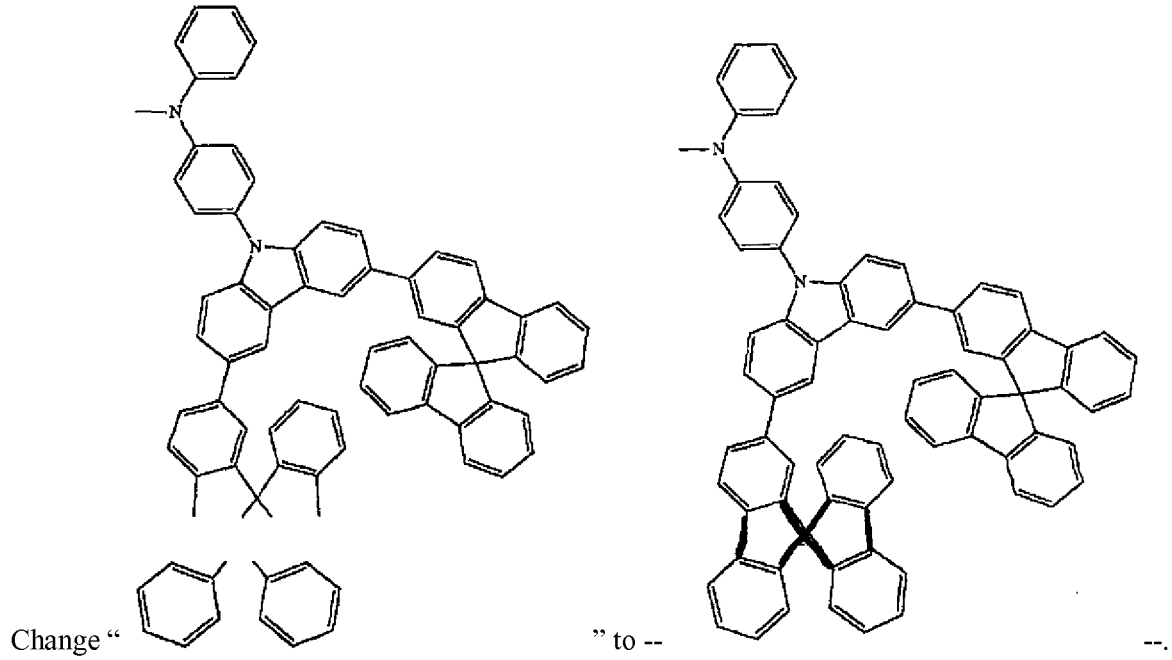

Column 42, Lines 50 to 67 and Column 43, Lines 1 to 13;

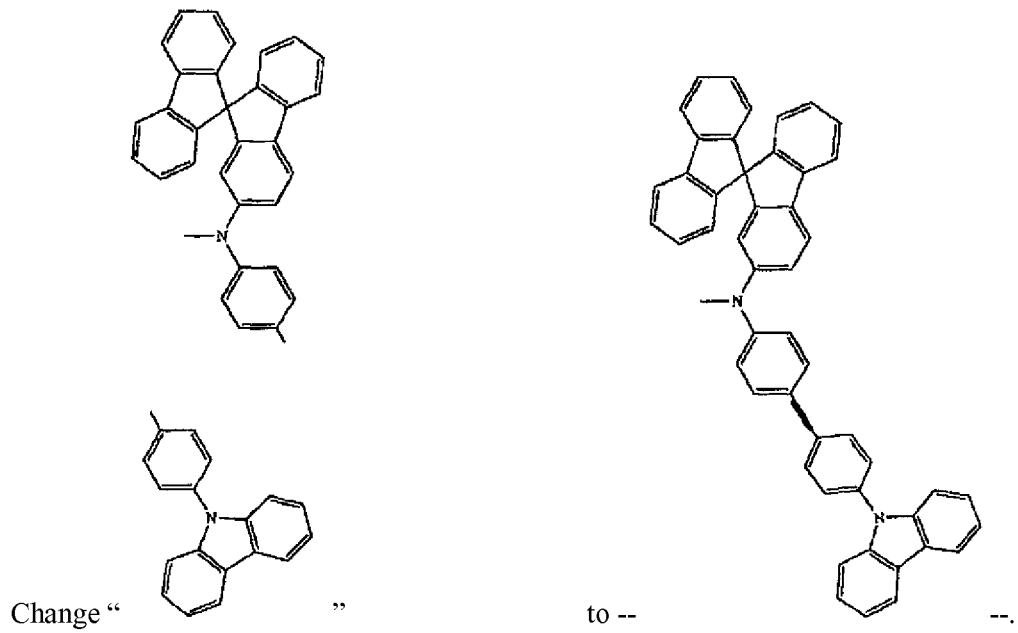

Column 121, Line 33; Change "(BaOx); or" to (BaOx), or--.

Column 123, Line 21; Change "(III)" to --(111)--.

Column 129, Line 38; Change "(I)" to --(1)--.

In the Specification:

CERTIFICATE OF CORRECTION (continued)
U.S. Pat. No. 8,686,159 B2

Column 139, Line 54; Change "(II)" to --(ii)--.

Column 139, Line 58; Change "(III)" to --(iii)--.

Column 139, Line 61; Change "(Iv)" to --(iv)--.

Column 141, Line 51; Change "1$r$(ppy)$_2$(acac)" to --I$r$(ppy)$_2$(acac)--.

Column 143, Line 34; Change "1$r$(Fdpq)$_2$(acac)" to --I$r$(Fdpq)$_2$(acac)--.

Column 156, Line 21; Change "mYGAO11, were" to --mYGA011 were--.

Column 157, Line 6; Change "30 mm." to --30 nm.--.

Column 157, Line 9; Change "Alg$_3$" to --Alq$_3$--.